United States Patent
Marban et al.

(10) Patent No.: US 11,357,799 B2
(45) Date of Patent: Jun. 14, 2022

(54) CARDIOSPHERE-DERIVED CELLS AND EXOSOMES SECRETED BY SUCH CELLS IN THE TREATMENT OF MUSCULAR DYSTROPHY

(71) Applicant: Cedars-Sinai Medical Center, Los Angeles, CA (US)

(72) Inventors: Eduardo Marban, Santa Monica, CA (US); Mark Amin Aminzadeh, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 204 days.

(21) Appl. No.: 15/516,658

(22) PCT Filed: Oct. 2, 2015

(86) PCT No.: PCT/US2015/053853
§ 371 (c)(1),
(2) Date: Apr. 3, 2017

(87) PCT Pub. No.: WO2016/054591
PCT Pub. Date: Apr. 7, 2016

(65) Prior Publication Data
US 2017/0290860 A1 Oct. 12, 2017

Related U.S. Application Data

(60) Provisional application No. 62/059,308, filed on Oct. 3, 2014.

(51) Int. Cl.
| | |
|---|---|
| *A61K 35/34* | (2015.01) |
| *A61K 9/00* | (2006.01) |
| *A61P 21/00* | (2006.01) |
| *A61P 9/10* | (2006.01) |
| *A61K 31/713* | (2006.01) |
| *A61K 38/17* | (2006.01) |
| *C12N 15/113* | (2010.01) |

(52) U.S. Cl.
CPC ............ *A61K 35/34* (2013.01); *A61K 9/0019* (2013.01); *A61K 31/713* (2013.01); *A61K 38/1709* (2013.01); *A61P 9/10* (2018.01); *A61P 21/00* (2018.01); *C12N 15/113* (2013.01); *C12N 2310/141* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,028,588 A | 7/1991 | Hoffman et al. |
| 5,052,402 A | 10/1991 | Bencini et al. |
| 5,104,787 A | 4/1992 | Lindstrom et al. |
| 5,175,004 A | 12/1992 | Matsurnura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |

(Continued)

FOREIGN PATENT DOCUMENTS

| | | |
|---|---|---|
| CA | 2488346 | 12/2003 |
| CN | 1537646 | 10/2004 |

(Continued)

OTHER PUBLICATIONS

Kaspar et al., (J Am Acad Nurse Pract. May 2009; 21(5): 241-249.*
Barile et al., Stem Cells International (2013), vol. 2013, Article ID 916837, 10 pages.*
Edelberg et al., "Platelet-Derived Growth Factor-AB Limits the Extent of Myocardial Infarction in a Rat Model: Feasibility of Restoring Impaired Angiongeic Capacity in the Aging Heart", Curculation , 2002, vol. 150, No. 5, pp. 608-613 (Year: 2002).*

(Continued)

*Primary Examiner* — Scott Long
*Assistant Examiner* — Evelyn Y Pyla
(74) *Attorney, Agent, or Firm* — Knobbe, Martens, Olson & Bear, LLP

(57) ABSTRACT

Described herein are compositions and techniques related to generation and therapeutic application of cardiosphere-derived cells (CDCs) and CDC-derived exosomes. These cells and their secreted vesicles contain a unique milieu of biological factors, including cytokines, growth factors, transcription factors, nucleic acids including non-coding nucleic acids such as microRNAs, that serve to initiate and promote many therapeutic effects. Exosomes and their "cargo" contents, such as microRNAs can favorably modulate apoptosis, inflammation and fibrosis in the injured heart. Thus, CDC-derived exosomes represent a novel "cell-free" therapeutic candidate for tissue repair.

7 Claims, 79 Drawing Sheets

(56) References Cited

U.S. PATENT DOCUMENTS

| | | |
|---|---|---|
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,743 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Roseman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenalan et al. |
| 6,997,363 B1 | 2/2006 | Handy et al. |
| 7,026,121 B1 | 4/2006 | Wohlgernuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenalan et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1 | 7/2004 | Schneider et al. |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |

(56) References Cited

U.S. PATENT DOCUMENTS

| | | |
|---|---|---|
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Aisberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091426 A1 | 4/2011 | Anversa |
| 2011/0091448 A1 | 4/2011 | Moon et al. |
| 2011/0092961 A1 | 4/2011 | Hyde et al. |
| 2011/0110397 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0189780 A1 | 7/2013 | Shoemaker et al. |
| 2013/0266543 A1 | 10/2013 | Nadal-Ginard |
| 2013/0280205 A1 | 10/2013 | Mozaffari et al. |
| 2013/0288962 A1 | 10/2013 | Anversa et al. |
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhaegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0140658 A1 | 5/2015 | Kamp et al. |
| 2015/0246030 A1 | 9/2015 | Armer et al. |
| 2015/0273113 A1 | 10/2015 | Marbán et al. |
| 2015/0328263 A1 | 11/2015 | Kaushal |
| 2016/0158291 A1 | 6/2016 | Kreke et al. |
| 2016/0244723 A1 | 8/2016 | Giacomello et al. |
| 2017/0037375 A1 | 2/2017 | Palecek et al. |
| 2017/0049793 A1 | 2/2017 | Moon et al. |
| 2017/0087087 A1 | 3/2017 | Leonard et al. |
| 2017/0304368 A1 | 10/2017 | Marbán et al. |
| 2018/0100149 A1 | 4/2018 | Marbán et al. |
| 2019/0000888 A1 | 1/2019 | Marbán et al. |
| 2019/0062740 A1 | 2/2019 | Zhu |

(56) References Cited

U.S. PATENT DOCUMENTS

| | | |
|---|---|---|
| 2019/0160111 A1 | 5/2019 | Marbán et al. |
| 2019/0255119 A1 | 8/2019 | Marbán et al. |
| 2020/0024604 A1 | 1/2020 | Marbán et al. |
| 2020/0121727 A1 | 4/2020 | Marban et al. |
| 2020/0316226 A1 | 10/2020 | Marban et al. |
| 2021/0032598 A1 | 2/2021 | Ibrahim et al. |
| 2021/0085724 A1 | 3/2021 | Marban et al. |
| 2021/0207145 A1 | 7/2021 | Marban et al. |

FOREIGN PATENT DOCUMENTS

| | | |
|---|---|---|
| CN | 1772300 | 5/2006 |
| CN | 1785430 | 6/2006 |
| EP | 1 254 952 | 11/2002 |
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |
| EP | 1 650 293 | 12/2010 |
| EP | 2 371 370 | 10/2011 |
| EP | 2 385 120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 687 219 | 1/2014 |
| JP | 2005-506845 | 3/2005 |
| JP | 2005-110565 | 4/2005 |
| JP | 2006-006125 | 1/2006 |
| JP | 2008-504816 | 2/2008 |
| JP | 2008-518730 | 6/2008 |
| KR | 100830889 | 5/2008 |
| KR | 10-1818560 | 1/2018 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 1/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2003/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |
| WO | WO 2014/013258 | 1/2014 |
| WO | WO-2014028493 A2 * | 2/2014 ........... C12N 15/111 |
| WO | WO 2014/114465 | 7/2014 |
| WO | WO 2014/160153 | 10/2014 |
| WO | WO 2015/055857 | 4/2015 |
| WO | WO 2015/085096 | 6/2015 |
| WO | WO 2015/092020 | 6/2015 |
| WO | WO 2015/120150 | 8/2015 |
| WO | WO 2016/054591 | 4/2016 |
| WO | WO 2016/057560 | 4/2016 |
| WO | WO 2017/160884 | 9/2017 |
| WO | WO 2017/173034 | 10/2017 |
| WO | WO 2019/015702 | 1/2019 |
| WO | WO 2019/028223 | 2/2019 |
| WO | WO 2019/050071 | 3/2019 |
| WO | WO 2019/126068 | 6/2019 |
| WO | WO 2019/152549 | 8/2019 |
| WO | WO 2020/227489 | 11/2020 |
| WO | WO 2021/178514 | 9/2021 |
| WO | WO 2021/188899 | 9/2021 |

OTHER PUBLICATIONS

Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.

Abela et al.; "A New Method for Isolation of Cardiac Myocytes by Percutaneous Endomyocardial Biopsy"; Catheterization and Cardiovascular Diagnosis, 1996, vol. 37, pp. 227-230.

(56) References Cited

OTHER PUBLICATIONS

Ajijola et al., "Ventricular Tachycardia in Ischemic Heart Disease Substrates", Indian Heart Journal, 2014, pp. S24-S34, S28 & S30, vol. 66, Supplement 1.
Albini et al., "A Rapid in Vitro Assay for Quantitating the Invasive Potential of Tumor Cells", Cancer Research, Jun. 15, 1987, pp. 3239-3245, vol. 47.
Ames et al., "Oxidants, Antioxidants, and the Degenerative Diseases of Aging", Proceedings of the National Academy of Sciences of the United States of America, Sep. 1993, vol. 90, pp. 7915-7922.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Andersen et al., "Murine 'Cardiospheres' Are Not a Source of Stem Cells with Cardiomyogenic Potential," Stem Cells, 2009, vol. 27, No. 7, pp. 1571-1581.
Anversa et al., "Primitive Cells and Tissue Regeneration", Circulation Research, 2003, vol. 92, pp. 579-582.
Assmus et al., "Transplantation of Progenitor Cells arid Regeneration Enhancement in Acute Myocardial Infarction (TOPCARE-AMI)", Circulation, Dec. 10, 2002, vol. 106, pp. 3009-3017.
"ATS/ACCP Statement on Cardiopulmonary Exercise Testing", American Thoracic Society/American College of Chest Physicians, American Journal of Respiratory and Critical Care Medicine, 2003, vol. 167, pp. 211-277.
Ausma et al., "Dedifferentiation of Atrial Cardiomyocytes: From in Vivo to in Vitro", Cardiovascular Research, Jul. 2002; vol. 55, No. 1, pp. 9-12.
Baker et al. "Adaptation to Culture of Human Embryonic Stem Cells and Oncogenesis in Vivo" Nature Biotechnology, Feb. 2007, vol. 25, No. 2, pp. 207-215.
Balser et al., "Global Parameter Optimization for Cardiac Potassium Channel Gating Models", Biophysical Journal, Mar. 1990, vol. 57, pp. 433-444.
Balser et al., "Local Anesthetics as Effectors of Allosteric Gating", Journal of Clinical Investigation, Dec. 1996, vol. 98, No. 12, pp. 2874-2886.
Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.
Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.
Barile et al., "Endogenous Cardiac Stem Cells"; Progress in Cardiovascular Diseases, Jul.-Aug. 2007, vol. 50, No. 1, pp. 31-48.
Barr et al., "Efficient Catheter-Mediated Gene Transfer Into the Heart Using Replication-Defective Adenovirus", Gene Therapy, Jan. 1994, vol. 1, No. 1, pp. 51-58.
Barry et al., "Differential Expression of Voltage-Gated $K^+$ Channel Subunits in Adult Rat Heart", Circulation Research, 1995, vol. 77, pp. 361-369.
Barth et al., "Lentiviral Vectors Bearing the Cardiac Promoter of the $Na^+$—$Ca^{2+}$ Exchanger Report Cardiogenic Differentiation in Stem Cells", Molecular Therapy, May 2008, vol. 16, No. 5, pp. 957-964.
Bearzi et al., "Human Cardiac Stem Cells", Proceedings of the National Academy of Sciences of the United States of America (PNAS), Aug. 28, 2007, pp. 14068-14073, vol. 104, No. 35.
Beltrami et al., "Adult Cardiac Stem Cells are Multipotent and Support Myocardial Regeneration", Cell, Sep. 19, 2003, vol. 114, No. 6, pp. 763-776.
Beltrami et al., "Evidence That Human Cardiac Myocytes Divide After Myocardial Infarction", The New England Journal of Medicine, Jun. 7, 2001, vol. 344, pp. 1750-1757.
Beltrami et al., "Multipotent Cells Can be Generated in Vitro from Several Adult Human Organs (Heart, Liver and Bone Marrow)", Stem Cells in Hematology, Blood, 2007, pp. 3438-3446, vol. 110, No. 9.
Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.
Bergmann et al., "Evidence for Cardiomyocyte Renewal in Humans", Science, Apr. 3, 2009, vol. 324, pp. 98-102.
Bernanke et al., "Effects of Hyaluronic Acid on Cardiac Cushion Tissue Cells in Collagen Matrix Cultures", Texas Reports on Biology and Medicine, 1979, pp. 271-285, vol. 39.
"Bioptome.com", Scholten Surgical Instruments, Inc., downloaded from <http://www.bioptome.com/pages.php?page=Products>, 2001, first date of publication unknown, printed on Nov. 1, 2005, pp. 2.
Bird et al., "The Human Adult Cardiomyocyte Phenotype", Cardiovascular Research, May 1, 2003, vol. 58, No. 2, pp. 423-434.
Birks et al., "Left Ventricular Assist Device and Drug Therapy for the Reversal of Heart Failure", The New England Journal of Medicine, 2006, vol. 355, No. 18, pp. 1873-1884.
Bjelakovic et al., "Mortality in Randomized Trials of Antioxidant Supplements for Primary and Secondary Prevention: Systematic Review and Meta-Analysis", JAMA, 2007, vol. 297, pp. 842-857.
Bosnali et al., "Generation of Transducible Versions of Transcription Factors Oct4 and Sox2", Biological Chemistry, Jul. 2008, vol. 389, pp. 851-861.
Bredemeyer et al., "ATM Stabilizes DNA Double-Strand-Break Complexes During V(D)J Recombination", Nature, Jul. 27, 2006, vol. 442, pp. 466-470.
Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.
Cai et al., "Injectable Glycosaminoglycan Hydrogels for Controlled Release of Human Basic Fibroblast Growth Factor," Biomaterials, 2005, vol. 26, pp. 6054-6067.
"CArdiosphere-Derived aUtologous StemCElls to Reverse ventricUlar dysfunction (CADUCEUS)", ClinicalTrials.gov, Identifier NCT00893360, 2009, pp. 6.
Chambers et al., "Functional Expression Cloning of Nanog, a Pluripotency Sustaining Factor in Embryonic Stem Cells", Cell, May 30, 2003, vol. 113, No. 5, pp, 643-655.
Chen et al., "Enhanced Turnorigenesis in p53 Knockout Mice Exposed in Utero to High-Dose Vitamin E", Carcinogenesis, 2006, vol. 27, No. 7, pp. 1358-1368.
Chen et al., "Mesenchymal Stem Cell Secretes Microparticles Enriched in Pre-MicroRNAs", Nucleic Acids Research, 2010, vol. 38, No. 1, pp. 215-224.
Chen et al., "Reduced Tumorigenesis in p53 Knockout Mice Exposed in Utero to Low-Dose Vitamin E", Cancer, Apr. 1, 2009, vol. 115, pp. 1563-1575.
Chen et al., "The Role of Notch 1 Activation in Cardiosphere Derived Cell Differentiation", Stem Cells and Development, 2012, pp. 2122-2129, vol. 21, No. 12.
Chen et al., "Vascular Endothelial Growth Factor Promotes Cardiomyocyte Differentiation of Embryonic Stem Cells", American Journal of Physiology-Heart and Circulatory Physiology, Oct. 2006, vol. 291, No. 4, pp. H1653-H1658.
Cheng et al., "Functional Performance of Human Cardiosphere-Derived Cells Delivered in an in situ Polymerizable Hyaluronan-Gelatin Hydrogel", Biomaterials, 2012, pp. 8.
Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.
Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.
Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.
Chimenti et al., "Abstract 3182: Paracrine Contribution versus Direct Regeneration in Cardiosphere-Derived Cell Therapy for Acute Myocardial Infarction", Circulation, 2009, vol. 120, p. S756.

(56) References Cited

OTHER PUBLICATIONS

Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.

Chlopčíková et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.

Cho et al., "Secondary Sphere Formation Enhances the Functionality of Cardiac Progenitor Cells", Molecular Therapy, Sep. 2012, vol. 20, No. 9, pp. 1750-1766.

Christman et al., "Biomaterials for the Treatment of Myocardial Infarction", Journal of the American College of Cardiology, 2006, vol. 48, No. 5, pp. 907-913.

Conkright et al., "A Gene Encoding an Intestinal-Enriched Member of the Krüppel-Like Factor Family Expressed in Intestinal Epithelia Cells", Nucleic Acids Research, 1999, vol. 27, No. 5, pp. 1263-1270.

Crisostomo et al., "Embryonic Stem Cells Attenuate Myocardial Dysfunction and Inflammation After Surgical Global Ischemia via Paracrine Actions", American Journal of Physiology-Heart and Circulatory Physiology, 2008, vol. 295, pp. H1726-H1735.

Csete, Marie, "Oxygen in the Cultivation of Stem Cells", Annals New York Academy of Sciences, 2005, vol. 1049, pp. 1-8.

"Culture Media Database", EGM-2 (Endothelial Growth Medium 2)—ID 63, downloaded from <http://bio.lonza.com/3018.html#ext-comp-1003:tab_63:change>, printed on Jan. 14, 2013, p. 1.

Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.

Davis et al., "Validation of the Cardiosphere Method to Culture Cardiac Progenitor Cells from Myocardial Tissue", PLoS One; 2009, vol. 4, No. 9, e7195; pp. 1-8.

Davis et al., "Human Cardiospheres are a Source of Stem Cells with Cardiomyogenic Potential", Stem Cells, 2010, vol. 28, No. 5, pp. 903-904.

De Bakker et al, "Slow Conduction in the Infarcted Human Heart 'Zigzag' Course of Activation", Circulation, Sep. 1993, pp. 915-926, vol. 88, No. 3.

De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.

De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.

Deal et al., "Molecular Physiology of Cardiac Potassium Channels", Physiological Reviews, Jan. 1996, vol. 76, No. 1, pp. 49-67.

Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.

Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.

DeRossi et al., "The Third Helix of the Antennapedia Homeodomain Translocates through Biological Membranes", The Journal of Biological Chemistry, Apr. 8, 1994, vol. 269, No. 14, pp. 10444-10450.

Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.

Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.

Dispersyn et al., "Dissociation of Cardiornyocyte Apoptosis and Dedifferentiation in Infarct Border Zones", European Heart Journal, 2002, vol. 23, pp. 849-857.

Dixon et al., "Quantitative Analysis of Potassium Channel mRNA Expression in Atrial and Ventricular Muscle of Rats", Circulation Research, Aug. 1994, vol. 75, No. 2, pp. 252-260.

Dixon et al., "Role of the Kv4.3 $K^+$ Channel in Ventricular Muscle", Circulation Research, 1996, vol. 79, pp. 659-668.

Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.

Donahue et al., "Ultrarapid, Highly Efficient Viral Gene Transfer to the Heart", Proceedings of the National Academy of Sciences of the United States of America, Apr. 1997, vol. 94, pp. 4664-4668.

Dong et al., "Islet Cel and Extrapancreatic Expression of the LIM Domain Homeobox Gene isl-1", Molecular Endocrinology, 1991, vol. 5, No. 11, pp. 1633-1641.

Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.

Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.

Driesen et al., "Structural Remodeling of Cardiomyocytes in the Border Zone of Infarcted Rabbit Heart", Molecular and Cellular Biochemistry, 2007, pp. 225-232, vol. 302.

Duff et al., "CD105 is Important for Angiogenesis: Evidence and Potential Applications," FASEB Journal, Jun. 2003, vol. 17, No. 9, pp. 984-992.

Eguchi, Masakatsu, "Recent Advances in Selective Opioid Receptor Agonists and Antagonists", Medicinal Research Reviews, 2004, vol. 24, No. 2, pp. 182-212.

Elliott et al., "Intercellular Trafficking and Protein Delivery by a Herpesvirus Structural Protein", Cell, Jan. 24, 1997, vol. 88, pp. 223-233.

Elliott et al., "Intercellular Trafficking of VP22-GFP Fusion Proteins", Gene Therapy, 1999, vol. 6, pp. 149-151.

Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.

Engel et al., "p38 MAP Kinase Inhibition Enables Proliferation of Adult Mammalian Cardiomyocytes", Genes & Development, May 2005, vol. 19, No. 10, pp. 1175-1187.

Eppenberger-Eberhardt et al., "Reexpression of α-Smooth Muscle Acting Isoforrn in Cultured Adult Rat Cardiomyocytes", Developmental Biology, Jun. 1990, vol. 139, No. 2, pp. 269-278.

Eschenhagen et al., "Engineering Myocardial Tissue", Circulation Research, 2005, vol. 97, pp. 1220-1231.

Falck et al., "Conserved Modes of Recruitment of ATM, ATR and DNA-PKcs to Sites of DNA Damage", Nature, Mar. 31, 2005, vol. 434, pp. 605-611.

Fehrer et al., "Reduced Oxygen Tension Attenuates Differentiation Capacity of Human Mesenchymal Stem Cells and Prolongs their Lifespan", Aging Cell, 2007, vol. 6, pp. 745-757.

Fiset et al., Shal-Type Channels Contribute to the $Ca^{2+}$—Independent Transient Outward $K^+$ Current in Rat Ventricle, Journal of Physiology, 1997, vol. 500, No. 1, pp. 51-64.

Foreman et al., "Reactive Oxygen Species Produced by NADPH Oxidase Regulate Plant Cell Growth", Nature, Mar. 27, 2003, vol. 422, pp. 442-446.

Frankel et al., "Cellular Uptake of the Tat Protein from Human Immunodeficiency Virus", Cell, vol. 55, Dec. 23, 1988, pp. 1189-1193.

Freyman et al., "A Quantitative, Randomized Study Evaluating Three Methods of Mesenchymal Stem Cell Delivery Following Myocardial Infarction", European Heart Journal, 2006, vol. 27, pp. 1114-1122.

(56) References Cited

OTHER PUBLICATIONS

Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.
Gallet et al, "Intracoronary Delivery of Self-Assembling Heart-Derived Microtissues (Cardiospheres) for Prevention of Adverse Remodeling in a Pig Model of Convalescent Myocardial Infarction", <http://circinterventions.ahajournals.org>, Dec. 8, 2015, pp. 21.
Galli et al., "Neural Stem Cells: An Overview", Circulation Research, 2003, vol. 92, No. 6, pp. 598-608.
Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.
George et al, "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.
Gibco, "Insulin-Transferrin-Selenium", Product Sheet, 2014.
Gibco, "Insulin-Transferrin-Selenium: 100X (for General Tissue Culture Applications)", Product Sheet, Form No. 2672, Jun. 2001, p. 1.
Gidh-Jain et al., Differential Expression of Voltage-Gated $K^+$ Channel Genes in Left Ventricular Remodeled Myocardium After Experimental Myocardial Infarction, Circulation Research, 1996, vol. 79, pp. 669-675.
Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology—Heart and Circulatory Physiology, Apr. 2005, vol. 288, No. 4, pp. H1851-H1858.
Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.
Good et al., "β-Amyloid Peptide Blocks the Fast-Inactivating $K^+$ Current in Rat Hippocarnpal Neurons", Biophysical Journal, Jan. 1996, vol. 70, pp. 296-304.
Goumans et al., "TGF-β1 Induces Efficient Differentiation of Human Cardiomyocyte Progenitor Cells into Functional Cardiomyocytes in Vitro", Stem Cell Research, 2008, vol. 1, pp. 136-149.
Grayson et al. "Hypoxia Enhances Proliferation and Tissue Formation of Human Mesenchymal Stem Cells", Biochemical and Biophysical Research Communications, 2007, vol. 358, pp. 948-953.
Green et al, "Autonomous Functional Domains of Chemically Synthesized Human Immunodeficiency Virus Tat Trans-Activator Protein", Dec. 23, 1988, Cell, vol. 55, pp. 1179-1188.
Grigorian-Shamagian et al., "Cardiac and Systemic Rejuvenation After Cardiosphere-Derived Cell Therapy in Senescent Rats", European Heart Journal, Oct. 14, 2017, pp. 2957-2967, vol. 38, No. 39.
Grossman et al., "Contractile State of the Left Ventricle in Man as Evaluated from End-Systolic Pressure-Volume Relations", Circulation, vol. 56, No. 5, Nov. 1977, pp. 845-852.
Gu, Ylping, "Bispecific Antibody Targeted Stem Cell Therapy for Myocardial Repair", Dissertation, University of California San Francisco and University of California Berkeley, 2008, pp. 94.
Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.
Hacein-Bey-Abina et al., "LMO2—Associated Clonal T Cell Proliferation in Two Patients after Gene Therapy for SCID-X1", Science, Oct. 17, 2003, vol. 302, pp. 415-419 with Erratum in 1 page.
Hagège, MD, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. I108-I113.
Haider et al., "Bone Marrow Stem Cell Transplantation for Cardiac Repair", American Journal of Physiology—Heart and Circulatory Physiology, 2005, H2557-H2567, vol. 288.
Hainsworth et al., "The Nitrone Disodium 2,4-Sulphophenyl-N-Tert-Butylnitrone is Without Cytoprotective Effect on Sodium Nitroprusside-Induced Cell Death in N1E-115 Neuroblastoma Cells in vitro", Journal of Cerebral Blood Flow & Metabolism, 2008, vol. 28, pp. 24-28.
Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.
Harvey, "Molecular Determinants of Cardiac Development and Congenital Disease," Mouse Development, Patterning, Morphogenesis, and Organogensis, 2002, pp. 331-370, Chapter 16.
Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.
Hergenreider et al., "Atheroprotective Communication Between Endothelial Cells and Smooth Muscle Cells Through miRNAs", Nature Cell Biology, Mar. 2012, vol. 14, No. 3, pp. 249-256.
Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.
Hierlihy et al., "The Post-Natal Heart Contains a Myocardial Stern Cell Population", FEBS Letters, 2002, vol. 530, No. 1-3, pp. 239-243.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hochedlinger et al., "Nuclear Reprogramming and Pluripotency", Nature, Jun. 29, 2006, vol. 441, pp. 1061-1067.
Hu et al., "MicroRNA-210 as a Novel Therapy for Treatment of Ischemic Heart Disease", Circulation, Sep. 14, 2010, vol. 122, Supplement 11, S124-S131, pp. 17.
Hullinger et al., Inhibition of miR-15 Protects Against Cardiac Ischemic Injury, Circulation Research, Jan. 6, 2012, vol. 110, No. 1, pp. 71-81.
Ibrahim et al., "Exosomes as Critical Agents of Cardiac Regeneration Triggered by Cell Therapy", Stem Cell Reports, May 6, 2014, vol. 2, pp. 606-619.
Ibrahim et al., "Exosomes: Fundamental Biology and Roles in Cardiovascular Physiology", Annual Review of Physiology, 2016, vol. 78, pp. 67-83.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
International Search Report and Written Opinion received in PCT Application No. PCT/US2015/053853, dated Dec. 29, 2015 in 9 pages.
International Preliminary Report on Patentability and Written Opinion received in PCT/US2015/053853, dated Apr. 13, 2017 in 8 pages.
Ivanovic, Zoran, "Hypoxia or in Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal of Clinical Investigation, Jun. 2001, pp. 1395-1402, vol. 107, No. 11.
Jayawardena et al., MicroRNA-Mediated in Vitro and in Vivo Direct Reprogramming of Cardiac Fibroblasts to Cardiomyocytes, Circulation Research, 2012, vol. 110, No. 11, pp. 1465-1473.
Johnston, MD, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.

(56) References Cited

OTHER PUBLICATIONS

Jutkiewicz, Emily, The Antidepressant-Like Effects of Delta-Opioid Receptor Agonists, Molecular Interventions, 2006, vol., No. 3, pp. 162-169.

Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.

Kamdar et al., "Dystrophin-Deficient Cardiomyopathy", Journal of the American College of Cardiology, 2016, vol. 67, No. 21, pp. 2533-2546.

Karlsson et al., "Insulin Gene Enhancer Binding Protein lsl-1 is a Member of a Novel Class of Proteins Containing Both a Homeo-and a Cys-His Domain", Nature, Apr. 26, 1990, vol. 344, pp. 879-882.

Karoubi et al., "Single-Cell Hydrogel Encapsulation for Enhanced Survival of Human Marrow Stomal Cells", Biomaterials, 2009, vol. 30, pp. 5445-5455.

Kawaguchi et al., "Cell Shape and Cardiosphere Differentiation: A Revelation by Proteomic Profiling"; Hindawi Publishing Corporation, Biochemistry Research International, vol. 2013, Article ID 730874, pp. 1-9.

Kim et al., "Generation of Human Induced Pluripotent Stem Cells by Direct Delivery of Reprogramming Proteins", Cell Stem Cell, Jun. 5, 2009, vol. 4, No. 6, pp. 472-476.

Kisselbach et al., "CD90 Expression on Human Primary Cells and Elimination of Contaminating Fibroblasts from Cell Cultures", Cytotechnology, 2009, pp. 31-44, vol. 59.

Kühn et al., "Periostin Induces Proliferation of Differentiated Cardiomyocytes and Promotes Cardiac Repair", Nature Medicine, Aug. 2007, vol. 13, No. 8, pp. 962-969.

Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. I167-I173.

Kwon et al., "Cellular Manipulation of Human Embryonic Stem Cells by TAT-PDX1 Protein Transduction," Molecular Therapy, Jul. 1, 2005, vol. 12, No. 1, pp. 28-32.

Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.

LaFlamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.

Lai et al., "Exosome Secreted by MSC Reduces Myocardial Ischemia/Reperfusion Injury", Stem Cell Research, 2010, vol. 4, pp. 214-222.

Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.

Landázuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.

Lavon et al., "Derivation of Euploid Human Embryonic Stem Cells from Aneuploid Embryos", Stem Cells, 2008, vol. 26, pp. 1874-1882.

Lee et al., "Antibody Targeting of Stem Cells to Infarcted Myocardium", Stem Cells: Translational and Clinical Research, 2007, pp. 712-717, vol. 25.

Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.

Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.

Leferovich et al., "Heart Regeneration in Adult MRL Mice", Proceedings of the National Academy of Sciences of the United States of America (PNAS), Aug. 14, 2001, vol. 98, No. 17, pp. 9830-9835.

Leor, MD, et al., "Transplantation of Fetal Myocardial Tissue Into the Infarcted Myocardium of Rat", Circulation, Nov. 1, 1996, vol. 94, No. 9, II-332-II-336.

Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.

Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.

Li et al., "Cardiospheres Recapitulate a Niche-Like Microenvironment Rich in Stemness and Cell-Matrix Interactions, Rationalizing Their Enhanced Functional Potency for Myocardial Repair", Stem Cells: Translational and Clinical Research, 2010, pp. 2088-2098, vol. 28.

Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.

Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.

Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.

Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105. No. 12, p, e58.

Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.

Li, MD, PhD et al., "Imaging Survival and Function of Transplanted Cardiac Resident Stem Cells", Journal of the American College of Cardiology, Apr. 7, 2009, vol. 53, No. 14, pp. 1229-1240.

Liao et al., "Enhanced Efficiency of Generating Induced Pluripotent Stem (iPS) Cells from Human Somatic Cells by a Combination of Six Transcription Factors", Cell Research, 2008, vol. 18, pp. 600-603.

Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.

Lindsay, Mark A., "Peptide-Mediated Cell Delivery: Application in Protein Target Validation", Current Opinion in Pharmacology, 2002, vol. 2, pp. 587-594.

Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.

Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.

Liu et al. "Autologous Stem Cell Transplantation for Myocardial Repair", American Journal of Physiology, Heart and Circulatory Physiology, 2004, pp. H501-H511, vol. 287.

Liu et al., "Osteochondral Defect Repair with Autologous Bone Marrow-Derived Mesenchymal Stem Cells in an Injectable, in Situ, Cross-Linked Synthetic Extracellular Matrix", Tissue Engineering, 2006, pp. 3405-3416, vol. 12, No. 12.

(56) References Cited

OTHER PUBLICATIONS

Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.
Lum et al., "The New Face of Bispecific Antibodies: Targeting Cancer and Much More", Experimental Hematology, 2006, pp. 1-6, vol. 34.
Lyngbaek et al., "Cardiac Regeneration by Resident Stem and Progenitor Cells in the Adult Heart", Basic Research in Cardiology, 2007, vol. 102, pp. 101-114.
Maitra et al, Genomic Alterations in Cultured Human Embryonic Stem Cells, Nature Genetics, Oct. 2005, vol. 37, No. 10, pp. 1099-1103.
Maletic-Savatic et al., "Differential Spatiotemporal Expression of $K^+$ Channel Polypeptides in Rat Hippocampal Neurons Developing in Situ and in Vitro", The Journal of Neuroscience, May 1995, vol. 15, No. 5, pp. 3840-3851.
Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.
Marbán, Eduardo, "Big Cells, Little Cells, Stem Cells: Agents of Cardiac Plasticity", Circulation Research, 2007, vol. 100, No. 4, pp. 445-446.
Marshall et al., "The Jellyfish Green Fluorescent Protein: A New Tool for Studying Ion Channel Express and Function", Neuron, Feb. 1995, vol. 14, pp. 211-215.
Martens et al., "Percutaneous Cell Delivery Into the Heart Using Hydrogels Polymerizing in Situ", Cell Transplantation, 2009, vol. 18, No. 3, pp, 297-304.
Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.
McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.
Mehmel et al., "The Linearity of the End-Systolic Pressure-Volume Relationship in Man and its Sensitivity for Assessment of Left Ventricular Function", Circulation, 1981, vol. 63, pp. 1216-1222.
Messina et al., "Isolation and Expansion of Adult Cardiac Stem Cells from Human and Murine Heart", Oct. 29, 2004, Circulation Research, Cellular Biology, American Heart Association, vol. 95, pp. 911-921.
Miller III, et al., Meta-Analysis: High-Dosage Vitamin E Supplementation May Increase All-Cause Mortality, Annals of Internal Medicine, 2005, vol. 142, pp. 37-46.
Miltenyi et al., "High Gradient Magnetic Cell Separation With MACS¹", Cytometry, 1990, pp. 231-238, vol. 11.
Mitsui et al., "The Homeoprotein Nanog is Required for Maintenance of Pluripotency in Mouse Epiblast and ES Cells", Cell, May 30, 2003, vol. 113, No. 5, pp. 631-642.
Miyazono et al. "Latent High Molecular Weight Complex of Transforming Growth Factor β1", May 5, 1988, vol. 263, No. 13, pp. 6407-6415.
Montessuit et al., "Regulation of Glucose Transporter Expression in Cardiac Myocytes: p38 MAPK is a Strong inducer of GLUT4", Cardiovascular Research, Oct. 1, 2004, vol. 64, No. 1, pp. 94-104.
Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.
Moss et al., "Conservation of the Heterochronic Regulator Lin-28, its Developmental Expression and MicroRNA Complementary Sites", Developmental Biology, 2003, vol. 258, No. 2, pp. 432-442.
Moss, M.D., et al., Prophylactic Implantation of a Defibrillator in Patients with Myocardial Infarction and Reduced Ejection Fraction, the New England Journal of Medicine, Mar. 21, 2002, vol. 346, No. 12, pp. 877-883.

Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.
Nadal-Ginard et al, "Myocyte Death, Growth, and Regeneration in Cardiac Hypertrophy and Failure", Circulation Research, 2003, vol. 92, pp. 139-150.
Nadal-Ginard et al., "A Matter of Life and Death: Cardiac Myocyte Apoptosis and Regeneration", Journal of Clinical Investigation, May 2003, vol. 111, No. 10, pp. 1457-1459.
Naka et al., "Regulation of Reactive Oxygen Species and Genomic Stability in Hematopoietic Stem Cells", Antioxidants & Redox Signaling, 2008, vol. 10, No. 11, pp. 1883-1894.
Nakagawa et al., "Generation of Induced Pluripotent Stem Cells without Myc from Mouse and Human Fibroblasts", Nature Biotechnology, Jan. 2008, vol. 26, No. 1, pp. 101-106.
Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.
Nelson et al., "CXCR4$^+$/FLK-1$^{30}$ Biomarkers Select a Cardiopoietic Lineage from Embryonic Stem Cells", Stem Cells, 2008, vol. 26, pp. 1464-1473.
Nelson, MD, PhD et al., "Repair of Acute Myocardial Infarction with iPS Induced by Human Stemness Factors", Circulation, Aug. 4, 2009, vol. 120, No. 5, pp. 408-416.
Niethammer et al., "A Tissue-Scale Gradient of Hydrogen Peroxide Mediates Rapid Wound Detection in Zebrafish", Nature, Jun. 16, 2009, vol. 459, pp. 996-999.
Noguchi et al., "Protein Transduction Technology: A Novel Therapeutic Perspective", Acta Medica Okayama, 2006, vol. 60, No. 1, pp. 1-11.
Nussbaum et al., "Transplantation of Undifferentiated Murine Embryonic Stem Cells in the Heart: Teratoma Formation and Immune Response", The FASEB Journal, Research Communication, May 2007, vol. 21; No. 7, pp. 1345-1357.
Odelberg et al., "Dedifferentiation of Mammalian Myotubes Induced by msx1", Cell, Dec. 22, 2000, vol. 103, No, 7, pp. 1099-1109.
Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.
Offord et al., "Photoprotective Potential of Lycopene,—Carotene, Vitamin E, Vitamin C and Carnosic in UVA-Irradiated Human Skin Fibroblasts", Free Radical Biology & Medicine, 2002, vol. 32, No. 12, pp. 1293-1303.
Oh et al., "Cardiac Muscle Plasticity in Adult and Embryo by Heart-Derived Progenitor Cells", Annals of the New York Academy of Sciences, 2004, vol. 1015, pp. 182-189.
Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, pp. 12313-12318, vol. 100, No. 21.
Okita et al., Generation of Mouse Induced Pluripotent Stem Cells Without Viral Vectors, Nov. 7, 2008, Science, vol. 322, pp. 949-953.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, <http://circ.ahajournals.org/content.1132/Suppl_3/A13881.short>.
Owusu-Ansah et al., "Reactive Oxygen Species Prime *Drosophila* Haematopoietic Progenitors for Differentiation", Nature, Sep. 24, 2009, vol. 461, pp. 537-541.
Park et al., "Reprogramming of Human Somatic Cells to Pluripotency with Defined Factors", Nature, Jan. 10, 2008, vol. 451, pp. 141-146.
Passier et al., "Stem-Cell-Based Therapy and Lessons from the Heart", May 15, 2008, Nature, vol. 453, pp. 322-329.
Passier et al., "Origin and Use of Embryonic and Adult Stem Cells in Differentiation and Tissue Repair", Cardiovascular Research, 2003, vol. 58, No. 2, pp. 324-335.
Payne, Anthony G., "Using Immunomagnetic Technology and Other Means to Facilitate Stem Cell Homing", Medical Hypotheses, 2004, pp. 718-720, vol. 62.

(56) References Cited

OTHER PUBLICATIONS

Peterson, MD, MPH, et al., "Risk Stratification After Myocardial Infarction", Annals of Internal Medicine, 1997, vol. 126, No, 7, pp. 561-582.

Pike et al., "Heparin-Regulated Release of Growth Factors in Vitro and Angiogenic Response in Vivo to Implanted Hyaluronan Hydrogels Containing VEGF and bFGF," Biomaterials, 2006, vol. 27, pp. 5242-5241.

Piper et al. "Determinants of Cardiomyocyte Development in Long-Term Primary Culture", Journal of Molecular and Cellular Cardiology, 1988, vol. 20, pp. 825-835.

Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.

Potapova et al., "Enhanced Recovery of Mechanical Function in the Canine Heart by Seeding an Extracellular Matrix Patch with Mesenchymal Stem Cells Committed to a Cardiac Lineage", American Journal of Physiology—Heart and Circulatory Physiology, 2008, vol. 295, pp. H2257-H2263.

Prestwich et al., "The Translational Imperative: Making Cell Therapy Simple and Effective", Acta Biomaterialia, 2012, vol. 8, pp. 4200-4207.

Prunier et al., "Delayed Erythropoietin Therapy Reduces Post-MI Cardiac Remodeling Only at a Dose that Mobilizes Endothelial Progenitor Cells", American Journal of Physiology—Heart and Circulatory Physiology, 2007, vol. 292; pp. H522-H529.

Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.

QiN et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.

Quaini et al., "Chimerism of the Transplanted Heart", The New England Journal of Medicine, Jan. 3, 2002, vol. 346, No. 1, pp. 5-15.

Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United States of America (PNAS), Aug. 18, 2009, vol. 106, No. 33, pp. 14022-14027.

Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.

Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.

Reiffel, James A., MD, FACC, "Ten Pearls for the Use of Antiarrhythmic Drugs for Atrial Fibrillation", Aug. 17, 2012, Retrieved from <http://www.acc.org/latest-in-cardiology/articles/2014/07/18/15/12/ten-pearls-for-the-use-of-antiarrhythmic-drugs-for-atrial-fibrillation>, pp. 17.

Riazifar et al., "Stem Cell Extracellular Vesicles: Extended Messages of Regeneration", Reviews in Advance, Oct. 19, 2016, vol. 14, No. 1, pp. 1-30.

Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.

Risebro et al., "Hand1 Regulates Cardiomyocyte Proliferation Versus Differentiation in the Developing Heart", Development, Nov. 2006, vol. 133, No. 22, pp. 4595-4606.

Rossi et al., "Deficiencies in DNA Damage Repair Limit the Function of Haematopoietic Stem Cells with Age", Nature, Jun. 7, 2007, vol. 447, pp. 725-729.

Rotwein et al., "Organization and Sequence of the Human Insulin-Like Growth Factor I Gene", The Journal of Biological Chemistry, Apr. 15, 1986, vol. 261, No. 11, pp. 4828-4832.

Rubio et al., "Spontaneous Human Adult Stem Cell Transformation", Cancer Research, 2005, vol. 65, pp. 3035-3039.

Rücker-Martin et al., "Dedifferentiation of Atrial Myocytes During Atrial Fibrillation: Role of Fibroblast Proliferation in Vitro", Cardiovascular Research, 2002, vol. 55, pp. 38-52.

Rudy, B. "Diversity and Ubiquity of K Channels", Neuroscience, 1988, vol. 25, No. 3, pp. 729-749.

Saito et al., "Cell Death Caused by Selenium Deficiency and Protective Effect of Antioxidants", The Journal of Biological Chemistry, Oct. 10, 2003, vol. 278, No. 41, pp. 39428-39434.

Sareen et al., Chromosome 7 and 19 Trisomy in Cultured Human Neural Progenitor Cells, PLoS One, Oct. 2009, vol. 4, No. 10, e7630, pp. 12.

Sasano et al., "Molecular Ablation of Ventricular Tachycardia after Myocardial Infarction", Natural Medicine, 2006, vol. 12, No. 11, pp. 1256-1258.

Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.

Scaria et al., "Host-Virus Genome Interactions: Marco Roles for MicroRNAs", Cellular Microbiology, 2007, vol. 9, No. 12, pp. 2784-2794.

Seifried et al., "A Review of the Interaction Among Dietary Antioxidants and Reactive Oxygen Species", Journal of Nutritional Biochemistry, 2007, vol. 18, pp. 567-579.

Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.

Serôdio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.

Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.

Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.

Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.

Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.

Shen et al. "Isolation of an Insulin-Like Growth Factor II cDNA with a Unique 5' Untranslated Region from Human Placenta", Mar. 1988, Proceedings of the National Academy of Sciences of the United States of America (PNAS), vol. 85, pp. 1947-1951.

Shenje et al., "Lineage Tracing of Cardiac Explant Derived Cells", PLoS One, Apr. 2008, vol. 3, No. 4, e1929, pp. 10.

Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.

Shu et al., "Disulfide-Crosslinked Hyaluronan-Gelatin Hydrogel Films: A Covalent Mimic of the Extracellular Matrix for in Vitro Cell Growth", Biomaterials, 2003, vol. 24, pp. 3825-3834.

Sigma-Aldrich, Inc., "Nutrient Mixture F12 Ham Kaighn's Modification (F12K)", Product Description, May 2007, pp. 2.

Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.

Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.

Singh, et al. "High-Dose α-Tocopherol Therapy Does Not Affect HDL Subfractions in Patients with Coronary Artery Disease on Statin Therapy", Clinical Chemistry, 2007, vol. 53, No. 3, pp. 525-528.

(56) References Cited

OTHER PUBLICATIONS

Slaughter, MD et al., "Clinical Management of Continuous-Flow Left Ventricular Assist Devices in Advanced Heart Failure", The Journal of Heart and Lung Transplantation, Apr. 2010, vol. 29, No. 4S, pp. S1-S39.
Smart et al., "De Novo Cardiomyocytes from Within the Activated Adult Heart After Injury", Nature, Jun. 30, 2011, vol. 474, pp. 640-646.
Smith, PhD et al., "Stem Cells in the Heart: What's the Buzz all About? Part 1: Preclinical Considerations", Heart Rhythm, May 2008, vol. 5, No. 5, pp. 749-757.
Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.
Smith et al., "Regenerative Potential of Cardiosphere-Derived Cells Expanded From Percutaneous Endomyocardial Biopsy Specimens", Circulation, Feb. 5, 2007, pp. 896-908, vol. 115.
Smith et al., "Unique Phenotype of Cardiospheres Derived from Human Endomyocardial Biopsies", Circulation, Supplement II, Oct. 25, 2005, pp. 2, vol. 112, No. 17.
Smith et al., "Unselected Human Cardiosphere-derived Cells are Functionally Superior to c-Kit- or CD90—Purified Cardiosphere-Derived Cells", Circulation, Supplement 2, Oct. 28, 2008, vol. 118, No. 17, p. 1.
Smits, Anke Maria, "Cell-Based Cardiac Repair", Thesis, Utrecht University, the Netherlands, 2009, pp. 180.
Srivastava et al., "Thymosin β4 Is Cardioprotective after Myocardial Infarction", Annals of the New York Academy of Sciences, Sep. 2007, vol. 1112, pp. 161-170. Abstract only.
Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.
Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.
Sussman, Mark A., "Myocardial Aging and Senescence: Where Have the Stem Cells Gone?" Annual Review of Physiology, 2004, vol. 66, pp. 29-48.
Takahashi et al., "Induction of Pluripotent Stem Cells from Adult Human Fibroblasts by Defined Factors," Cell, vol. 131, Nov. 30, 2007, pp. 861-872.
Takahashi et al., "Induction of Pluripotent Stem Cells from Fibroblast Cultures, Nature Protocols", 2007, vol. 2 No. 12, pp. 3081-3089.
Takeda et al., "Human Oct3 Gene Family: cDNA Sequences, Alternative Splicing, Gene Organization, Chromosomal Location, and Expression at Low Levels in Adult Tissues", Nucleic Acids Research, 1992, vol. 20, No. 17, pp. 4613-4620.
Takehara, MD, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.
Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.
Tateishi et al., "Clonally Amplified Cardiac Stem Cells are Regulated by Sca-1 Signaling for Efficient Cardiovascular Regeneration", Journal of Cell Science; 2007; vol. 120, No. 10, pp. 1791-1800.
Ten Dijke et al. "Identification of Another Member of the Transforming Growth Factor Type β Gene Family", Proceedings of the National Academy of Sciences of the United States of America (PNAS), 1988, vol. 85, pp. 4715-4719.
Terrovitis, MD, et al., "Assessment and Optimization of Cell Engraftment after Transplantation into the Heart", Circulation Research, Feb. 19, 2010, vol. 106, No. 3, pp. 479-494.

Terrovitis, MD, et al., "Noninvasive Quantification and Optimization of Acute Cell. Retention by in Vivo Positron Emission Tomography after Intramyocardial Cardiac-Derived Stem Cell Delivery", Journal of the American College of Cardiology, Oct. 20, 2009, vol. 54, No. 17, pp. 1619-1626.
The Exosomes Derived from CDCs Experimental Data to Show that Unexpectedly Improved Characteristics are Exhibited, p. 1.
Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.
Torella et al., "Cardiac Stem Cell and Myocyte Aging, Heart Failure, and Insulin-Like Growth Factor-1 Overexpression", Circulation Research, 2004, vol. 95, pp. 514-524.
Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.
Trevethick et al., "Treating Lung Inflammation with Agonists from the Adenosine A2A Receptor: Promises, Problems and Potential Solutions", British Journal of Pharmacology, 2008, vol. 155, pp. 463-474.
Tsagalou, MD, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.
Tseliou et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
Uemura et al., "Bone Marrow Stem Cells Prevent Left Ventricular Remodeling of Ischemic Heart Through Paracrine Signaling", Circulation Research, 2006, vol. 98, pp. 1414-1421.
Ueno et al., "Biphasic Role for Wnt/β-Catenin Signaling in Cardiac Specification in Zebrafish and Embryonic Stem Cells", Proceedings of the National Academy of Sciences of the United States of America (PNAS), Jun. 5, 2007, vol. 104, No. 23, pp. 9685-9690.
Ulloa-Montoya et al., "Culture Systems for Pluripotent Stem Cells", Journal of Bioscience and Bioengineering, 2005, vol. 100, No. 1, pp. 12-27.
Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.
Urbanek, et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.
Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.
Van Der Geest et al., "Quantification in Cardiac MRI", Journal of Magnetic Resonance Imaging, 1999, vol. 10, pp. 602-608.
Van Gent et al., "Chromosomal Stability and the DNA Double-Stranded Break Connection", Nature, Mar. 2001, vol. 2, pp. 196-206.
Van Vliet et al., "Progenitor Cells Isolated from the Human Heart: a Potential Cell Source for Regenerative Therapy", Netherlands Heart Journal, May 2008, vol. 16, No. 5, pp. 163-169.
Van Winkle et al, "Cardiogel: A Biosynthetic Extracellular Matrix for Cardiomyocyte Culture", In Vitro Cellular & Developmental Biology—Animal, Sep. 1996, vol. 21; pp. 478-485.
Vela et al., "Quest for the Cardiovascular Holy Grail: Mammalian Myocardial Regeneration", Cardiovascular Pathology, 2008, vol. 17, No. 1-5.
Ventura et al., "Hyaluronan Mixed Esters of Butyric and Retinoic Acid Drive Cardiac and Endothelial Fate in Term Placenta Human

(56) References Cited

OTHER PUBLICATIONS

Mesenchymal Stem Cells and Enhance Cardiac Repair in Infarcted Rat Hearts", The Journal of Biological Chemistry, May 11, 2007, vol. 282, No. 19, pp. 14243-14252.
Von Harsdorf, R., "Can Cardiomyocytes Divide?" Heart, 2001, vol. 86, pp. 481-482.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Wagner, Richard, "The State of the Art in Antisense Research", Nature Medicine, Nov. 1995, vol. 1, No. 11, pp. 1116-1118.
Walder et al., "Up-Regulation of Neural Stem Cell Markers Suggests the Occurrence of Dedifferentiation in Regenerating Spinal Cord", Development Genes and Evolution, 2003, vol. 213, pp. 625-630.
Walravens et al., "Cardiosphere-Derived Cell and Mesenchymal Stem Cell Extracellular Vesicles Contain Distinct RNA Cargo", Scientific Program, ISEV2017, Dec. 2017, p. 173.
Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.
Wang et al., "Establishment of New Mouse Embryonic Stem Cell Lines is Improved by Physiological Glucose and Oxygen", Cloning and Stem Cells, 2006, vol. 8, No. 2, pp. 108-116.
Wernig el al., "c-Myc Is Dispensable for Direct Reprogramming of Mouse Fibroblasts", Cell Stem Cell, Jan. 2008, vol. 2, pp. 10-12.
White et al. "Intrinsic Cardiac Origin of Human Cardiosphere-Derived Cells", European Heart Journal, 2013, vol. 34, pp. 68-75.
Wilmut et al., "Viable Offspring Derived from Fetal and Adult Mammalian Cells", Nature, Feb. 27, 1997, vol. 385, pp. 810-813.
Wilson et al., "Bioluminescence Reporter Gene Imaging of Human Embryonic Stem Cell Survival, Proliferation, and Fate", Methods in Molecular Biology, 2009, vol. 574, pp. 87-103.
Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.
Wu et al., "Cellular Therapy and Myocardial Tissue Engineering: The Role of Adult Stem and Progenitor Cells", European Journal of Cardio-Thoracic Surgery, 2006, vol. 30, pp. 770-781.
Yamada et al., "Type V Collagen-Induced Oral Tolerance Plus Low-Dose Cyclosporine Prevents Rejection of MHC Class I and II Incompatible Lung Allografts", The Journal Immunology, Jul. 1, 2009, vol. 183, No. 1, pp. 237-245.
Yang et al., "Human Cardiovascular Progenitor Cells Develop from a $KDR^+$ Embryonic-Stem-Cell-Derived Population", Nature, May 22, 2008, vol. 453, pp. 524-528.
Yau MD et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.
Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", PLOS One, Dec. 2, 2014, pp. 1-29.
Yu et al., "Induced Pluripotent Stem Cell Lines Derived from Human Somatic cells," Science, Dec. 21, 2007, vol. 318, pp. 1917-1920.
Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.
Zammit et al., "The Skeletal Muscle Satellite Cell: Stem Cell or Son of Stem Cell?" Differentiation, 2001, vol. 68, pp. 193-204.
Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.
Zhang et al., "Do Cardiac Stem Cells Arise from Cardiomyocyte Dedifferentiation?" Circulation Research, Nov. 2006, vol. 99, No. 11, p. 1276. Abstract only.
Zhao et al., "Targeting Human $CD34^+$ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.
Zhou et al., "Down-Regulation of microRNA-26a Promotes Mouse Hepatocyte Proliferation During Liver Regeneration", PLoS One, Apr. 2012, vol. 7, No. 4, e33577, pp. 1-7.
Zhou et al., "Generation of Induced Pluripotent Stem Cells Using Recombinant Proteins", Cell Stem Cell, May 1, 2009, vol. 4, No. 5, pp. 381-384.
Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.
Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.
Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, pp. 99624-99636.
Haderk et al., "Tumor-Derived Exosomes Modulate PD-L1 Expression in Monocytes", Science Immunology, Jul. 28, 2017, vol. 2, No. 13, pp. 1-11.
Kooijmans et al., "PEGylated and Targeted Extracellular Vesicles Display Enhanced Cell Specificity and Circulation Time", Journal of Controlled Release, 2016, vol. 224, pp. 77-85.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.
Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.
Aminzadeh et al., "Exosome-Mediated Benefits of Cell Therapy in Mouse and Human Models of Duchenne Muscular Dystrophy" Stem Cell Reports, Mar. 13, 2018, vol. 10, pp. 942-955.
Gallet et al, "Cardiosphere-Derived Cells Reverse Heart Failure With Preserved Ejection Fraction in Rats by Decreasing Fibrosis and Inflammation", JACC: Basic to Translational Science, Jan. 1, 2016, vol. 1, No. 1-2, pp. 14-28.
Li et al., "IL-6 Contributes to the Defective Osteogenesis of Bone Marrow Stromal Cells from the Vertebral Body of the Glucocorticoid-Induced Osteoporotic Mouse", PLoS One, Apr. 29, 2016, vol. 11, No. 4, pp. 19.
Makkar et al., "Intracoronary Cardiosphere-Derived Cells for Heart Regeneration After Myocardial Infarction (CADUCEUS): A Prospective, Randomised Phase 1 Trial", Lancet, Mar. 10, 2012, vol. 379, pp. 895-904.
Malliaras et al., "Intracoronary Cardiosphere-Derived Cells After Myocardial Infarction", Journal of the American College of Cardiology, 2014, vol. 63, No. 2, pp. 110-121.
Matsumura, Tsuyoshi, "Cardiaphal Association in Muscular Dystrophy", Nanbyo to Zaitaku Care (Intractable Diseases and Home Care), 2013, vol. 19, No. 8, pp. 55-57.
Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.
North et al., "The Intersection Between Aging and Cardiovascular Disease", Circulation Research, Apr. 13, 2012, pp. 1097-1108.
Takeda et al., "Induced Pluripotant Stem(IPS) Cell-Based Cell Therapy for Duchenne Muscular Dystrophy", History of Medicine, Dec. 31, 2011, vol. 239, No. 14, pp. 1440-1444.
Agrahari et al., "How Are We Improving the Delivery to Back of the Eye? Advances and Challenges of Novel Therapeutic Approaches", Expert Opinion on Drug Delivery, 2017, vol. 14, No. 10, pp. 1145-1162.
Cooper et al., "Immunobiological Barriers to Xenotransplantation", International Journal of Surgery, 2015, vol. 23, pp. 211-216.

(56) References Cited

OTHER PUBLICATIONS

Dib et al., "Cell Therapy for Cardiovascular Disease: A Comparison of Methods of Delivery", Journal of Cardiovascular Translational Research, 2011, vol. 4, pp. 177-181.
Ikehara et al., "Grand Challenges in Stem Cell Treatments", Frontiers in Cell and Developmental Biology, Oct. 10, 2013, vol. 1, No. 2, p. 2.
Liu et al., "The Immunogenicity and Immune Tolerance of Pluripotent Stem Cell Derivatives", Frontiers in Immunology, Jun. 2017, vol. 3, No. 645, pp. 1-6.
Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.
Tsutsui, Hiroyuki, "Cardiomyopathy: Progress in Diagnosis and Treatments Topics: 1. New classification based on etiology of cardiomyopathy; 1. Classification of cardiomyopathy-its past and present status", The Japanese Society of Internal Medicine, Feb. 2014, vol. 103, No. 2, pp. 277-284.
Wu et al., "Cell Delivery in Cardiac Regenerative Therapy", Ageing Research Reviews, 2012, vol. 11, pp. 32-40.
Aminzadeh et al., "Mitigation of Skeletal Myopathy After Intramyocardial Injection of Cardiosphere-derived Cells in the Mdx Mouse Model of Duchenne Muscular Dystrophy", Circulation Research, Dec. 4, 2015, No. 22919, pp. e122-e127.
Gallet et al., "Exosomes Secreted by Cardiosphere-Derived Cells Reduce Scarring, Attenuate Adverse Remodeling, and Improve Function in Acute and Chronic Porcine Myocardial Infarction", European Heart Journal, Jan. 14, 2017, vol. 38, pp. 201-211.
Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1,p. 3.
Bryan et al., "Implications of Protein Fold Switching", Current Comments, posted Feb. 4, 2013, printed in 4 pages. https://web.archive.org/web/20160628060217/http://www.elsevierblogs.com/currentcomments/?p=962.
Carr et al., "Cardiosphere-Derived Cells Improve Function in the Infarcted Rat Heart for at Least 16 Weeks - an MRI Study", PLoS One, Oct. 2011, vol. 6, No. 10, pp. 1-10.
Cheng et al., "Focus on Mesenchymal Stem Cell-Derived Exosomes: Opportunities and Challenges in Cell-Free Therapy", Hindawi, Stem Cells International, 2017, Article ID 6305295, p. 10.
Edelberg et al., "Platelet-Derived Growth Factor-AB Limits the Extent of Myocardial Infarction in a Rat Model: Feasibility of Restoring Impaired Angiogenic Capacity in the Aging Heart", Circulation, 2002, vol. 150, No. 5, pp. 608-613.
Fernandez-Aviles et al., "Experimental and Clinical Regenerative Capability of Human Bone Marrow Cells After Myocardial Infarction", Circulation Research, 2004, vol. 95, pp. 742-748.
Heng et al., "Strategies for Directing the Differentiation of Stem Cells into the Cardiomyogenic Lineage in Vitro", Cardiovascular Research, 2004, vol. 62, pp. 34-42.
Hoppe et al., "Distinct Gene-Specific Mechanisms of Arrhythmia Revealed by Cardiac Gene Transfer of Two Long QT Disease Genes, HERG and KCNE1", Proceedings of the National Academy of Sciences of the United States of America, Apr. 24, 2001, vol. 98, No. 9, pp. 5335-5340.
Kobashigawa et al., "A Randomized Active-Controlled Trial of Mycophenolate Mofetil in Heart Transplant Recipients", Transplantation, Aug. 27, 1998, vol. 66, No. 4, pp. 507-515.
Limana et al., "Exogenous High-Mobility Group Box 1 Protein Induces Myocardial Regeneration after Infarction via Enhanced Cardiac C-Kit+ Cell Proliferation and Differentiation", Circulation Research, Oct. 14, 2005, vol. 97, No. 8, pp. 73-83.
Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, vol. 23, No. 17 & 18, 2017, pp. 989-1000.

Magarotto et al., "Muscle Functional Recovery is Driven by Extracellular Vesicles Combined with Muscle Extracellular Matrix in a Volumetric Muscle Loss Murine Model", Biomaterials 269, 2021, pp. 1-15.
Maqbool et al., The Substrate-Binding Protein in Bacterial ABC Transporters: Dissecting Roles in the Evolution of Substrate Specificity, Biochemical Society Transactions, 2015, vol. 43, Part 5, pp. 1011-1017.
Menasche et al., "Autologous Skeletal Myoblast Transplantation for Severe Postinfarction Left Ventricular Dysfunction", Journal of the American College of Cardiology, vol. 41, No. 7, Apr. 2, 2003, pp. 1078-1083.
Pfeffer et al., "Myocardial Infarct Size and Ventricular Function in Rats", Circulation Research, Apr. 1979, vol. 44, No. 4, pp. 503-512.
Pilia et al., "Transplantation and Perfusion of Microvascular Fragments in a Rodent Model of Volumetric Muscle Loss Injury", European Cells and Materials, vol. 28, 2014, pp. 11-24.
Schächinger et al., "Transplantation of Progenitor Cells and Regeneration Enhancement in Acute Myocardial Infarction: Final One-Year Results of the TOPCARE-AMI Trial", Journal of the American College of Cardiology, Oct. 19, 2004, vol. 44, No. 8, pp. 1690-1699.
Shimasaki et al., "Exosome Research and Co-culture Study", Biological and Pharmaceutical Bulletin, vol. 40, No. 9, 2018, pp. 1311-1321.
Sicari et al., "An Acellular Biologic Scaffold Promotes Skeletal Muscle Formation in Mice and Humans with Volumetric Muscle Loss", Science Translational Medicine, Apr. 30, 2014, vol. 6, No. 234, pp. 1-10.
Siminiak et al., "Autologous Skeletal Myoblast Trans plantation for the Treatment of Postinfarction Myocardial Injury: Phase I Clinical Study with 12 Months of Follow-Up", American Heart Journal, Sep. 2004, vol. 148, No. 3, pp. 531-537.
Smits et al., "Catheter-Based Intramyocardial Injection of Autologous Skeletal Myoblasts as a Primary Treatment of Ischemic Heart Failure: Clinical Experience with Six-Month Follow-Up", Journal of the American College of Cardiology, 2003, vol. 42, No. 12, pp. 2063-2069.
Strauer et al., "Repair of infarcted Myocardium by Autologous Intracoronary Mononuclear Bone Marrow Cell Transplantation in Humans", Circulation, Oct. 8, 2002, vol. 106, No. 15, pp. 1913-1918.
Taylor et al., "A Randomized, Multicenter Comparison of Tacrolimus and Cyclosporine Immunosuppressive Regimens in Cardiac Transplantation: Decreased Hyperlipidemia and Hypertension with Tacrolimus", Journal Heart Lung Transplant, Apr. 1, 1999, vol. 18, No. 4, pp. 336-345.
Bioptome.com, Scholten Surgical Instruments, Inc., downloaded from hts//www.blogtome.com, 2001, first date of publication unknown, printed on Nov. 1, 2005, p. 2.
Zeger et al., "Longitudinal Data Analysis for Discrete and Continuous Outcomes", Biometrics, Mar. 1986, vol. 42, No. 1, pp. 121-130.
Anastasiou-Nana et al., "Relative Efficiency and Risk of Endomyocardial Biopsy: Comparisons in Heart Transplant and Nontransplant Patients," Catheter Cardiovascular Diagnosis Journal, Sep. 1989, vol. 18, No. 1, pp. 7-11.
Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.
Catalano, Mariadelva, "Engineering Exosomes Toward Folate Receptor Expressing Cells", Dec. 7, 2017, p. 3.
Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.
Declaration of Rachel Smith, PH.D., Curriculum Vitae, Exhibit A U.S. Application No. 13/412,051, 13 pages.
Girard et al., "A Germline-Specific Class of Small RNAs Binds Mammalian Piwi Proteins", Nature, Jul. 13, 2006, vol. 442, pp. 199-202.
Kasai-Brunswick et al., "Cardiosphere-Derived Cells do not Improve Cardiac Function in Rats with Cardiac Failure," Stem Cell Research & Therapy, 2017, vol. 8, No. 36, 9 pages.

(56) References Cited

OTHER PUBLICATIONS

Kim, PhD et al., "Engineering Macrophage-Derived Exosomes for Targeted Paclitaxel Delivery to Pulmonary Metastases:in Vitroandin Vivoevaluations", Nanomedicine, Nanotechnology, Biology, and Medicine, vol. 14, 2018, pp. 195-204.

Kim, PhD et al., "Exosome Mediated Delivery of Paclitaxel for the Treatment of Multi Drug Resistant Pulmonary Metastases", Dissertation, Chapel Hill, Dec. 31, 2016, p. 112.

Mason, "Techniques for Right and Left Ventricular Endomyocardial Biopsy", American Journal of Cardiology, 1978, vol. 41, No. 5, pp. 887-892.

Shen et al., "The Early Cryptic Transmission and Evolution of SARS-CoV-2 in Human Hosts", Available at SSRN 3724275, Aug. 2019, https://www.oyeyeah.com/wp-content/uploads/2020/11/SSRN-is3724275.pdf, p. 22.

Smyth et al., "Surface Functionalization of Exosomes Using Click Chemistry", Bioconjugate Chemistry, vol. 25, No. 10, Sep. 30, 2014, pp. 1777-1784.

USPTO Patent Trial and Appeal Board., "Decision on Appeal", in U.S. Appl. No. 13/412,051, dated Jun. 8, 2020, 12 pages.

USPTO Patent Trial and Appeal Board., "Declaration of Rachel R. Smith, PhD," in U.S. Appl. No. 13/412,051, dated Oct. 13, 2017, 32 pages.

Vella et al., "PIWI-lnteracting RNA (piRNA) Signatures in Human Cardiac Progenitor Cells", The International Journal of Biochemistry & Cell Biology, 2016, vol. 76, pp. 1-11.

Wan et al., "Aptamer-Conjugated Extracellular Nanovesicles for Targeted Drug Delivery", Cancer Research, vol. 78, No. 3, Dec. 7, 2017, pp. 798-808.

Wang et al., Challenges in the Development and Establishment of Exosome-Based Drug Delivery Systems, Journal of Controlled Release, 2021, vol. 329, pp. 894-906.

Wang et al., "The Use of RGD-Engineered Exosomes for Enhanced Targeting Ability and Synergistic Therapy Toward Angiogenesis", Nanoscale, vol. 9, No. 40, Jan. 1, 2017, p. 15598-15605.

Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.

Zhao et al., "Exosomes as Drug Carriers for Cancer Therapy and Challenges Regarding Exosome Uptake" Biomedicine & Pharmacotherapy, 2020, vol. 128, 9 pages.

De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).

Ibrahim et al., "Augmenting Canonical Wnt Signaling in Therapeutically Inert Cells Converts them into Therapeutically Potent Exosome Factories", Nature Biomedical Engineering, Sep. 2019, vol. 3, pp. 695-705.

Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, p. 7.

\* cited by examiner

B

A

B h

CARDIOSPHERE-DERIVED CELLS AND EXOSOMES SECRETED BY SUCH CELLS IN THE TREATMENT OF MUSCULAR DYSTROPHY

CROSS-REFERENCE TO RELATED APPLICATIONS

This application is a National Phase of International Application No. PCT/US2015/053853 filed Oct. 2, 2015, which designated the U.S. and that International Application was published under PCT Article 21(2) in English, which also includes a claim of priority under 35 U.S.C. § 119(e) to U.S. provisional patent application No. 62/059,308 filed Oct. 3, 2014, the entirety of which is hereby incorporated by reference.

STATEMENT REGARDING FEDERALLY SPONSORED RESEARCH OR DEVELOPMENT

This invention was made with government support under Grant No. HL083109 awarded by the National Institutes of Health. The government has certain rights in the invention.

FIELD OF THE INVENTION

This invention relates to the use of cells and their extracts, specifically cellular exosomes, for therapeutic use, including treatment of heart disease.

BACKGROUND

Duchenne muscular dystrophy (DMD) afflicts ~20,000 boys and young men in the USA. The central cause is a genetic abnormality in the dystrophin complex, with secondary damage to skeletal muscle and heart tissue. Although virtually all patients are treated with corticosteroids, no treatment has been proven effective. Heart failure (HF) secondary to DMD afflicts virtually all DMD patients aged >15 years, and is often the cause of death. DMD-associated HF aggressively progresses from the initial insult (a genetic abnormality in the dystrophin complex), to asymptomatic abnormalities in cardiac structure and function (stage B), to overt symptomatic HF (stage C), to advanced HF (stage D) and death. Progression of HF is associated with high risk of hospitalization and intense overall health care resource utilization. Modes of death during the course of DMD-associated HF include sudden cardiac death (which increases as HF worsens), or progressive HF culminating in circulatory collapse. Moreover, much of the disability in the later years of DMD is due to HF rather than to skeletal muscle disease. Thus, DMD HF represents an important, neglected target for innovative therapy.

A highly promising avenue of therapy for cardiac-related diseases and conditions includes cardiosphere-derived cells (CDCs) that are capable of stimulating regeneration, angiogenesis, and functional improvement in infarcted myocardium. Previous or ongoing trials involving CDCs target adult patients in stage B; wherein heart function is depressed, but symptoms of HF have yet to appear. In DMD-associated HF, therapeutic approaches may be most dramatic for stages C and D. These later stages of disease are associated with high mortality (>20% per year) despite optimal medical therapy, which have also never been shown to actually slow the progression of disease in DMD patients. Because of exclusionary comorbidities, heart transplantation is not an option for DMD patients. These patients are also not candidates for mechanical circulatory support devices. In summary, no treatment modality currently available addresses the underlying pathophysiology of DMD-associated HF, which is a loss of functional heart muscle and conversion of living heart muscle to scar.

Interestingly, growing evidence suggests that the positive therapeutic benefits of CDCs occur through indirect mechanisms, with most of the newly regenerated myocardium and vasculature being of endogenous origin. Perhaps due to the fact that CDCs are rich biological factories that secrete many growth factors and cytokines, the beneficial therapeutic effects of CDCs manage to persist long after the injected cells have been cleared. Of critical interest is understanding whether these positive factors may exist in cellular exosomes produced by CDCs, the lipid bilayer nanovesicles secreted by cells when multivesicular endosomes fuse with the plasma membrane. Confirming a role for secreted exosomes in these processes has yet to be considered, and understanding these processes governing CDC-initiated regeneration may open new avenues therapeutic approaches. Because no existing therapy can reverse the progression of DMD HF, CDC-derived exosomes may effectively address a major unmet medical need, by recruiting various synergistic mechanisms of benefit that have been observed in animal models of HF. This includes the ability to attract endogenous stem cells to sites of myocardial injury, promote differentiation into heart muscle and vessels, and potentially reversing the pathophysiology of HF. The potential benefits of an exosome-based approach as an alternative to cell therapy is particularly compelling given the unavailability of conventional therapy to late stage patients. The possibility exists that CDC-derived exosomes may fundamentally alter the natural history of the disease.

Described herein are compositions and techniques related to generation and therapeutic application of CDC-derived exosomes. These biological molecules contain a unique milieu of biological factors, including cytokines, growth factors, transcription factors, nucleic acids including non-coding nucleic acids such as microRNAs that serve to initiate and promote many of the therapeutic effects of CDCs. The Inventors' work demonstrates that exosomes and their constituent microRNAs favorably modulate apoptosis, inflammation and fibrosis in the injured heart, leading to functional recovery and increase tissue viability. Thus, CDC-derived exosomes represent a novel "cell-free" therapeutic candidate for tissue repair.

SUMMARY OF THE INVENTION

Described herein is a method of treatment, including selecting a subject in need of treatment for heart failure secondary to a chronic degenerative muscular disease and administering a composition including a plurality of exosomes to the subject, wherein the plurality of the exosomes are isolated from cardiosphere-derived cells (CDCs) grown in serum-free media, include exosomes with a diameter of about 90 nm to about 200 nm and are CD81+, CD63+, or both, and further wherein administration of the composition treats the subject. In other embodiments, the chronic degenerative muscular disease is Duchenne muscular dystrophy. In other embodiments, administering a composition includes about 1 to about 100 mg exosome protein in a single dose. In other embodiments, a single dose is administered multiple times to the subject. In other embodiments, administering a composition includes injection. In other embodiments, the injection includes percutaneous injection. In other embodiments, the injection is directly into heart muscle. In other embodiments, administering a composition includes myocardial infusion. In other embodiments, myocardial infusion is intra-arterial or intravenous. In other embodiments, treatment of the subject results in decreased fibrosis, decreased inflammation, increased mitochondrial function and/or increased cardiomyogenesis. In other embodiments, decreased fibrosis includes a reduction in collagen accumulation. In other embodiments, collagen includes collagen I and/or collagen III. In other embodiments, decreased inflammation includes an increase in cytoplasmic nuclear factor (erythroid-derived 2)-like 2 (Nrf2), reduction in fatty acid peroxidation end products, reduced numbers of inflammatory cells, and/or upregulated expression of antioxidants. In other embodiments, antioxidants include heme oxygenase-1 (HO-1), catalase, superoxide dismutase-2 (SOD-2), and glutamate-cystein ligase catalytic (GCLC) subunit. In other embodiments, inflammatory cells include CD68+ macrophages and CD3+ T-cells. In other embodiments, increased mitochondrial function includes increased mitochondrial ultrastructure and/or increased mitochondrial biogenesis. In other embodiments, increased mitochondrial function includes increased nuclear PPAR-γ co-activator-1 (PGC-1) expression. In other embodiments, the exosomes include one or more microRNAs selected from the group consisting of: microRNAs miR-146a, miR148a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a.

Further described herein is method of treatment, including selecting a subject in need of treatment for heart failure secondary to a chronic muscular disease and administering a composition including cardiosphere-derived cells (CDCs), wherein administration of the composition treats the subject. In other embodiments, the chronic muscular disease is Duchenne muscular dystrophy. In other embodiments, administering a composition includes about $1\times10^5$ to about $1\times10^8$ or more CDCs in a single dose. In other embodiments, administering a composition includes myocardial infusion. In other embodiments, myocardial infusion is intracoronary. In other embodiments, myocardial infusion is intra-arterial or intravenous. In other embodiments, treatment of the subject results in decreased fibrosis, decreased inflammation, increased mitochondrial function and/or increased cardiomyogenesis. In other embodiments, decreased fibrosis includes a reduction in collagen accumulation. In other embodiments, collagen includes collagen I and/or collagen III. In other embodiments, decreased inflammation includes an increase in cytoplasmic nuclear factor (erythroid-derived 2)-like 2 (Nrf2), reduction in fatty acid peroxidation end products, reduced numbers of inflammatory cells, and/or upregulated expression of antioxidants. In other embodiments, antioxidants include heme oxygenase-1 (HO-1), catalase, superoxide dismutase-2 (SOD-2), and glutamate-cystein ligase catalytic (GCLC) subunit. In other embodiments, inflammatory cells include CD68+ macrophages and CD3+ T-cells. In other embodiments, increased mitochondrial function includes increased mitochondrial ultrastructure and/or increased mitochondrial biogenesis. In other embodiments, increased mitochondrial function includes increased nuclear PPAR-γ co-activator-1 (PGC-1) expression.

DETAILED DESCRIPTION

Figure 1:
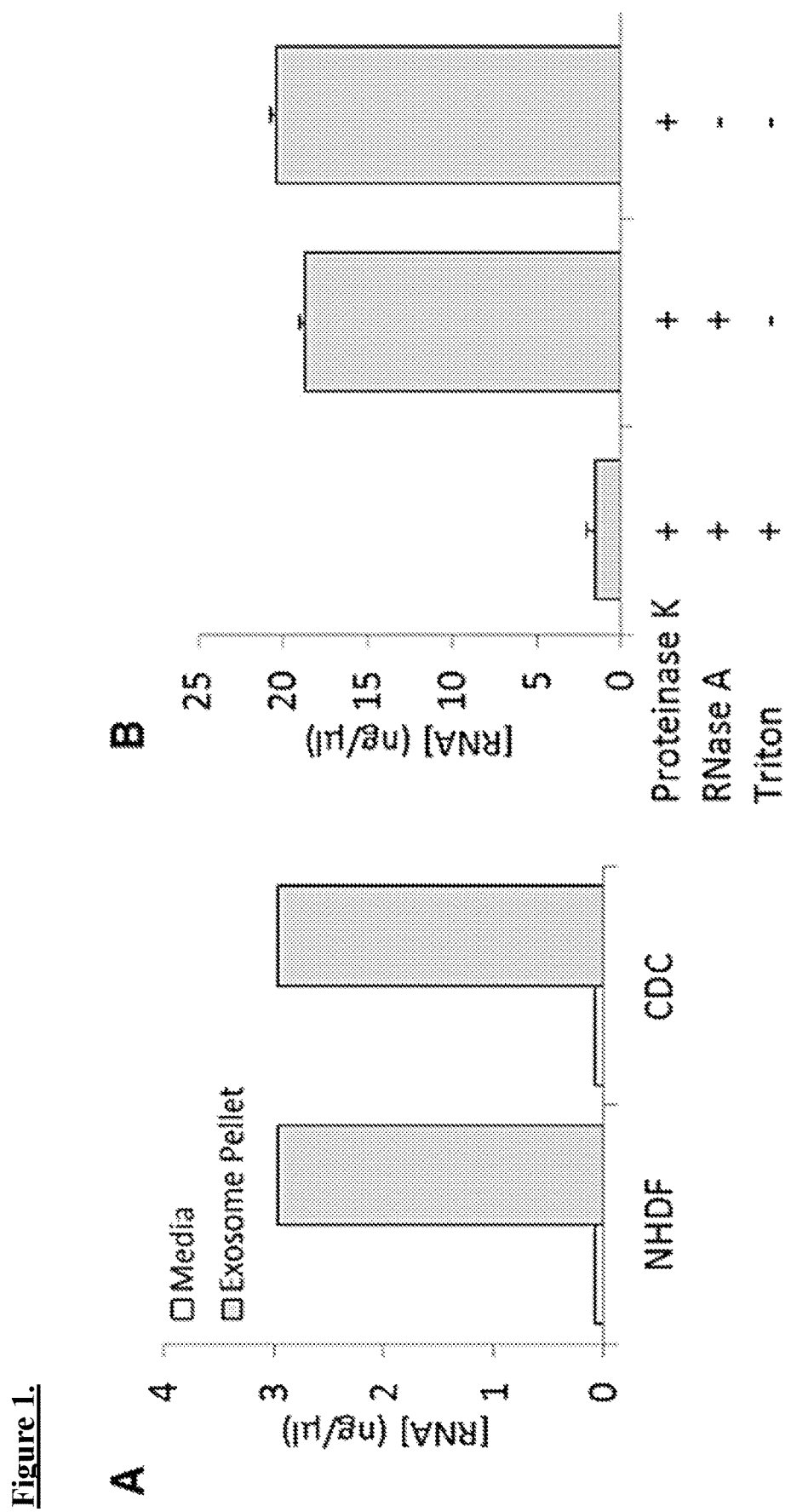
FIG. 1. Characterization of Cardiosphere-Derived Cells Exosomes. (A) RNA content measured in exosome pellets derived from cardiosphere-derived cells (CDCs) and normal human dermal fibroblasts (NHDF) compared to conditioned media from both samples. (B) Exosomal RNA is protected from RNase degradation by the lipid bilayer membrane of exosomes. Exosome pellets were treated with RNase A in the presence or absence of triton to assess protection from RNase-mediated degradation. All samples were treated with proteinase K to dissociate complexes which might otherwise shield RNA (n=4 technical replicates). (C) CDC and NHDF exosomes express ubiquitous exosome markers as revealed by mass spectrometry. (D) Exosome quantification from CDC- and NHDF-conditioned media based on expression of the conserved CD63 marker (n=3 technical repeats). (E) Exosomes isolated from CDCs Visualized by transmission electron microscopy. Three populations (by size) are illustrated. (F) Size distribution of exosomes derived from CDCs, measured from transmission electron microscopic images; n=100 exosomes counted. CDC exosomes enhance angiogenesis and promote neonatal rat cardiomyocyte (NRCM) survival and proliferation in vitro.
Figure 1:
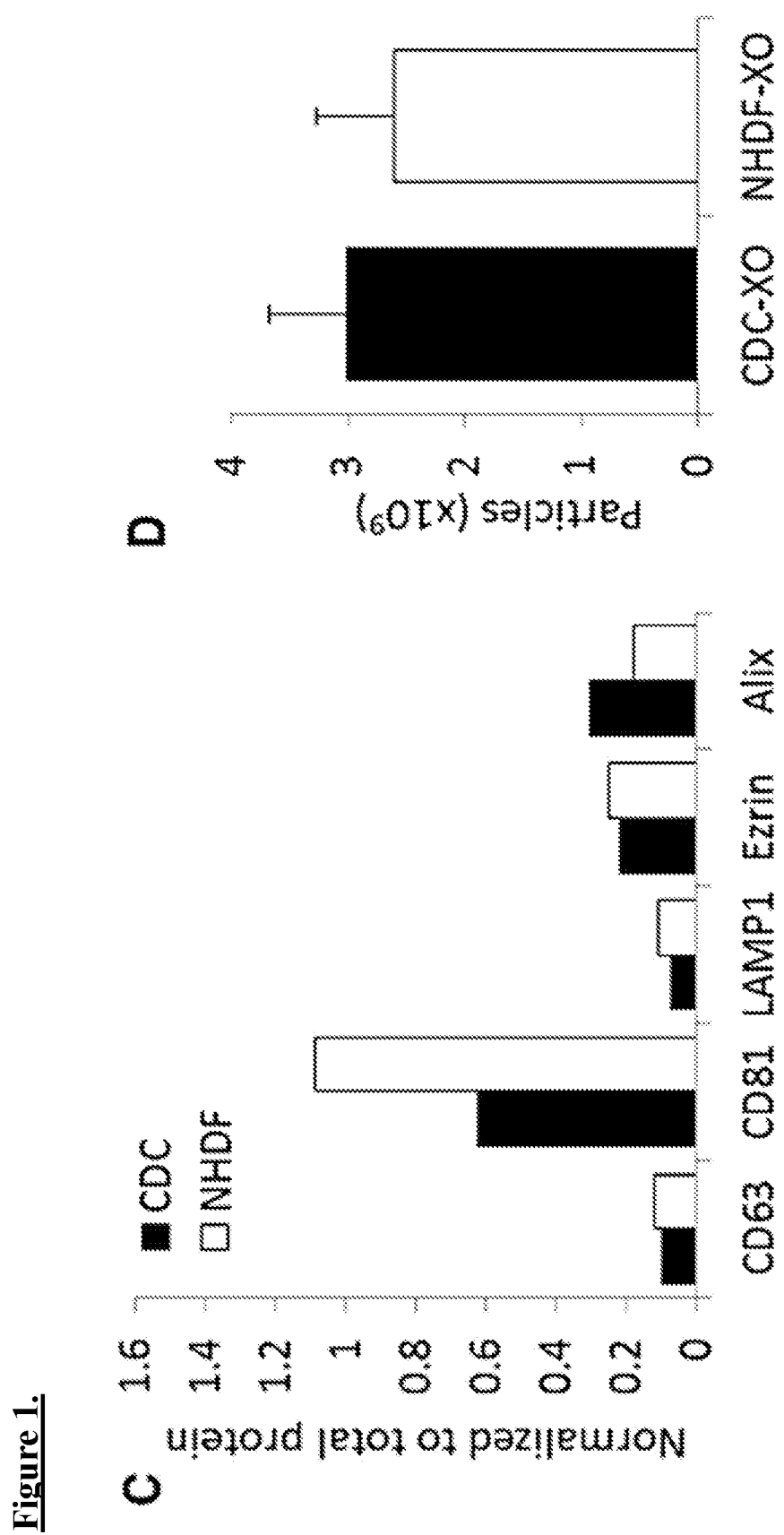
Figure 1:
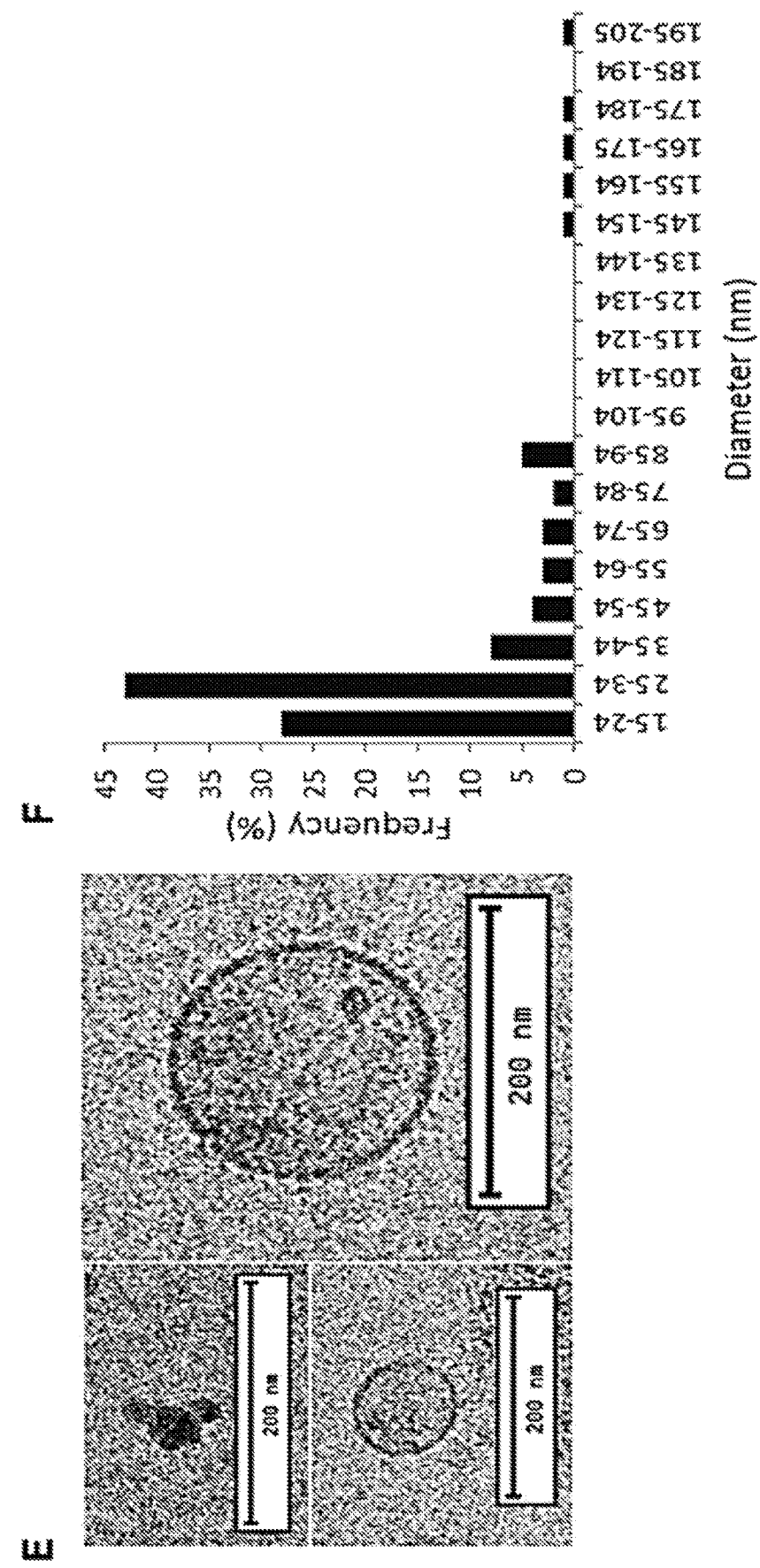
Figure 1:
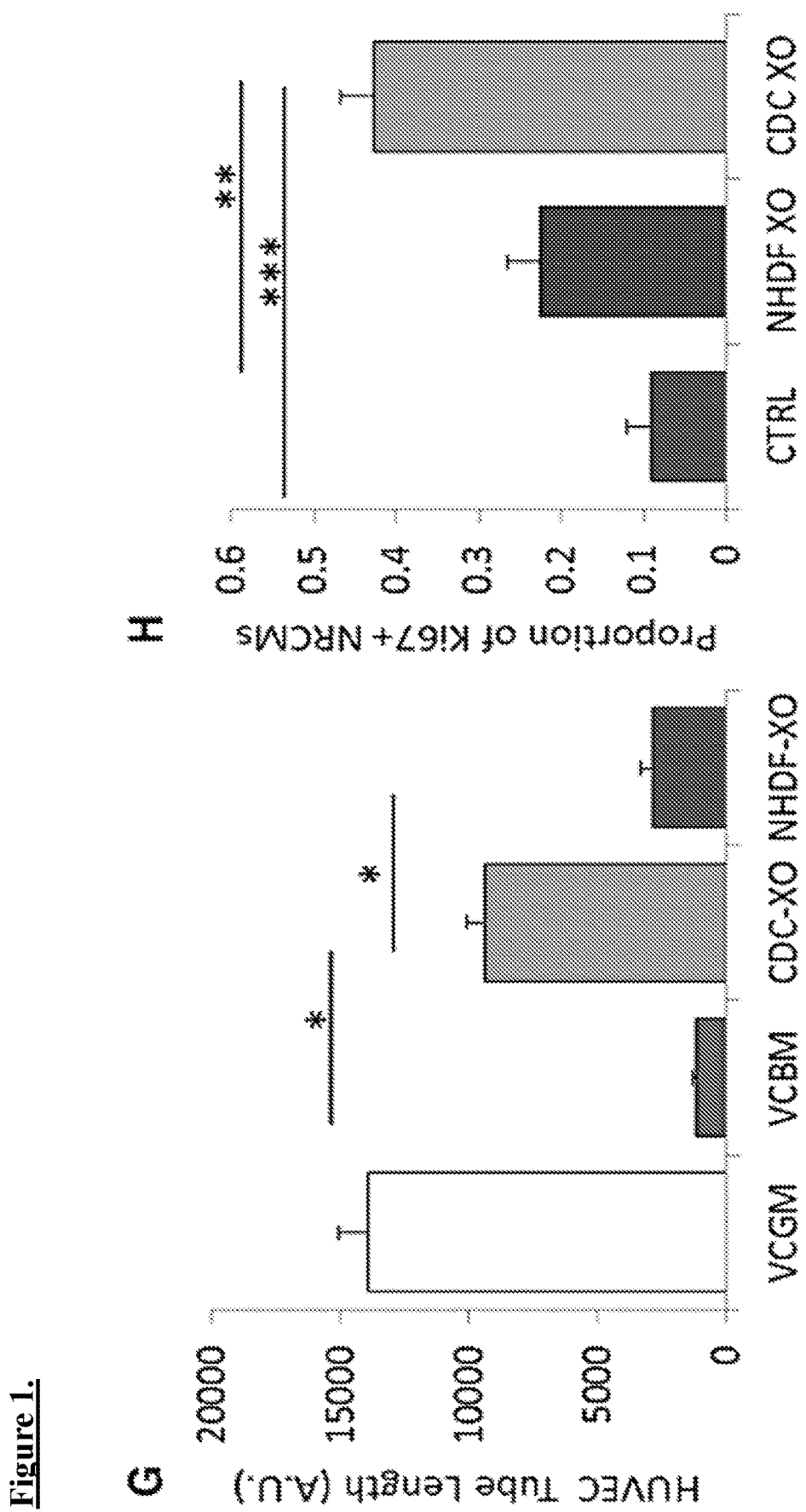
Figure 1:
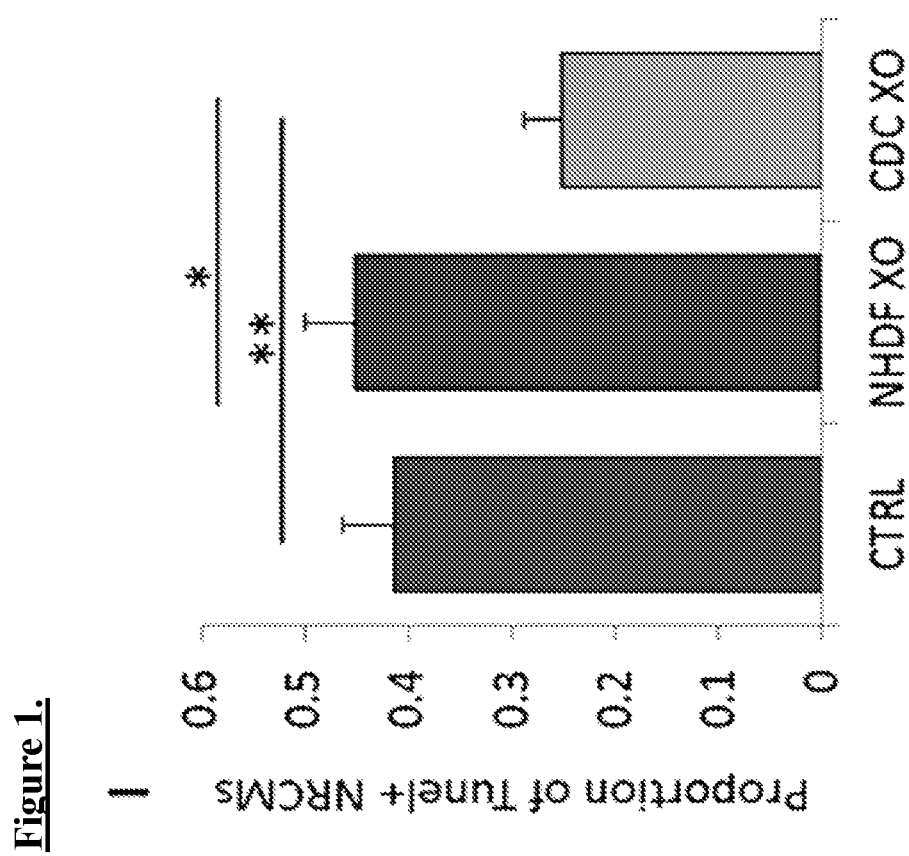

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Duchenne muscular dystrophy, a crippling genetic disease leading to premature death, affects the heart as well as skeletal muscle. Indeed, cardiomyopathy is the leading cause of death in Duchenne patients. There are no approved treatments for the cardiomyopathy, and novel Duchenne-specific experimental approaches such as exon skipping do not benefit the heart. Here the Inventors demonstrate that cardiosphere-derived cells (CDCs), in advanced clinical testing for therapeutic regeneration after myocardial infarction, reverse the key pathophysiological hallmarks of Duchenne cardiomyopathy (oxidative stress, inflammation, fibrosis and mitochondrial dysfunction) in mdx mice. Exosomes secreted by human CDCs reproduce the benefits of CDCs in mdx mice, and reverse abnormalities of calcium cycling and mitochondrial respiration in human Duchenne cardiomyocytes.

Absence of dystrophin in Duchenne muscular dystrophy (DMD) leads to membrane fragility and secondary damage to muscle (both skeletal and cardiac). Early disability is due predominantly to the skeletal myopathy, but heart failure is the most common cause of death. No currently available treatment modality addresses the underlying pathophysiology of DMD-associated heart failure, a loss of functional heart muscle and conversion of living heart muscle to scar. Cardiosphere-derived cells (CDCs) may represent a viable therapeutic option. Healthy heart muscle regrew and scar decreased in the first-in-human CADUCEUS trial of CDCs in myocardial infarction; these findings are now being further tested in a randomized, placebocontrolled multicenter clinical trial of allogeneic CDCs. Preclinical studies show that CDCs are not only regenerative, but also anti-inflammatory and anti-fibrotic; they work indirectly via the secretion of exosomes laden with noncoding RNA including microRNAs (miRs). In a murine model of myocardial infarction, CDC-exosomes mimic the functional and structural benefits of CDCs, while blockade of exosome biosynthesis renders CDCs ineffective. Given the clinical data and the mechanism of action, the Inventors reasoned that CDCs might be useful in treating Duchenne cardiomyopathy. The goal is not to replace dystrophin, but rather to offset the pathophysiological consequences of dystrophin deletion, by recruiting regeneration, reversing fibrosis and targeting inflammation.

Exosomes, secreted lipid vesicles containing a rich milieu of biological factors, provide powerful paracrine signals by which stem cells potentiate their biological effects to neighboring cells, including diseased or injured cells. Through the encapsulation and transfer of proteins, bio-active lipid and nucleic acid "cargo", there is increasing recognition that these natural delivery devices are capable of inducing significant phenotypic and functional changes in recipient cells that lead to activation of regenerative programs. The role of such indirect mechanisms to in stem cell initiated regeneration is strongly suggested by growing evidence that after stem cell administration and clearance from delivery sites in tissue and organs, regeneration processes nevertheless persist and arise from endogenous tissues.

The "paracrine hypothesis" of stem cell regenerative activity has created a paradigm shift by which clinical applications based on exosomes secreted by the stem cells may prove superior, or provide distinct advantages, when compared to transplant and delivery of stem cells themselves. Stem cell-derived exosomes have been identified and isolated from supernatants of several cell types with demonstrated therapeutic potential, including mesenchymal stromal (MSC), (bone marrow stem cells) mononuclear (MNC) cells, immune cells (dendritic and CD34+), human neural stem cells (hNSCs), among others. In the context of heart disease, human cardiosphere derived cells (CDCs) are known to improve myocardium and vasculature. Stem cell-derived exosomes, including those produced by CDCs, may provide a potent and rich source for developing "cell-free" therapies.

In addition, exosome-based, "cell-free" therapies, in contrast to cell therapy, provide distinct advantages in regenerative medicine. As non-viable entities, with reduced or non-existent immunogenic or tumorigenic potential, these features significantly obviate safety issues. For example, stem cell-derived exosomes are less immunogenic than parental cells, as a result of a lower content of membrane-bound proteins, including MHC complex molecules. Replacing the administration of live cells with their secreted exosomes, mitigates many of the safety concerns and limitations associated with the transplantation of viable replicating cells. In addition, exosome encapsulation of bioactive components in lipid vesicles allows protection of contents from degradation in vivo, thereby potentially negating obstacles often associated with delivery of soluble molecules such as cytokines, growth factors, transcription factors and RNAs. This comparative ease of administration may ultimately allow for repeated and sustained delivery to patients, thereby maximizing the potential for regeneration and repair of diseased and/or dysfunctional tissue.

Also, exosome production under defined conditions allows for easier manufacture and scale-up opportunity. Manufacture of exosomes is akin to conventional biopharmacological product manufacture, allowing for standardization in production and quality control for dosage and biological activity testing. Further, the durability of exosomes in culture allows for the acquisition of large quantities of exosomes through their collection from a culture medium in which the exosomes are secreted over periods of time.

While it is now well-established that exosomes are involved in intercellular communication between different cell types, much remains to be discovered in regard to the mechanisms of their production within parental cells of origin and effects on target recipient cells. Exosomes have been reported to be involved in numerous cellular, tissue and physiological processes, including immune modulating processes, angiogenesis, migration of endothelial cells in connection with tumor growth, or reducing damage in ischemia reperfusion injury. Of critical scientific interest in establishing whether exosomes secreted by cells, such as cardiosphere-derived cells (CDCs), are capable of reproducing the therapeutic benefits of their parental cells, or possibly, are indispensable in effectuating such therapeutic benefits.

General Features of Exosomes.

Secreted by a wide range of cell types, exosomes are lipid bilayer vesicles that are enriched in a variety of biological factors, including cytokines, growth factors, transcription factors, lipids, and coding and non-coding nucleic acids. Exosomes are found in blood, urine, amniotic fluid, interstitial and extracellular spaces. These exocytosed vesicles of endosomal origin can range in size between 30-200 nm, including sizes of 40-100 nm, and possess a cup-shaped morphology, as revealed by electron microscopy. Their initial formation begins with inward budding of the cell membrane to form endosomes, which is followed by invagination of the limiting membrane of late endosomes to form multivesicular bodies (MVB). Fusion of the MVB with the plasma membrane results in the release of the internal vesicles to the extracellular space, through the formation of vesicles thereafter known as exosomes.

As described, the "cargo" contents of exosomes reflect their parental cellular origin, as containing distinct subsets of biological factors in connection with their parent cellular origin, including the cell regulatory state of the parental cells when formed. The rich biological milieu of different proteins, including cytokines and growth factors, lipids, coding and noncoding RNA molecules, within exosomes are all necessarily derived from their parental cells. In addition to containing a rich array of cytosolic derivatives, exosomes further express the extracellular domain of membrane-bound receptors at the surface of the membrane.

The described encapsulation and formation processes necessarily create heterogeneity in exosome compositions based on parental cellular origin and regulatory state at time of formation. Nevertheless, generic budding formation and release mechanisms establish a common set of features as a consequence of their origin, such as endosome-associated proteins (e.g., Rab GTPase, SNAREs, Annexins, and flotillin), proteins that are known to cluster into microdomains at the plasma membrane or at endosomes (four transmembrane domain tetraspanins, e.g., CD63, CD81, CD82, CD53, and CD37), lipid raft associated proteins (e.g., glycosylphosphatidylinositol-anchored proteins and flotillin), cholesterol, sphingomyelin, and hexosylceramides, as examples.

In addition to these core components reflecting their vesicle origin, a critical property of exosomes is a demonstrated capability to contain both mRNA and microRNA associated with signaling processes, with both cargo mRNA being capable to translation in recipient cells, or microRNA functionally degrading target mRNA in recipient cells. Other noncoding RNAs, capable for influencing gene expression, may also be present in exosomes. While the processes governing the selective incorporation of mRNA or microRNA populations into exosomes is not entirely understood, it is clear that RNA molecules are selectively, not randomly incorporated into exosomes, as revealed by studies reporting enrichment of exosome cargo RNAs when compared to the RNA profiles of the originating cells. Given the growing understanding of how such RNA molecules play a role in disease pathogenesis and regenerative processes, the presence of RNA molecules in exosomes and apparent potency in affecting target recipient cells suggests critical features that can be deployed in therapeutic approaches.

Importantly, the natural bilayer membrane encapsulation of exosomes provides a protected and controlled internal microenvironment that allows cargo contents to persist or migrate in the bloodstream or within tissues without degradation. Their release into the extracellular environment allows for interaction with recipient cells via adhesion to the cell surface mediated by lipid-ligand receptor interactions, internalization via endocytic uptake, or by direct fusion of the vesicles and cell membrane. These processes lead to the release of exosome cargo content into the target cell.

The net result of exosome-cell interactions is modulation of genetic pathways in the target recipient cell, as induced through any of several different mechanisms including antigen presentation, the transfer of transcription factors, cytokines, growth factors, nucleic acid such as mRNA and microRNAs. In the stem cell context, embryonic stem cell (ESC)-derived exosomes have been demonstrated to shuttle/transfer mRNA and proteins to hematopoietic progenitors. Other studies have shown that adult stem cell-derived exosomes also shuttle selected patterns of mRNA, microRNA and pre-microRNA associated with several cellular functions involved in the control of transcription, proliferation and cell immune regulation.

Isolation and Preparation of Exosomes.

Exosome isolation relies on exploiting their generic biochemical and biophysical features for separation and analysis. For example, differential ultracentrifugation has become a leading technique wherein secreted exosomes are isolated from the supernatants of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm. Differences in flotation velocity further allows for separation of differentially sized exosomes. In general, exosome sizes will possess a diameter ranging from 30-200 nm, including sizes of 40-100 nm. Further purification may rely on specific properties of the particular exosomes of interest. This includes, for example, use of immunoadsorption with a protein of interest to select specific vesicles with exoplasmic or outward orientations.

Among current methods (differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/ml) or application of a discrete sugar cushion in preparation.

Importantly, ultrafiltration can be used to purify exosomes without compromising their biological activity. Membranes with different pore sizes—such as 100 kDa molecular weight cut-off (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. HPLC can also be used to purify exosomes to homogeneouslysized particles and preserve their biological activity as the preparation is maintained at a physiological pH and salt concentration.

Other chemical methods have exploit differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media.

Beyond these techniques relying on general biochemical and biophysical features, focused techniques may be applied to isolated specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

Exosome-Based Therapies.

A chief goal of developing exosome-based therapy is the creation of "cell-free" therapies, wherein the benefits of cellular therapeutics can be provided with reduced risks or in scenarios in which cell therapy would be unavailable. For example, Duchenne muscular dystrophy (DMD) associated heart failure (HF), particularly at later stages, presents significant exclusionary comorbidities, wherein cell, tissue, heart or mechanical transplantation may not be an option for late stages C and D. As described, the therapeutic benefits of cell-based therapies such as cardiosphere-derived cells (CDCs) appear to occur through indirect mechanisms involving regenerated myocardium and vasculature arising from endogenous origin. Cellular exosomes produced by CDCs may allow for production and delivery of growth factors, transcription factors, cytokines and nucleic acids for new therapeutic approaches in a manner that not only ameliorates progression of the disease, but repairs and regenerates disease and/or dysfunctional tissue. In this regard, CDC-derived exosomes may effectively address a major unmet medical need, by recruiting synergistic mechanisms to attract endogenous stem cells to sites of myocardial injury, promote differentiation into heart muscle and vessels, thereby reversing the pathophysiology of HF.

More specifically, DMD is an X-linked recessive disorder characterized by myopathy (cell membrane damage in muscle fiber) as exemplified by a variety of pathological features. this includes skeletal muscle weakness starting 3-5 years from onset, progressive weakness, wheelchair dependency at approximately 13 years from onset. Importantly, cardiomyopathy is observed to take hold in ⅓ of patients from less than 13 years from onset, increasing to ½ of patients less than 18 years from onset, and in all patients after 18 years. Dilated cardiomyopathy includes left ventricle posterobasal fibrosis; conduction abnormalities are mainly intra-atrial: SVT with abnormal AV nodal conduction. Patients may further suffer from smooth muscle myopathy including vascular dysfunction, further including GI and urinary tract systems involvement. Common prognosis is death from respiratory insufficiency or cardiomyopathy. Underlying these clinical features is dystrophin gene mutation (deletion) wherein loss of dystrophin results in cellular membrane damage and leakage of extracellular $Ca^{2+}$ into the cell. Elevated intracellular levels ultimately result in increased oxidative and/or nitrosative stress and inflammation, and activation of calpain. The combination of these effects results in muscle proteolysis and apoptosis, leading to the degradative features described above.

Based on this pathophysiology of DMD patients, including an environment of increased oxidative and/or nitrosative stress, elevated inflammation, pro-apoptotic and remodeling states, therapeutic approaches involving CDCs may provide significant benefits in reversing the course of the disease. CDCs have been demonstrated as promoting anti-oxidative, anti-inflammatory, anti-apoptotic, anti-remodeling effects, in addition to enhancing regenerative capacity. In this regard, it is suggested that CDC administration is beneficial in retarding/reversing DMD, and exosome populations derived from CDCs may allow for these benefits to be delivered, while avoiding obstacles associated with cell-based therapy.

In particular, stem cell-derived exosomes are likely to be less immunogenic than parental cells. The possibility of replacing the administration of live cells with secreted exosomes, mitigates many of the safety concerns and limitations associated with the transplantation of viable cells. In addition, exosome encapsulation of bioactive components in lipid vesicles allows protection of contents from degradation in vivo, thereby potentially negating obstacles often associated with delivery of soluble molecules such as cytokines, growth factors, transcription factors and RNAs, while potentially allowing for increased concentrations to be provided. Particularly for chronic conditions, such as DMD, repeated and sustained delivery to patients may maximize the potential for regeneration and repair of diseased and/or dysfunctional tissue, in a manner that would be difficult or unsafe with a cell-based therapy. Fully realizing these benefits requires an improved understanding of whether exosomes secreted by cells such as CDCs, are alone capable of reproducing therapeutic benefits of their parental cells, or possibly indispensable in these processes. Confirming the role of exosomes in such processes will allow their application in new therapeutic approaches, including "cell-free" use in subjects for which cellular transplant or administration is unavailable (e.g., late stage heart disease), as pharmacological, device-based intervention or surgery may not be prudent treatment modalities for such subject. There is a great need in the art for identifying means by which to deliver the benefits of stem cell regeneration, without resorting to mechanisms involving administration or transplant of the cell themselves.

Described herein are compositions and methods and compositions providing significant benefits in the repair or regeneration of damaged or diseased tissues via "cell-free" methods involving exosomes. Specifically, human cardiosphere-derived cells (CDC)-derived exosomes are demonstrated as effective in reducing scar size and regenerating viable myocardium. Such results confirm that the major benefits of CDC cell therapy are mediated by exosomes, including specific microRNAs identified by the Inventors as enriched in CDCs.

Described herein is a method of treatment, including selecting a subject in need of treatment for heart failure secondary to a chronic degenerative muscular disease and administering a composition including a plurality of exosomes to the subject, wherein the plurality of the exosomes are isolated from cardiosphere-derived cells (CDCs) grown in serum-free media, include exosomes with a diameter of about 90 nm to about 200 nm and are CD81+, CD63+, or both, and further wherein administration of the composition treats the subject. In other embodiments, the chronic degenerative muscular disease is Duchenne muscular dystrophy. In other embodiments, administering a composition includes about 1 to about 100 mg exosome protein in a single dose. In other embodiments, a single dose is administered multiple times to the subject. In other embodiments, administering a composition includes injection. In other embodiments, the injection includes percutaneous injection. In other embodiments, the injection is directly into heart muscle. In other embodiments, administering a composition includes myocardial infusion. In other embodiments, myocardial infusion is intra-arterial or intravenous. In other embodiments, treatment of the subject results in decreased fibrosis, decreased inflammation, increased mitochondrial function and/or increased cardiomyogenesis. In other embodiments, decreased fibrosis includes a reduction in collagen accumulation. In other embodiments, collagen includes collagen I and/or collagen III. In other embodiments, decreased inflammation includes an increase in cytoplasmic nuclear factor (erythroid-derived 2)-like 2 (Nrf2), reduction in fatty acid peroxidation end products, reduced numbers of inflammatory cells, and/or upregulated expression of antioxidants. In other embodiments, antioxidants include heme oxygenase-1 (HO-1), catalase, superoxide dismutase-2 (SOD-2), and glutamate-cystein ligase catalytic (GCLC) subunit. In other embodiments, inflammatory cells include CD68+ macrophages and CD3+ T-cells. In other embodiments, increased mitochondrial function includes increased mitochondrial ultrastructure and/or increased mitochondrial biogenesis. In other embodiments, increased mitochondrial function includes increased nuclear PPAR-γ co-activator-1 (PGC-1) expression. In other embodiments, the exosomes include one or more microRNAs selected from the group consisting of: microRNAs miR-146a, miR148a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a.

Further described herein is method of treatment, including selecting a subject in need of treatment for heart failure secondary to a chronic muscular disease and administering a composition including cardiosphere-derived cells (CDCs), wherein administration of the composition treats the subject. In other embodiments, the chronic muscular disease is Duchenne muscular dystrophy. In other embodiments, administering a composition includes about $1 \times 10^5$ to about $1 \times 10^8$ or more CDCs in a single dose. In another example, the number of administered CDCs includes intracoronary 25 million CDCs per coronary artery (i.e., 75 million CDCs total) as another baseline for exosome dosage quantity. In various embodiments, the numbers of CDCs includes $1 \times 10^5$, $1 \times 10^6$, $1 \times 10^7$, $1 \times 10^8$, $1 \times 10^9$ CDCs in a single dose as another baseline for exosome dosage quantity. In certain instances, this may be prorated to body weight (range 100,000-1M CDCs/kg body weight total CDC dose). In other embodiments, administering a composition includes myocardial infusion. In other embodiments, myocardial infusion is intracoronary. In other embodiments, myocardial infusion is intra-arterial or intravenous. In other embodiments, treatment of the subject results in decreased fibrosis, decreased inflammation, increased mitochondrial function and/or increased cardiomyogenesis. In other embodiments, decreased fibrosis includes a reduction in collagen accumulation. In other embodiments, collagen includes collagen I and/or collagen III. In other embodiments, decreased inflammation includes an increase in cytoplasmic nuclear factor (erythroid-derived 2)-like 2 (Nrf2), reduction in fatty acid peroxidation end products, reduced numbers of inflammatory cells, and/or upregulated expression of antioxidants. In other embodiments, antioxidants include heme oxygenase-1 (HO-1), catalase, superoxide dismutase-2 (SOD-2), and glutamate-cystein ligase catalytic (GCLC) subunit. In other embodiments, inflammatory cells include CD68+ macrophages and CD3+ T-cells. In other embodiments, increased mitochondrial function includes increased mitochondrial ultrastructure and/or increased mitochondrial biogenesis. In other embodiments, increased mitochondrial function includes increased nuclear PPAR-γ co-activator-1 (PGC-1) expression. Further examples are found in U.S. applicaton Ser. No. 11/666,685, 12/622,143, and 12/622,106, which are herein incorporated by reference.

Described herein is a composition including a plurality of exosomes. In certain embodiments, the plurality of exosomes are generated by a method including providing a population of cells, and isolating a plurality of exosomes from the population of cells.

In various embodiments, the cells are stem cells, progenitors and/or precursors. In other embodiments, the stem cells, progenitors and/or precursors are cardiosphere-derived cells (CDCs). In other embodiments, the stem cells, progenitors and/or precursors are pluripotent stem cells (pSCs), such as embryonic stem cells (ESCs) and induced pluripotent stem cells (iPSCs) derived from any one of various somatic sources in the body such as fibroblasts, blood and hematopoietic stem cells (hSCs), immune cells, bone and bone marrow, neural tissue, among others. In other embodiments, the stem cells, progenitors and/or precursors include hSCs, mesenchymal stem cells (MSCs), or endothelial precursor cells (EPCs). In various embodiments, the cells are stem cells, progenitors and/or precursors derived from human biopsy tissue. In various embodiments, the cells are stem cells, progenitors and/or precursors are a primary culture. In various embodiments, the cells are stem cells, progenitors and/or precursors which may constitute a cell line capable of serial passaging.

In various embodiments, the plurality of exosomes is isolated from the supernatants of the population of cells. This includes, for example, exosomes secreted into media as conditioned by a population of cells in culture, further including cell lines capable of serial passaging. In certain embodiments, the cells are cultured in serum-free media. In certain embodiments, the cells in culture are grown to 10, 20, 30, 40, 50, 60, 70, 80, 90, or 90% or more confluency when exosomes are isolated. In certain embodiments, the population of cells has been genetically manipulated. This includes, for example, knockout (KO) or transgenic (TG) cell lines, wherein an endogenous gene has been removed and/or an exogenous introduced in a stable, persistent manner. This further includes transient knockdown of one or more genes and associated coding and non-coding transcripts within the population of cells, via any number of methods known in the art, such as introduction of dsRNA, siRNA, microRNA, etc. This further includes transient expression of one or more genes and associated coding and non-coding transcripts within the population of cells, via any number of methods known in the art, such as introduction of a vector, plasmid, artificial plasmid, replicative and/or non-relicative virus, etc. In other embodiments, the population of cells has been altered by exposure to environmental conditions (e.g., hypoxia), small molecule addition, presence/absence of exogenous factors (e.g., growth factors, cytokines) at the time, or substantially contemporaneous with, isolating the plurality of exosomes in a manner altering the regulatory state of the cell. For example, one may add a differentiation agent to a population of stem cells, progenitors and/or precursors in order to promote partial or full differentiation of the cell, and thereafter derive a plurality of exosomes. In various embodiments, altering the regulatory state of the cell changes composition of one or more exosomes in the plurality of exosomes.

In various embodiments, the plurality of exosomes include one or more exosomes that are about 10 nm to about 250 nm in diameter, including those about 10 nm to about 15 nm, about 15 nm to about 20 nm, about 20 nm to about 25 nm, about 25 nm to about 30 nm, about 30 nm to about 35 nm, about 35 nm to about 40 nm, about 40 nm to about 50 nm, about 50 nm to about 60 nm3 about 60 nm to about 70 nm, about 70 nm to about 80 nm, about 80 nm to about 90 nm, about 90 nm to about 95 nm, about 95 nm to about 100 nm, about 100 nm to about 105 nm, about 105 nm to about 110 nm, about 110 nm to about 115 nm, about 115 nm to about 120 nm, about 120 nm to about 125 nm, about 125 nm to about 130 nm, about 130 nm to about 135 nm, about 135 nm to about 140 nm, about 140 nm to about 145 nm, about 145 nm to about 150 nm, about 150 to about 200 nm, about 200 nm to about 250 nm, about 250 nm or more.

In various embodiments, the plurality of exosomes includes one or more exosomes expressing a biomarker. In certain embodiments, the biomarkers are tetraspanins In other embodiments, the tetraspanins are one or more selected from the group including CD63, CD81, CD82, CD53, and CD37. In other embodiments, the exosomes express one or more lipid raft associated proteins (e.g., glycosylphosphatidylinositol-anchored proteins and flotillin), cholesterol, sphingomyelin, and/or hexosylceramides.

In several embodiments, the plurality of exosomes includes one or more exosomes containing a biological protein. In various embodiments, the biological protein includes transcription factors, cytokines, growth factors, and similar proteins capable of modulating signaling pathways in a target cell. In various embodiments, the biological protein is capable of facilitating regeneration and/or improved function of a tissue. In various embodiments, the biological protein is capable of modulating pathways related to Irak1, Traf6, toll-like receptor (TLR) signaling pathway, NOX-4, SMAD-4, and/or TGF-β. In other embodiments, the biological protein related to exosome formation and packaging of cytosolic proteins such as Hsp70, Hsp90, 14-3-3 epsilon, PKM2, GW182 and AGO2.

In other embodiments, the plurality of exosomes includes one or more exosomes containing a signaling lipid. This includes ceramide and derivatives. In other embodiments, the plurality of exosomes includes one or more exosomes containing a coding and/or non-coding nucleic acid.

In several embodiments, the plurality of exosomes includes one or more exosomes containing microRNAs. In various embodiments, these microRNAs can include miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and/or miR-23a. In several embodiments, the plurality of exosomes include one or more exosomes enriched in at least one of miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and/or miR-23a. In several embodiments, the plurality of exosomes includes one or more exosomes enriched in at least one of miR-146a, miR-22, miR-24. Enrichment can be measured by, for example, comparing the amount of one or more of the described microRNAs when derived from cells providing salutary benefit in a therapeutic setting (e.g., cardiosphere-derived cells (CDCs) compared to cells that do not provide such a salutary benefit (e.g., fibroblasts). Enrichment may also be measured in absolute or relative quantities, such as when compared to a standardized dilution series.

In other embodiments, the plurality of exosomes can include one or more exosomes containing microRNAs. This includes various microRNAs known in the art, such as miR-23a, miR-23b, miR-24, miR-26a, miR27-a, miR-30c, let-7e, mir-19b, miR-125b, mir-27b, let-7a, miR-19a, let-7c, miR-140-3p, miR-125a-5p, miR-132, miR-150, miR-155, mir-210, let-7b, miR-24, miR-423-5p, miR-22, let-7f, and/or miR-146a.

In other embodiments, the plurality of exosomes can include one or more exosomes containing microRNAs. This includes various microRNAs known in the art, such as miR-17, miR-21, miR-92, miR92a, miR-29, miR-29a, miR-29b, miR-29c, miR-34, mi-R34a, miR-150, miR-451, miR-145, miR-143, miR-144, miR-193a-3p, miR-133a, miR-155, miR-181a, miR-214, miR-199b, miR-199a, miR-210, miR-126, miR-378, miR-363 and miR-30b, and miR-499. Other microRNAs known in the art include miR-92, miR-17, miR-21, miR-92, miR92a, miR-29, miR-29a, miR-29b, miR-29c, miR-34, mi-R34a, miR-150, miR-451, miR-145, miR-143, miR-144, miR-193a-3p, miR-133a, miR-155, miR-181a, miR-214, miR-199b, miR-199a, miR-126, miR-378, miR-363 and miR-30b, and/or miR-499.

In several embodiments, isolating a plurality of exosomes from the population of cells includes centrifugation of the cells and/or media conditioned by the cells. In several embodiments, ultracentrifugation is used. In several embodiments, isolating a plurality of exosomes from the population of cells is via size-exclusion filtration. In other embodiments, isolating a plurality of exosomes from the population of cells includes use of discontinuous density gradients, immunoaffinity, ultrafiltration and/or high performance liquid chromatography (HPLC).

In certain embodiments, differential ultracentrifugation includes using centrifugal force from 1000-2000×g, 2000-3000×g, 3000-4000×g, 4000-5000×g, 5000×g-6000×g, 6000-7000×g, 7000-8000×g, 8000-9000×g, 9000-10,000×g, to 10,000×g or more to separate larger-sized particles from a plurality of exosome derived from the cells. In certain embodiments, differential ultracentrifugation includes using centrifugal force from 10,000-20,000×g, 20,000-30,000×g, 30,000-40,000×g, 40,000-50,000×g, 50,000×g-60,000×g, 60,000-70,000×g, 70,000-80,000×g, 80,000-90,000×g, 90,000-100,000×g, to 10,000×g or more to separate larger-sized particles from a plurality of exosome derived from the cells.

In other embodiments, isolating a plurality of exosomes from the population of cells includes use of filtration or ultrafiltration. In certain embodiments, a size exclusion membrane with different pore sizes is used. For example, a size exclusion membrane can include use of a filter with a pore size of 0.1-0.5 µM, 0.5-1.0 µM, 1-2.5 µM, 2.5-5 µM, 5 or more µM. In certain embodiments, the pore size is about 0.2 µM. In certain embodiments, filtration or ultrafiltration includes size exclusion ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In other embodiments, filtration or ultrafiltration includes size exclusion includes use of hollow fiber membranes capable of isolating particles ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In other embodiments, a molecular weight cut-off (MWCO) gel filtration capable of isolating particles ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In various embodiments, such systems are used in combination with variable fluid flow systems.

In other embodiments, isolating a plurality of exosomes from the population of cells includes use of tangential flow filtration (TFF) systems are used purify and/or concentrate the exosome fractions. In other embodiments, isolating a plurality of exosomes from the population of cells includes use of (HPLC) can also be used to purify exosomes to homogeneously sized particles. In various embodiments, density gradients as used, such as centrifugation in a sucrose density gradient or application of a discrete sugar cushion in preparation.

In other embodiments, isolating a plurality of exosomes from the population of cells includes use of a precipitation reagent. For example, a precipitation reagent, ExoQuick®, can be added to conditioned cell media to quickly and rapidly precipitate a population of exosomes. In other embodiments, isolating a plurality of exosomes from the population of cells includes use of volume-excluding polymers (e.g., polyethylene glycols (PEGs)) are used. In another embodiment, isolating a plurality of exosomes from the population of cells includes use of flow field-flow fractionation (FlFFF), an elution-based technique.

In certain embodiments, isolating a plurality of exosomes from the population of cells includes use of one or more capture agents to isolate one or more exosomes possessing specific biomarkers or containing particular biological molecules. In one embodiment, one or more capture agents include at least one antibody. For example, antibody immunoaffinity recognizing exosome-associated antigens is used to capture specific exosomes. In other embodiments, the at least one antibody are conjugated to a fixed surface, such as magnetic beads, chromatography matrices, plates or microfluidic devices, thereby allowing isolation of the specific exosome populations of interest. In other embodiments, isolating a plurality of exosomes from the population of cells includes use of one or more capture agents that is not an antibody. This includes, for example, use of a "bait" molecule presenting an antigenic feature complementary to a corresponding molecule of interest on the exosome surface, such as a receptor or other coupling molecule. In one embodiment, the non-antibody capture agent is a lectin capable of binding to polysaccharide residues on the exosome surface.

In various embodiments, the CDCs are mammalian. In other embodiments, the CDCs are human. As disclosed above, in some embodiments, synthetic exosomes are generated, which can be isolated by similar mechanisms as those above. In various embodiments, the composition that is a plurality of exosomes is a pharmaceutical composition further including a pharmaceutically acceptable carrier.

In various embodiments, the plurality of exosomes range in size from 30 to 300 nm. In various embodiments, the plurality of exosomes range in size from 40 to 100 nm. In certain embodiments, the plurality of exosomes is cardiosphere-derived cell (CDC) exosomes. In certain embodiments, the plurality of exosomes includes exosomes that are CD63+. In various embodiments, the exosomes include microRNAs miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and/or miR-23a. In other embodiments, the exosomes are 2-5 kDa, such as 3 kDa. Other examples or embodiments relating to the composition and techniques involving exosomes are presented, in PCT Pub. No. WO 2014/028,493, which is fully incorporated herein by reference.

Described herein is a method for treatment including, selecting a subject in need of treatment, administering a composition including a plurality of exosomes to the individual, wherein the administration of the composition treats the subject. In certain embodiments, the subject is in need to treatment for a disease and/or condition involving tissue damage or dysfunction. In other embodiments, the disease and/or condition involving tissue damage or dysfunction is heart disease. In other embodiments, the plurality of exosomes includes exosomes including one or more microRNAs.

In certain embodiments, the plurality of exosomes are generated by a method including providing a population of cells, and isolating a plurality of exosomes from the population of cells. In various embodiments, the cells are stem cells, progenitors and/or precursors. In other embodiments, the stem cells, progenitors and/or precursors are cardiosphere-derived cells (CDCs). In other embodiments, the stem cells, progenitors and/or precursors are pluripotent stem cells (pSCs), such as embryonic stem cells (ESCs) and induced pluripotent stem cells (iPSCs) derived from any one of various somatic sources in the body such as fibroblasts, blood and hematopoietic stem cells (hSCs), immune cells, bone and bone marrow, neural tissue, among others. In other embodiments, the stem cells, progenitors and/or precursors includes hSCs, mesenchymal stem cells (MSCs), or endothelial precursor cells (EPCs). In various embodiments, the cells are stem cells, progenitors and/or precursors derived from human biopsy tissue. In various embodiments, the cells are stem cells, progenitors and/or precursors are a primary culture. In various embodiments, the cells are stem cells, progenitors and/or precursors are a cell line capable of serial passaging. In certain embodiments, the exosomes are synthetic.

In various embodiments, the plurality of exosomes is derived from cardiosphere-derived cells (CDCs). In other embodiments, the plurality of exosomes includes exosomes including one or more biological molecules. In other embodiments, the plurality of exosomes includes exosomes enriched for one or more biological molecules when derived from CDCs compared to exosome derived from non-CDC sources. In various embodiments, the one or more biological molecules are proteins, growth factors, cytokines, transcription factors and/or morphogenic factors. In other embodiments, the plurality of exosomes includes exosomes enriched for one or more biological molecules includes microRNAs, further including microRNAs that are enriched when derived from CDCs compared to exosome derived from non-CDC sources. In various embodiments, these microRNAs can include miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and/or miR-23a. In several embodiments, the plurality of exosomes includes one or more exosomes enriched in at least one of miR-146a, miR-22, miR-24.

In various embodiments, the CDCs are mammalian. In other embodiments, the CDCs are human. In certain embodiments, the exosomes are synthetic. In certain embodiments, the synthetic exosomes possess substantially similar content (e.g., microRNAs, biological molecules) as exosomes derived from CDCs.

In various embodiments, administration of the plurality of exosomes alters gene expression in the damaged or dysfunctional tissue, improves viability of the damaged tissue, and/or enhances regeneration or production of new tissue in the individual. In various embodiments, the quantities of exosomes that are administered to achieved these effects range from $1\times10^6$ to $1\times10^7$, $1\times10^7$ to $1\times10^8$, $1\times10^8$ to $1\times10^9$, $1\times10^9$ to $1\times10^{10}$, $1\times10^{10}$ to $1\times10^{11}$, $1\times10^{11}$ to $1\times10^{12}$, $1\times10^{12}$ or more. In other embodiments, the numbers of exosomes is relative to the number of cells used in a clinically relevant dose for a cell-therapy method. For example, it has been demonstrated that 3 mL/$3\times10^5$ CDCs, is capable of providing therapeutic benefit in intracoronary administration, and therefore, a plurality of exosomes as derived from that number of cells in a clinically relevant dose for a cell-therapy method. In various embodiments, administration can be in repeated doses. In another example, the number of administered CDCs includes intracoronary 25 million CDCs per coronary artery (i.e., 75 million CDCs total) as another baseline for exosome dosage quantity. In various embodiments, the numbers of CDCs includes $1\times10^5$, $1\times10^6$, $1\times10^7$, $1\times10^8$, $1\times10^9$ CDCs in a single dose as another baseline for exosome dosage quantity. In certain instances, this may be prorated to body weight (range 100,000-1M CDCs/kg body weight total CDC dose). In various embodiments, exosome quantity may be defined by protein quantity, such as dosages including 1-10, 10-25, 25-50, 50-75, 75-100, or 100 or more mg exosome protein.

Defining an effective dose range, dosing regimen and route of administration, may be guided by studies using fluorescently labeled exosomes, and measuring target tissue retention, which can be >10×, >50×, or >100× background, as measured 5, 10, 15, 30, or 30 or more min as a screening criterion. In certain embodiments, >100× background measured at 30 mins is a baseline measurement for a low and high dose that is then assess for safety and bioactivity (e.g., using MRI endpoints: scar size, global and regional function). In various embodiments, single doses are compared to two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition.

In various embodiments, administration of exosomes to the subject occurs through any of known techniques in the art. In some embodiments, this includes percutaneous delivery. In other embodiments, myocardial infusion is used, for example, the use of intracoronary catheters. In various embodiments, delivery can be intra-arterial or intravenous. Additional delivery sites include any one or more compartments of the heart, such as arterial, venous, and/or ventricular locations. In certain embodiments, administration can include delivery to a tissue or organ site that is different from the site or diseased and/or dysfunctional tissue. In certain embodiments, the delivery is via inhalation or oral administration.

In various embodiments, administration of the plurality of exosomes alters gene expression in the damaged or dysfunctional tissue, improves viability of the damaged tissue, and/or enhances regeneration or production of new tissue in the individual. In various embodiments, administration of the exosomes results in functional improvement in the tissue. In several embodiments, the damaged or dysfunctional tissue includes cardiac tissue.

For example, in certain embodiments in which cardiac tissue is damaged or dysfunctional, functional improvement may include increased cardiac output, contractility, ventricular function and/or reduction in arrhythmia (among other functional improvements). For other tissues, improved function may be realized as well, such as enhanced cognition in response to treatment of neural damage, improved blood-oxygen transfer in response to treatment of lung damage, improved immune function in response to treatment of damaged immunological-related tissues.

In various embodiments, administration of the plurality of exosomes alters gene expression in the damaged or dysfunctional tissue, improves viability of the damaged tissue, and/or enhances regeneration or production of new tissue in the individual. In various embodiments, administration of the exosomes results in functional improvement in the tissue. In several embodiments, the damaged or dysfunctional tissue includes skeletal muscle tissue.

For example, in certain embodiments in which skeletal muscle tissue is damaged or dysfunctional, functional improvement may include increased contractile strength, improved ability to walk (for example, and increase in the six-minute walk test results), improved ability to stand from a seated position, improved ability to sit from a recumbent or supine position, or improved manual dexterity such as pointing and/or clicking a mouse.

In various embodiments, the damaged or dysfunctional tissue is in need of repair, regeneration, or improved function due to an acute event. Acute events include, but are not limited to, trauma such as laceration, crush or impact injury, shock, loss of blood or oxygen flow, infection, chemical or heat exposure, poison or venom exposure, drug overuse or overexposure, and the like. In other embodiments, the damaged tissue is cardiac tissue and the acute event includes a myocardial infarction. In some embodiments, administration of the exosomes results in an increase in cardiac wall thickness in the area subjected to the infarction.

In other embodiments, tissue is also subject to damage due to chronic disease, such as for example congestive heart failure, including as conditions secondary to diseases such as Duchenne muscular dystrophy, ischemic heart disease, hypertension, valvular heart disease, dilated cardiomyopathy, infection, diabetes, and the like. In various embodiments, the administration can be in repeated doses, such as two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition.

Other sources of damage also include, but are not limited to, injury, age-related degeneration, cancer, and infection. In several embodiments, the regenerative cells are from the same tissue type as is in need of repair or regeneration. In several other embodiments, the regenerative cells are from a tissue type other than the tissue in need of repair or regeneration.

In certain embodiments, the method of treatment includes, selecting a subject in need of treatment for a heart related disease and/or condition, administering a composition including a plurality of exosomes to the individual, wherein the administration of the composition treats thesubject. In various embodiments, the heart related disease and/or condition includes heart failure, further including Duchenne muscular dystrophy related heart failure. In various embodiments, the plurality of exosomes range in size from 30 to 300 nm. In various embodiments, the plurality of exosomes range in size from 40 to 100 nm. In certain embodiments, the plurality of exosomes are cardiosphere-derived cell (CDC) exosomes. In certain embodiments, the plurality of exosomes include exosomes that are CD63+. In various embodiments, the exosomes include microRNAs miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and/or miR-23a. In other embodiments, the exosomes are 2-5 kDa, such as 3 kDa. In other embodiments, administering a composition includes a dosage of $1\times10^8$, $1\times10^8$ to $1\times10^9$, $1\times10^9$ to $1\times10^{10}$, $1\times10^{10}$ to $1\times10^{11}$, $1\times10^{11}$ to $1\times10^{12}$, $1\times10^{12}$ or more exosomes. For example, it has been demonstrated that 3 mL/$3\times10^5$ CDCs, is capable of providing therapeutic benefit in intracoronary administration, and therefore, a plurality of exosomes as derived from that number of cells in a clinically relevant dose for a cell-therapy method. In various embodiments, administration can be in repeated doses. In another example, the number of administered CDCs includes intracoronary 25 million CDCs per coronary artery (i.e., 75 million CDCs total) as another baseline for exosome dosage quantity. In various embodiments, the numbers of CDCs includes $1\times10^5$, $1\times10^6$, $1\times10^7$, $1\times10^8$, $1\times10^9$ CDCs in a single dose. In certain instances, this may be prorated to body weight (range 100,000-1M CDCs/kg body weight total CDC dose). In various embodiments, exosome quantity may be defined by protein quantity, such as dosages including 1-10, 10-25, 25-50, 50-75, 75-100, or 100 ore more mg exosome protein. In various embodiments, administering a composition includes multiple dosages of the exosomes. In various embodiments, the repeated or sequentially-applied doses are provided for treatment of an acute disease and/or condition. In various embodiments, the repeated or sequentially-applied doses are provided for treatment of a chronic disease and/or condition. In other embodiments, administering a composition includes percutaneous injection. In other embodiments, administering a composition includes myocardial infusion. In other embodiments, administering a composition includes use of a intracoronary catheter. In other embodiments, administration a composition includes intra-arterial or intravenous delivery.

Further described herein is a method of improving cardiac performance in a subject including, selecting a subject, administering a composition including a plurality of exosomes to the individual, wherein the administration of the composition improves cardiac performance in the subject. In other embodiments, improving cardiac performance can be demonstrated, by for example, improvements in baseline ejection volume. In other embodiments, improving cardiac performance relates to increases in viable tissue, reduction in scar mass, improvements in wall thickness, regenerative remodeling of injury sites, enhanced angiogenesis, improvements in cardiomyogenic effects, reduction in apoptosis, and/or decrease in levels of pro-inflammatory cytokines.

In certain embodiments, the method of improving cardiac performance includes, selecting a subject in need of treatment for a heart related disease and/or condition, administering a composition including a plurality of exosomes to the individual, wherein the administration of the composition treats thesubject. In various embodiments, the heart related disease and/or condition includes heart failure, further including Duchenne muscular dystrophy related heart failure. In various embodiments, the plurality of exosomes range in size from 30 to 300 nm. In various embodiments, the plurality of exosomes range in size from 40 to 100 nm. In certain embodiments, the plurality of exosomes are cardiosphere-derived cell (CDC) exosomes. In certain embodiments, the plurality of exosomes include exosomes that are CD63+. In various embodiments, the exosomes include microRNAs miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and/or miR-23a. In other embodiments, the exosomes are 2-5 kDa, such as 3 kDa. In other embodiments, administering a composition includes a dosage of $1\times10^8$, $1\times10^8$ to $1\times10^9$, $1\times10^9$ to $1\times10^{10}$, $1\times10^{10}$ to $1\times10^{11}$, $1\times10^{11}$ to $1\times10^{12}$, $1\times10^{12}$ or more exosomes. For example, it has been demonstrated that 3 mL/$3\times10^5$ CDCs, is capable of providing therapeutic benefit in intracoronary administration, and therefore, a plurality of exosomes as derived from that number of cells in a clinically relevant dose for a cell-therapy method. In various embodiments, administration can be in repeated doses. In another example, the number of administered CDCs includes intracoronary 25 million CDCs per coronary artery (i.e., 75 million CDCs total) as another baseline for exosome dosage quantity. In various embodiments, the numbers of CDCs includes $1\times10^5$, $1\times10^6$, $1\times10^7$, $1\times10^8$, $1\times10^9$ CDCs in a single dose. In certain instances, this may be prorated to body weight (range 100,000-1M CDCs/kg body weight total CDC dose). In various embodiments, exosome quantity may be defined by protein quantity, such as dosages including 1-10, 10-25, 25-50, 50-75, 75-100, or 100 or more mg exosome protein. In various embodiments, administering a composition includes multiple dosages of the exosomes. In various embodiments, the repeated or sequentially-applied doses are provided for treatment of an acute disease and/or condition.

In various embodiments, the repeated or sequentially-applied doses are provided for treatment of a chronic disease and/or condition. In other embodiments, administering a composition includes percutaneous injection. In other embodiments, administering a composition includes myocardial infusion. In other embodiments, administering a composition includes use of a intracoronary catheter. In other embodiments, administration a composition includes intra-arterial or intravenous delivery.

Herein the Inventors demonstrate that cardiosphere-derived cells (CDCs), in advanced clinical testing for therapeutic regeneration after myocardial infarction, reverse the key pathophysiological hallmarks of Duchenne cardiomyopathy (oxidative stress, inflammation, fibrosis and mitochondrial dysfunction) in mdx mice. Exosomes secreted by human CDCs reproduce the benefits of CDCs in mdx mice, and reverse abnormalities of calcium cycling and mitochondrial respiration in human Duchenne cardiomyocytes. Both CDCs and their exosomes improve heart function in mdx mice; a single injection of CDCs suffices to increase maximal exercise capacity and improve survival. Delivery of a microRNA enriched in CDC exosomes, miR-148a, mimics key effects of CDCs and CDC exosomes. Thus, CDCs ameliorate Duchenne cardiomyopathy via exosome-mediated transfer of signaling molecules including miR-148a. The present findings motivate clinical testing of CDCs in patients with Duchenne cardiomyopathy.

Example 1

CDC Culture

Endomyocardial biopsies from the right ventricular aspect of the interventricular septum are obtained from healthy hearts of deceased tissue donors. Cardiosphere-derived cells were derived as described previously. See Makkar et al., (2012). "Intracoronary cardiosphere-derived cells for heart regeneration after myocardial infarction (CADUCEUS): a prospective, randomized phase 1 trial." *Lancet* 379, 895-904 (2012), which is fully incorporated by reference herein.

In brief, heart biopsies are minced into small fragments and briefly digested with collagenase. Explants were then cultured on 20 mg/ml fibronectin-coated dishes. Stromal-like flat cells and phase-bright round cells grow out spontaneously from tissue fragments and reach confluence by 2-3 weeks. These cells are harvested using 0.25% trypsin and cultured in suspension on 20 mg/ml poly d-lysine to form self-aggregating cardiospheres. cardiosphere-derived cells (CDCs) are obtained by seeding cardiospheres onto fibronectin-coated dishes and passaged. All cultures are maintained at 5% CO2 at 37° C., using IMDM basic medium supplemented with 20% FBS, 1% penicillin/streptomycin, and 0.1 ml 2-mercaptoethanol.

Example 2

Media Conditioning and Exosome Purification

Exosomes are harvested from CDCs at passage 4. One can also isolate exosomes from normal human dermal fibroblasts (NHDF), cells that have been previously utilized as controls providing no salutary benefit, as a control.

CDCs and NHDFs are conditioned in serum-free media for 15 days at 100% confluence. Aspirated media is then centrifuged at 3,000×g for 15 min to remove cellular debris Exosomes were then isolated using EXOQUICK™ Exosome Precipitation Solution.

Exosome pellets are resuspended in the appropriate media and used for assays. Expression of the conserved exosome marker CD63 is verified using ELISA. RNA content of exosome pellets can also be quantified using a Nanodrop spectrophotometer. For generation of miR-146a-deficient exosomes, CDC are transfected in suspension with miRIDIAN miR-146a hairpin inhibitor or a miRIDIAN hairpin control and seeded on to fibronectin-coated flasks. Exosomes are isolated from serum-free conditioned media (48 hr conditioning).

Example 3

Exosomal RNA Degradation

Exosomal RNA degradation is performed by suspending exosome pellets in 2 ml of PBS. To one sample. 100 ml of TRITON™ X-100 (Sigma Aldrich) is added to achieve 5% triton concentration. Exosomes are treated with 0.4 mg/ml RNase A treatment for 10 min at 37° C. Samples are further treated with 0.1 mg/ml Proteinase K for 20 min at 37° C. RNA is purified from samples using an microRNA isolation kit. RNA levels are measured using Nanodrop.

Example 4

Mass Spectrometry Analysis on Exosome Pellets

Proteins are prepared for digestion using the filter-assisted sample preparation (FASP) method. Concentrations re measured using a Qubitfluorometer. Trypsin is added at a 1:40 enzyme-to-substrate ratio and the sample incubated overnight on a heat block at 37° C. The device was centrifuged and the filtrate collected. Digested peptides are desalted using C18 stop-and-go extraction (STAGE) tips. Peptides are fractionated by strong anion exchange STAGE tip chromatography. Peptides re eluted from the C18 STAGE tip and dried. Each fraction is analyzed with liquid chromatography-tandem mass spectrometry. Samples are loaded to a 2 cm×100 mm I.D. trap column. The analytical column is 13 cm×75 mm I.D. fused silica with a pulled tip emitter. The mass spectrometer is programmed to acquire, by data-dependent acquisition, tandem mass spectra from the top 15 ions in the full scan from 400 to 1,400 m/z. Mass spectrometer RAW data files re converted to MGF format using msconvert. MGF files re searched using X!Hunter against the latest spectral library available on the GPM at the time. MGF files are also searched using X!!Tandem using both the native and k-score scoring algorithms and by OMSSA. Proteins re required to have one or more unique peptides with peptide E-value scores of 0.01 or less from X!!Tandem, 0.01 or less from OMSSA, 0.001 or less and theta values of 0.5 or greater from X!Hunter searches, and protein E-value scores of 0.0001 or less from X!!Tandem and X!Hunter.

Example 5

Myocyte Isolation, Angiogenesis Assay

For studies establishing the effects of exosome application, a variety of cell types can be used. For example, neonatal rat cardiomyoctes (NRCMs) can be isolated from 1- to 2-day-old Sprague Dawley rat pups and cultured in monolayers. Another useful source includes human vein umbilical vein endothelial cells plated on growth factor-deprived MATRIGEL® (BD Biosciences) to assay angiogenesis.

Cells are then incubated with $7 \times 10^8$ and $4.0 \times 10^8$ CDC exosomes or NHDF exosomes, respectively. Difference in doses reflects the different exosome output from cells during conditioning. Cells were allowed to produce exosomes under similar conditions such that the relative doses might be representative of the relative exosome production in vivo. Four hours later, tube formation was measured.

Example 6

In Vitro Cardiomyocyte Assay Exosome Treatment

The Inventors plated $1.5 \times 10^4$ NRCMs in fibronectin-coated eight-chamber slides. After 5 days, media is replaced with new fresh media containing 3 $5 \times 10^8$ or $2 \times 10^8$ CDC or NHDF exosomes, respectively. Cells are then fixed with 4% paraformaldehyde for 30 min at 4° C. Chambers are washed three times with cold P3S then blocked and permeabilized with Dako/0.1% Saponin (Invitrogen) for 1 hr at 37° C. Cells are incubated (overnight, 4° C.) with rabbit anti-Ki-67 (1.100) primary antibody and mouse anti-a-sarcomericacti-nin (Abcam). Cells are then washed three times with PBS and incubated with goat antimouse (Cy5) and goat antirabbit (FITC) in TUNEL stain solution for 1 hr at 37° C. Slides are then washed three times in PBS, stained with 1:8,000 40,6-diamidino-2-phenylindole stain solution, and mounted using PROLONG™ antifade solution (Invitrogen) Slides were imaged using confocal microscopy.

Example 7

Cardiomyocyte Stress Assay

One injury model can include use of NRCMs plated in a monolayer on fibronectin-coated 12-well plates and treated with either 40 nM of miR-146a or mimic for 24 hr. Media is then changed and cells were washed three times with PBS. Cells are then stressed using hydrogen peroxide (100 mM $H_2O_2$ in serum free media for 2 hr) or cobalt chloride (5 mMCoCl$_2$ in serum-free media for 2 hr). Viability is measured by washing cells with PBS and treating with 20 mM Calcein PBS solution for 20 min at 37° C. in dark conditions. Fluorescence is read using a SOFTMAX® Pro 5 Plate Reader (Molecular Devices) Data per well is the average of nine consecutive measurements.

A second model includes plating cardiomyocytes on 25 mm precoated glass coverslips (Fischer Scientific) in six-well plates. Cells are stressed using 50 mM H2O2 for 15 min followed incubation with transwell membrane inserts containing CDCs or incubation with CDC exosomes for 4 hr. Cells are then washed, fixed with paraformaldehyde, and stained for analysis as explained above.

Example 8

Exosome Inhibition in CDCs

CDCs are grown to confluence in T175 flasks. For in vitro studies, CDCs were conditioned for 15 days in 20 mM GW4869 (Sigma Aldrich), serum-free media, or serum-free media containing an equivalent volume of DMSO. For in vitro transwell insert assays of cardiomyocyte stress, one can treat CDCs with 20 mM GW4869 (Sigma Aldrich), or 5 mM Spiroepoxide (Santa Cruz Biotechnology) for 12 hr. CDCs are washed three times in PBS and supplanted with serum-free media. Inserts containing treated CDCs are added into six-well plates containing cardiomyocytes. For in vivo studies, CDCs are treated with 20 mM GW4869 or an equivalent volume of DMSO for 12 hr. Prior to injection, CDC flasks are washed twice with PBS, trypsinized, and counted; $10^5$ CDCs were injected per animal.

Example 9

Acute and Chronic Myocardial Infarction Model

Three-month-old male severe combined immunodeficient (SCID)-beige mice are anesthetized with isoflurane. Following surgical preparation, a 2 cm vertical incision is introduced in the midclavicular line for a lateral thoracotomy. The left anterior descending was ligated using 7-0 silk. Animals are injected with exosomes, microRNAs, CDCs, or media control at two peri-infarct sites with a volume of 40 ml per injection.

For the chronic model of MI, animals are infarcted as described above without any treatment administration. Three weeks later, the animals are given the treatment in the same manner as above. For exosome treatments, pellets are resuspended in Iscove's Modified Dulbecco's (IMDM) basal media. Animals are injected with $2.8 \times 10^9$ and $1.56 \times 10^9$ of CDC and NHDF exosomes, respectively. microRNA-treated animals are injected with 80 ng of miR-146a or microRNA mimic control. In brief, miRIDIAN miR-146a or miRIDIAN negative control is vortexed in DHARMA-FEC™ (Thermo Scientific) transfection reagent and IMDM basal media and incubated for 10 min at room temperature to allow complexes to form microRNA complexes are resuspended in IMDM for injection. For CDC treatments, animals are injected with $10^5$ CDCs as described.

Echocardiography SCID beige mice are evaluated via echocardiography 24 hr (baseline), 14 days, and 4 weeks after surgery using VEVO 770® Imaging System (Visual Sonics). After induction of light general anesthesia, hearts are 31) imaged in the long axis view at the level of maximum left ventricular diameter. Left ventricular ejection fraction can be measured with Visual Sonics version 1.3.8 software from 2D views of LV end-diastolic and LV end-systolic area. Each animal/time point is measured multiple times and the average used for statistical analysis.

Example 10

Histology

Animals are sacrificed 4 weeks after MI. Hearts are harvested and a transverse cut is made slightly above the MI suture. The apical portion is then imbedded in optimum cutting temperature solution in a base mold/embedding ring block. Blocks are immediately frozen by submersion in cold 2-methylbutane. Hearts are sectioned at a thickness of 5 mM.

Example 11

Masson's Trichrome Staining

Two slides containing a total of four sections per heart are stained using Masson's trichrome stain. In brief, sections are treated overnight in Bouin's solution. Slides are then rinsed for 10 min under running water and stained with Weigert's hematoxylin for 5 min. Thereafter, slides are then rinsed and stained with scarlet-acid fuchsin for 5 min and rinsed again. Slides are then further stained with phosphotungstic/phosphomolybdic, aniline blue, and 2% acetic acid for 5 min each. Slides were then rinsed, dried, and mounted using DPX mounting media.

Example 12

Morphometry

Morphometric analysis of heart sections was performed using Image J software.

Briefly, 2D images of stained sections are split into blue, red, and green channels (only the blue was used). Infarct size can be established by measuring area and intensity of blue in each section to calculate infarct size. Percent viable and infarct mass were calculated by averaging percent infarct across four sections analyzed per heart. Infarct and viable masses were calculated as the product of the infarct or viable tissue, the height of the average mouse heart (3 mm) and the specific gravity of heart tissue (1.05 g/ml). Infarct wall thickness is calculated by measuring the thinnest area of the infarct. In a chronic model of MI where significant hypertrophy and adverse remodeling took place, one can adjust the viable mass of each heart based on the derived mass of cardiomyocytes in the tissue.

Myocyte mass is obtained by measuring the cross-sectional area of perpendicularly sectioned cardiomyocytes (defined as round cells with red cytoplasm and a visible nucleus in the center). The Inventors measured at least 25 myocytes per heart. Myocyte volume is quantified using the simplifying assumption of a cylindrical shape; mass was derived by multiplying volumes by the specific gravity of a cardiomyocyte (1.15 mg/ml). The viable mass of each mouse heart was divided by the mass of the cardiomyocytes in that heart.

Example 13

Figure 7:
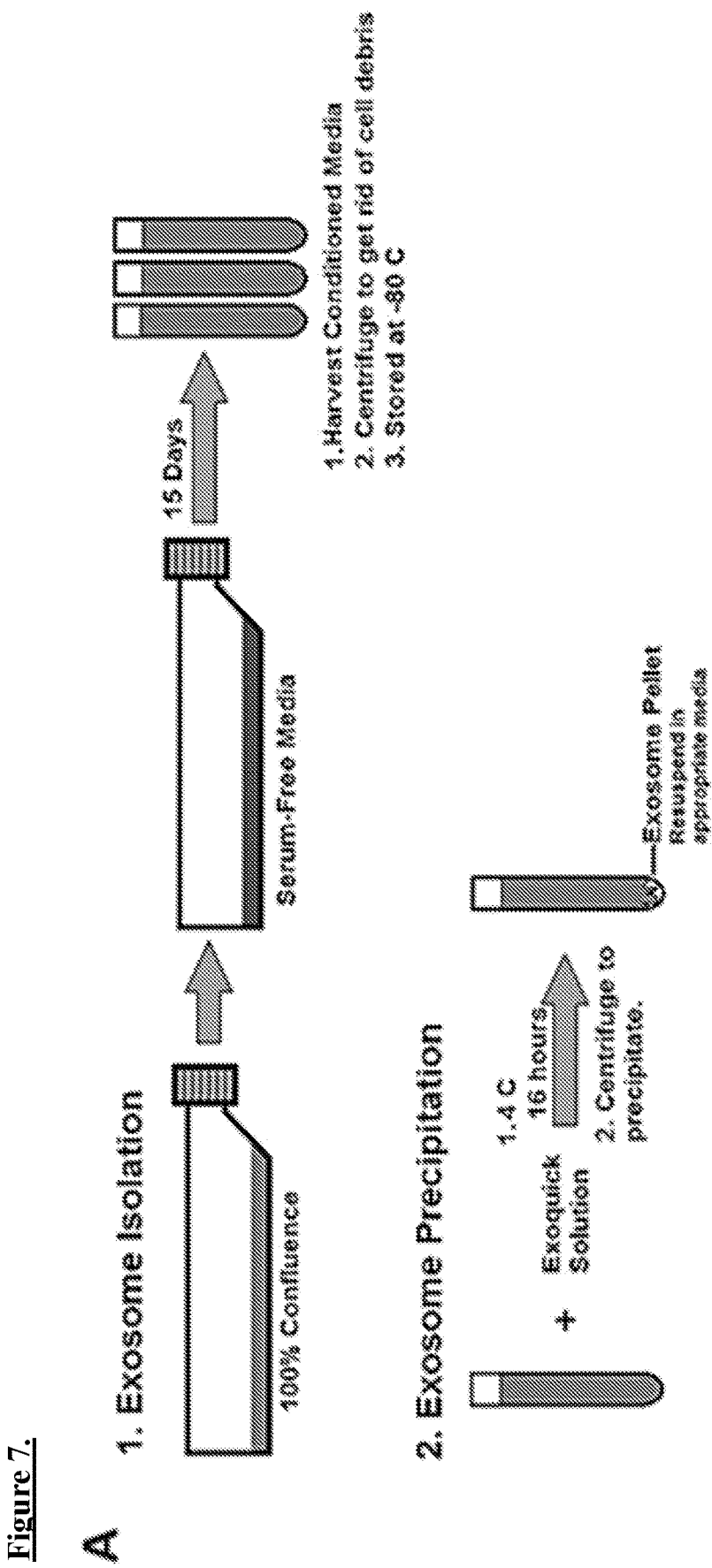
FIG. 7. Isolation of Exosomes from CDCs. (A) Graphical representation of exosome isolation and purification for exosomes. (B) Cell viability (calcein) and cell death (Ethidium homodimer-1) assay performed on CDCs over the 15 day serum-free conditioning period. (C) Representative images of CDCs before and after serum-free conditioning.
Figure 7:
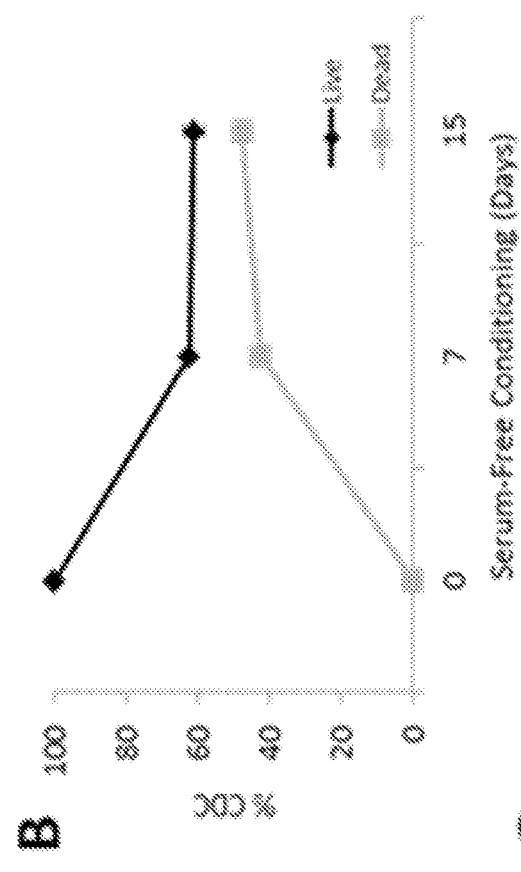
Figure 7:
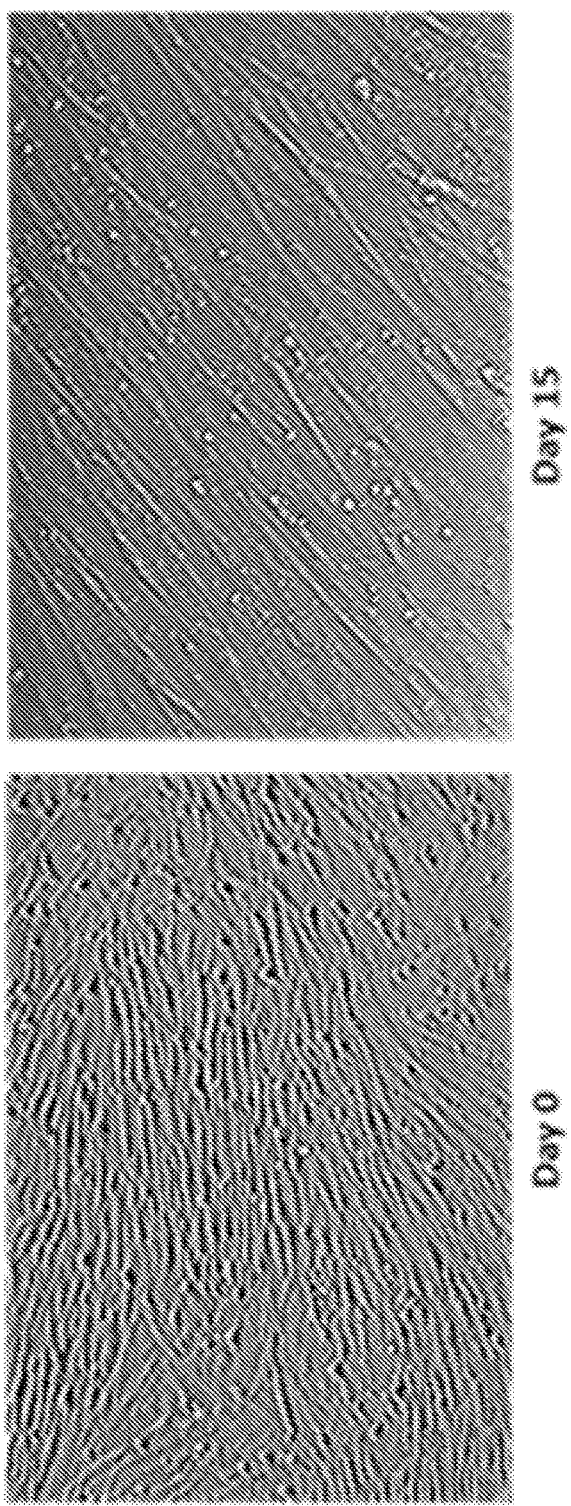

CDC Exosomes Enhance Angiogenesis and Promote Cardiomyocyte Survival and Proliferation Exosomes are isolated from serum-free media conditioned over 15 days by cultured human CDCs (or normal human dermal fibroblasts (NHDFs) as a therapeutically inert control) (FIG. 7 available online). By the end of the conditioning period, most of the CDCs remained alive despite the absence of regular media changes (FIGS. 7B and 7C). Purified exosome pellets were enriched in RNA (FIG. 1A). The Inventors confirmed that the RNA resides within exosomes by exposing the pellet to RNase A in the presence of 5% triton (FIG. 1B), with proteinase K added to dissociate protein complexes that may shield RNA. Mass spectrometry confirmed the presence of conserved exosomal biogenesis proteins (FIG. 1C) including CD63, which the Inventors used to quantify exosome yield (FIG. 1D). Transmission electron microscopy revealed most exosomes to be 30-90 nm in diameter, although smaller and larger particles were also present (FIGS. 1E and 1F), consistent with reports of exosomes derived from vascular cells. In vitro assays revealed major effects of CDC exosomes on angiogenesis, cardiomyocyte proliferation, and apoptosis.

CDC exosomes, but not NHDF exosomes, promoted tube formation in human umbilical cord endothelial cells, indicative of enhanced angiogenesis (FIG. 1G). CDC-exosome-treated neonatal cardiomyocytes proliferated more than those exposed to NHDF exosomes or media only, as evidenced by higher proportions of Ki67-positive nuclei (FIG. 1H). In addition, CDC-exosome-treated cardiomyocytes exhibited fewer terminal deoxynucleotidyltransferase nick end labeling (TUNEL)-positive nuclei (FIG. 1I). Thus, CDC exosomes stimulate angiogenesis, promote cardiomyocyte proliferation, and decrease programmed cell death. These effects reproduce those of the parent CDCs.

Example 14

CDC Exosomes Improve Cardiac Function, Impart Structural Benefits, and Increase Viable Mass after MI It is known that CDCs stimulate functional improvement and regeneration in the infarcted myocardium in both animals and humans, but of central important to the present technology is whether exosomes derived from CDCs can reproduce or are indispensable to these processes. To assess therapeutic efficacy in an established preclinical model, the Inventors induced acute MI in immunodeficient mice then injected CDC exosomes, NHDF exosomes, or serum-free media into the MI border zone.

Figure 2:
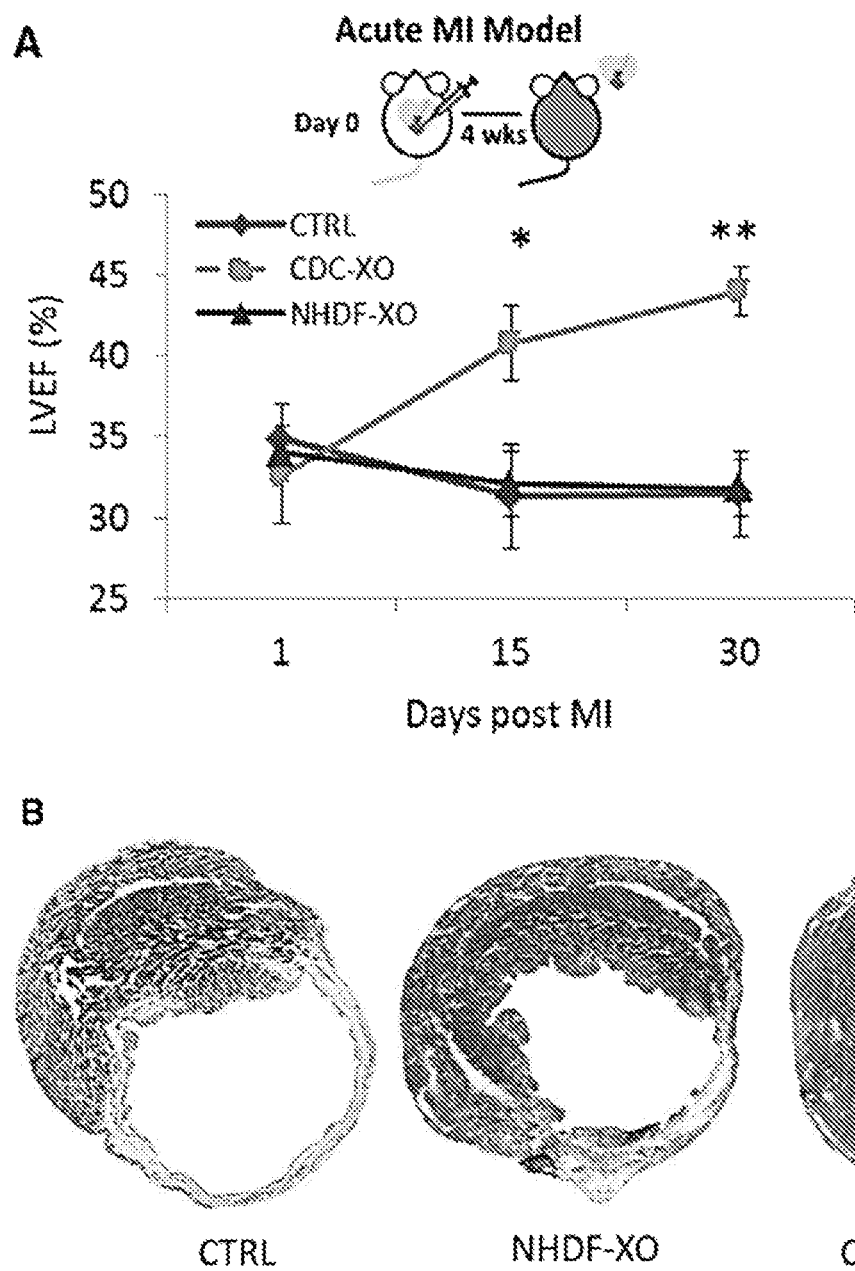
FIG. 2. CDC Exosomes Produce Structural and Functional Benefits in Mouse Hearts after MI. (A) In the acute model, SCID Beige mice underwent MI and hearts were injected with CDC exosomes, NHDF exosomes, or vehicle (control). Animals (n=8 animals per group) were echoed at days 1, 15, and 30 and were then sacrificed for histological analysis. CDC exosomes increase left ventricular ejection fraction (LVEF). (B-E) Structural benefits of CDC exosomes. Representative Masson's trichrome-stained sections of hearts from each of the three groups (B) and pooled morphometric analysis (C-E; n=3 hearts per group) reveal decreased scar and increased viable mass in hearts injected with CDC exosomes. (F) In the chronic model, 3-month-old SCID Beige mice (n=6 animals per group) underwent MI. Three weeks later, animals were injected intramyocardially with CDC exosomes or control. Functional measurements were taken 24 hr before injection (day 21) and 3 weeks later (day 42), after which animals were sacrificed for histological analysis. (G-J) As in the acute MI model, CDC exosomes produce functional and structural benefits in mouse hearts (n=4 hearts per group) in a model of chronic MI. *p<0.05, p<0.01, and *p<0.001 using one-way ANOVA with Tukey's post hoc test and two-tailed Student's t test. Data are represented as mean and SEM. See also FIGS. 8 and 9.
Figure 2:
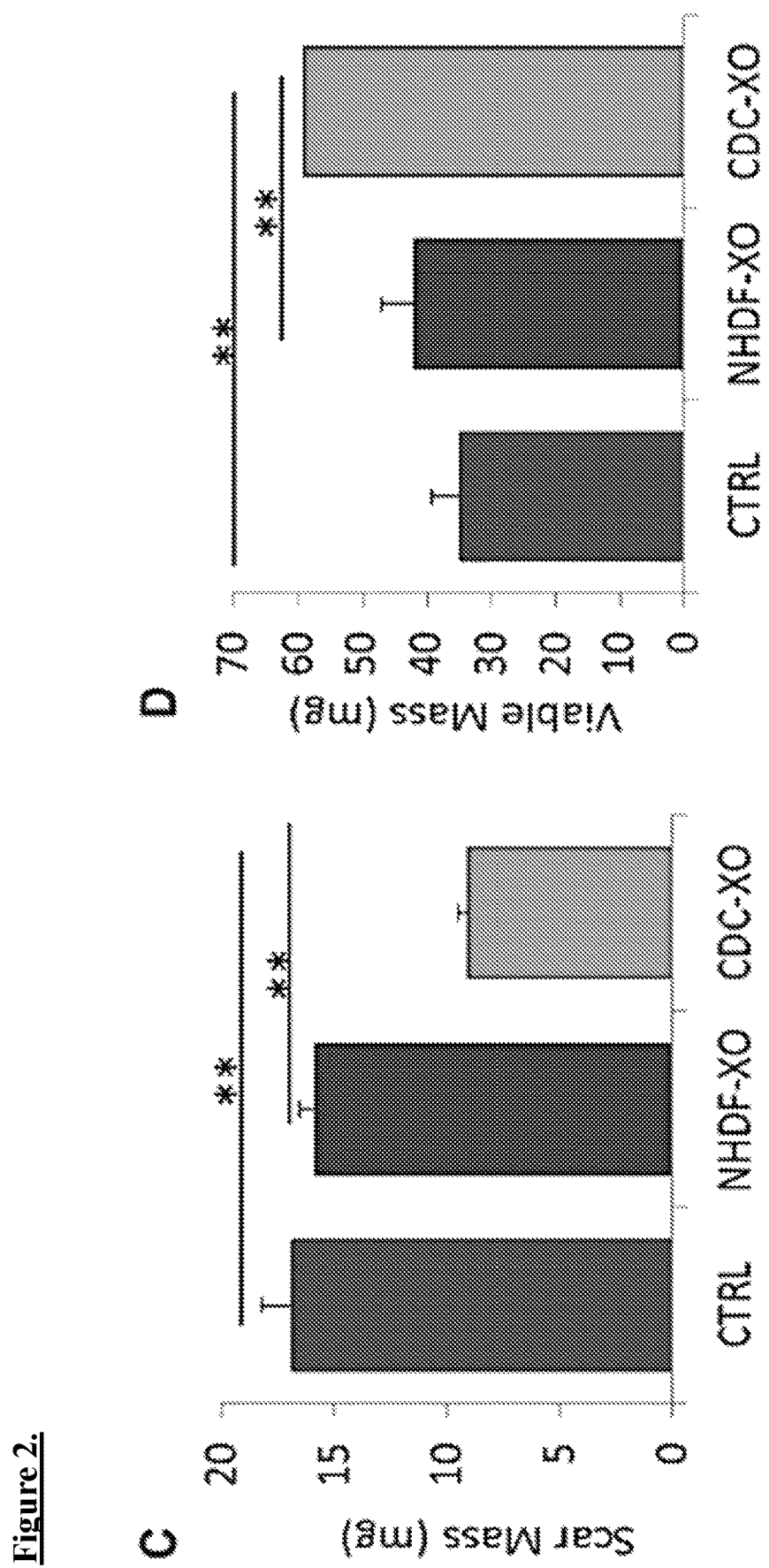
Figure 2:
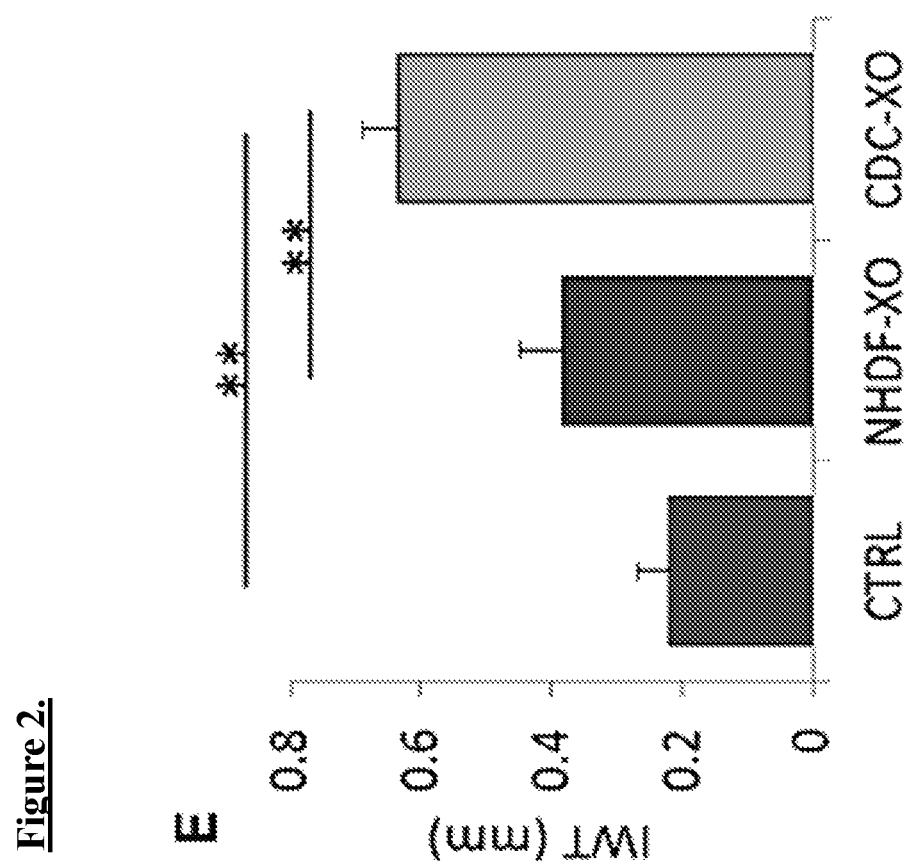
Figure 2:
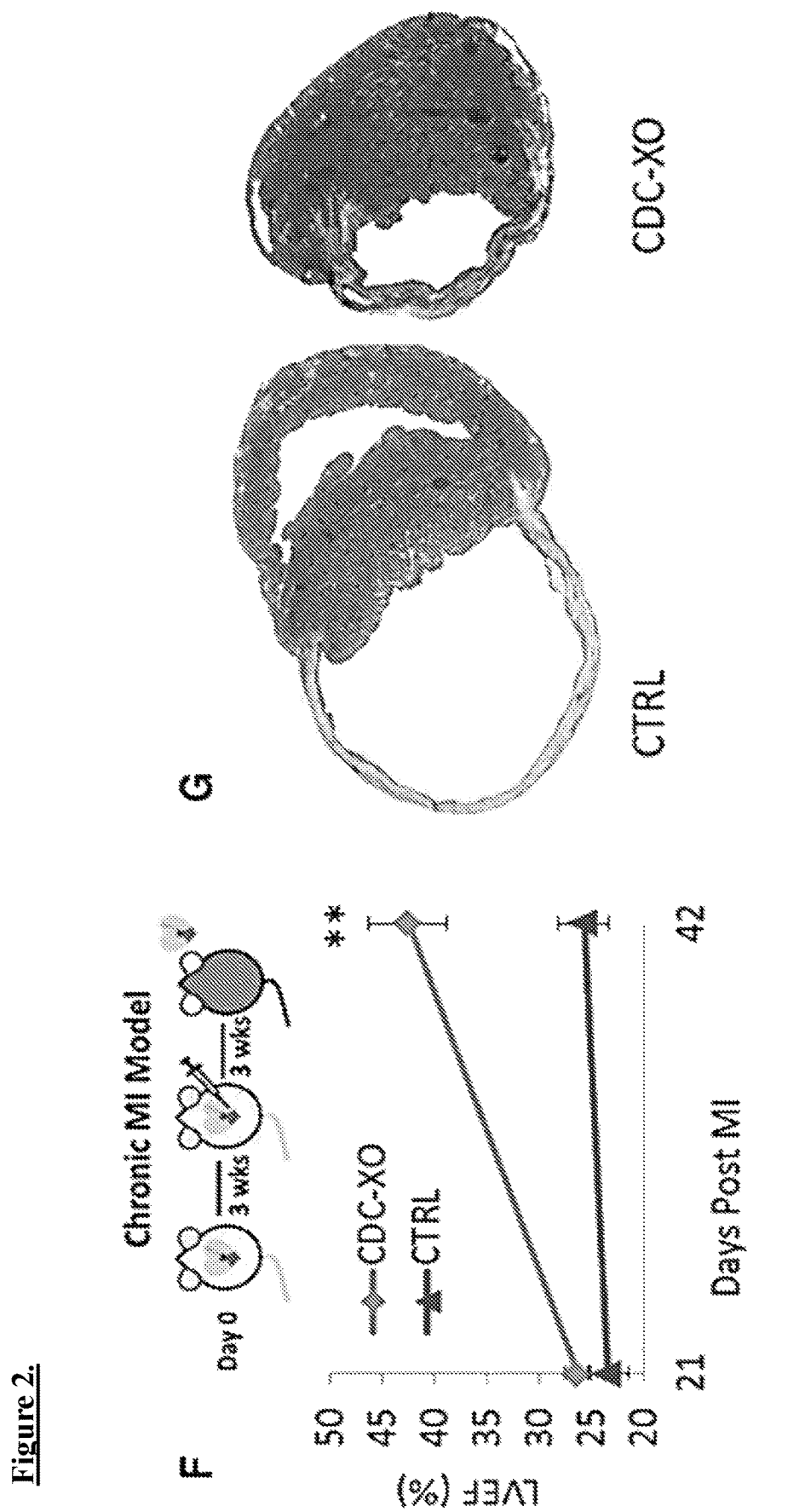
Figure 2:
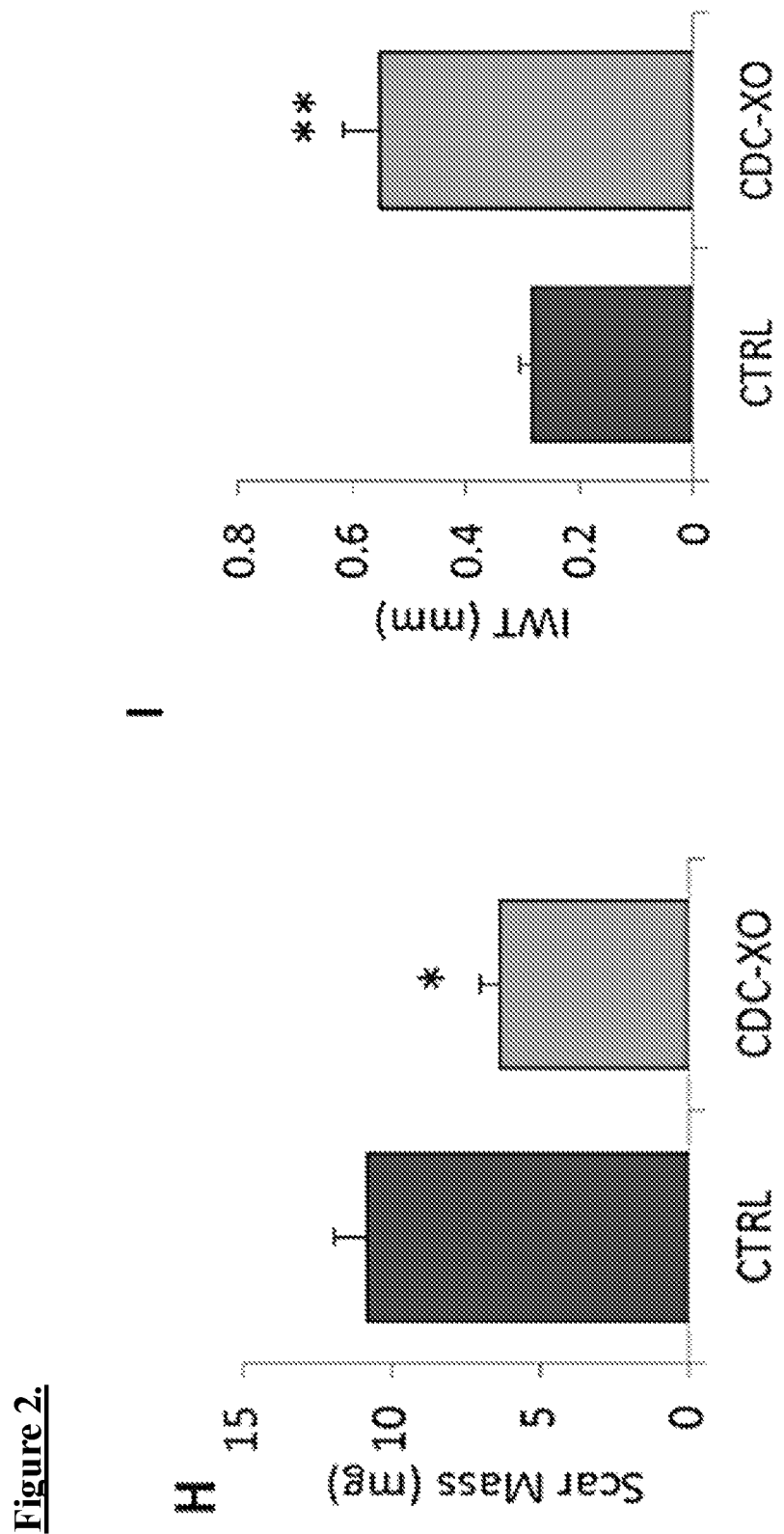
Figure 2:
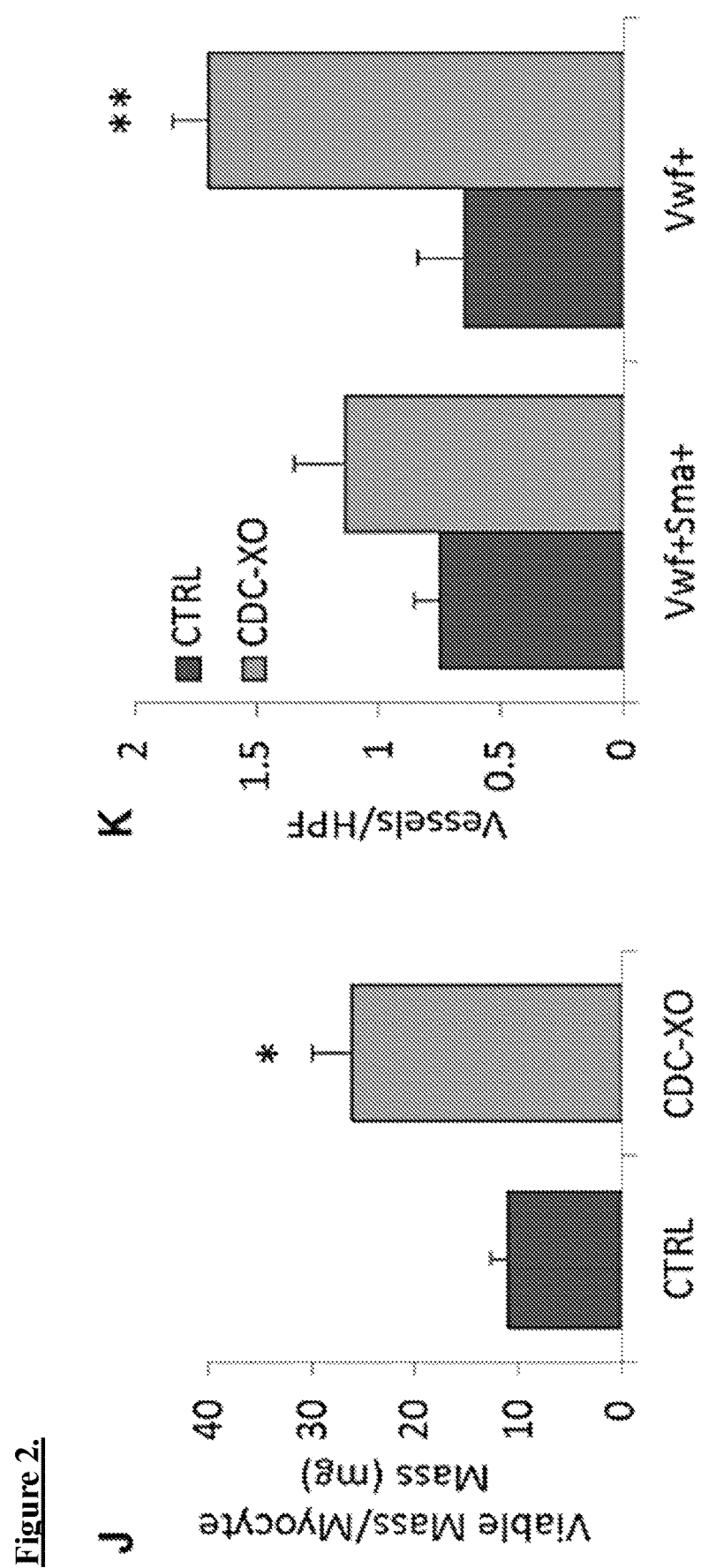
Figure 8:
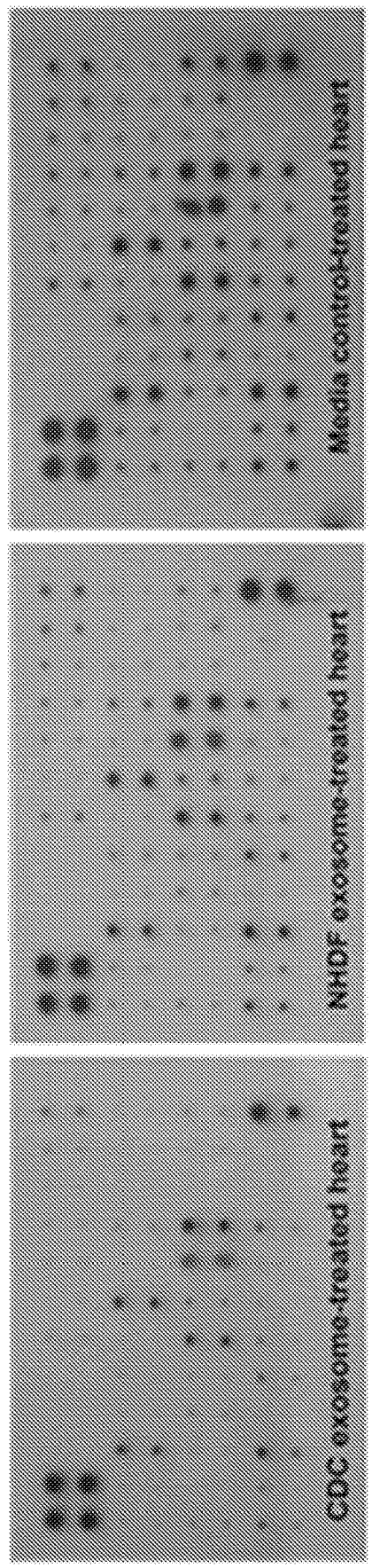
FIG. 8. CDC Exosomes Reduce Inflammation In A Mouse Model Of Acute MI. (A) Representative protein arrays for 40 pro-inflammatory markers. (B) Quantification of inflammatory proteins in mouse hearts treated with CDC-exosomes, NHDF-exosomes, or control. Data comes from three mouse hearts per group. Analysis was done using one-way ANOVA (95% CI) (n=3 hearts per group). Data represented as mean and standard error of the mean.
Figure 8:
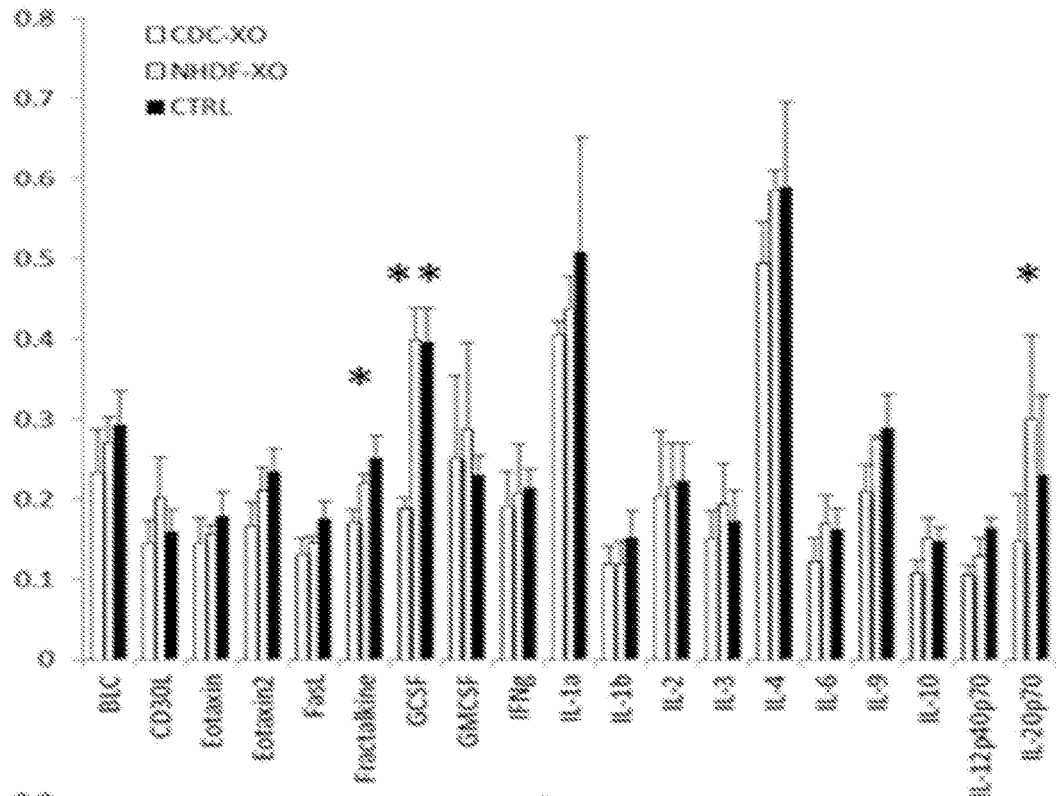
Figure 8:
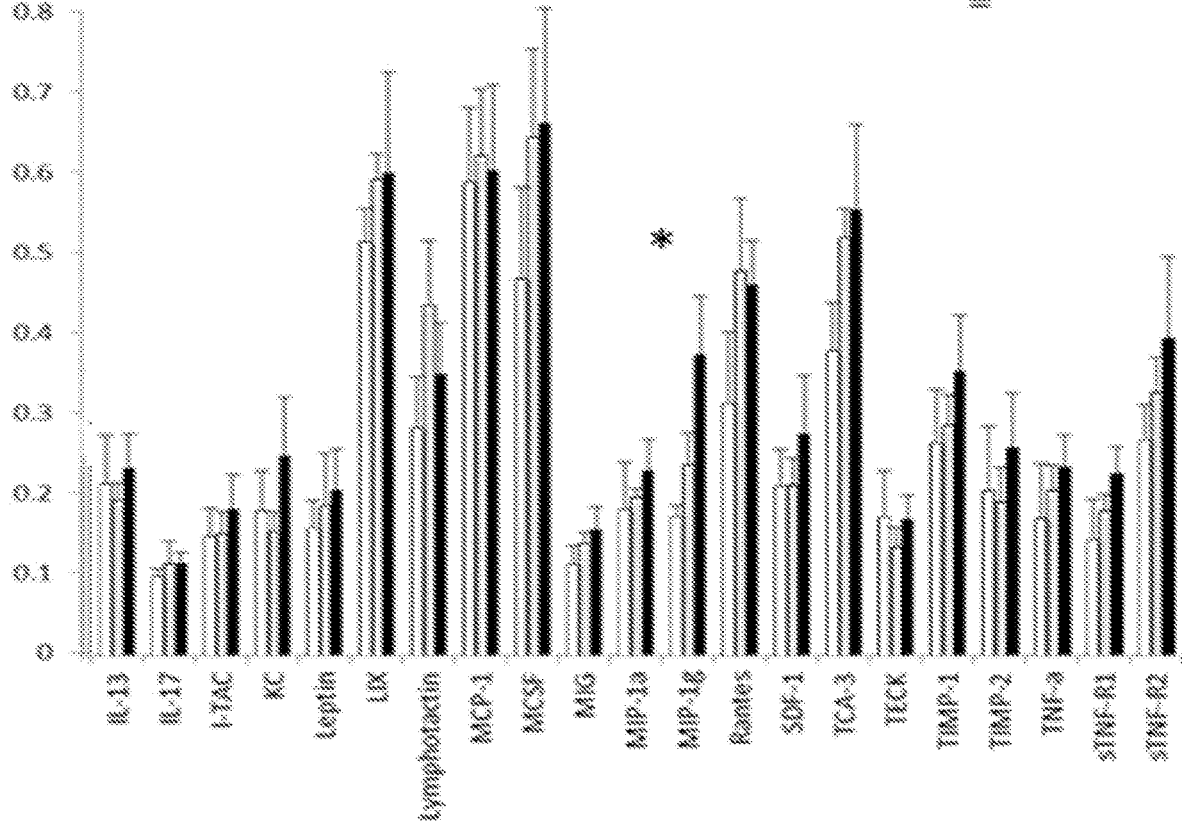

At 15 and 30 days after injection, global heart function was greater in animals injected with CDC exosomes compared with NHDF exosomes or media controls (FIG. 2A). At the histological level, CDC-exosome-treated hearts exhibited decreased scar mass, increased viable mass, and increased infarcted wall thickness compared to NHDF exosome and media controls (FIGS. 2B-2E). Proinflammatory cytokine levels were also lower in CDC-exosome-treated hearts (FIG. 8). In all these respects, CDC exosomes mimic the known benefits of CDCs themselves.

Figure 9:
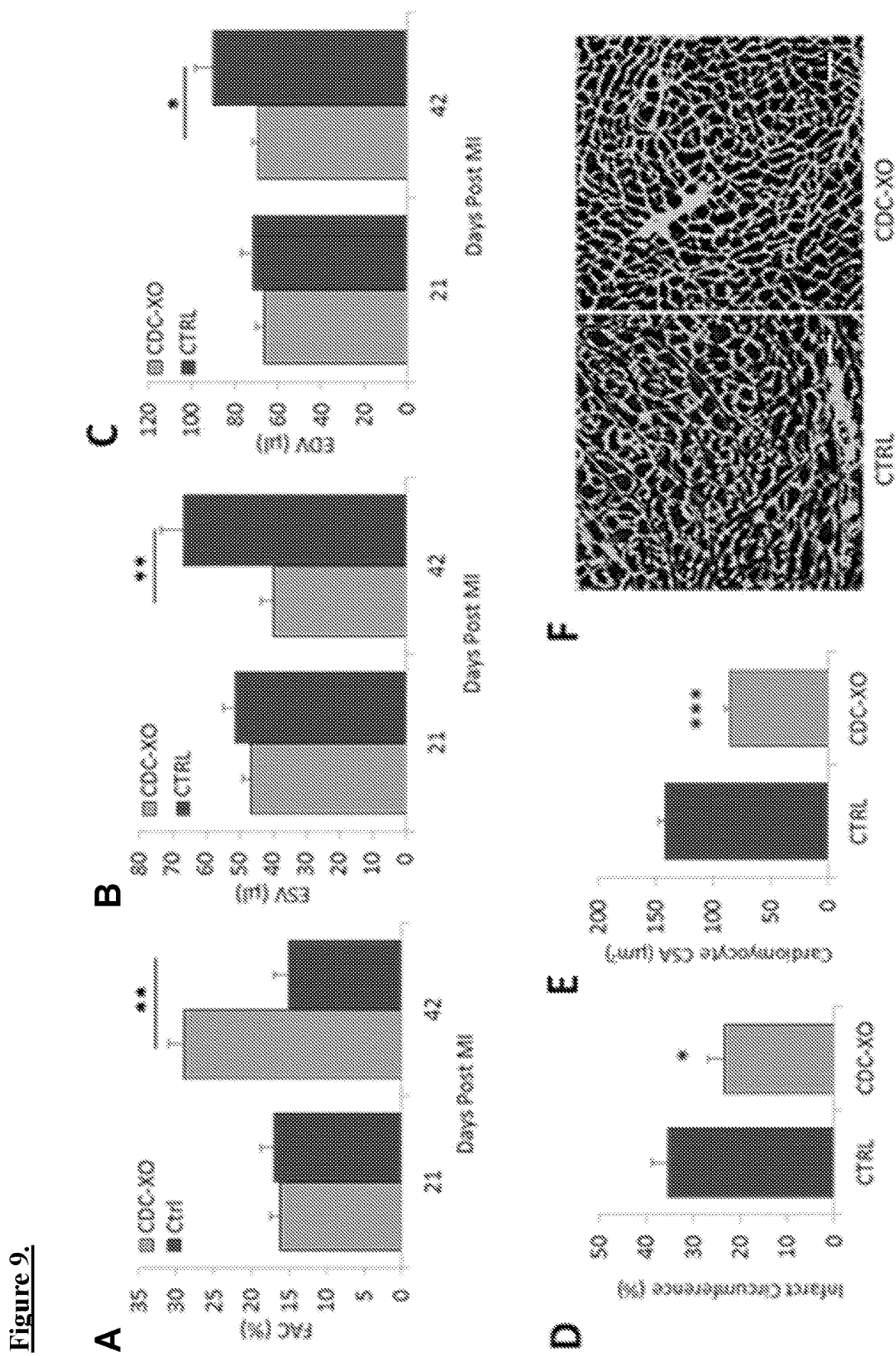
FIG. 9. CDC-Exosomes Produce Structural And Functional Benefits In Mouse Hearts After MI. CDC-exosomes stimulate functional improvement and attenuate adverse remodeling and cardiac hypertrophy in a mouse model of chronic MI. Animals treated with CDC-exosomes showed significant functional improvement compared to control as shown by fractional area change (A), end systolic volume (B) and end diastolic volume (C) (A-C, n=6 animals per group). Animals treated with CDCexosomes also showed structural improvements as noted as seen in percent of the circumference of tissue sections that are scar (D), decreased cardiomyocyte hypertrophy (E) as measured by staining with wheat germ agglutinin and DAPI (F) and increased angiogenesis in the infarct zone (G). Less cardiomyocyte death was observed in the border zone of CDC-exosome-treated animals compared to control. (H, I) (D-I n=4 hearts per group) *P<0.05, P<0.01, *P<0.001. using Student's t test, all scale bars represent 50 μm. Data represented as mean and standard error of the mean.
Figure 9:
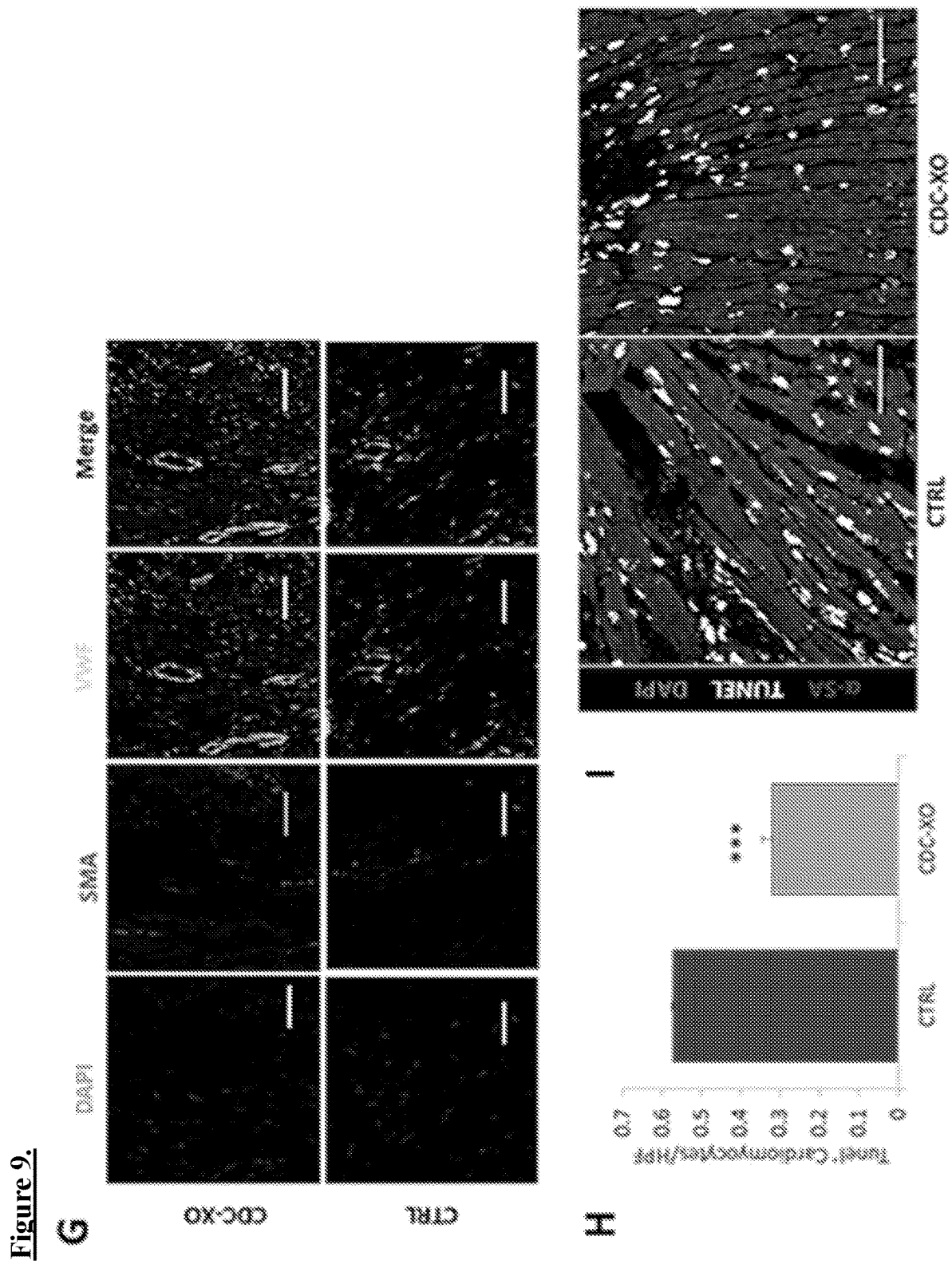

The acute MI model, while used extensively to assess bioactivity, cannot distinguish cardioprotective effects from genuine regeneration. To make this distinction, the Inventors performed another set of experiments in which the Inventors injected exosomes 21 days after MI, when myocardial scar is well established. Three weeks later, hearts injected with CDC exosomes showed multiple structural and functional benefits: improved ejection fraction (FIG. 2F; also improved fractional area change, FIG. 9A), lower scar mass (representative images in FIG. 2G and pooled data in FIG. 2H), higher viable mass (FIG. 2I), and thicker infarcted walls (FIG. 2J). Moreover, hearts treated with CDC exosomes exhibited less chamber dilation (FIGS. 9B and 9C), smaller infarct circumference (FIG. 9D), and diminished compensatory myocyte hypertrophy (FIGS. 9E and 9F) relative to the grossly distorted control hearts. The density of microvessels was increased (FIGS. 2K and 9G) and apoptotic cardiomyocyte nuclei were less frequent (FIGS. 9H and 9I) in CDC-exosome-treated hearts. The net growth of new myocardium in the setting of established scar fulfills the central criterion for therapeutic regeneration; the improvement in function and the attenuation of adverse remodeling attest to the physiological significance of the tissue changes. The Inventors conclude that CDC exosomes indeed mediate genuine cardiac regeneration, while favoring angiogenesis and tissue preservation.

Example 15

Inhibition of Exosome Secretion Attenuates CDC Benefit

If exosomes mediate the therapeutic effects of CDC transplantation, then inhibition of exosome secretion would logically be expected to block the benefits. To test this concept, the Inventors treated CDCs with GW4869, a reversible inhibitor of neutral sphingomyelinase that prevents exosome release. Exposure to GW4869 blocked exosome production in a dose-dependent manner (FIG. 3A), with complete suppression at 20 mM (a dose without apparent short-term cytotoxicity; e.g., no impairment of proliferation; FIG. 3B).

Figure 10:
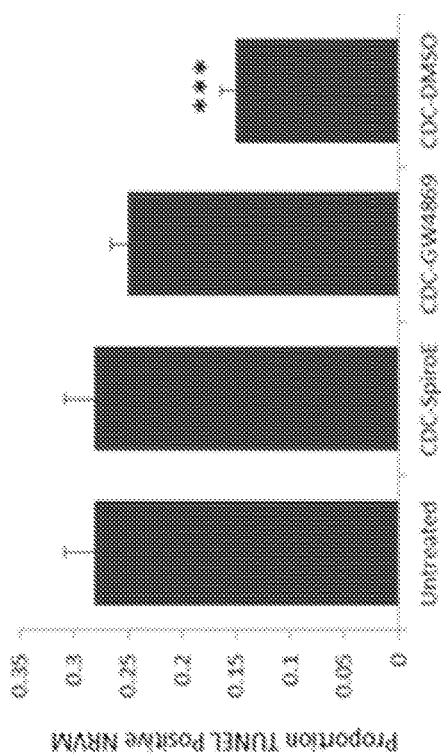
FIG. 10. Inhibition Of Exosome Secretion In CDCs Diminishes The Protective Effects Of CDCs In Vitro. Neonatal rat ventricular myocytes were stressed with 50 μM H2O2 for 15 minutes followed by trans-well treatment with CDCs pre-treated with 5 μM of Spiroepoxide, 20 μM of GW4869, or vehicle (DMSO). (A) Cell death was measured using TUNEL staining (red), Phalloidin (green), and DAPI (blue). (B) Pooled data of the four groups represented as proportion of TUNEL positive cardiomyocyte nuclei of total cells counted (n=3 technical replicates from neonatal rat cardiomyocytes derived from 20-30 rat pups from 3 different mothers) (B). *P<0.05, P<0.01, *P<0.001 using Student's t test, all scale bars represent 50 μm. Data represented as mean and standard error of the mean.
Figure 10:
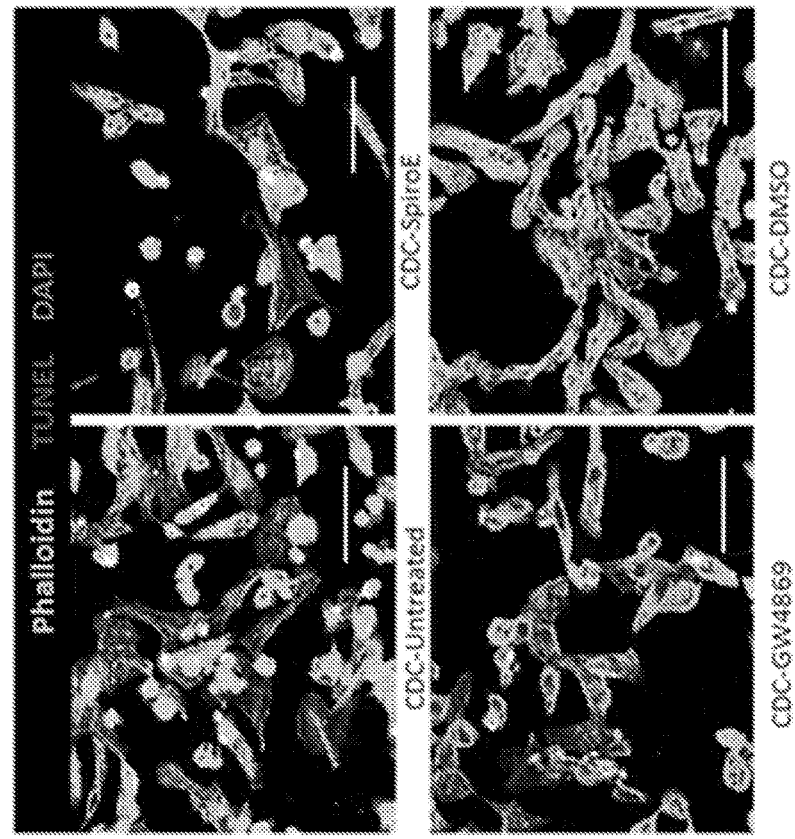

Suppression of exosome release abrogated the indirect benefits of CDCs in vitro because media conditioned by GW4869-treated CDCs did not enhance cardiomyocyte proliferation or attenuate apoptosis (FIGS. 3C and 3D). Spiroepoxide, a specific irreversible inhibitor of neutral sphingomyelinase, mimicked the antiapoptotic effects of GW4869 on stressed cardiomyocytes (FIGS. 10A and 10B). In vivo, CDCs pretreated with GW4869 exerted no functional (FIG. 3E) or structural (FIGS. 3F-3I) benefits in acute MI, in contrast to vehicle-only (DMSO) controls that conferred all the expected therapeutic effects of CDCs. Thus, exosome secretion by CDCs is required for CDCmediated benefits in vitro and in vivo.

Example 16

Figure 4:
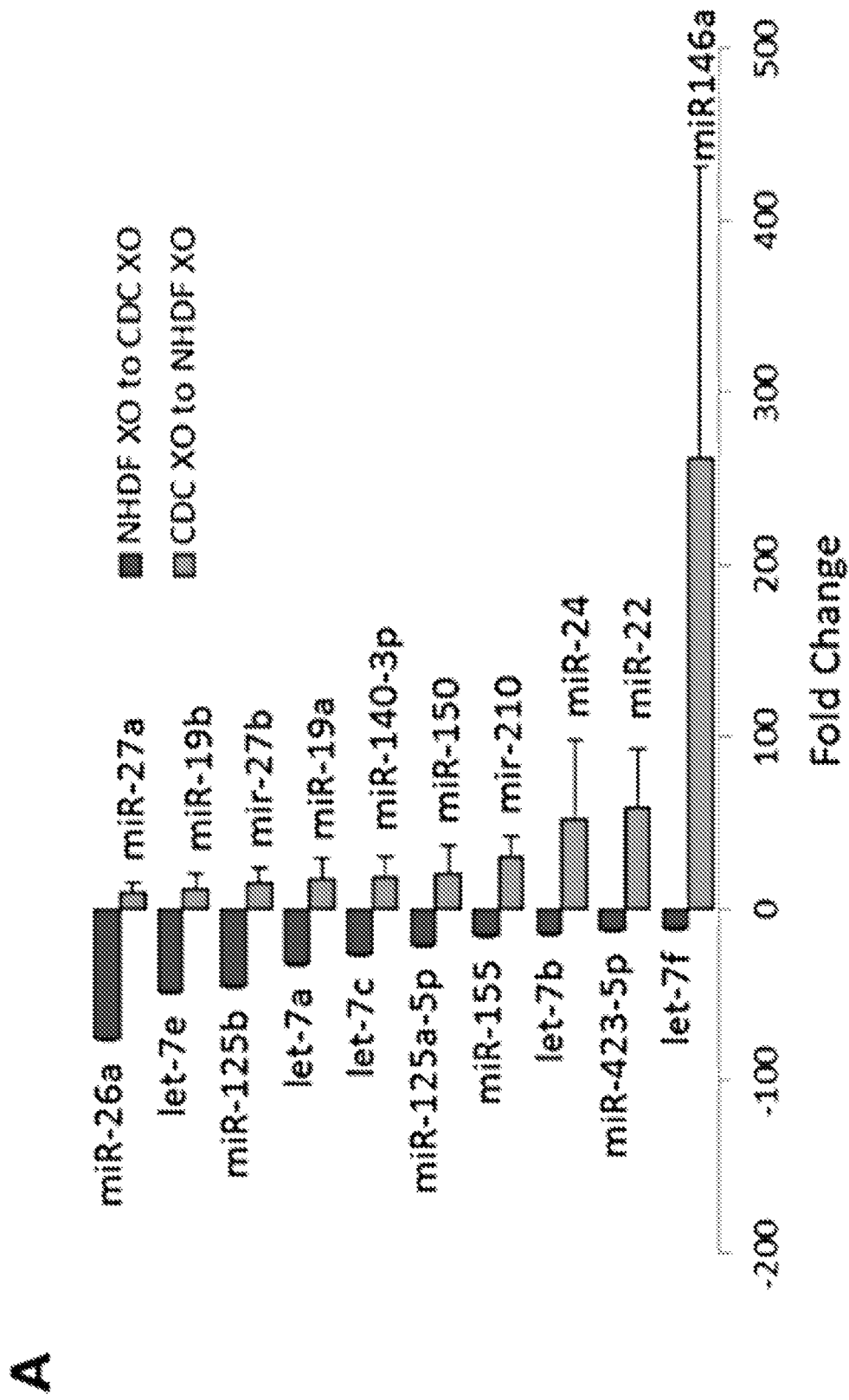
FIG. 4. miR-146a Is Highly Enriched in CDC Exosomes and Confers Therapeutic Benefit In Vitro and In Vivo. (A) Fold changes of microRNA abundance in CDC exosomes compared to NHDF exosomes (n=4 independent experiments). Total RNA (including microRNAs) was isolated from CDC exosomes and NHDF exosomes. qRT-PCR was performed on an microRNA array. (B) Venn diagram showing the variable microRNA profile between CDC and NHDF exosomes. Font size reflects the magnitude of differential expression of each microRNA. (C) Infarcted mouse hearts treated with CDC-derived exosomes have elevated levels of miR-146a compared to NHDF exosome-treated hearts (n=2 animals per group, three technical replicates per group). (D) miR-146a protects stressed neonatal rat cardiomyocytes. Cardiomyocytes were pretreated with 80 nM miR-146a mimic or mimic control then exposed to 100 mM hydrogen peroxide for 2.5 hr in serum-free media (n=4 technical replicates; neonatal rat cardiomyocytes under study were derived from 20 to 30 rat pups from three different mothers). (E) Microarray data showing fold differences in mRNA abundance between miR-146a and mimic-control treated cardiomyocytes. miR-146a suppresses Irak1 and Traf6 in stressed neonatal rat cardiomyocytes. (F) miR-146a-deficient animals have severely impaired cardiac function and structure following acute MI. Pooled data for left ventricular ejection fraction (n=8 animals per group). (G-J) Representative Masson's trichrome-stained sections of hearts from three groups (G) and pooled morphometric analysis (H-J; n=4 hearts per group) reveal impairment of CDC-mediated benefit as evident in pooled data for scar mass, viable mass, and infarct wall thickness (IWT) in hearts injected with GW869-treated CDCs. *p<0.05, {p<0.05; **p<0.01, and {{p<0.01 using Student's t test (*KO versus WT; {KO versus KO-R). Data are represented as mean and SEM. See also FIGS. 11 and 12.
Figure 4:
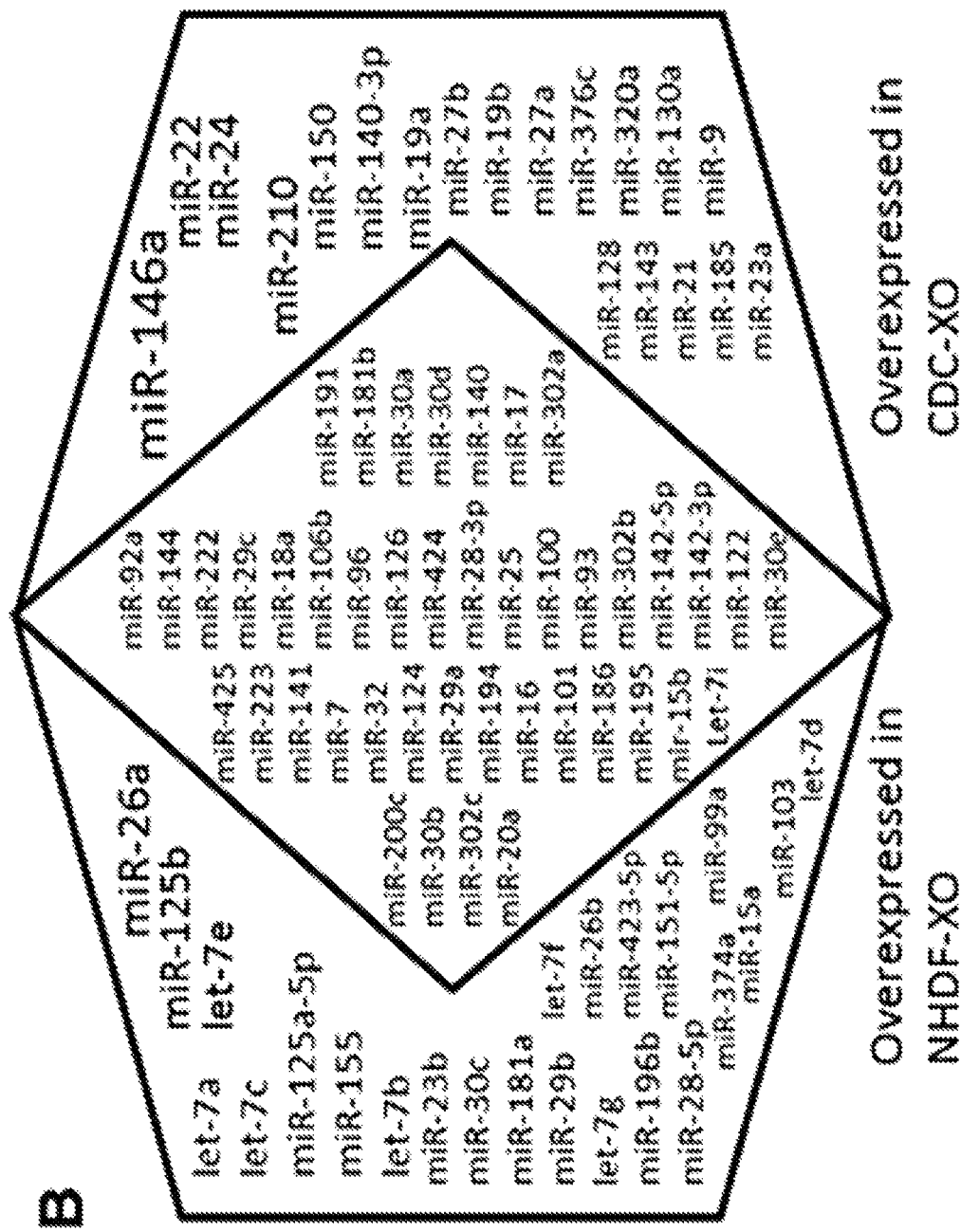
Figure 4:
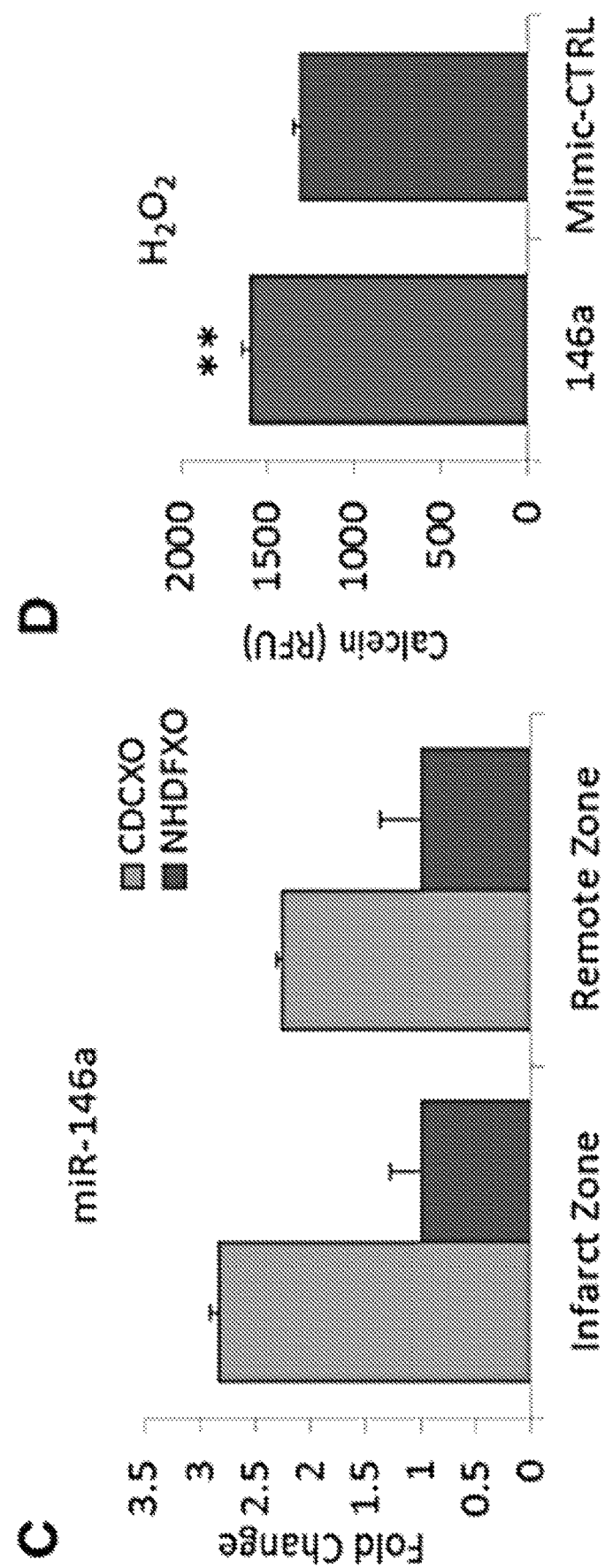
Figure 4:
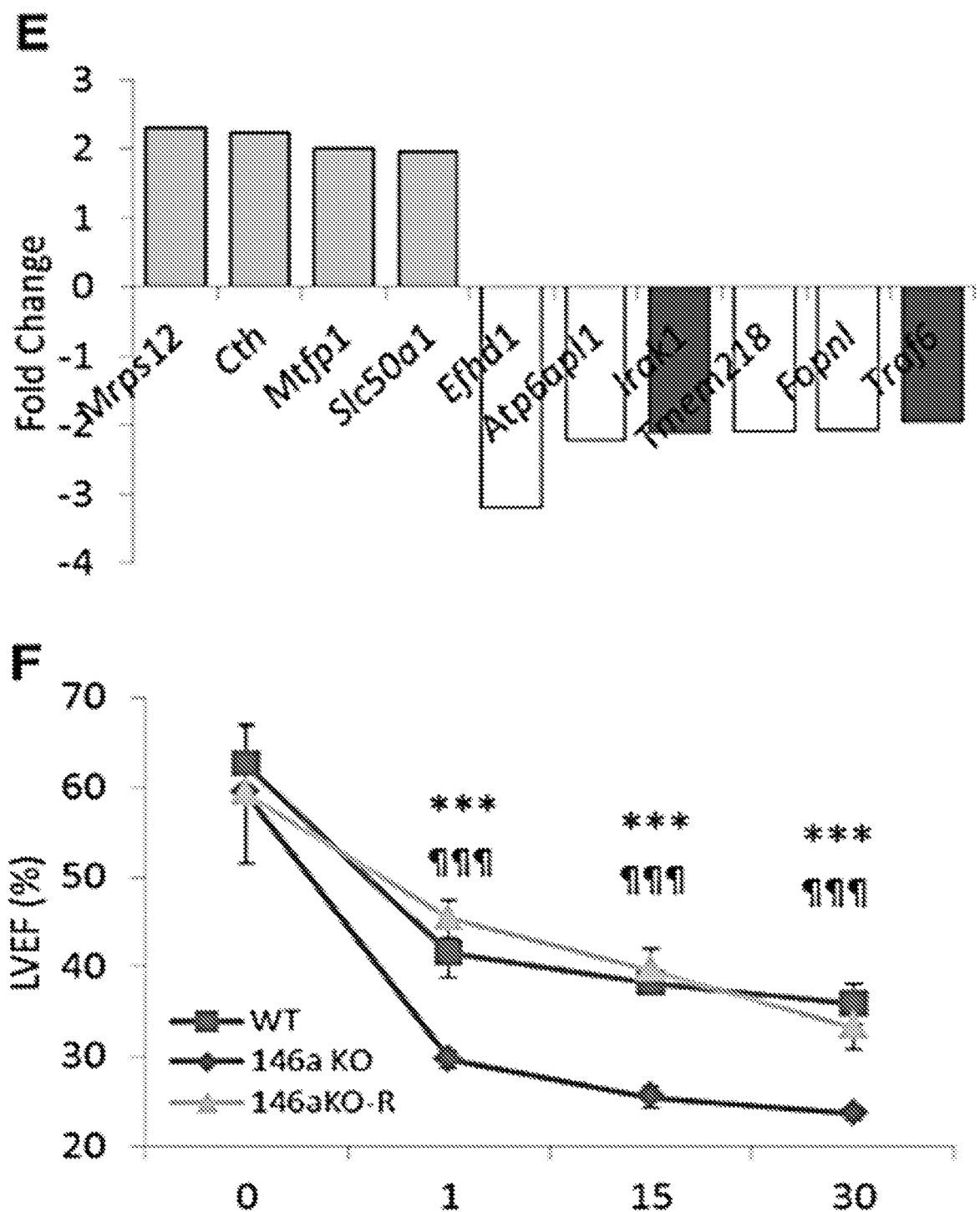
Figure 4:
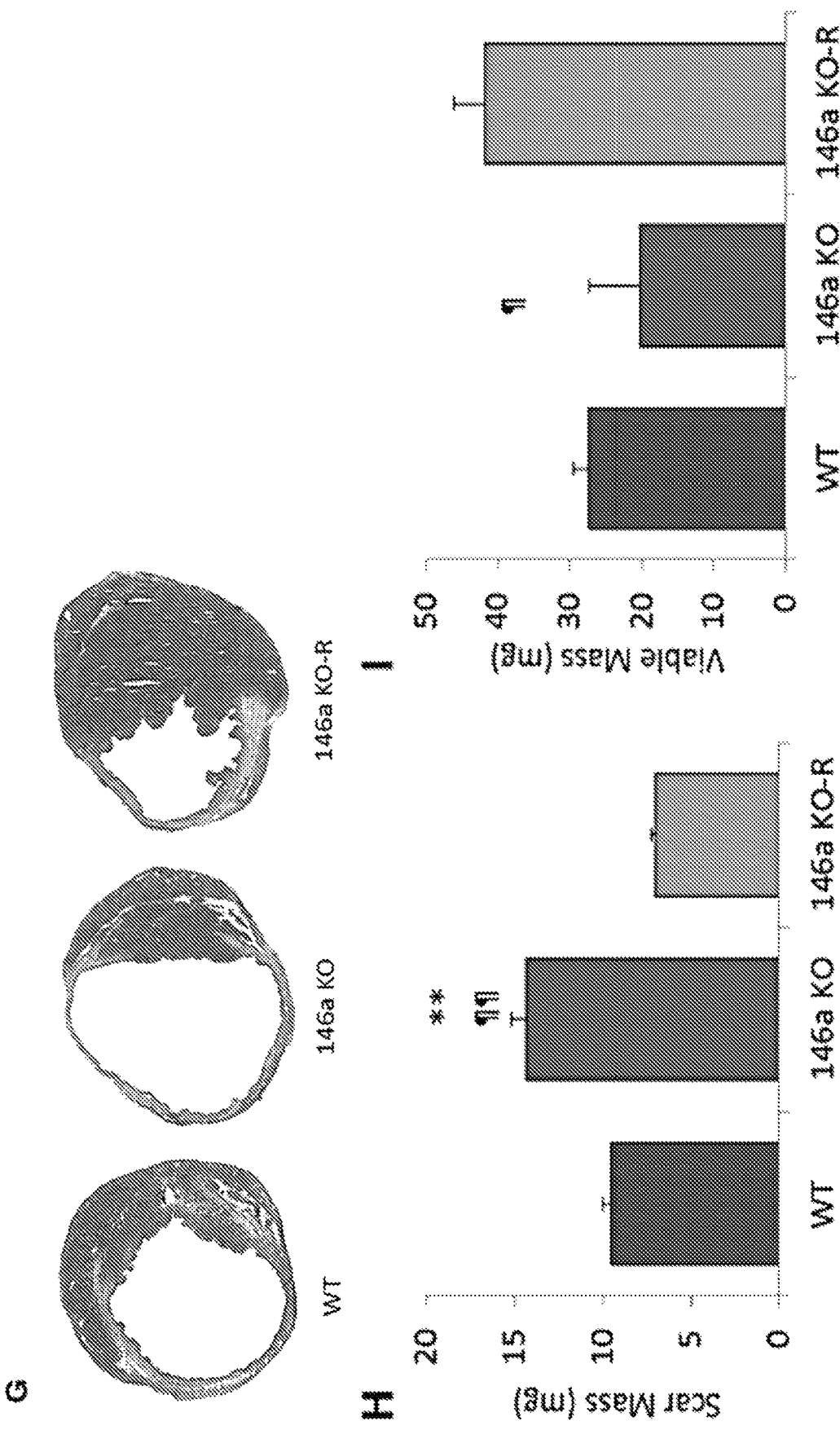
Figure 4:
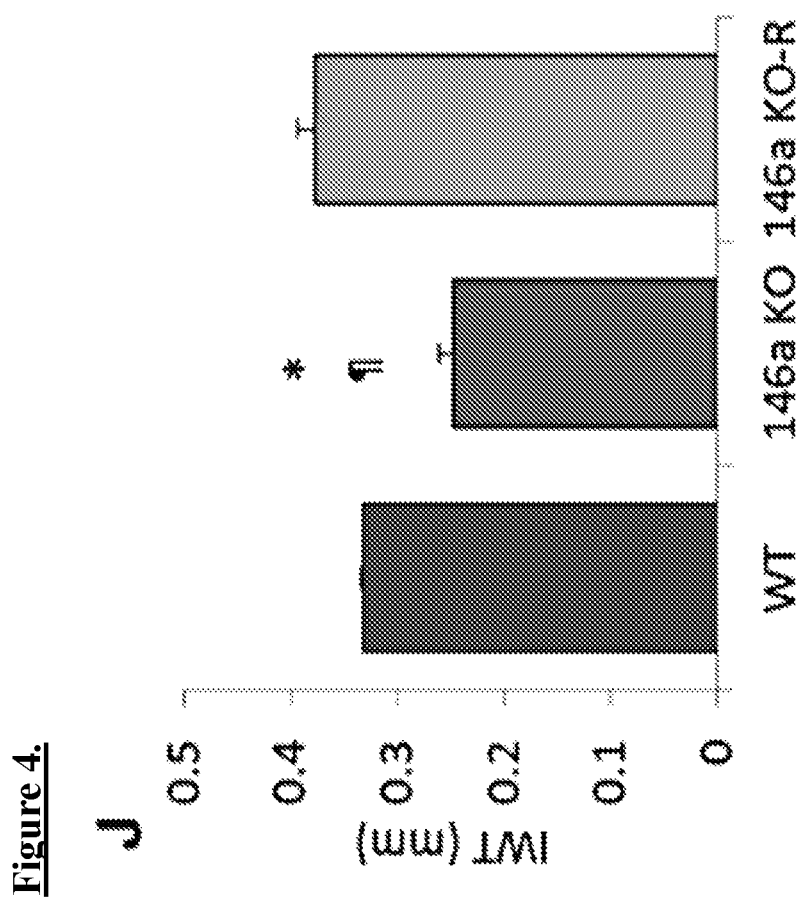
Figure 11:
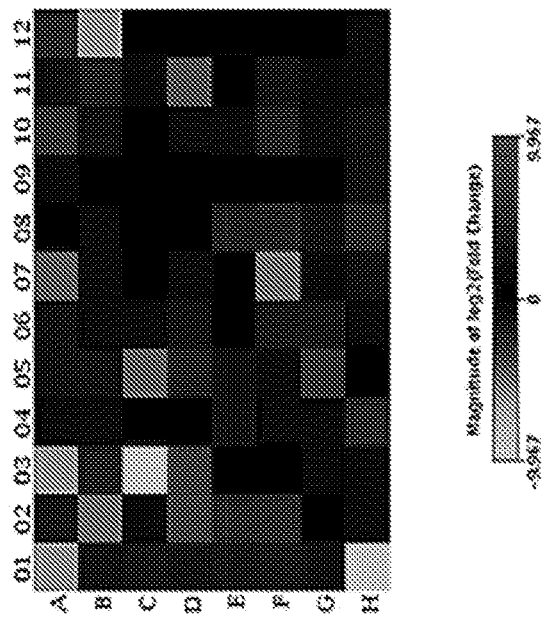
FIG. 11. Heat Map Of Mir PCR Array Identifies Mir-146a As The Most Differentially Expressed microRNA. Heat map showing fold regulation differential abundance data for transcripts between CDC exosomes and NHDF exosomes overlaid onto the PCR Array plate layout.
Figure 12:
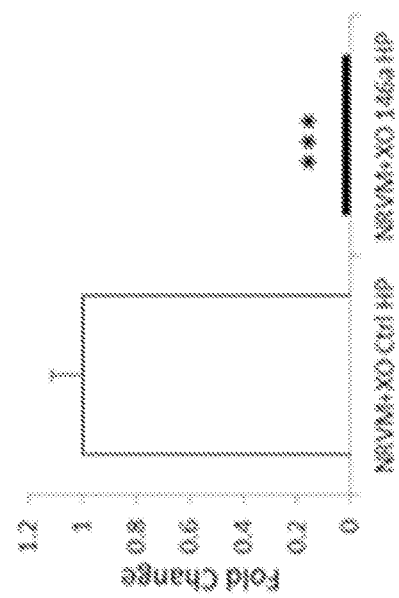
FIG. 12. miR-146a Protects Stressed Neonatal Rat Cardiomyocytes. (A) Cardiomyocytes were pre-treated with 80 nM miR-146a mimic or mimic-control then exposed to 5 mM cobalt chloride for 2 hours (n=4 technical replicates per group of neonatal rat cardiomyocytes derived from 20-30 rat pups from 3 different mothers) (B, C) CDC exosomes derived from CDCs transfected with mir-146a hairpin inhibitor. Exosomes were derived from conditioned media and mir146a knockdown confirmed by qPCR in exosomes. (C) Decreased levels of mir-146a in NRVMs treated with 146a-free exosomes compared to control (n=3 technical replicates per group of neonatal rat cardiomyocytes derived from 20-30 rat pups from 3 different mothers). Pathway analysis derived from transcriptome data showing affected pathways and (B) Pathway depiction showing MYC activation as a putative hub, based on microarray data analysis.
Figure 12:
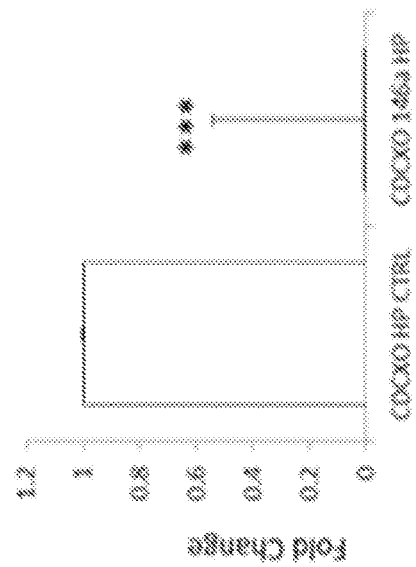
Figure 12:
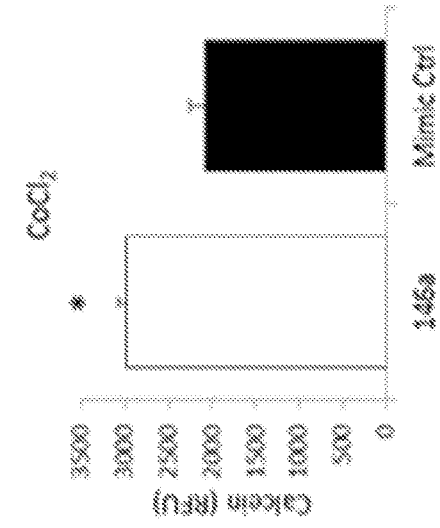
Figure 12:
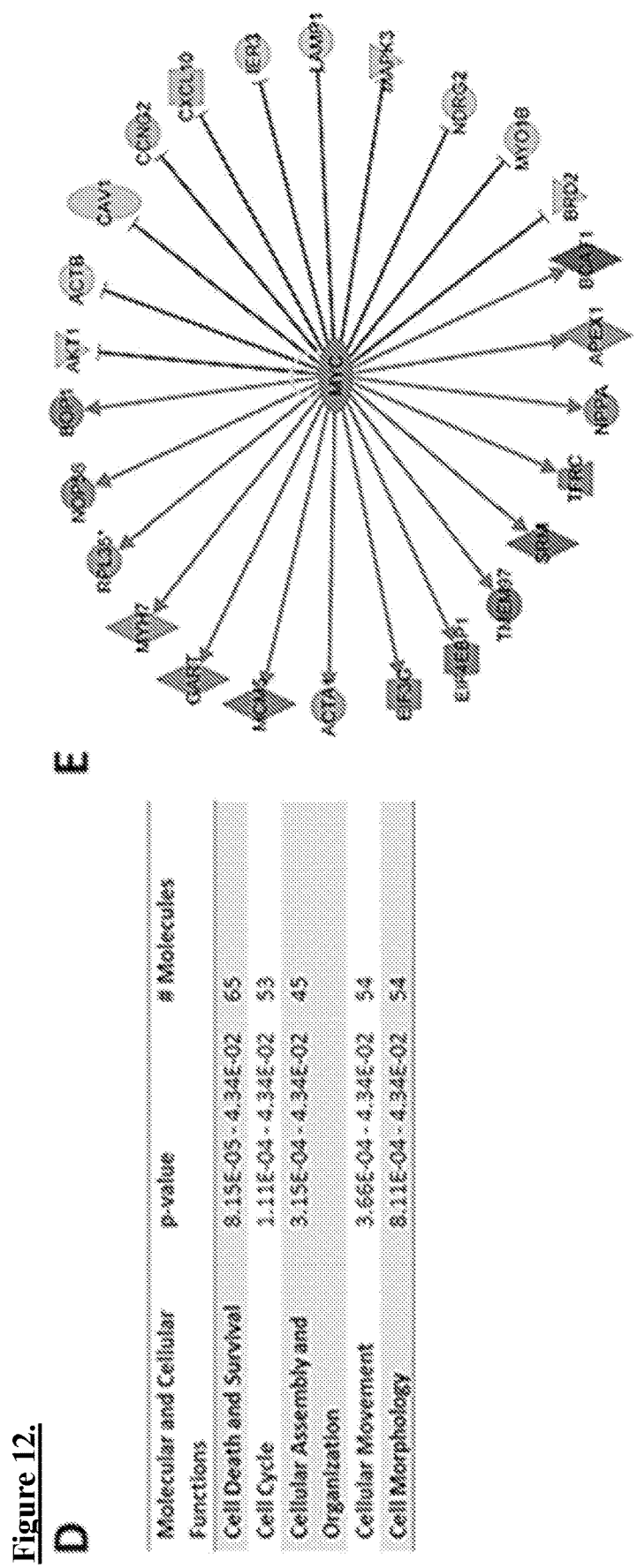

CDC Exosomes are Enriched in miR-146a, which Plays an Important Role in MI Pathology To investigate the basis of the therapeutic benefit of CDC exosomes, the Inventors compared their microRNA repertoire to that of NHDF exosomes using a PCR microarray of the 88 best-defined microRNAs. The microRNA content of the two cell types differed dramatically. Forty-three microRNAs were differentially present in the two groups; among these, miR-146a was the most highly enriched in CDC exosomes (262-fold higher than in NHDF exosomes; FIGS. 4A, 4B, and 11). Furthermore, miR-146a tissue levels were increased in post-MI hearts from animals injected with CDC exosomes relative to those injected with NHDF exosomes (FIG. 4C), rendering plausible the idea that CDC exosomes might act via miR-146a transfer. Exposure of neonatal rat cardiomyocytes to a miR-146a mimic increased cardiomyocyte viability and protected against oxidant stress (FIGS. 4D and 12A). Whole-transcriptome microarrays revealed downregulation of Irak1 and Traf6, two signaling mediators of the TLR-NFkB axis that are known targets of miR-146a (FIG. 4E). Ingenuity pathway analysis pointed to changes in pathways involved in cell survival, cell cycling, cellular organization, and morphology, all of which are relevant to ischemic injury (FIG. 11D) and share links to the basal transcription factor Myc (FIG. 11E). To probe the biological role of miR-146a in myocardial injury, the Inventors induced acute MI in miR-146a knockout (146a KO) mice and compared them with wild-type mice of the same strain (WT), as well as 146a KO mice "rescued" by injection of a miR-146a mimic at the time of MI (146a KO-R).

After MI, the 146a KO mice showed deeply impaired heart function and adverse remodeling compared to WTor 146a KO-R (FIGS. 4F and 4G). Histological analysis revealed significant increases in scar mass (FIG. 4H) and decreases in infarct wall thickness in the 146a KO, but not in WT or 146a KO-R (FIG. 4J). Viable mass was greatest in the 146a KO-R group (FIG. 4I), perhaps indicating a supraphysiological effect of the injected miR-146a mimic. These findings point to a critical role of miR-146a in MI and give reason to suspect that miR-146a may mediate some of the therapeutic benefits of CDC exosomes.

Figure 5:
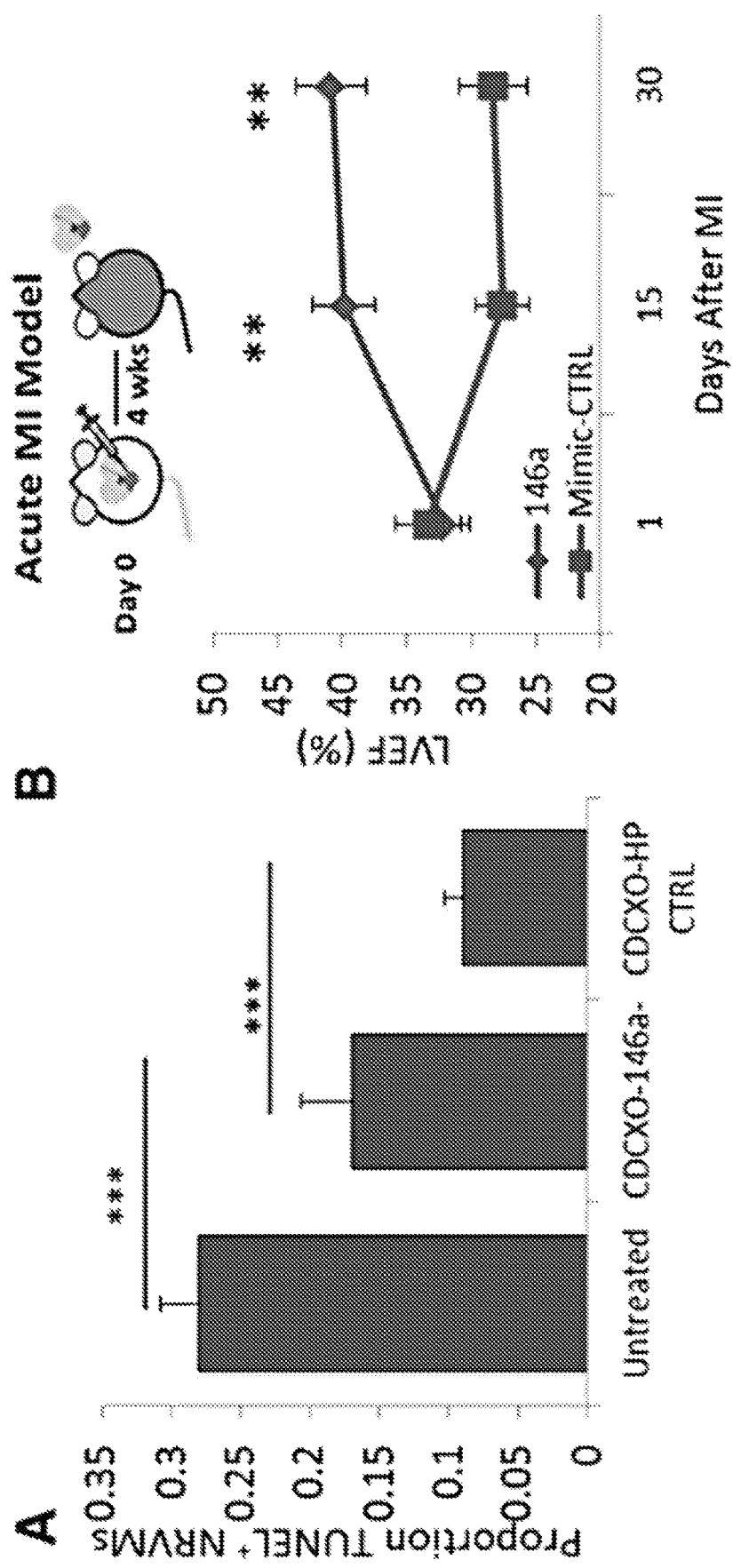
FIG. 5. miR-146a Improves Systolic Function in Acute and Chronic Mouse Models of MI. (A) miR-146a knockdown in CDC exosomes diminishes their capacity to protect stressed NRVMs in vitro (n=three technical replicates; neonatal rat cardiomyocytes were derived from 20 to 30 rat pups from three different mothers). CDCs were transfected with either a miR-146a inhibitor or a hairpin control with a sequence based on Caenorhabditis elegans microRNAs (HP-CTRL). (B-F) Acute MI protocol data. Time course of left ventricular ejection fraction (n=6 animals per group; B). Representative Masson's trichrome-stained sections of hearts from each of the two groups (C) and pooled morphometric analysis (n=4 hearts per group) reveal decreased scar mass, increased viable mass, and increased infarct wall thickness in animals treated with miR-146a compared to microRNA control (D-F). (G-L) miR-146a reproduces some of the structural and functional benefits seen in CDC-exosome-treated hearts in a mouse model of chronic MI (miR-146a mimic or mimic control injected on day 21 after MI; n=6 animals per group). Three weeks later (day 42), animals treated with miR-146a showed comparable cardiac function to control (G) but adverse remodeling was significantly attenuated (H). Scar mass was also similar (I). Viability and infarct wall thickness were significant structural benefits (J and K), but scar mass was not reduced (I). Analysis was done using Student's t test; *p<0.05, p<0.01, and *p<0.001. Data are represented as mean and SEM. See also FIGS. 12 and 13.
Figure 5:
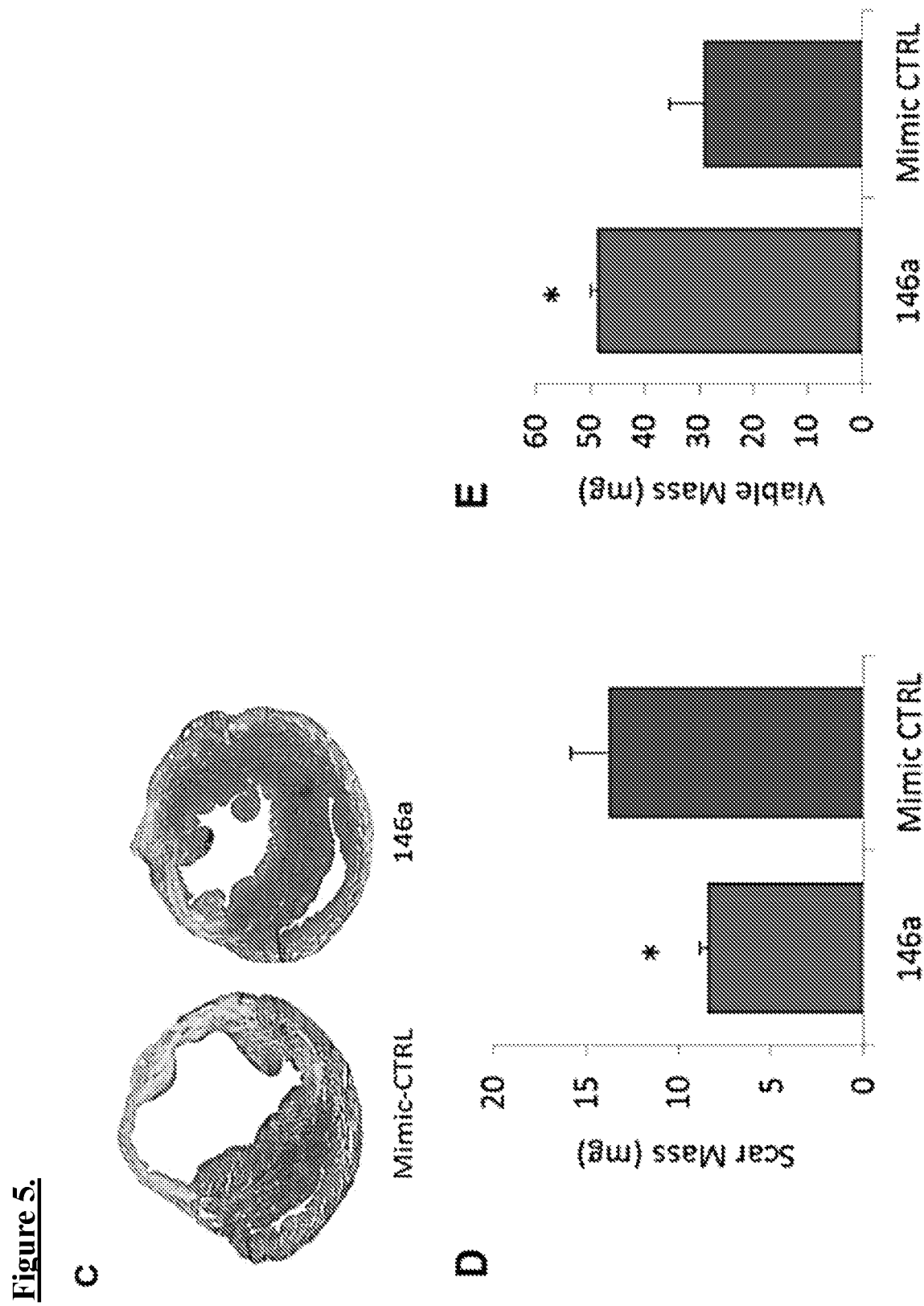
Figure 5:
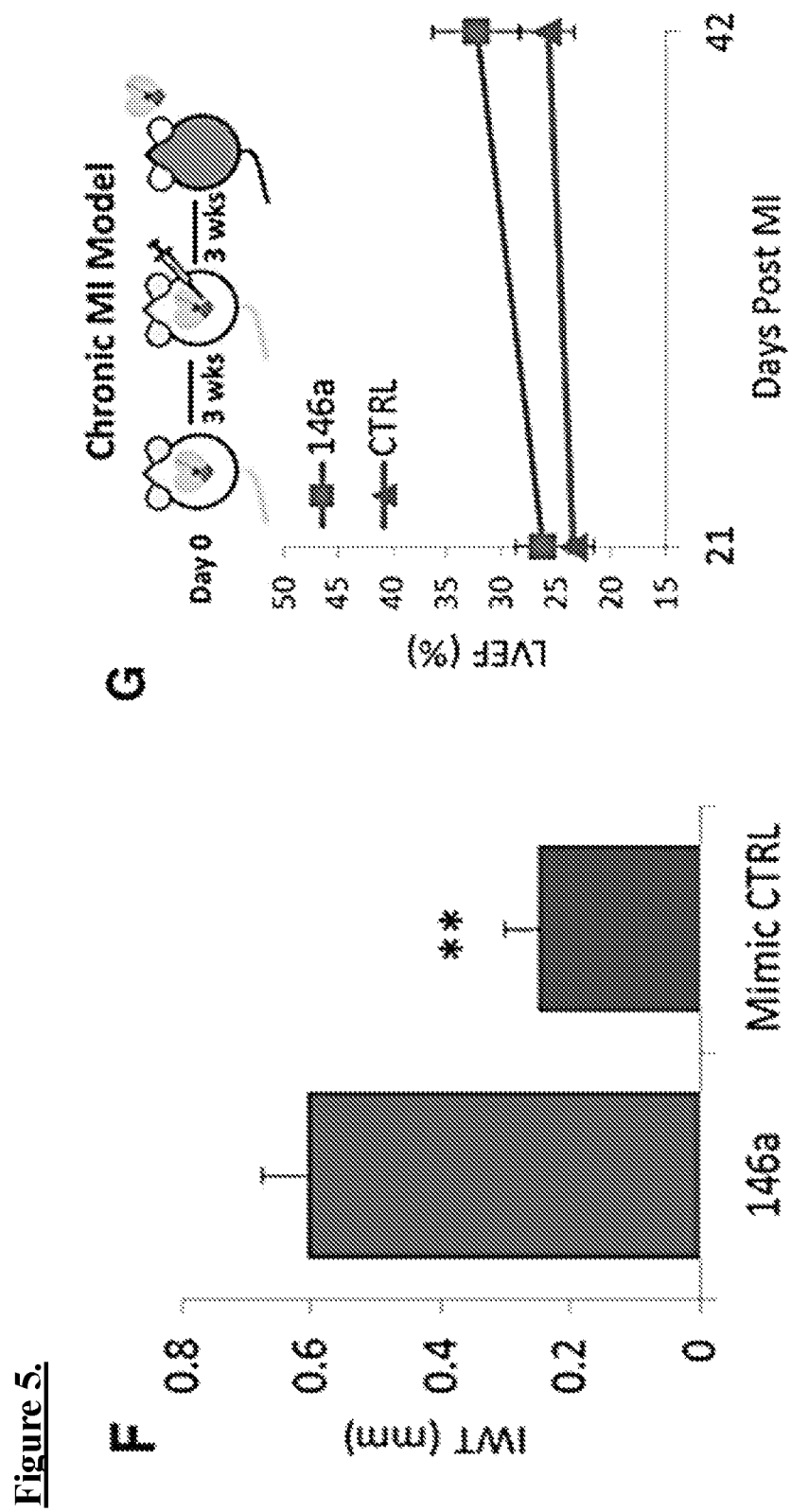
Figure 5:
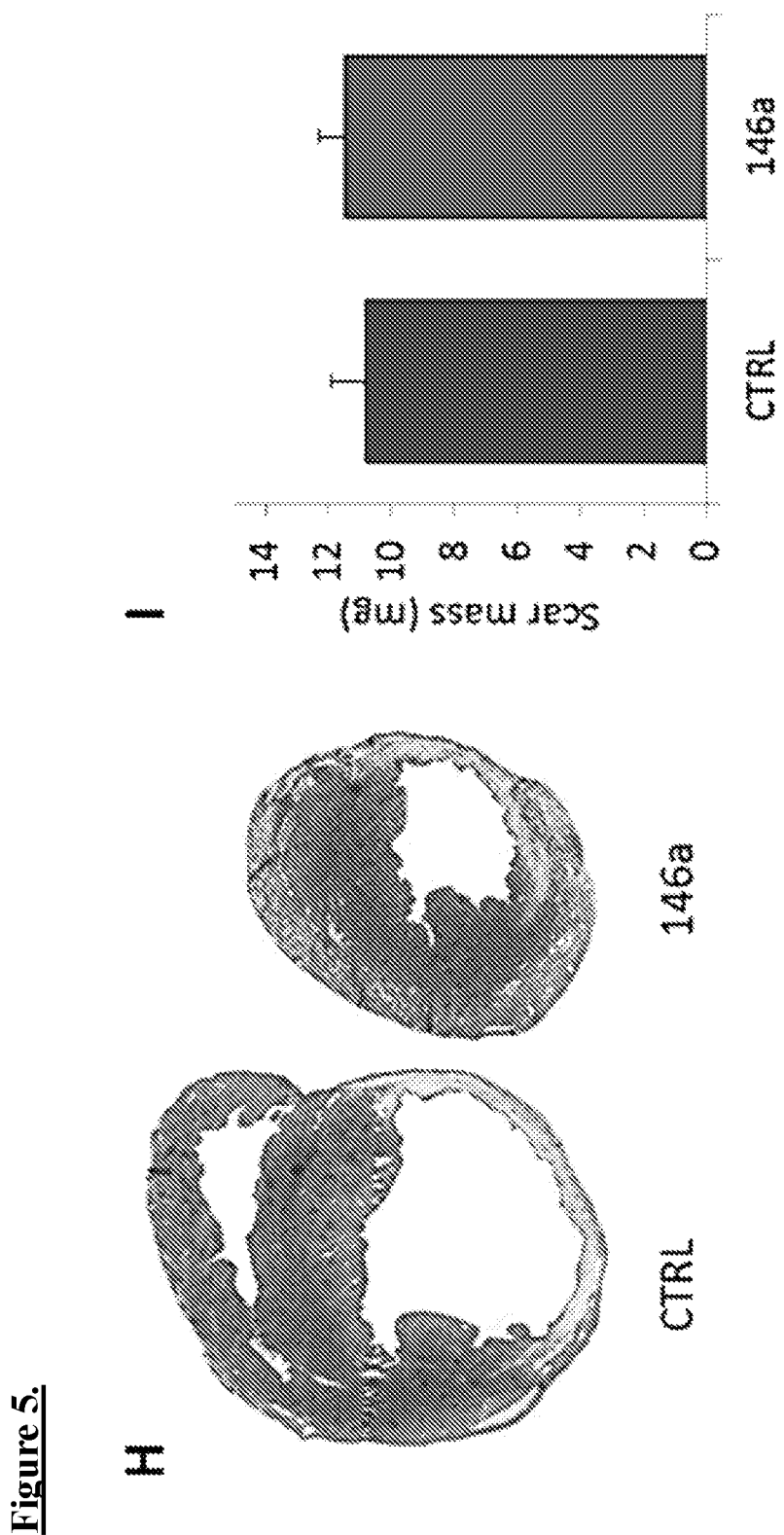
Figure 5:
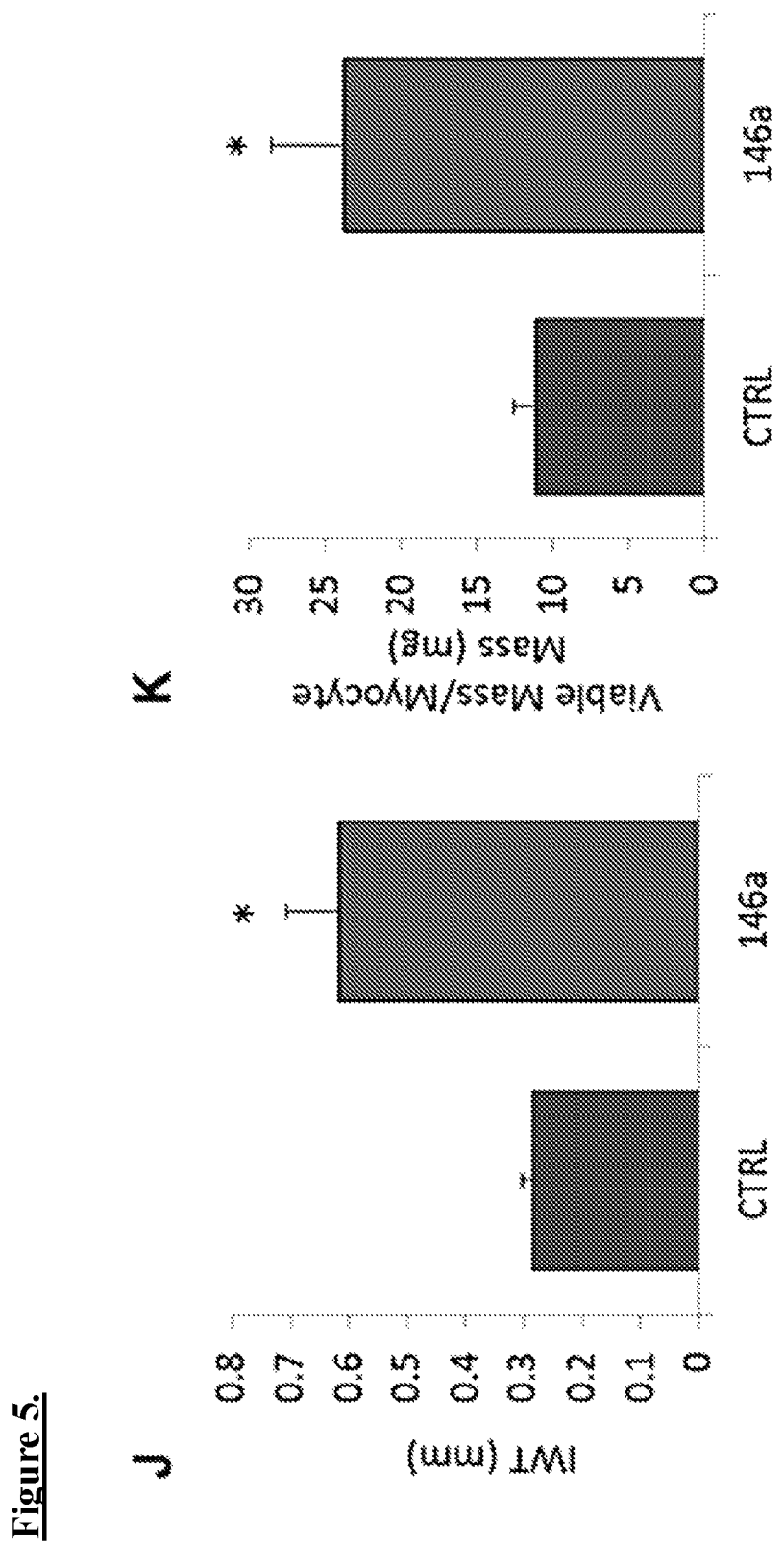
Figure 5:
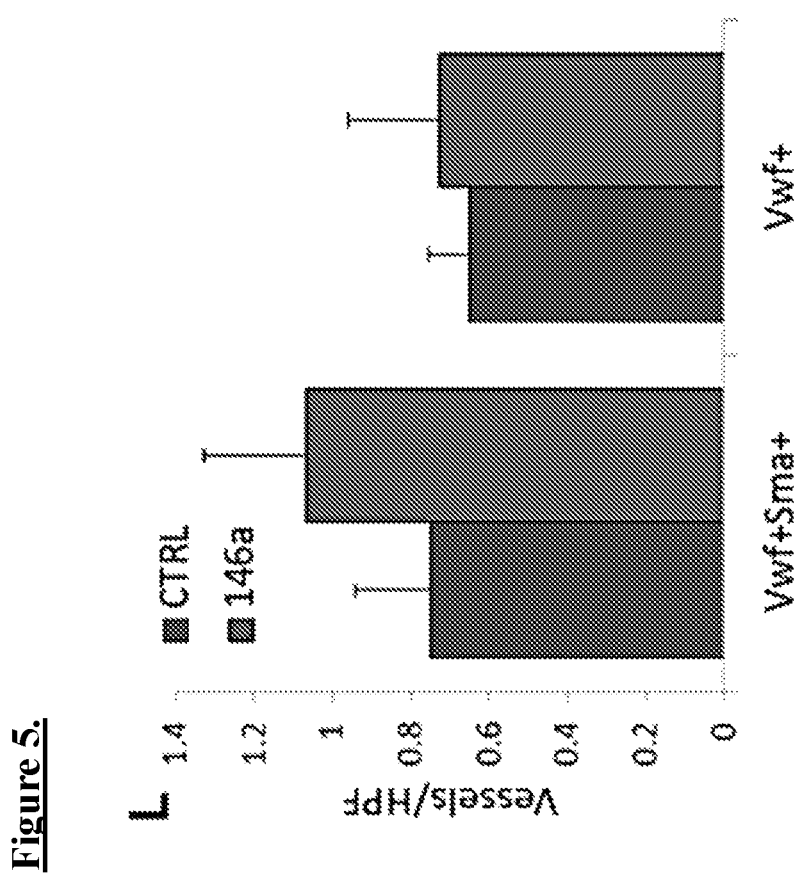
Figure 13:
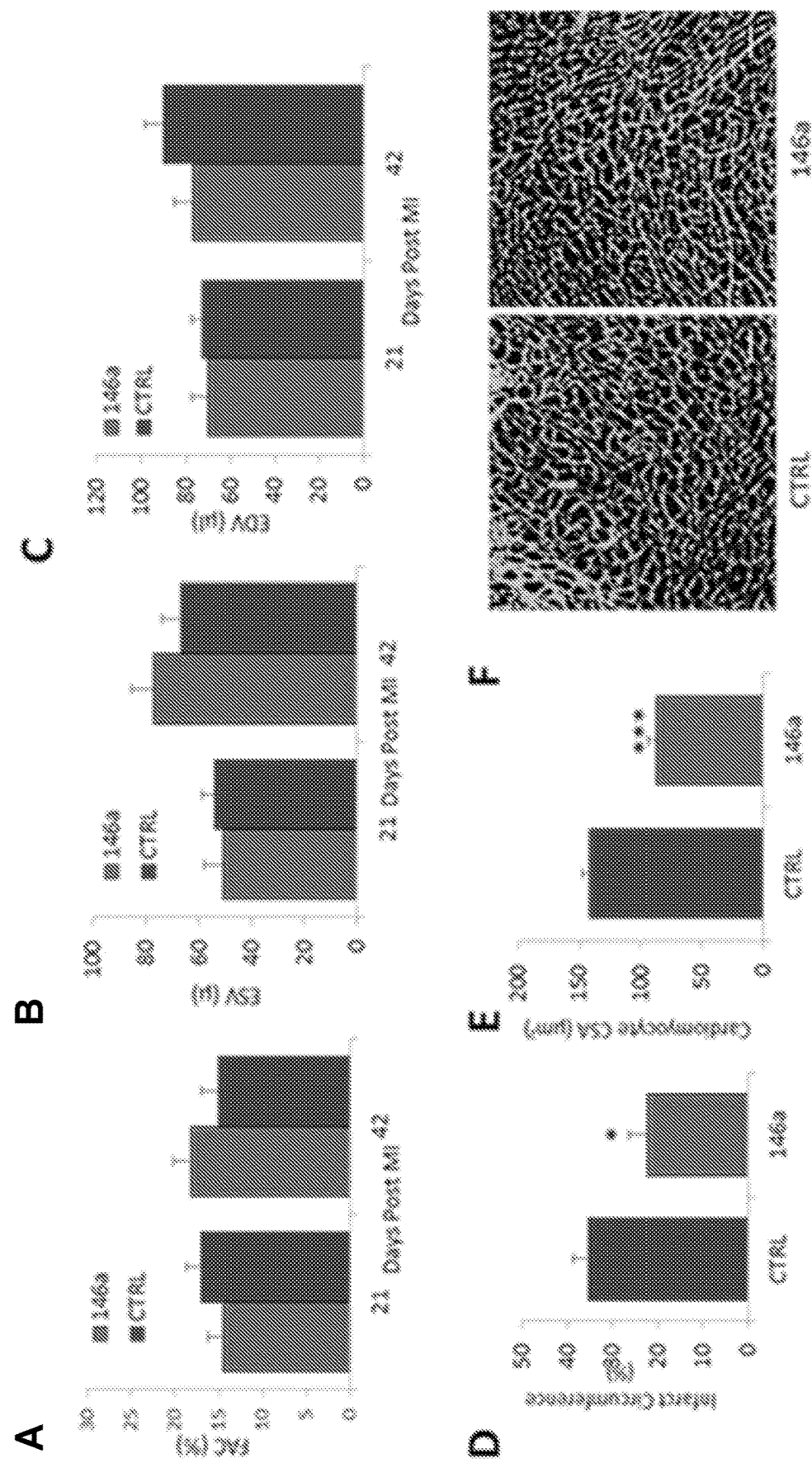
FIG. 13. miR-146a Reproduces Some But Not All The Effects Of CDC-Exosomes. miR-146a attenuates adverse remodeling and cardiac hypertrophy in a mouse model of chronic MI. (A,C) Animals treated with CDC-exosomes showed no significant functional improvement compared to control as shown by fractional area change (A), end systolic volume (B) and end diastolic volume (C) (AC, n=6 animals per group). Structural improvements however were noted as seen in percent of the circumference of tissue sections that are scar (D), and decreased cardiomyocyte hypertrophy (E) as measured by staining with wheat germ agglutinin and DAPI. No differences in angiogenesis were observed between the two groups (G). Less cardiomyocyte death was observed in the border zone of mir 146a-treated animals compared to control. (H, I) (D-I, n=4 hearts per group) *P<0.05, P<0.01, *P<0.001 using Student's t test, all scale bars represent 50 μm. Data represented as mean and standard error of the mean.
Figure 13:
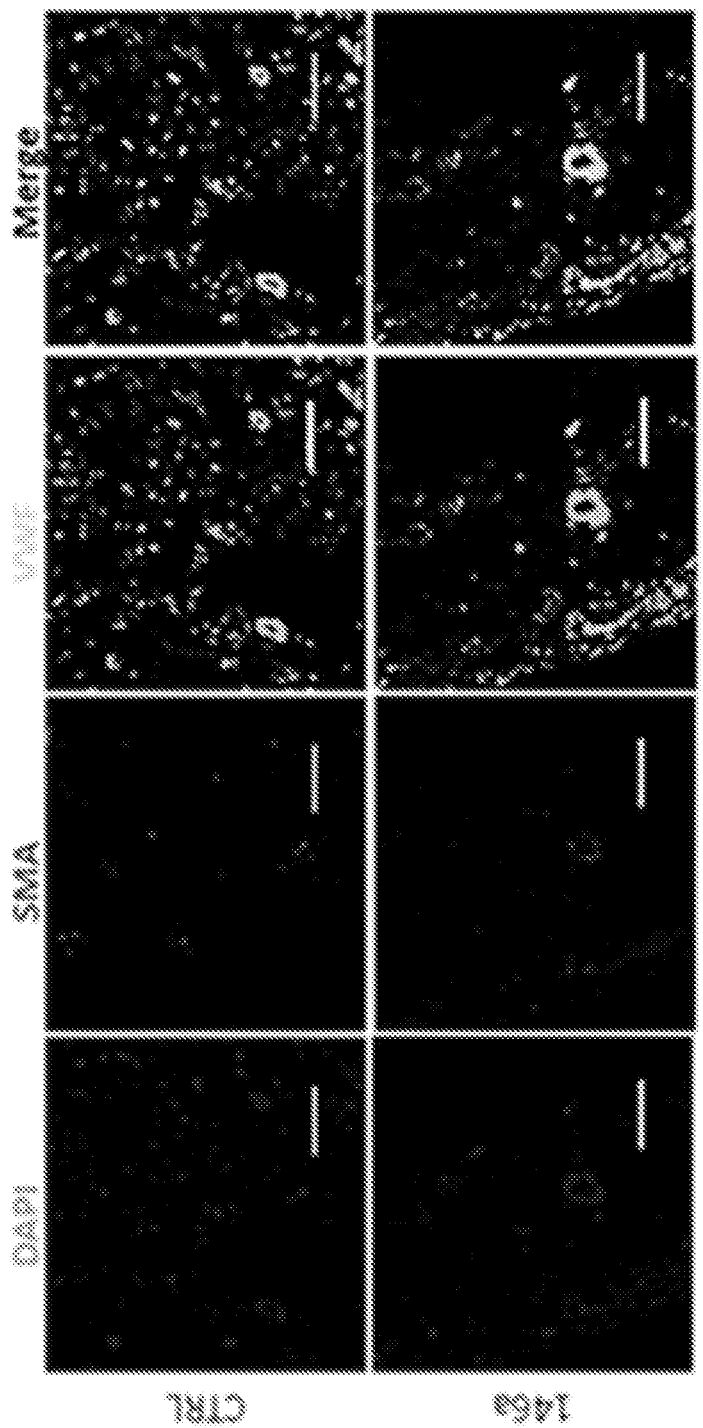
Figure 13:
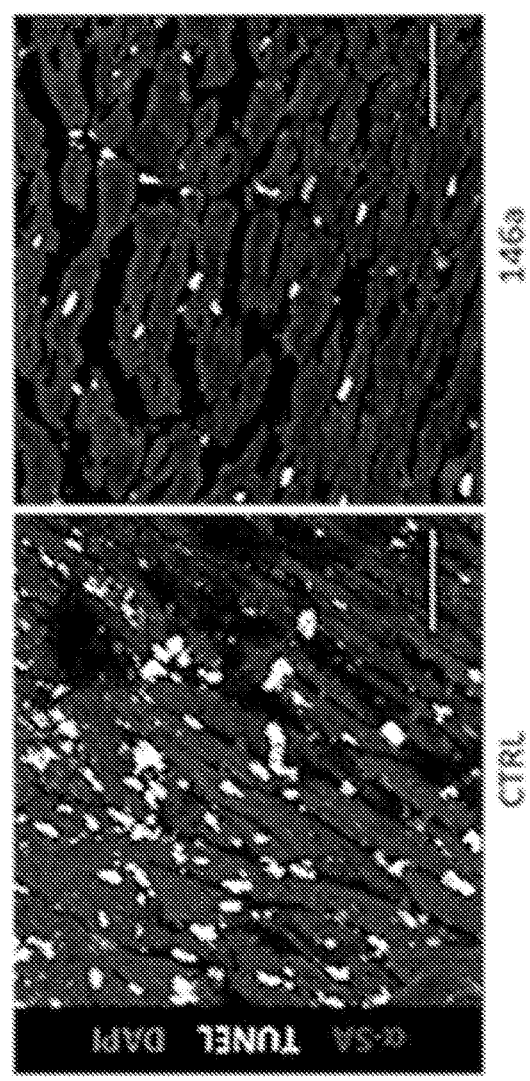
Figure 13:
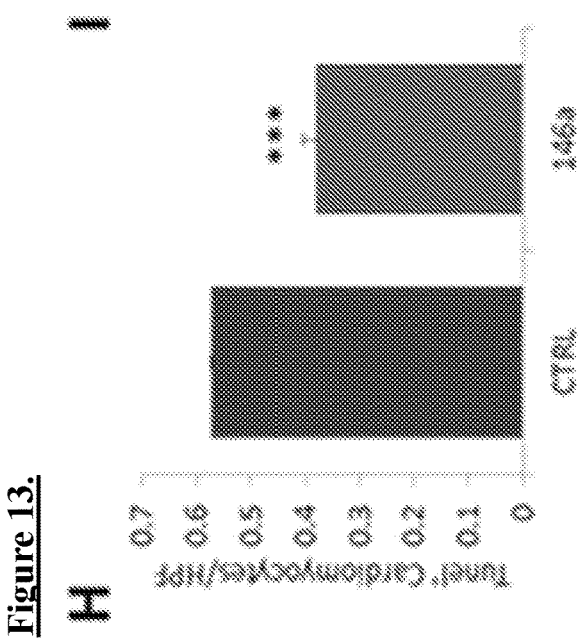
Figure 14:
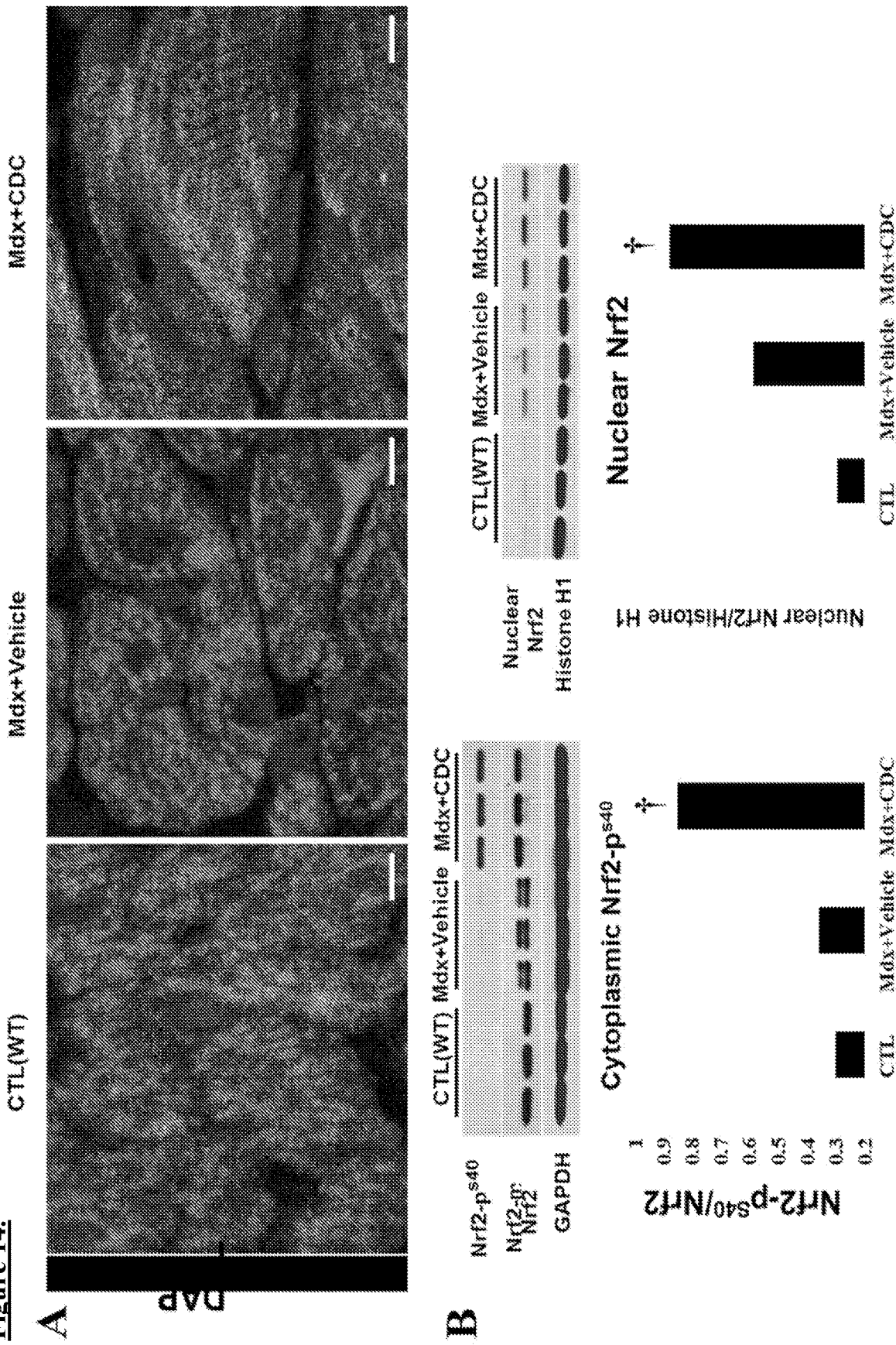
FIG. 14. CDC Treatment Heightened Activity Of Nrf2 Antioxidative Pathway And Increased Expression Of Nrf2 Downstream Gene Products. (A) Representative immunohistochemical images depicting Nrf2 in the mdx mouse hearts three weeks after treatment with vehicle (Mdx+Vehicle) or CDC (Mdx+CDC). Age-matched wild type mice (CTL) served as control. (B) and (C): Representative western blots and pool data demonstrating cytoplasmic and nuclear Nrf2 content (B) and the protein abundance of Nrf2 downstream-gene products (C): HO-1, modulatory (GCLM) and catalytic (GCLC) subunits of glutamate-cysteine ligase, SOD-1, catalase and SOD-2 in the mdx mouse hearts 3 weeks after treatment with vehicle or CDC. The experimental mice were recruited at 10 months of age. Marked increase in phosphorylated Nrf2 (Nrf2-ps40) in the cytoplasm was accompanied with augmented nuclear Nrf2 content and increased expression of Nrf2 downstream gene products in the CDC-treated mdx mice (B,C). Data are means±SEM; n=7 in each group. †P<0.05 vs. Mdx+Vehicle and control (CTL; wild type); Scale bars: 5 μm.
Figure 14:
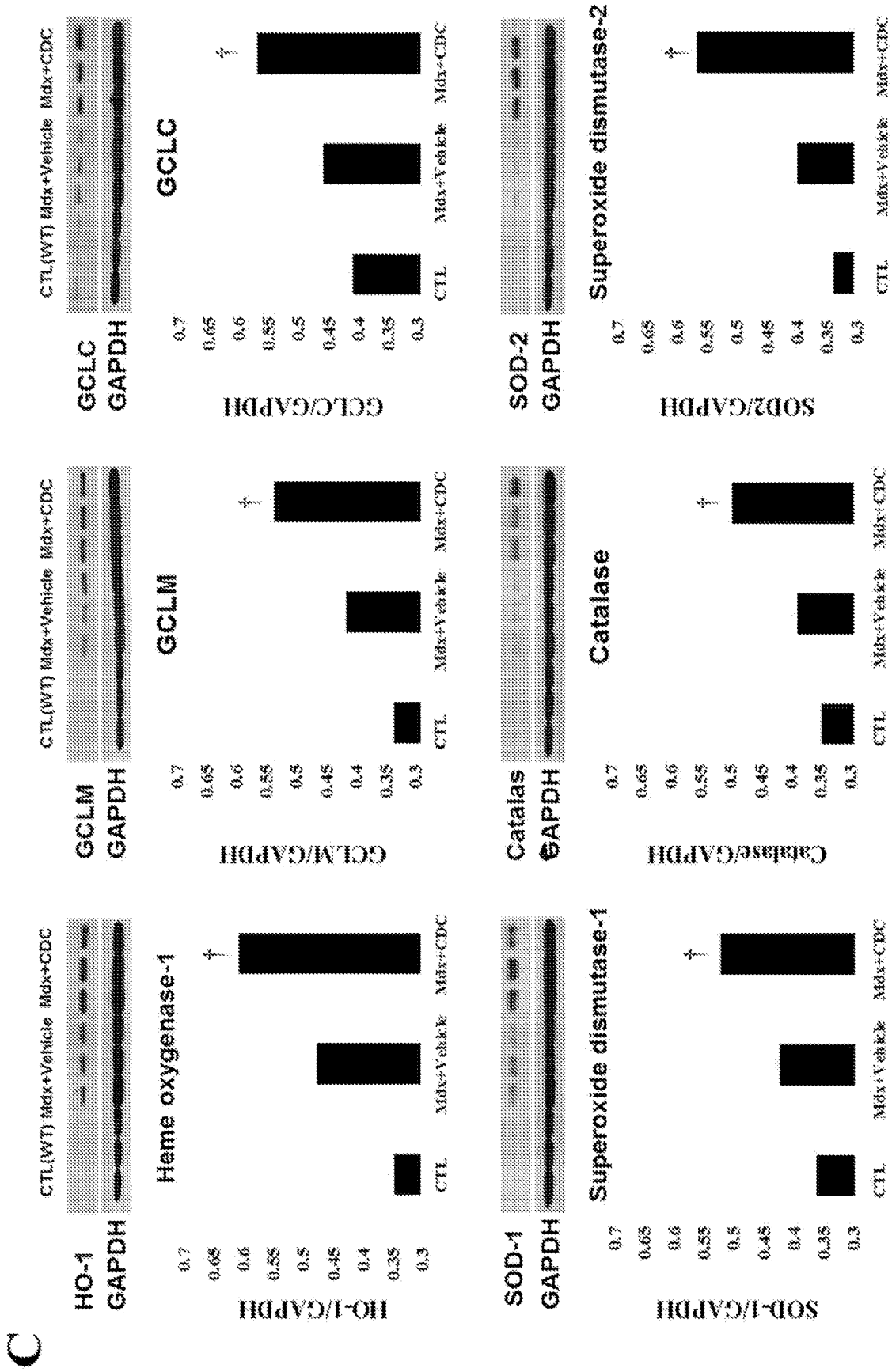
Figure 15:
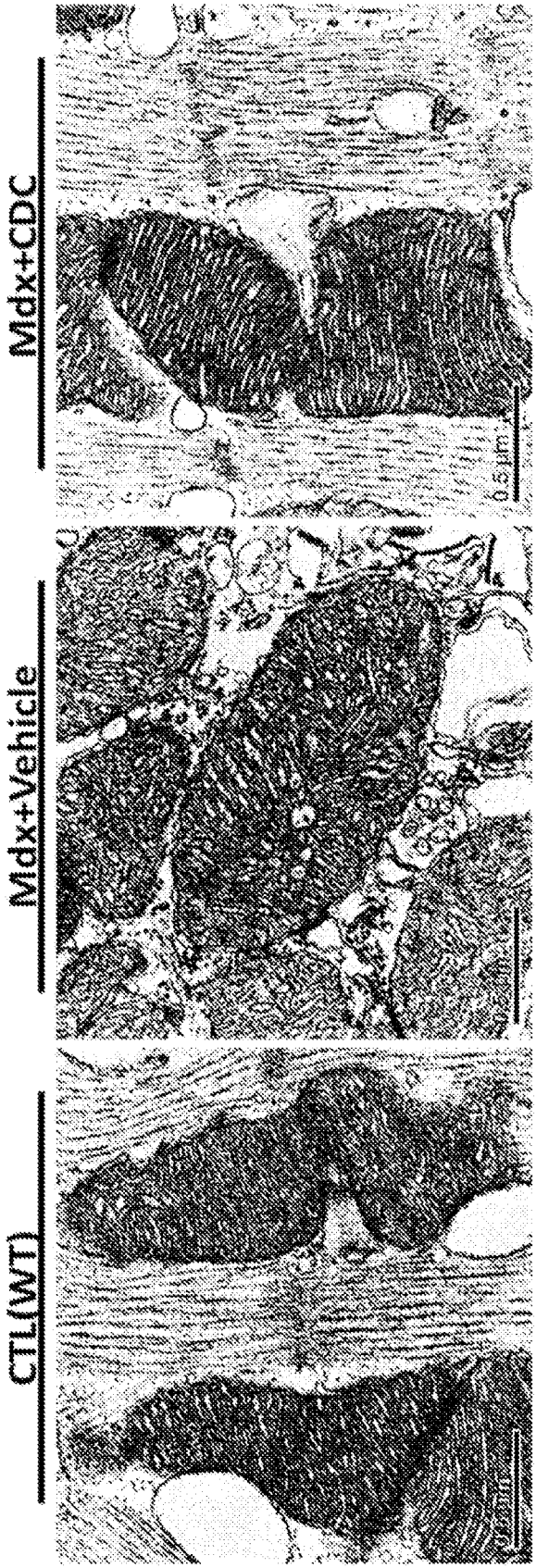
FIG. 15. CDC Treatment Markedly Restored Mitochondrial Structure And Content And, Enhanced Expression Of Respiratory Chain Subunits In The Heart Tissue Of Mdx Mice. (A): Representative images of transmission electron microscopy of cardiomyocyte mitochondria in mdx mice 3 weeks after treatment with vehicle (Mdx+Vehicle) or CDC (Mdx+CDC). Elongated mitochondria with altered (rounded/tubular) crista were predominant in the cardiomyocyte of mdx mice at 10 months of age. CDC treatment significantly restored cardiomyocyte mitochondrial size and crista structure (lamellar crista). (B): Representative western blots and pool data depicting nuclear Nrf1 protein content and protein abundance of cytoplasmic and nuclear mitochondrial transcription factor A (mtTFA) in the heart tissue of vehicle/CDC-treated Mdx mice and age-matched wild-type mice (CTL) 3 weeks after treatment. (C): Bar graph demonstrating mitochondrial DNA copy numbers per cell in the heart tissue of experimental animals 3 weeks after treatment. (D): Representative western blots and pool data showing protein content of mitochondrial respiratory chain subunits in the heart tissue of Mdx mice 3 weeks after treatment with vehicle (Mdx+vehicle) and CDC (Mdx+CDC). Concomitant upregulation of Nrf1 and mtTFA were associated with increased mitochondrial DNA copy numbers and accompanied with restored expression of mitochondrial respiratory chain subunits. PC*: positive control. Data are means±SEM; n=7 in each group. †P<0.05 vs. Mdx+Vehicle and control (CTL; wild type); ††P<0.001 vs. Mdx+CDC and control (CTL; wild type).
Figure 15:
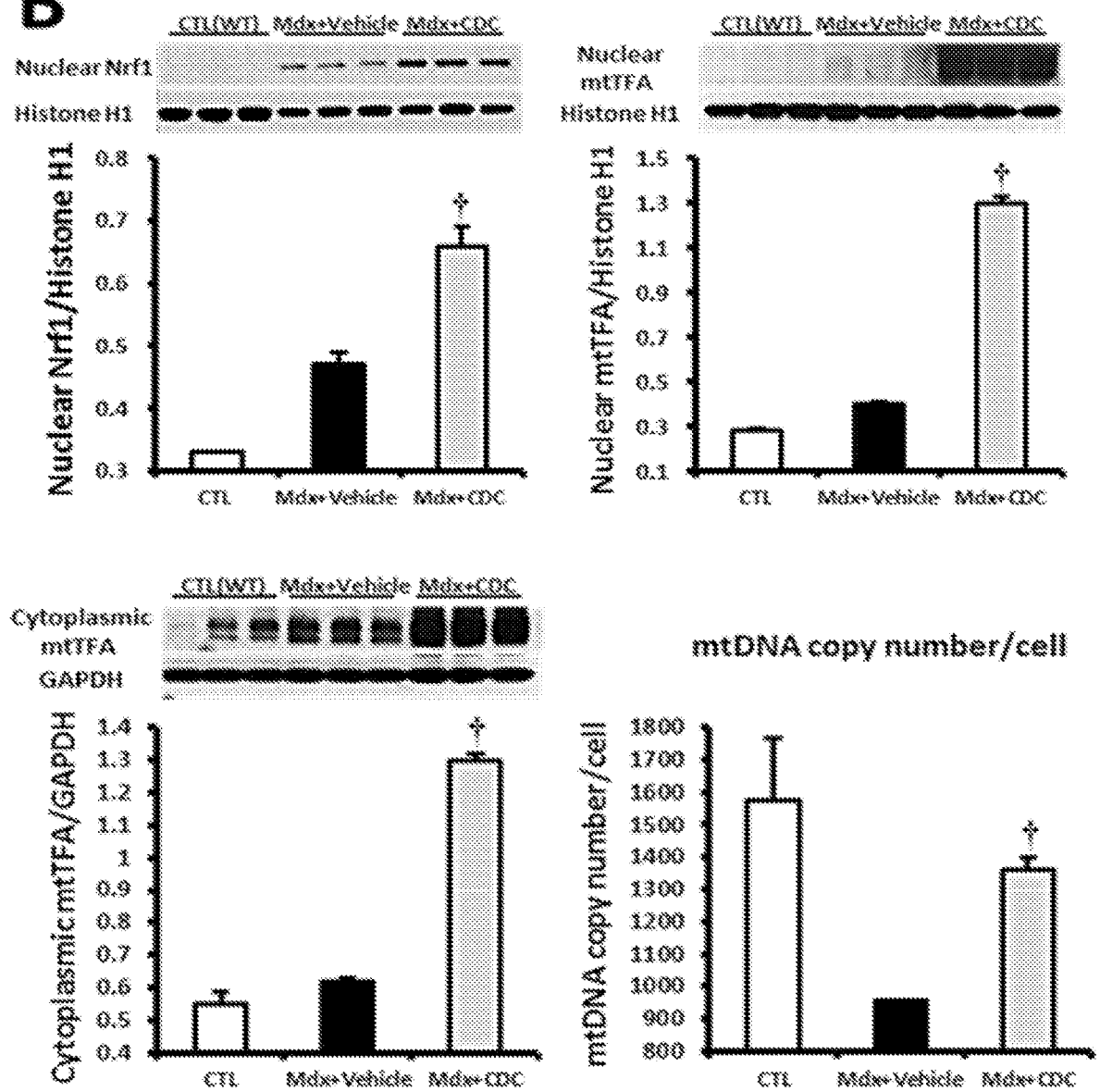
Figure 15:
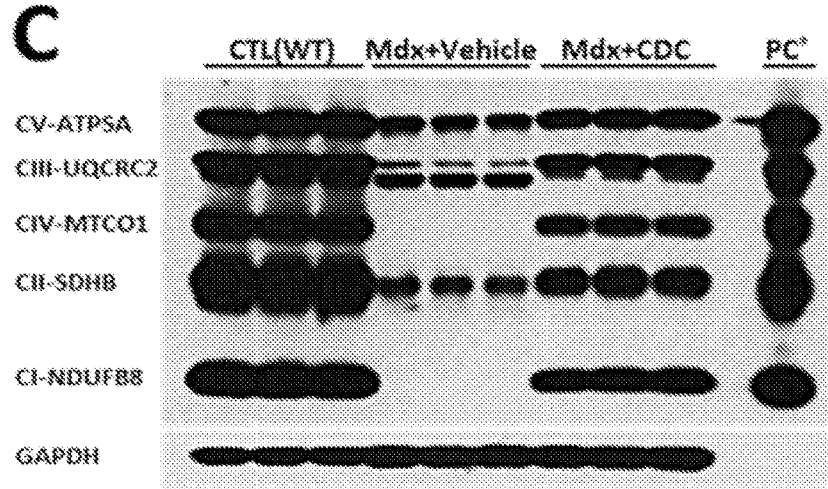
Figure 15:
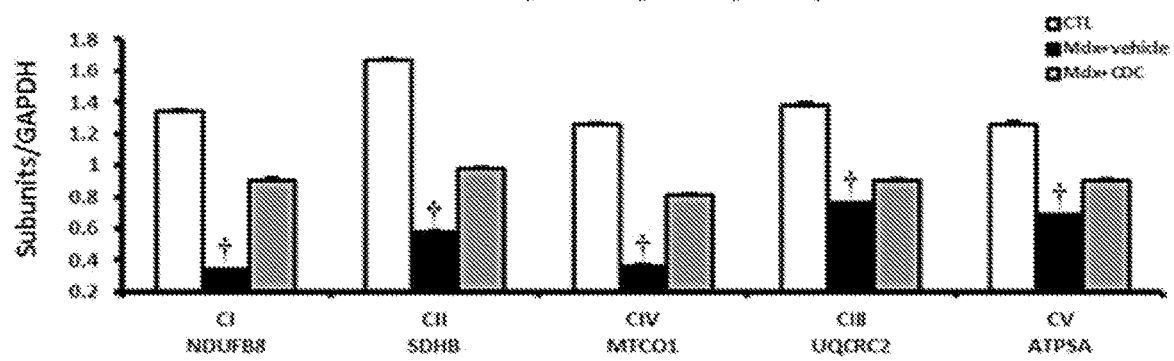
Figure 16:
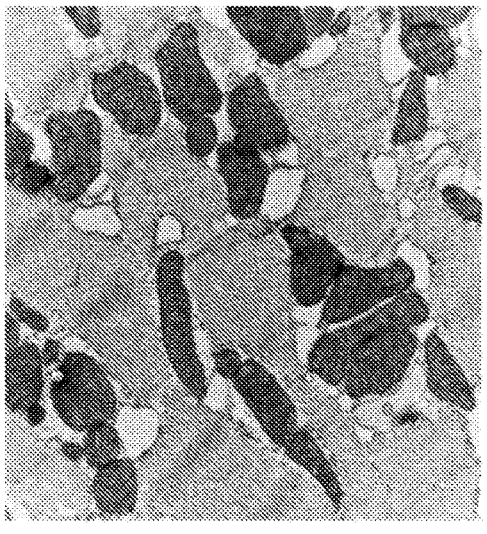
FIG. 16. Ultrastructeral Degenerative Alterations In The Heart Of 10-Month-Old Mdx Mice Diminished Markedly 3 Weeks After Treatment With CDC. (A): Representative images of transmission electron microscopy of cardiomyocytes illustrating intracellular accumulation of amorphous proteins, extensive sarcomeric disruption and irregularities (Z streaming) and disorganized altered interfibrillar mitochondria in the 10-month-old Mdx mice. CDC markedly decreased cardiomyocyte degenerative alterations 3 weeks after intramyocardial injection. (B): Bar graphs depicting average length of mitochondria and total number and percentage of rounded crista in mitochondria in wild type control mice (CTL) and in vehicle- (Mdx+vehicle) and CDC-treated Mdx mice (Mdx+CDC) 3 weeks after treatment. Data are means±SEM; †P<0.005 vs. Mdx+CDC and control (CTL; wild type); ††P<0.005 vs. Mdx+vehicle and control (CTL; wild type).
Figure 16:
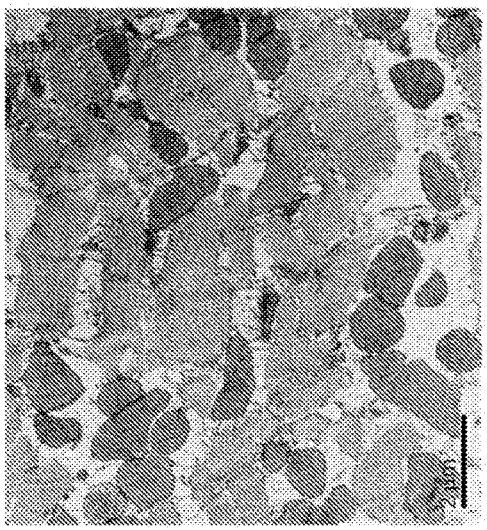
Figure 16:
Figure 16:
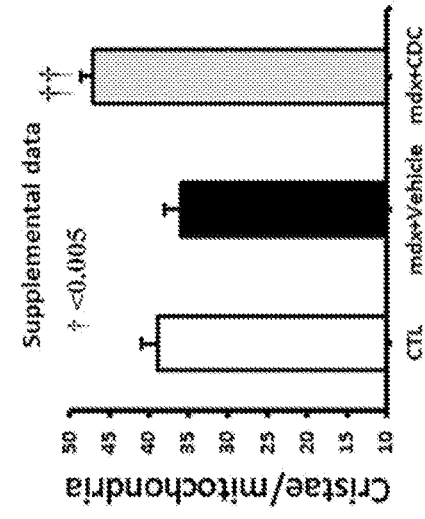
Figure 16:
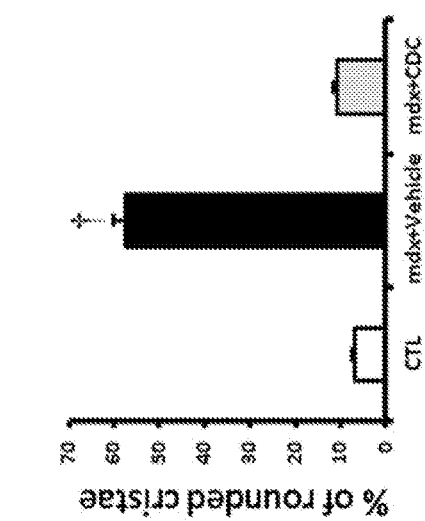
Figure 16:
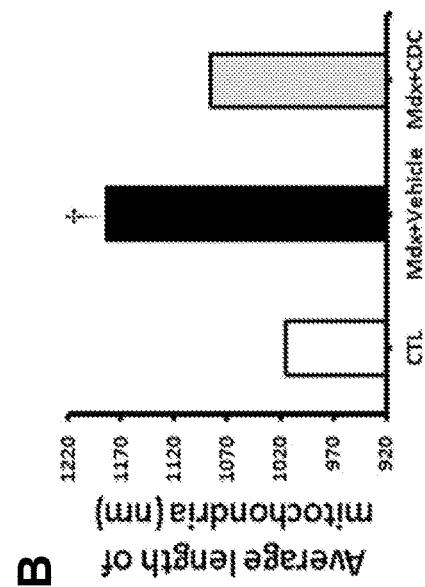
Figure 17:
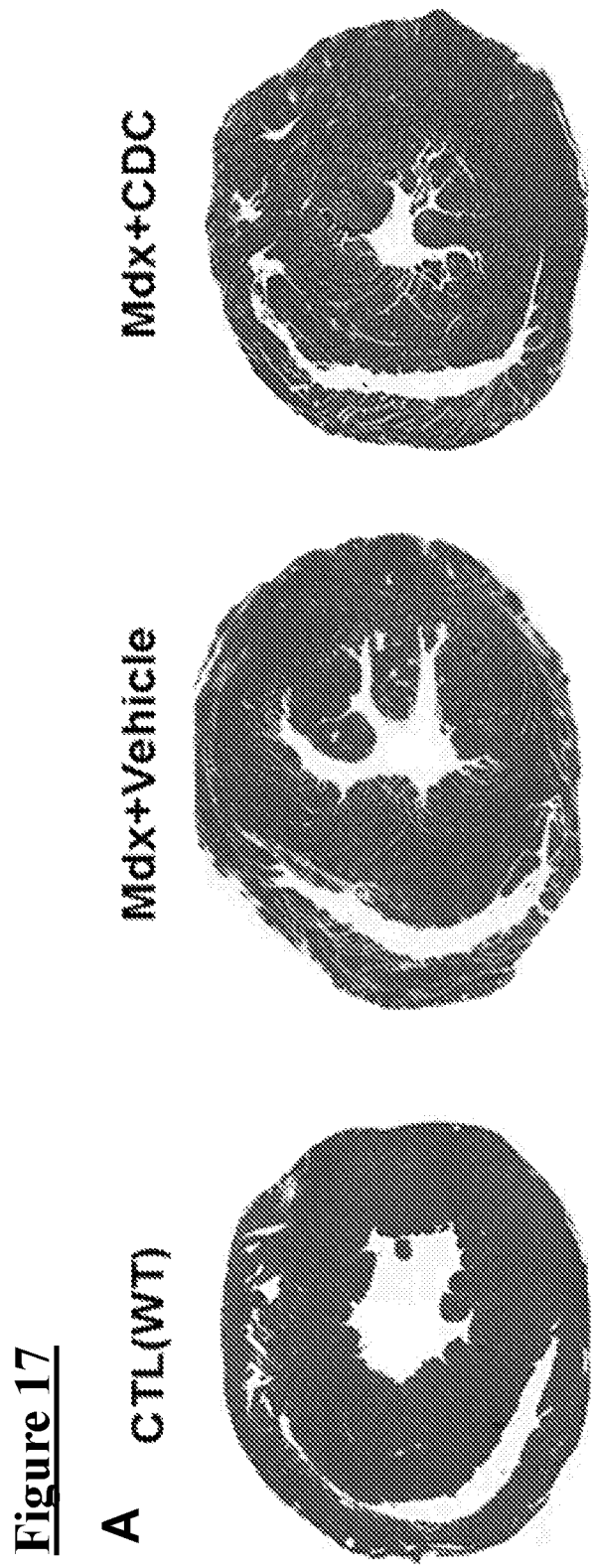
FIG. 17. CDC Treatment Reduced Cardiac Collagen Content And Fibrosis. Representative Masson trichrome images (A) and western blots and pooled data (B) representing fibrosis and collagen content in the mdx mouse hearts 3 weeks after treatment with vehicle (Mdx+Vehicle) or CDC (Mdx+CDC). Age-matched wild type mice (CTL) served as control. Collagen band size: 90-150 kDa. Data are means±SEM; n=7 in each group. †P<0.01 vs. Mdx+CDC and control (CTL; wild type). Scale bars: 1 mm FIG. 18. CDC Treatment Increased Cardiomyocyte Cycling And Proliferation And Augmented Number Of C-Kit Positive Cells Differentiating Into Cardiac Lineage (C-Kit+Nkx2.5+). Representative immunohistochemical images and pooled data ((A)-(C); CTL [wild type], vehicle and CDC-treated Mdx mouse hearts stained for Ki67 (A), aurora B (B), c-kit and Nkx2.5 (C)) from Mdx mice treated at 10 months of age. Arrows point to Ki67+ (A) and aurora B+(B) cardiomyocytes and the cells positive for both c-kit and Nkx2.5 (C). Fractions of cycling (Ki67+) and proliferating (Aurora B+) cardiomyocytes are expressed as the number of Ki67+ and aurora B+ cardiomyocytes divided by the total number of cardiomyocytes per high-power field (HPF), respectively (Pooled data (A), (B)). The portion of c-kit+Nkx2.5+ cells was calculated as the number of c-kit+Nkx2.5+ cells divided by the total number of cardiomyocytes per HPF (Pooled data (C)). WGA (Wheatgerm agglutinin) was applied for staining and delineation of cell membrane. Data are means±SEM; n=7 in each group. †P<0.01 vs. Mdx+Vehicle and control (CTL; wild type); Scale bars: 10 μm.
Figure 17:
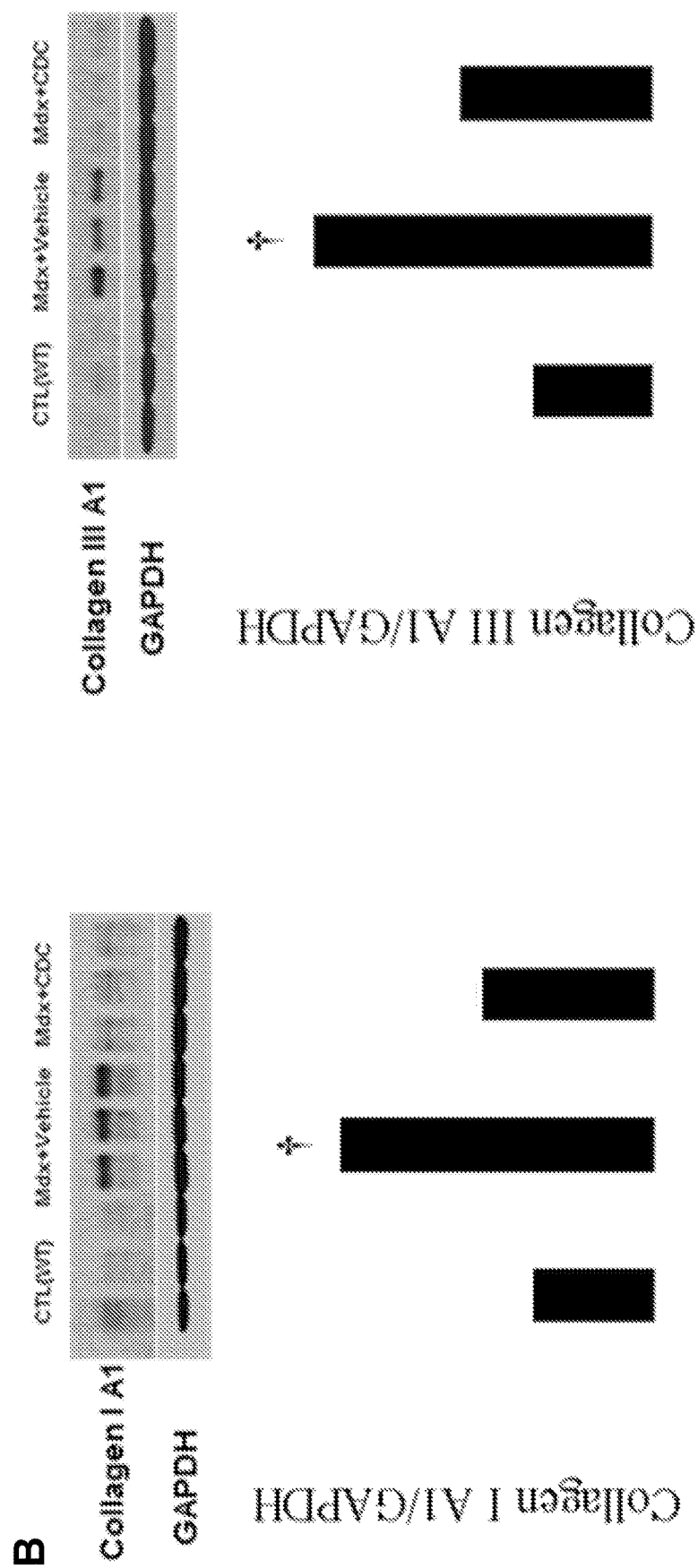
Figure 18:
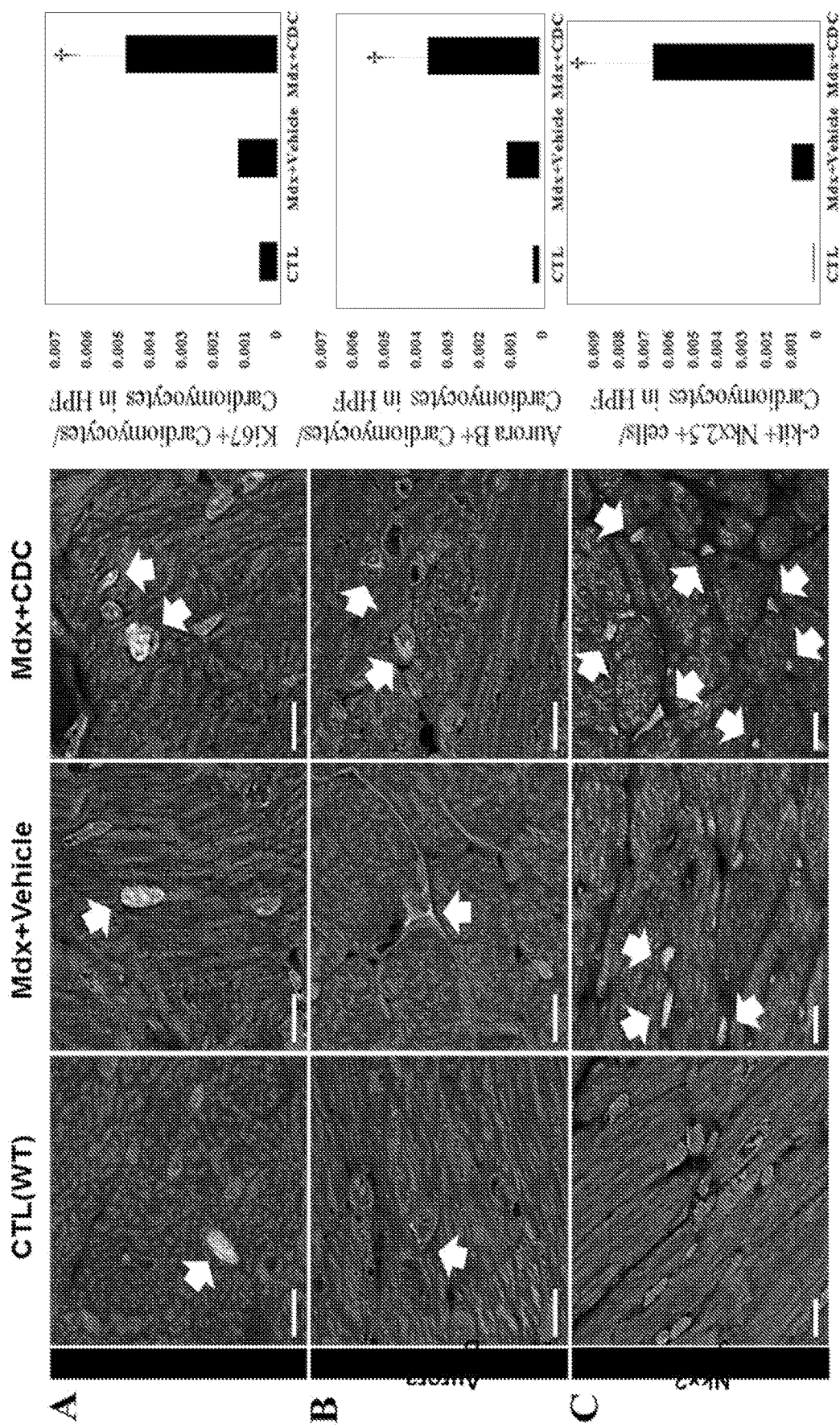
Figure 19:
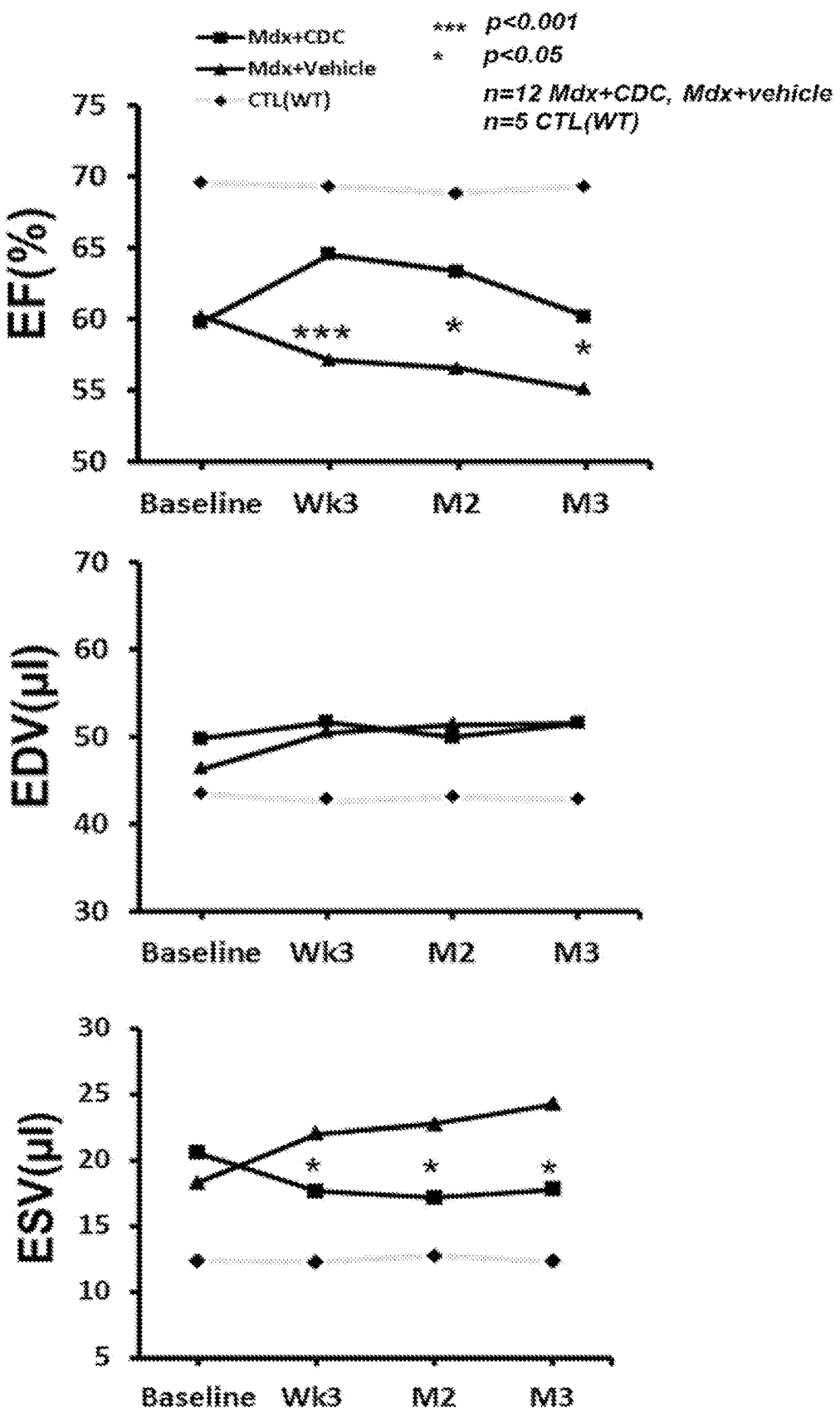
FIG. 19. Functional Benefits After Cardiosphere-Derived Cell (CDC) Transplantation. Pooled data for left ventricular ejection fraction (EF) and LV end-diastolic (LV EDV) and end-systolic (LV ESV) volumes show that CDC transplantation resulted in a sustained improvement of EF, LV EDV and LV ESV for 3 months in Mdx mice that received CDC at 10 months of age. Data are means±SEM; n=5 (control wild type) and n=12 (Mdx+vehicle, Mdx+CDC). *P<0.05 vs Gq+CDC; ***P<0.001 vs Gq+CDC.
Figure 20:
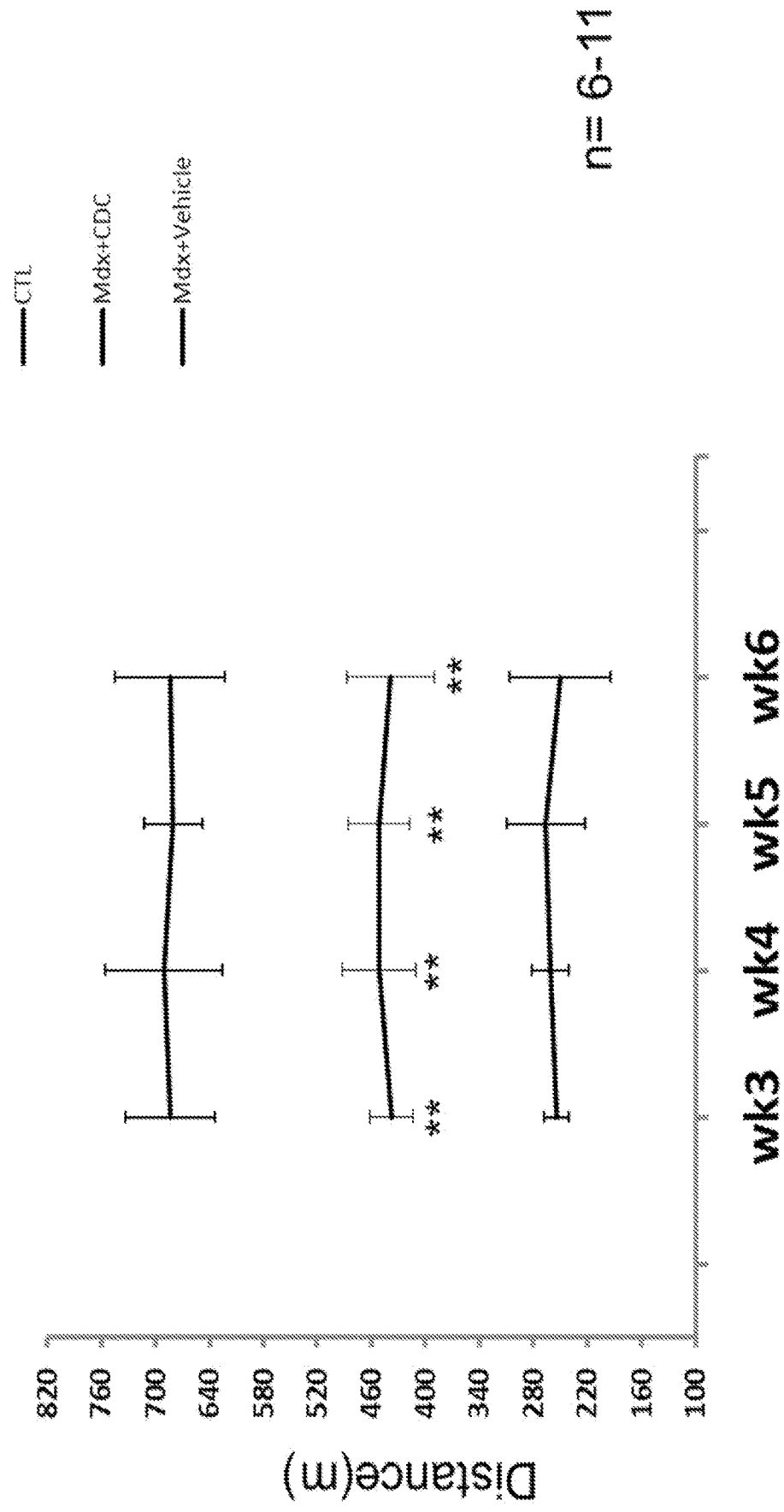
FIG. 20. Enhanced Maximal Exercise Capacity With CDC Treatment. Age-matched wild type mice (CTL) and 10-month-old Mdx mice treated with vehicle (Mdx+vehicle) or CDC (Mdx+CDC) were subjected to weekly high intensity exercise (stepwise increase in average speed every two minutes until exhaustion), starting 3 weeks after CDC/vehicle treatment. Sustained improvement of exercise capacity was observed in CDC-treated mdx mice relative to vehicle-treated mice. Data are means±SEM; n=6 (control wild type) and n=11 (Mdx+vehicle, Mdx+CDC). *P<0.05 vs Gq+Vehicle.
Figure 21:
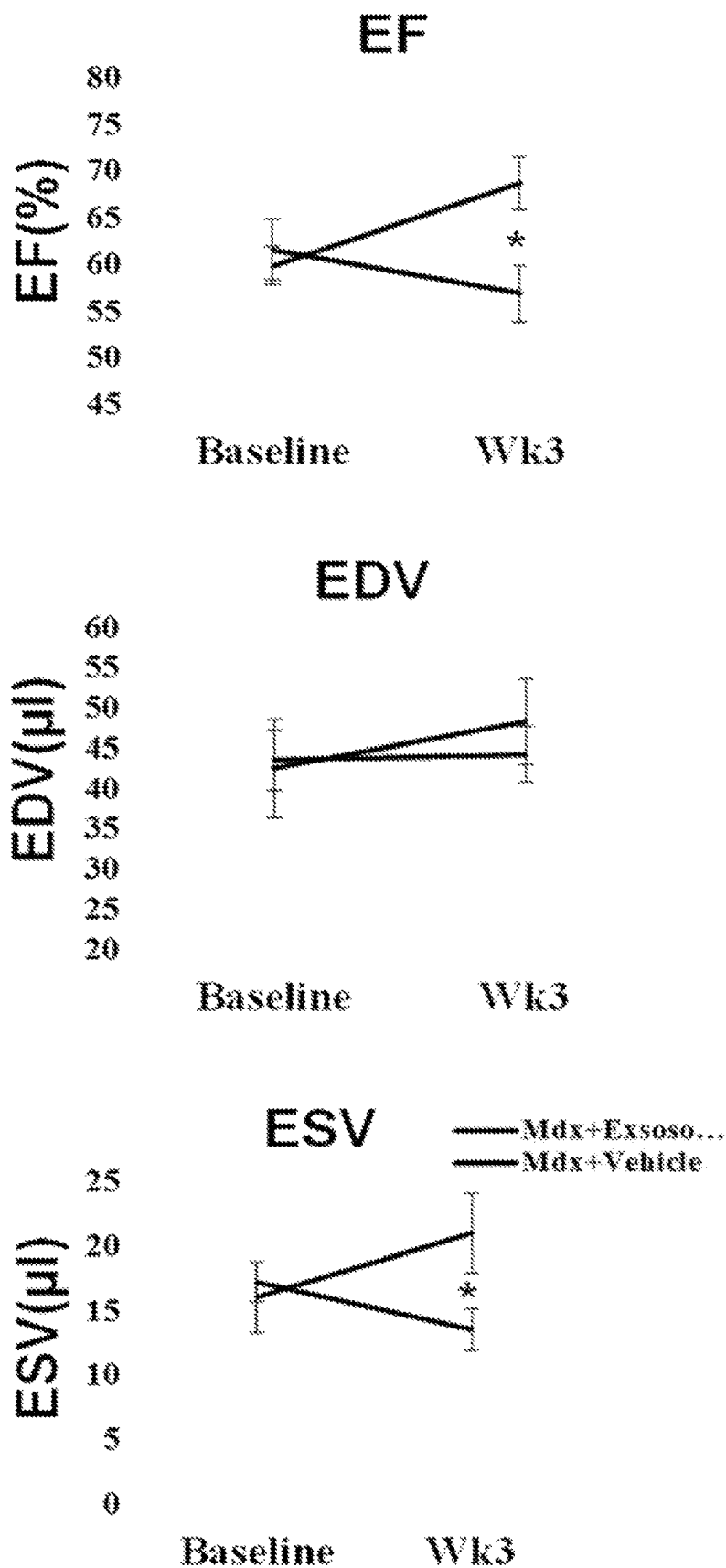
FIG. 21. Functional Benefits After Transplantation Of Human CDC-Derived Exosomes. Pooled data for left ventricular ejection fraction (EF) and LV end-diastolic (LV EDV) and end-systolic (LV ESV) volumes show that exosome transplantation resulted in improvement of EF, LV EDV and LV ESV three weeks after intramyocardial injection in 10-month-old Mdx mice. Data are means±SEM; n=11 in each group. *P<0.05 vs Gq+CDC.
Figure 22:
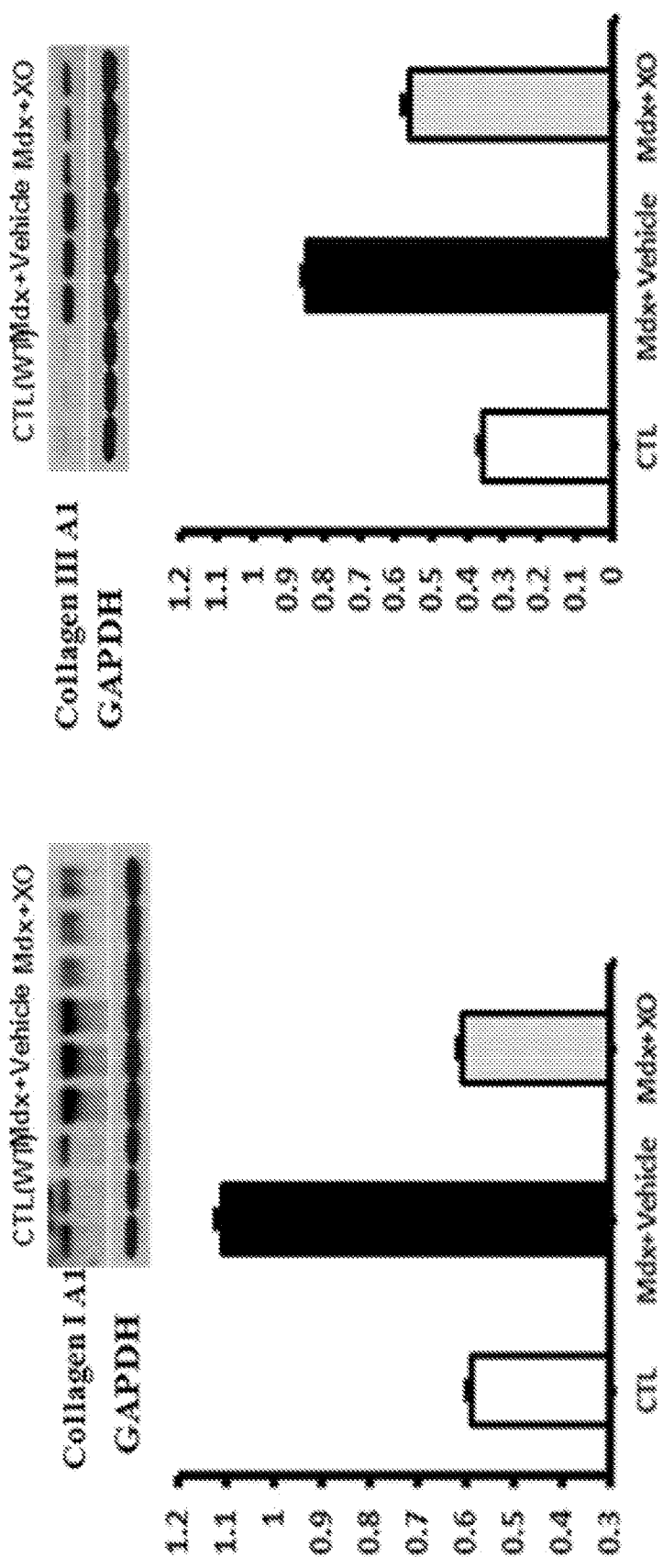
FIG. 22. CDC-Derived Exosomes Reduce Cardiac Collagen Content And Fibrosis. Representative western blots and pooled data depicting collagen I and III protein content in the mdx mouse hearts 3 weeks after treatment with vehicle (Mdx+Vehicle) or exosomes (Mdx+XO). Age-matched wild type mice (CTL) served as control. Collagen band size: 90-150 kDa. Data are means±SEM; n=7 in each group. †P<0.01 vs. Mdx+XO and control (CTL; wild type).

Importantly, the Inventors further established that miR-146a leads to thicker infarct wall thickness and increased viable tissue in a mouse model of myocardial infarct. To investigate the contribution of miR-146a to the greater exosome effect, the Inventors developed miR-146a-deficient exosomes by transfecting CDCs with a miR-146a hairpin inhibitor (or a control hairpin) followed by media conditioning and exosome isolation. Successful knockdown of miR-146a was confirmed by qPCR on resultant exosomes and on NRVMs exposed to either control or miR-146a depleted exosomes (FIGS. 12B and 12C). The antiapoptotic effect of CDC exosomes was evident by comparing TUNEL positivity in untreated NRVMs (left column, FIG. 5A) to that in NRVMs treated with control CDC exosomes (right column, FIG. 5A). Exosomes deficient in miR-146a conferred less protection from oxidant stress (middle column, FIG. 5A) than did control CDC exosomes, but still significantly suppressed apoptosis. These data hint that miR-146a underlies some, but not all, of the beneficial effect of CDC exosomes. To further probe this question in vivo, the Inventors implemented the same MI models as in FIG. 2 but injecting either a miR-146a mimic or a microRNA mimic control. Mice injected with miR-146a mimic during acute MI exhibited improved pump function (FIG. 5B), decreased scar mass, and increased viable heart tissue (FIGS. 5C-5F). In the chronic MI model, where regeneration can be studied more rigorously, animals treated with miR-146a showed only minor, statistically insignificant functional improvement (FIGS. 5G and 13A). Furthermore, histological analysis showed no difference in scar mass (FIGS. 5H and 5I). However, hearts treated with miR-146a mimic did show increased viable tissue, thicker infarcted walls (FIGS. 5J and 5K), and less adverse remodeling than controls (FIGS. 13B-13D). Evaluation of angiogenesis showed no significant differences between the two groups (FIGS. 5L and 13G). However, lower frequencies of cardiomyocyte apoptosis were observed in the miR-146a-injected hearts (FIGS. 13H and 13I), consistent with the in vitro data (FIG. 5A). Thus, in the chronic MI model, miR-146a reproduces the cardiomyogenic and antiapoptotic effects, but not the remaining functional and structural benefits, of CDC exosomes (cf. FIGS. 2F-2J and 9A-9C). Exogenous miR-146a is known to suppress ischemia/reperfusion injury via targeting of Irak-1 and Traf6, both involved in the toll-like receptor (TLR) signaling pathway. TLR signaling underlying innate immunity plays a major role in the pathology of sterile inflammation, including MI.

Figure 6:
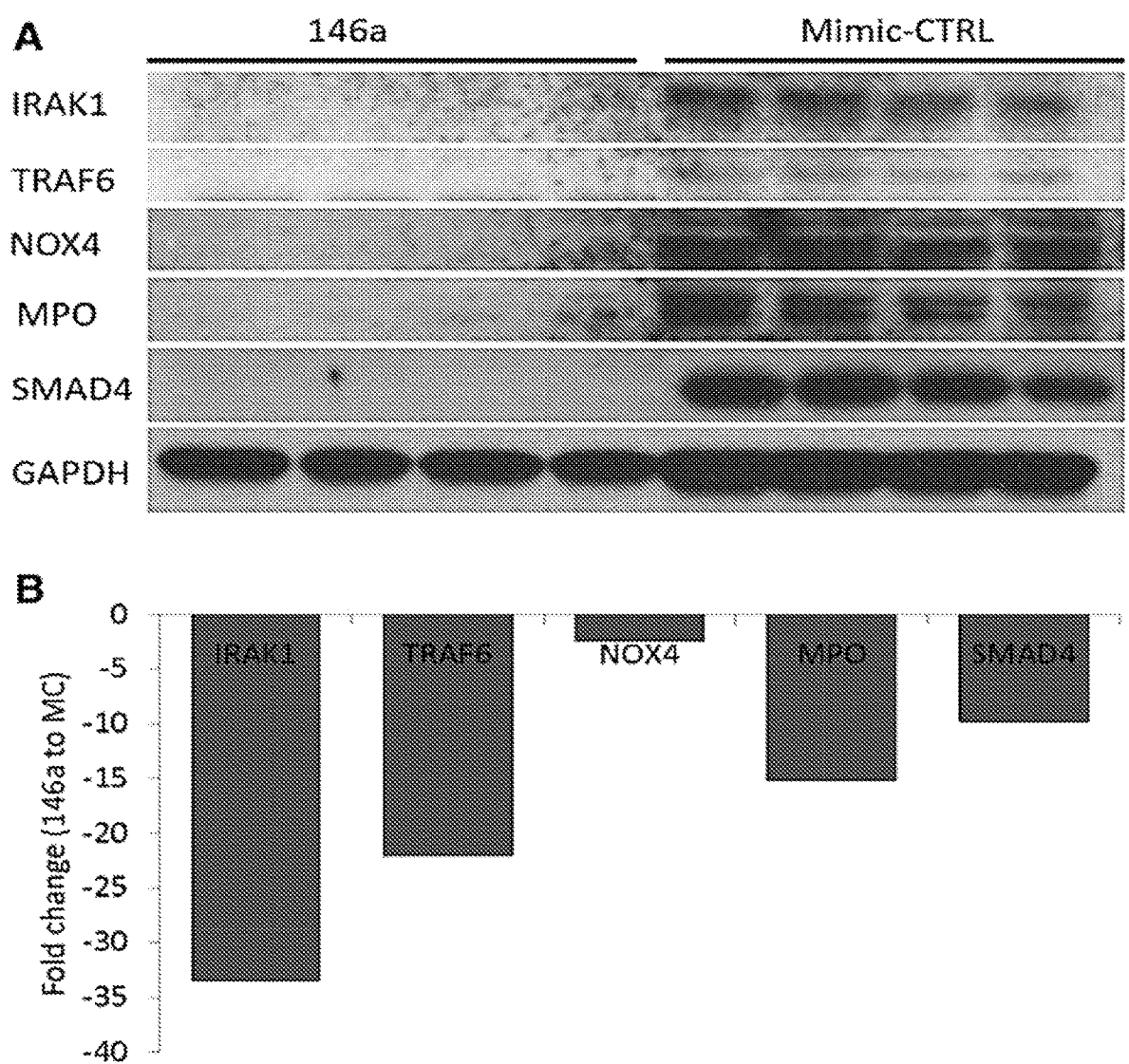
FIG. 6. miR-146a Targets Genes Involved in MI Pathology. (A and B) Downregulation of known miR-146a targets in chronic MI mouse hearts 7 days after injection of miR-146a or mimic control. (A) Western blot for IRAK, TRAF6, SMAD4, NOX4, and MPO (a marker of neutrophil infiltration). Each well is loaded with protein lysate pooled from two hearts per group, so that the blot represents pooled samples of two animals each with n=4 technical replicates. (B) Densitometric analysis of blot in (A) normalized to glyceraldehyde 3-phosphate dehydrogenase (GAPDH). (C) Schematic of the Inventors' working hypothesis. CDCs promote functional and structural benefits in the injured myocardium in a primarily paracrine manner. CDCs secrete exosomes that contain microRNAs that mediate benefits in the injured myocardium. These microRNAs target transcripts in the various compartments of the myocardium, which ultimately leads to increased cardiac function, increases in viable tissue, and decrease of scar after MI.
Figure 6:
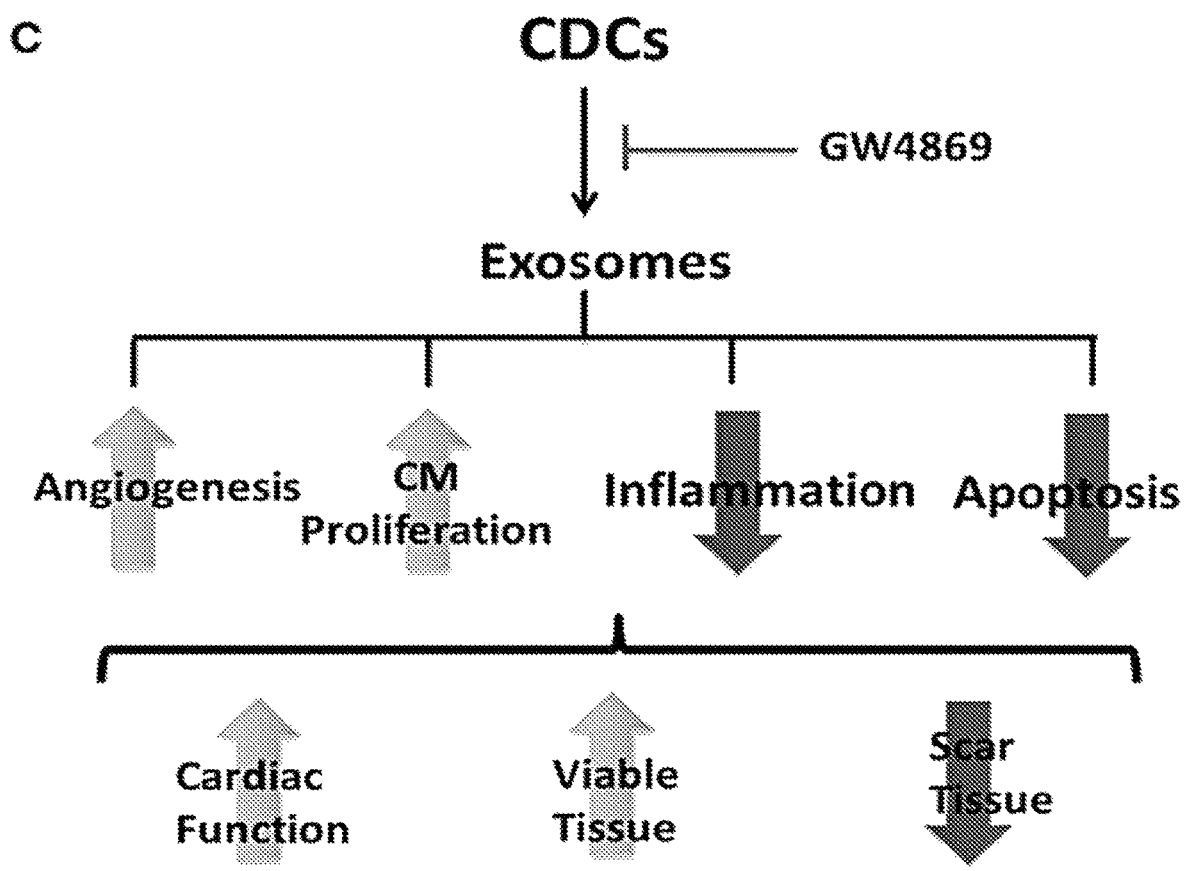

The CDC-exosome-mediated reductions of proinflammatory cytokines (FIG. 8) and suppression of Irak1 and Traf6 by miR-146a (which is augmented in hearts injected with CDC exosomes; FIG. 4C) are consistent with blunted TLR signaling. In addition, miR-146a suppresses NOX-4, which has been shown to impart oxidative stress and to potentiate cardiac injury, and SMAD4, a member of the transforming growth factor b (TGF-b) profibrotic pathway. To confirm that these targets are indeed downregulated, the Inventors performed western blots on chronic MI hearts 7 days after treatment with miR-146a. Indeed, all of the aforementioned targets were silenced in miR-146a-treated hearts compared to mimic control (FIGS. 6A and 6B). The Inventors also found lower levels of myeloperoxidase, a surrogate of neutrophil infiltration.

Example 17

Differences in Baseline Ejection Fraction Between Different Mouse Strains

The Inventors observed a noticeably high baseline ejection fraction for these animals. It was surmised that this difference is due to the different background strain of mice used in the knockouts (C57BL6). In all other experiments in the manuscript, the strain of mice used is SCID-Beige. SCID-Beige mice lack mature B and T cells as well as Natural Killer (NK) cells. This fundamental difference in immune competence likely accounts for the contrast in the baseline measurement as they respond to injury differently. In most of the experiments in this manuscript the Inventors chose the SCID-Beige mouse since they are permissive to human cells (which are the source of the CDC and the exosomes). However an appropriate control for the 146a KO mouse was a wild type from the same background strain which the BL6 background. This has been previously documented. Strain has previously been shown to be a significant determinant of wound healing after myocardial infarction.

Example 18

MiR-146a Effect on Immune Infiltration

Attenuating the inflammatory immune response is not necessarily abrogating it altogether. Innate immune cells including macrophages have been shown to play pro regenerative roles. Furthermore unpublished data from the Inventors' lab show that macrophage trafficking is not affected by CDC treatment, but macrophages treated with CDCs do switch from an M1 (proinflammatory) to an anti-inflammatory and pro-healing phenotype M2.

Example 19

Discussion

Figure 3:
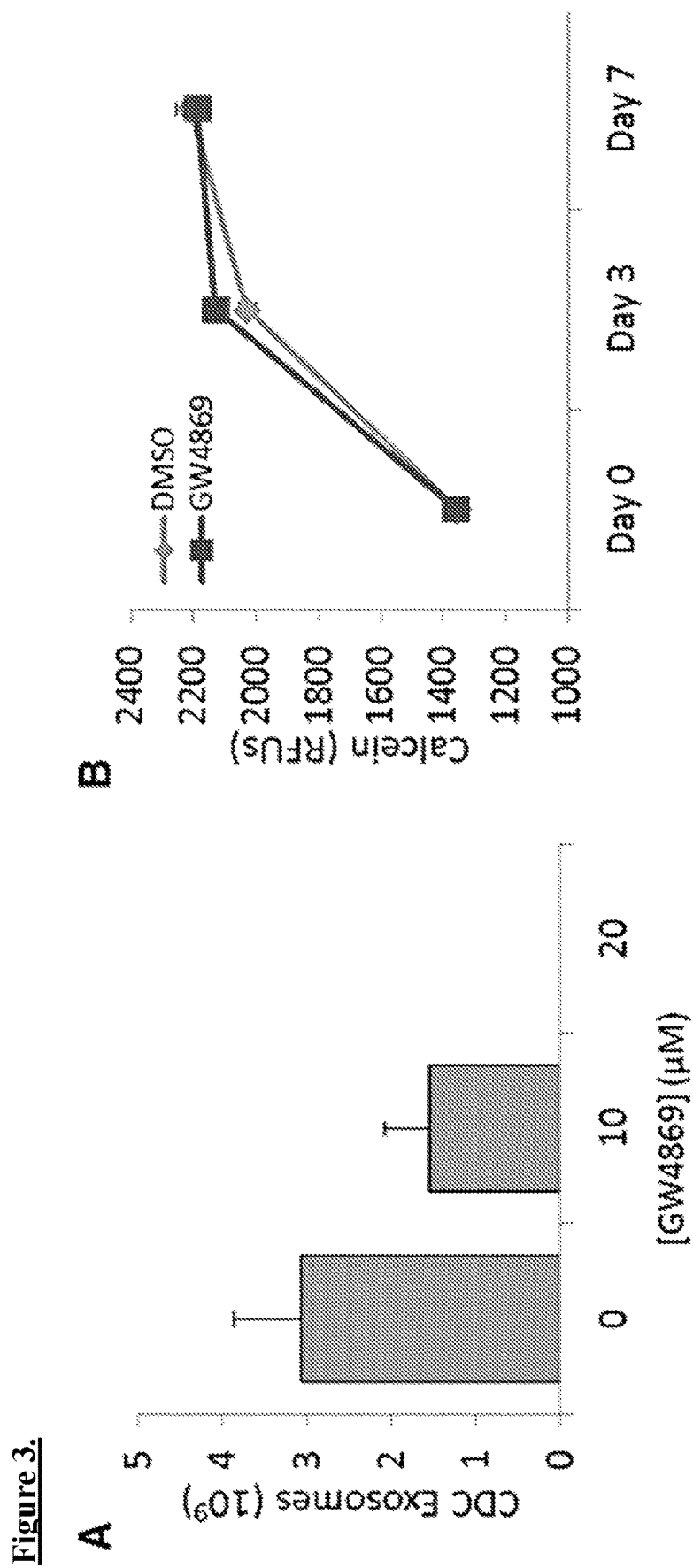
FIG. 3. Exosome Inhibition Attenuates CDC-Mediated Benefits. (A) GW4869 inhibited exosome production in CDCs in a dose-dependent manner (n=3 technical replicates). (B) GW4869 does not affect CDC viability as shown by calcein assay of CDCs treated with GW4869 or its solvent DMSO (n=4 technical replicates). (C and D) Neonatal rat cardiomyocytes (NRCMs) were cultured on chamber slides and treated with media conditioned by CDCs exposed to either GW4869 or DMSO. NRCMs were then treated with culture media and after 5 days, slides were stained for Ki67 and TUNEL to assess proliferation and apoptosis (n=4 technical replicates per group). (E) Pooled data for left ventricular ejection fraction (n=8 animals per group). (F-I) Representative Masson's trichrome-stained heart sections from two groups (F) and pooled morphometric analysis (G-I; n=4 hearts per group) reveal impairment of CDC-mediated benefit as evident in pooled data for scar mass, viable mass, and infarct wall thickness (IWT) in hearts injected with GW869-treated CDCs. *p<0.05 and **p<0.01 using Student's t test. Data are represented as mean and SEM. See also FIG. 10.
Figure 3:
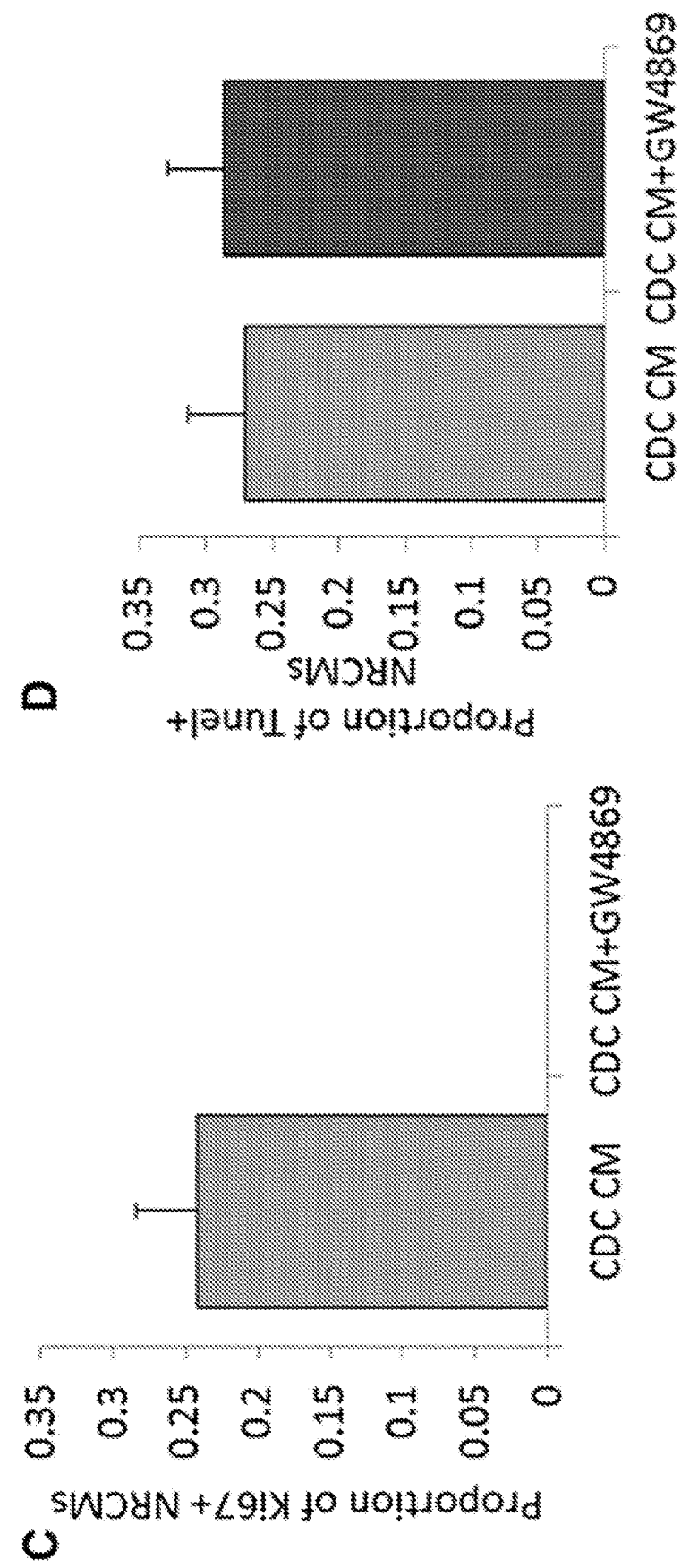
Figure 3:
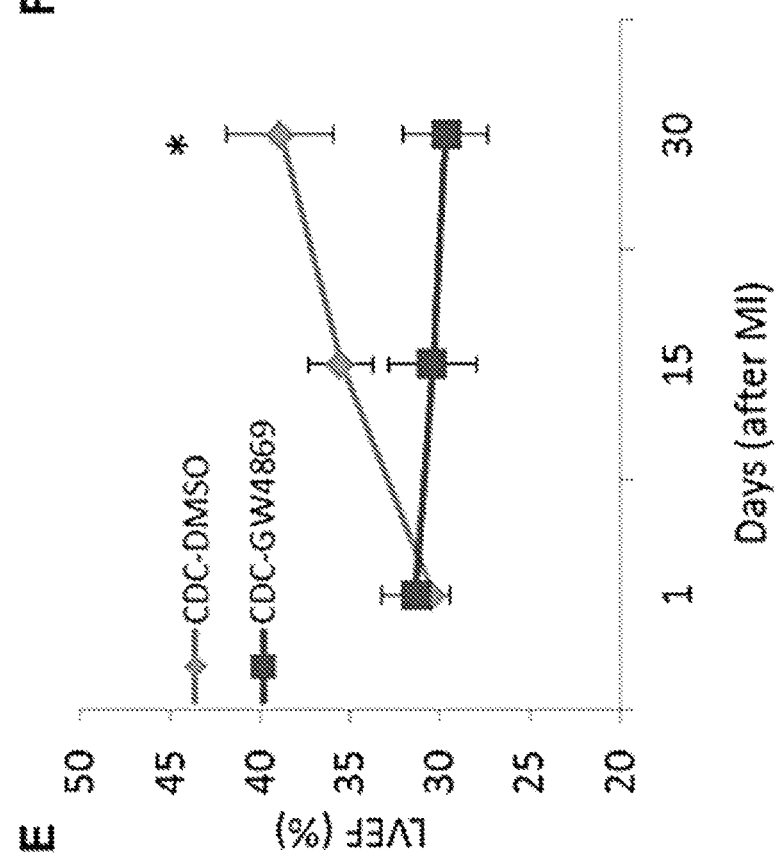
Figure 3:
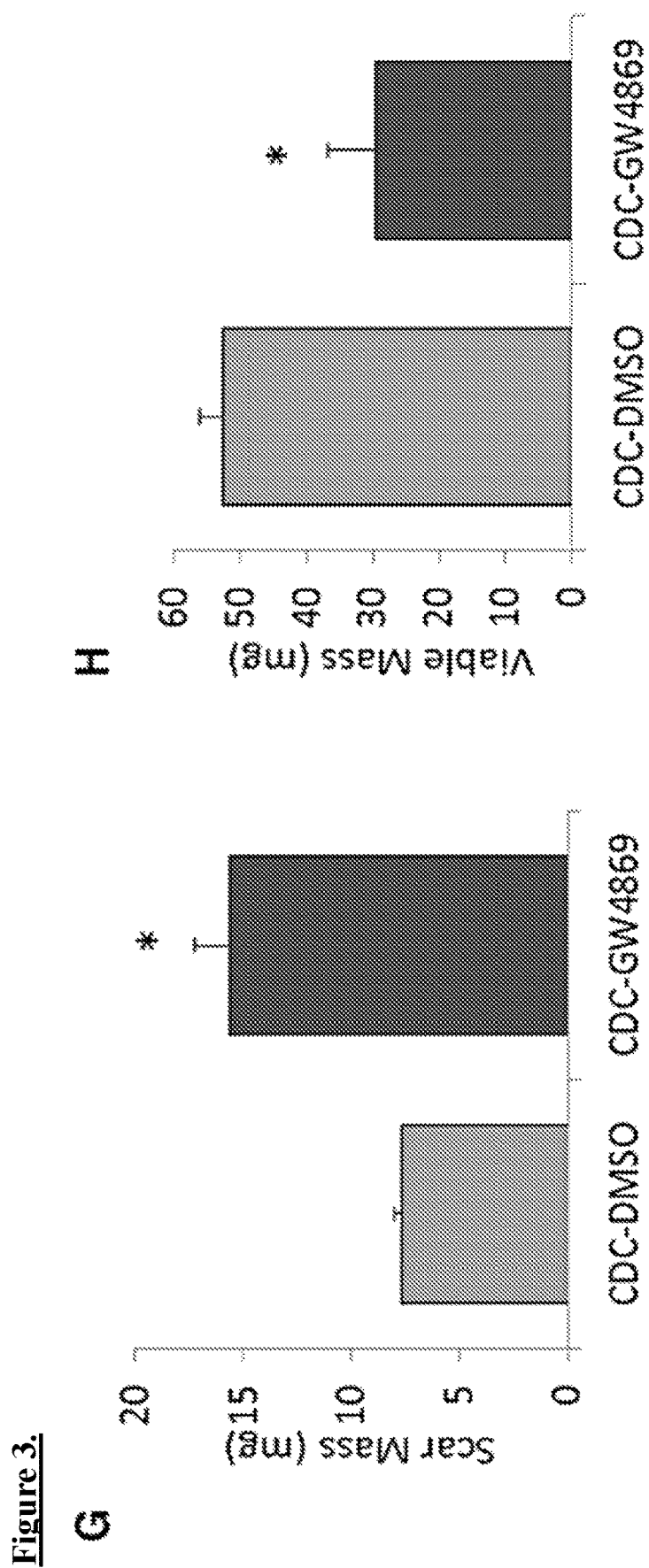
Figure 3:
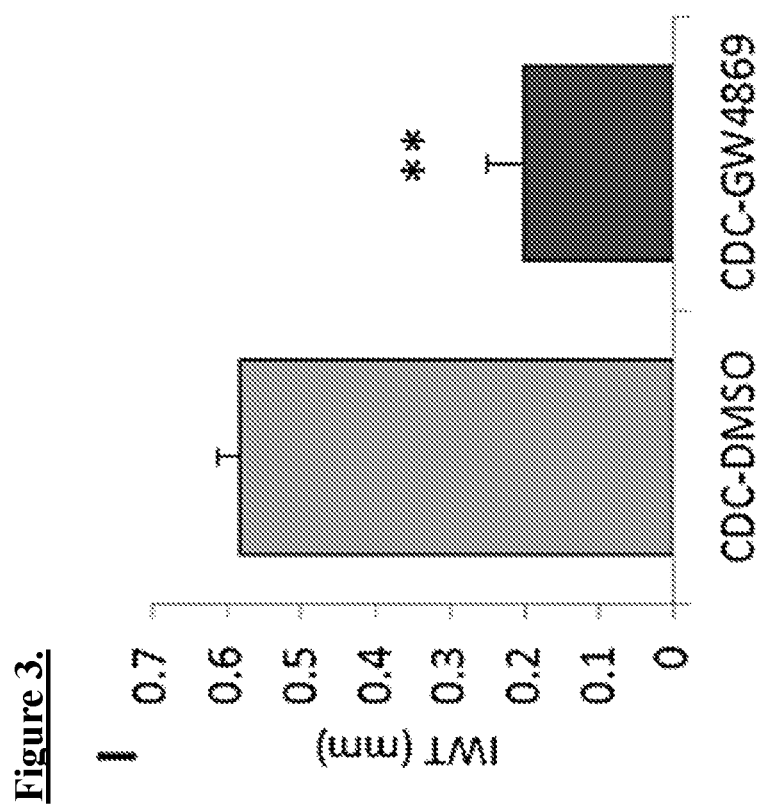

Cardiosphere-derived cells have been shown to induce therapeutic regeneration of the infarcted human heart. In a form of injury traditionally thought to be irreversible, CDCs led to shrinkage of scar and growth of new, functional myocardium. Similar effects have been corroborated in animal models. Here, the Inventors show that exosomes reproduce CDC-induced therapeutic regeneration, and that inhibition of exosome production undermines the benefits of CDCs. Exosomes contain microRNAs, which have the ability to alter cell behavior through paracrine mechanisms (FIG. 6B). Among these, the Inventors have identified miR-146a as being particularly enriched in CDC exosomes. When administered alone, miR-146a reproduces some, but not all, of the salient benefits of CDCs and of CDC exosomes (FIG. 3). Likewise, miR-146a-depleted exosomes were still able to suppress cardiomyocyte apoptosis (FIG. 5A), albeit more weakly than when miR-146a is present. Treating hearts with miR-146a in a chronic model of MI (after the scar is permanent) does reproduce the increase in viable mass that is the signature of therapeutic regeneration, but fails to mimic two key beneficial effects of CDC exosomes: decreased scar mass and improved global function. The increase in viable myocardium does not suffice to increase function, possibly because of inadequate angiogenesis elicited by miR-146a. The Inventors conclude that miR-146a plays an important part in mediating the effects of CDC exosomes, but alone does not suffice to confer comprehensive therapeutic benefit. Other microRNAs in the repertoire may exert synonymous or perhaps synergistic effects with miR-146a. For instance, miR-22 (another microRNA highly enriched in CDC exosomes) has been shown to be critical for adaptive responses to cardiac stress. Likewise, miR-24 (also identified in CDC exosomes) modulates cardiac fibrosis by targeting furin, a member of the profibrotic TGF-b signaling pathway; overexpression of miR-24 in a model of MI decreased myocardial scar formation. The possible roles of these microRNAs as mediators of CDC exosome benefits, alone or in combination with miR-146a, remain to be studied. Whereas dissection of the active principles within CDC exosomes is worthwhile, deconstruction of the nanovesicles may be counterproductive from a therapeutic perspective. CDC exosomes are naturally cell permeant, and their lipid bilayer coat protects their payloads from degradation as particles shuttle from cell to cell, so that the intact particles themselves may be well suited for disease applications.

Injection of CDC-derived exosomes into the injured heart mimics the structural and functional benefits of CDC transplantation; conversely, inhibition of exosome secretion by CDC s abrogates the therapeutic benefits of transplanted CDCs. Not all exosomes are salutary: Injection of exosomes from dermal fibroblasts, control cells which are therapeutically inert, had no benefit. DC-exosomes decreased acute cardiomyocyte death and inflammatory cytokine release, while attenuating left ventricular (LV) remodeling and fibrosis in the injured heart. MicroRNA arrays reveal several "signature microRNAs" that are highly up-regulated in CDC-exosomes. In contrast, mass spectrometry indicates that the protein composition of CDC-exosomes is conventional and comparable to that of fibroblast exosomes.

This work implicates exosomes, and the microRNAs they contain, as crucial mediators of CDC-induced cardiac regeneration. CDCs exert diverse but coordinated effects: they recruit endogenous progenitor cells and coax surviving heart cells to proliferate; on the other hand, injected CDCs suppress maladaptive LV remodeling, apoptosis, inflammation, and tissue fibrosis after MI. While it is possible that CDCs secrete a medley of individual growth factors and cytokines that collectively produce diverse benefits, the involvement of master-regulator microRNAs within exosomes would help tie together the various effects without postulating complex mixtures of numerous secreted protein factors. Moreover, microRNAs are known to confer long-lasting benefits and fundamental alterations of the injured microenvironment helping to rationalize the sustained benefits of CDCs despite their evanescent survival in the tissue. CDC exosomes contain rich signaling information conferred by a cell type that is the first shown to be capable of producing regeneration in a setting of "permanent" injury, and confer the same benefits as CDCs without transplantation of living cells. For all these reasons, CDC exosomes merit further development as cell-free therapeutic candidates.

Based on the results described herein, CDC-exosomes are demonstrated as capable of treating heart-related conditions, such as treat heart failure (HF) associated with Duchenne muscular dystrophy (DMD). Exosomes secreted by cells are capable of reproducing therapeutic benefits of their parental cells and based on the described knockdown studies, appear to be indispensable in effectuating such therapeutic benefits. Importantly, these results have further identified that within their rich biological cargo of various proteins and RNA, microRNAs play a central role in activating regenerative processes, suggesting compelling applications in clinical therapeutics. Exosomes have significant advantages over traditional cell-based therapies including manufacturing advantages, relative ease of definition and characterization, lack of tumorgenicity and immunogenicity, and possibility of administration in therapeutic scenarios for which cell, tissue, organ or mechanical transplant is not available. Thus, CDC-exosomes represent a significant advance in biologic therapy.

Example 20

Statistical Analysis

All results are presented as mean±SEM; results for alternans are presented as mean±SD. Normality and equality of variances of data sets were first tested using Kolmogorov-Smirnov and Levene's tests, respectively. If both were confirmed, t-test or analysis of variance followed by Bonferroni's post hoc test were used for determination of statistical significance; if either normality or equality of variances was not assured, nonparametric tests (Wilcoxon test or Kruskal-Wallis test followed by Dunn's post-test) were applied (SPSS II, SPSS Inc., Chicago, Ill.). No preliminary data were available for a power analysis. Experiments were planned with a sample size of 4 animals per group as an initial pilot project. Results from the pilot project allowed us to power subsequent studies. The study followed preclinical reporting standards, as described.

Example 21

Echocardiography

Echocardiographic studies were performed two days before (Baseline) and 3 weeks, 2 and 3 months after first CDC/CDC exosome (CDC-XO) injection and 3 weeks, 2 and 3 months after second CDC/CDC-XO injection using the Vevo 770 Imaging System (VisualSonics, Toronto, Canada). The same imaging system was used to perform echocardiographic studies at baseline (2 day before) and 3 weeks after miR148a mimic injection. After induction of light general anesthesia, the heart was imaged at the level of the greatest LV diameter. LV ejection fraction (LVEF) was measured with VisualSonics version 1.3.8 software from 2-dimensional long-axis views. Changes in left ventricular (LV) end diastolic and systolic volumes: First and second CDC or CDC-XO transplantation resulted in a sustained improvement of LV end-diastolic (LV EDV) and end-systolic (LV ESV) volumes in mdx mice, relative to placebo, for at least 6 months. Delivery of miR-148a partially improved LV EDV and LV ESV. CDC and CDC-XO transplantations resulted in a sustained improvement of LV EDV and LV ESV for 3 months after both first and second (3 months interval) injections in mdx mice, relative to placebo. Three weeks after miR-148 injection, LV EDV and LV ESV were partially improved. Data was collected for n=12 in each group. #P<0.05 vs Mdx+Vehicle.

Example 22

Treadmill Exercise Testing

Exercise capacity was assessed weekly with Exer-3/6 open treadmill (Columbus Instruments, Columbus, Ohio), beginning 3 weeks after CDC/vehicle injection (exercise capacity measured in a subset of mdx mice 1 week preoperatively was equivalent to that measured 3 weeks postoperatively in the Mdx+Vehicle group; data not shown). After an acclimation period (10 m/min for 20 min) stepwise increases in average speed (1 m/min) were applied every two minutes during treadmill exercise until the mouse became exhausted (spending >10 seconds on shocker; continuous nudging was used during treadmill to help mice stay on the track). Subsequently, the mouse was returned to the cage and the total distance recorded. After 3 months of weekly exercise, CDC/vehicle mdx mice along with wild-type age-matched mice were followed for assessment of mortality. The treadmill protocol conformed to guidelines from the American Physiological Society[3].

Example 23

Expansion of CDCs

Mouse CDCs were expanded from wild-type strain-matched mouse hearts (C57BL/10ScSnJ wild type mouse heart) as described. Briefly, ventricular tissues were minced into ~1 mm explants, partially digested enzymatically and plated on adherent (fibronectin-coated) culture dishes. These explants spontaneously yield outgrowth cells (explant-derived cells) which were harvested once confluent and plated in suspension culture ($10^5$ cells/mL on poly-D-lysine-coated dishes) to enable self-assembly of three-dimensional cardiospheres. Subsequent replating of cardiospheres on adherent culture dishes yielded CDCs which were used in all experiments at passage one.

Example 24

Assessment of CDC Engraftment by Real-Time Polymerase Chain Reaction

Quantitative polymerase chain reaction (PCR) was performed 1, 2 and 3 weeks after CDC injection to assess cell engraftment. Male CDCs were injected to enable detection of the SRY gene located on the Y chromosome as a marker of engraftment using the TAQMAN™ assay (Applied Biosystems, Foster City, Calif.). The whole mouse heart was harvested, weighed, and homogenized. A standard curve was generated with multiple dilutions of genomic DNA isolated from the injected CDCs. All samples were spiked with equal amounts of genomic DNA from non-injected mouse hearts as a control For each reaction, 50 ng of genomic DNA was used Real-time PCR was performed in triplicate. Engraftment was quantified from the standard curve. Percentage engraftment of CDCs at 1 week was ~8% and <1% at 2 weeks. By 3 weeks, no surviving CDCs could be detected. Percentage engraftment of CDCs at 1 week was ~8% and <1% at 2 weeks. By 3 weeks, no surviving CDCs could be detected. n=3 for each time point.

Example 25

Cardiomyocyte Proliferation and Cardiac Collagen Content after CDC Injection Paraffin-embedded sections from apical, middle and basal parts of each heart were used for Masson's trichrome staining and immunostaining with antibodies against Ki67 and aurora B. Myocardial abundance of collagen I A1 and collagen III A1 was measured by Western blot analysis. Enhanced cardiomyogenesis and diminished cardiac fibrosis and collagen content was noted 3 weeks after CDC injection in mdx mice. Representative immunohistochemical images were gathered and pooled data was collected (for wild type, vehicle and CDC-treated; mdx mouse hearts were stained for Ki67 and Aurora B; n=4–6 per group). Representative Masson trichrome images and western blots and pooled data were gathered as was data for cardiac collagen IA and IIIA. †P<0.05 vs. Mdx+Vehicle and CTL (control); #P<0.05 vs. Mdx+CDC and CTL (control).

Example 26

Exosomes

Exosomes were isolated from serum-free media conditioned overnight (24 hr) by cultured human CDCs (CDC-XO) [or normal human dermal fibroblasts (NHDF) as a control] in hypoxia (2% $O_2$; default condition) or normoxia (20% $O_2$, solely for studies comparing RNA content of exosomes). Ultracentrifugation (100,000 g for 1 hr) was used to isolate exosomes from conditioned media after sequential centrifugations at 300 g (10 min) and 10,000 g (30 min) and filtration with 0.22 micron filters. Isolated exosomes underwent RNA extraction and subsequently RNA sequencing or were re-suspended in PBS (for in vivo and in vitro experiments) and the ratio of exosome to protein was measured using Micro BCA Protein Assay Kit (Life technologies, Grand Island, N.Y.) and Nanosight particle counter, respectively. The fold changes of microRNAs in CDC exosomes isolated from hypoxic conditioned was measured (under hypoxic conditions (2% $O_2$) compared to CDC normoxic conditioned media): change >10 and <20. NEBNext Small RNA Library Prep kit (New England Bio-Labs, Ipswich, MA) was used for miRNA-seq library preparation of extracted small RNAs from the exosomes. RNAs were extracted from exosomes using miRNeasy Serum/Plasma Kit (QIAGEN, Germantown, MD). Preliminary dose-response studies identified $2 \times 10^7$ and $1 \times 10^9$ exosomes/n protein from hypoxic CDCs as effective doses for in vitro and in vivo experiments, respectively Similar concentrations of exosomes were used for the experiments in which NHDF exosomes were applied. Preliminary pilot in vivo experiments were performed using exosomes isolated by ultracentrifugation or EXOQUICK™ kit (SBI, Mountain View, Calif.) as described, yielding similar results with the two isolation methods. Isolated exosomes collected by ultracentrifugation were analyzed by nanoparticle tracking. Using the NanoSight NS300 system (NanoSight Ltd, UK), videos were collected and analyzed using NTAsoftware (version 2.3), with the minimal expected particle size, minimum track length, and blur setting, all set to automatic. Camera shutter speed was fixed at 30.01 ms and camera gain was set to 500. Camera sensitivity and detection threshold were set close to maximum (15 or 16) and minimum (3 or 4), respectively, to reveal small particles. Ambient temperature was recorded manually, ranging from 24 to 27° C. For each sample, five videos of 60 seconds duration were recorded, with a 10-second delay between recordings, generating five replicate histograms that were averaged.

Example 27

CDC, CDC-Exosome and miR-148 Injections

To optimize the process of CDC transplantation, preliminary dose-response experiments were performed, which identified $1 \times 10^5$ cells in first injection and $1 \times 10^4$ cells in second injection (3 months after first injection) as effective doses, consistent with prior dose-ranging experiments in ischemic and nonischemic mouse models. A total of $1 \times 10^5$ cells/40 µL phosphate-buffered saline (PBS; first injection) or $1 \times 10^4$ cells/40 µL PBS (second injection) or PBS alone were injected into left ventricular (LV) myocardium divided equally among 4 points as described. The LV was visually divided into three zones: basal, middle, and apical, with one injection in the basal, two in the middle and one in the apical zone. 10-month-old CDC/mdx and vehicle/mdx mice were injected with CDCs (Mdx+CDC, n=12) or vehicle [placebo: Mdx+Vehicle (PBS), n=12] twice (3 months interval), respectively. Injections were during open-chest thoracotomy via a 28½ gauge-needle. All surgical procedures were carried out while the animals were under general anesthesia (Dexmedetomidine (0.5 mg/kg)/Ketamine (75 mg/kg); IP; once before surgery). Similar protocols were used for injection of CDC-exosomes and miR-148 into myocardium. A miR-148a mimic (hsa-miR-148a-3p, 2 µg; Sigma-Aldrich, St. Louis, Mo.) was mixed with RNAiMAX transfection reagent (life technologies, Grand Island, N.Y.) for 30 min at room temperature at a total volume of 40 µl and injected into 4 points per heart as described above.

Example 28

Histology

Mice were sacrificed 3 weeks (CTL: n=4; Mdx+Vehicle: n=6; Mdx+CDC/Mdx+CDC-XO: n=6 each) or 3 months (CTL: n=4; Mdx+Vehicle: n=6; Mdx+CDC/Mdx+CDC-XO: n=6) after first CDC/CDC-XO injections and 3 weeks after miR-148 injection (n=6). Paraffin-embedded sections from apical, middle and basal parts of each heart were used for histology. Masson's trichrome staining (HT15 Trichrome Stain [Masson] Kit; Sigma-Aldrich, St. Louis, Mo.) was performed for evaluation of fibrosis. T cells, B cells and macrophages were assessed by immunostaining with antibodies against mouse CD3, CD20 and CD68, respectively, and the average number of cells in each heart was calculated from counting cells in 10 fields (20× magnification) from each of 10 sections selected randomly from the apical (3 sections; 50 µm interval), middle (4 sections; 50 µm interval) and basal (3 sections; 50 µm interval) regions of each heart. Actively-cycling and proliferating (Ki67$^+$ & Aurora B$^+$) cardiomyocytes were counted in the same manner, and the cycling and proliferating fractions were expressed as the number of Ki67$^+$ and Aurora B$^+$ cardiomyocytes divided by the total number of cardiomyocytes per high-power field (HPF), respectively, as described. Measurements were averaged for each heart. Immunofluorescence staining: Heat-induced epitope retrieval in low pH buffer (DAKO, Carpinteria, Calif.) was followed by 2 hours permeabilization/blocking with Protein Block Solution (DAKO, Carpinteria, Calif.) contained 1% saponin (Sigma, St. Louis, Mo.; Protein Block Solution contained 3% saponin was applied for immunofluorescence staining of Ki67). Subsequently, primary antibodies in Protein Block Solution were applied overnight in 4° C. for immunofluorescence staining of 5-nm sections from apical, middle and basal parts of each heart. After 3× wash with PBS, each 10 minutes, Alexa Fluor secondary antibodies (Life Technologies, Grand Island, N.Y.) were used for detection. Images were taken by a Leica TCS SP5× confocal microscopy system. Immunofluorescence staining was conducted using antibodies against mouse Ki-67 (SP6; 1:50; Thermo Fisher Scientific, Fremont, Calif.), WGA (Wheat germ agglutinin; 1:200; Life Technologies, Grand Island, N.Y.), Nrf2 (C20; 1:50; Santa Cruz Biotechnology, Santa Cruz, Calif.), aurora B (1:250; BD Biosciences, San Jose, Calif.). Immunoperoxidase staining: Immunohistochemical detection of CD3, CD20 and CD68 was performed on 5-µm sections using prediluted rabbit monoclonal antibodies from Ventana Medical System (Tuscon, Ariz.; CD68) and Cell Marque (Rocklin, Calif.; CD3, CD20). Staining was conducted on the Leica Bond-Max Ventana automated slide stainer (Chicago, Ill.) using onboard heat-induced epitope retrieval method in high pH ER2 buffer (Leica Biosystems, Buffalo Grove, Ill.). The staining was visualized using the Dako Envision+ rabbit detection System and Dako DAB (Carpinteria, Calif.). The slides were subsequently counterstained with mayer's hematoxylin for 1 minute and coverslipped. Electron microscopy: Apical (1 cube), middle (3 cubes from right, middle and left subparts) and basal (3 cubes from right, middle and left subparts) parts of posterior wall from each heart (CTL: n=3; Mdx+Vehicle: n=3; Mdx+CDC: n=3) were fixed by immersion of 1 mm² cubes in 2% glutaraldehyde, postfixed in osmium, and embedded in epon. Sections were cut at silver thickness, stained with uranyl acetate and lead citrate, and viewed with JEOL 1010 equipped with AMT digital camera system.

Example 29

Western Blots

Western blot analysis was performed to compare myocardial abundance of target proteins contributing to Nrf2 signaling [Nrf2, phospho-Nrf2 (Nrf2-$p^{s40}$) and Nrf2 downstream gene products: heme oxygenase-1 (HO-1), catalase, superoxide dismutase-2 (SOD-2), and catalytic subunit of glutamate-cysteine ligase (GCLC)], Nrf2 phosphorylation [phospho-Akt (Akt-$p^{308}$)], oxidative phosphorylation [CI (NDUFB8 subunit), CII (SDHB subunit), CIV (MTCO1 subunit), CIII (UQCRC2 subunit) and CV (ATPSA subunit)], mitochondrial biogenesis (PGC-1), mitophagy (PINK1), inflammation (NF-κB and MCP-1) and fibrosis (Collagen IA1 and collagen IIIA1). Myocardial density of malondialdehyde protein adducts, a marker of oxidative stress, was also measured by Western blotting (WB). Samples from apical, middle and basal parts of each heart (each 1 mm-thick transverse section) were mixed and homogenized. and nuclear and cytoplasmic fractions were extracted per manufacturer's instructions CELYTIC™ NUCLEAR™ Extraction Kit, Sigma-Aldrich, St. Louis, Mo.). Mitochondria were extracted from fresh whole hearts (CTL: n=3; Mdx+Vehicle n=8; Mdx+CDC n=8) as described in respirometry section. Cytoplasmic, nuclear and mitochondrial extracts for WB analysis were stored at −80° C. The protein concentrations in extracts were determined by the Micro BCA Protein Assay Kit (Life technologies, Grand Island, N.Y.). Target proteins in the cytoplasmic, nuclear and mitochondrial fractions were measured by Western blot analysis using the following antibodies. antibodies against mouse Nrf2, HO-1, catalase, SOD-2, GCLC, collagen IA1, and collagen IIIA1, and PGC-1 were purchased from Santa Cruz Biotechnology (Santa Cruz, Calif.), phospho-Nrf2 (Nrf2-$p^{s40}$; Biorbyt, San Francisco, Calif.), respiratory chain subunits (Total OXPHOS Rodent WB Antibody Cocktail antibody), malondialdehyde, citrate synthase and TBP (Abcam, Cambridge, Mass.), Akt and Akt-$p^{T308}$, IκB-α, p-IκB-α, (Cell Signaling Technology, Denver, Colo.). PINK1, MCP-1 and NF-κB p65 (Sigma-Aldrich, St. Louis, Mo.) antibodies were purchased from the cited sources. Antibodies to TBP (TATA binding protein) and citrate synthase were used for measurements of the housekeeping proteins for nuclear (TBP), cytosolic and mitochondrial (citrate synthase) target proteins. Western blot methods: Briefly, aliquots containing 20 μg proteins were fractionated on 8, 10 and 4-12% Bis-Tris gel (Life technologies, Grand Island, N.Y.) at 120 V for 2 h and transferred to a PVDF membrane (Life technologies, Grand Island, N.Y.). The membrane was incubated for 1 h in blocking buffer (1 TBS, 0.05% Tween-20 and 5% nonfat milk) and then overnight in the same buffer containing the given antibodies at optimal dilutions listed in Table 1.

TABLE 1

Antibodies and the optimal dilutions applied in Western blot analyses.

| Antibody | p-Akt | Akt | Malondialdehyde | NF-κB p65 | Nrf2 | HO-1 | p-Nrf2 |
|---|---|---|---|---|---|---|---|
| Dilution | 1:500 | 1:1000 | 1:1000 | 1:1000 | 1:500 | 1:500 | 1:250 |
| Antibody | TBP | Collagen I | Collagen III | Citrate syn. | p-IκB-α | IκB-α | PGC-1 |
| Dilution | 1:2000 | 1:500 | 1:500 | 1:2000 | 1:500 | 1:1000 | 1:500 |
| Antibody | Catalase | SOD-2 | GCLC | MCP | OXPHOS | PINK1 | |
| Dilution | 1:500 | 1:500 | 1:500 | 1:100 | 1:500 | 2 μg/ml | |

The membrane was washed 3 times for 5 min in 1×TBS, 0.05% Tween-20 before a 2-h incubation in a buffer (1×TBS, 0.05% Tween-20 and 3% nonfat milk) containing horseradish peroxidase-linked anti-rabbit IgG, anti-mouse IgG (Cell Signaling Technology, Denver, Colo.) and anti-goat IgG (Sigma-Aldrich, St. Louis, Mo.) at 1:1000-3000 dilution. The membrane was washed 3 times for 5 min in 1×TBS, 0.05% Tween-20 and developed by autoluminography using the ECL chemiluminescent agents (Super Signal West Pico Chemiluminescent Substrate; Life Technologies, Grand Island, N.Y.). Citrate synthase and TBP were used as housekeeping proteins against which expressions of the proteins of interest were normalized. Phosphorylated Akt, Nrf2 and IκB-α were normalized to total Akt, Nrf2 and IκB-α. Western blot analyses of collagen I and collagen III were conducted under non-reducing, non-denaturing condition.

Example 30

Mitochondrial DNA

Extracted DNAs (QIAMP® DNA Mini Kit, QIAGEN, Germantown, Md.) from whole heart tissue were used to measure mitochondrial to nuclear DNA ratio using PCR format per manufacturer's instructions (NOVAQUANT™ Mouse Mitochondrial to Nuclear Ratio kit, EMD Millipore, Billerica, Mass.).

Example 31

Respirometry

Mice were sacrificed via cervical dislocation after isofluorane anesthesia. Hearts were immediately excised, rinsed in PBS and homogenized via polytron in 1 mL ice cold HES buffer (250 mM sucrose, 1 mM EDTA, 10 mM HEPES, pH 7.4). Lysates were spun down at 1000 g for 5 min at 4° C. to remove unbroken cells and large debris. Supernatant was then spun down at 7000 g for 10 min at 4° C. to separate mitochondria-enriched fraction from crude cytosol. Pellet was resuspended in 1 mL HES buffer (A subportion in lysis buffer for WB). Protein quantification was performed and adjustment with HES buffer to obtain sample containing 10 µg protein in 50 µL buffer which was loaded into a 24-well Seahorse cell culture plate, which was spun down at 2000 g for 20 min at 4° C. to allow mitochondria adherence to the plate surface. 450 µL MAS buffer (70 mM sucrose, 220 mM mannitol, 5 mM KH2PO4, 5 mM MgCl2, 1 mM EGTA, 0.2% fatty acid-free BSA, pH 7.4) was then added prior to Seahorse XF24 mitochondria stress test. 5 mM/5 mM pyruvate/malate and 0.25 mM ADP was used to stimulate mitochondrial oxidative phosphorylation followed by 1 µM oligomycin, 1 µM FCCP, and a mixture of 1 µM antimycin, 500 nM rotenone. Citrate synthase activity was measured in sample lysates to normalize for actual amount of mitochondria loaded for test. Seahorse respirometry on normal and human Duchenne iPs cell derived cardiomyocytes was performed using Seahorse™ XF96 Extracellular Flux analyzer as described.

Example 32

Intracellular Ca2+ Recordings iPS-derived cardiomyocytes were loaded for 30 min with 5 µM of the fluorogenic calcium-sensitive dye, Cal-520 (AAT Bioquest, Sunnyvale, Calif.) and paced via field stimulation at a frequency of 1 Hz using an Ion-Optix Myopacer (IonOptix Corp) delivering 0.2 ms square voltage pulses with an amplitude of 20 V via two platinum wires placed on each side of the chamber base (~1 cm separation). The Inventors used the xyt mode (2D) of a Leica TCS-SP5-II (Leica Microsystems Inc.; Wetzlar, Germany) to image intracellular $Ca^{2+}$. Cal 520 was excited with a 488 nm laser and its emission (>505 nm) was collected with a 10× objective (Leica: N PLAN 10×/0.25) at scan speeds ranging from 36 to 7 ms per frame depending on the field size. The fluorescence intensity (F) proportional to $Ca^{2+}$ concentration was normalized to baseline fluorescence, F0 (F/F0). Time to peak and $Ca^{2+}$ transient amplitude (F/F0) were analyzed with the software Clampfit (ver. 10.2, Molecular Devices, Inc.). Beat-to-beat alternans in each group calculated over the 5-10 sec interval of pacing at 1 Hz. The amplitude of each transient from each cell (n=10 cells in each group) was measured during pacing and mean and standard deviation were calculated and compared among groups.

Example 33

Figure 23:
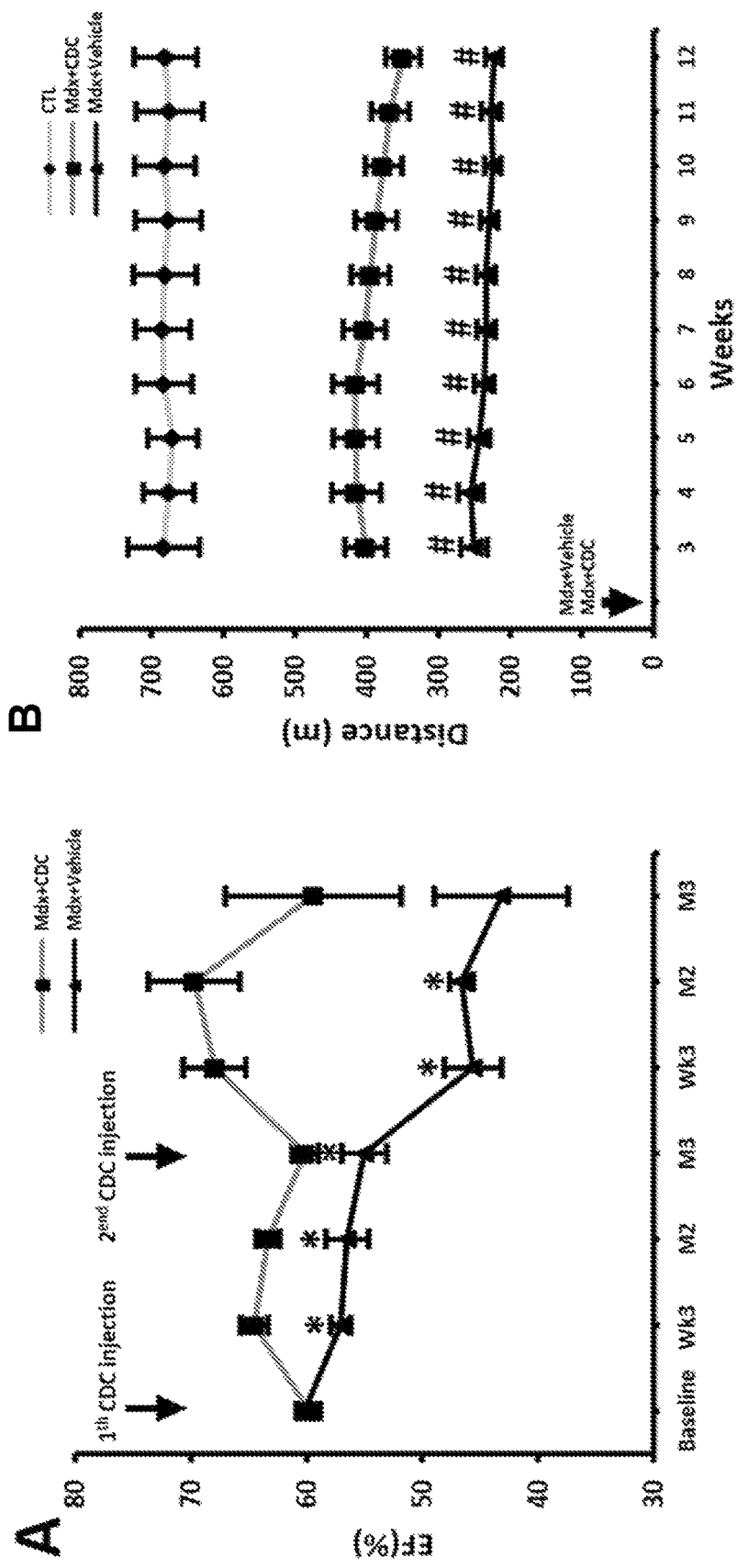
FIG. 23. Function, survival and antioxidant pathways improved by CDC transplantation in mdx mice. A: Ejection fraction (EF) in CDC-injected mdx mice (Mdx+CDC) and vehicle-injected mdx mice (Mdx+Vehicle) in response to injections at baseline (10 mos of age) and 3 months later (n=12 each). B: Exercise capacity in mice subjected to weekly high-intensity treadmill exercise, starting 3 weeks after CDC or vehicle administration (CTL: n=7; Mdx+Vehicle & Mdx+CDC: n=11 each). C: Kaplan-Meier analysis of survival in the same animals as B shows lower survival in vehicle-treated mdx mice than in CDC-treated mdx mice or wild-type controls (p<0.001, log rank test); the latter two groups, however, were statistically comparable. D: Immunohistochemical images of Nrf2 in mdx mouse hearts 3 weeks after administration of vehicle or CDCs. Age-matched wild-type mice (CTL) served as control. Scale bars: 10 μm. E: Western blots and pooled data for protein abundance of phospho-Akt (Akt-$p^{T308}$), cytoplasmic phospho-Nrf2 (Nrf2-$p^{S40}$), nuclear Nrf2 and downstream gene products: heme oxygenase-1 (HO-1), catalase, superoxide dismutase2 (SOD-2), and catalytic subunit of glutamate-cysteine ligase (GCLC) in mdx mouse hearts 3 weeks after administration of vehicle or CDCs (n=4-6). F: Pooled data and representative western blot of myocardial malondialdehyde protein adducts 3 weeks after injections as indicated, showing attenuation of oxidative stress in Mdx+CDC. Pooled data are means±SEM. *P<0.05 vs. Mdx+CDC; # P<0.005 vs. Mdx+CDC; tP<0.05 vs. Mdx+Vehicle and CTL (WT, wild type mice); ‡P<0.002 vs. Mdx+CDC and CTL (WT, wild type mice).
Figure 23:
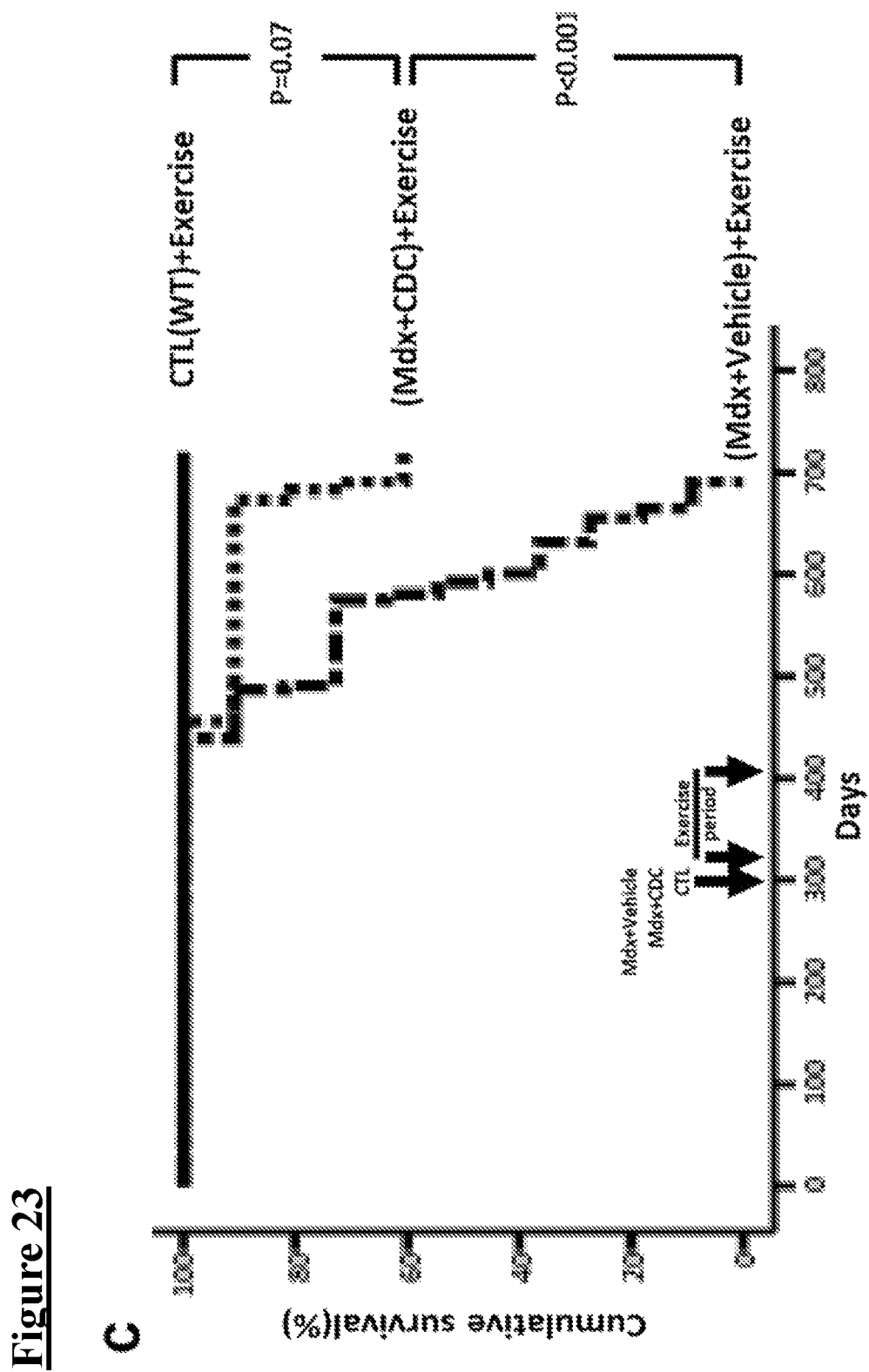
Figure 23:
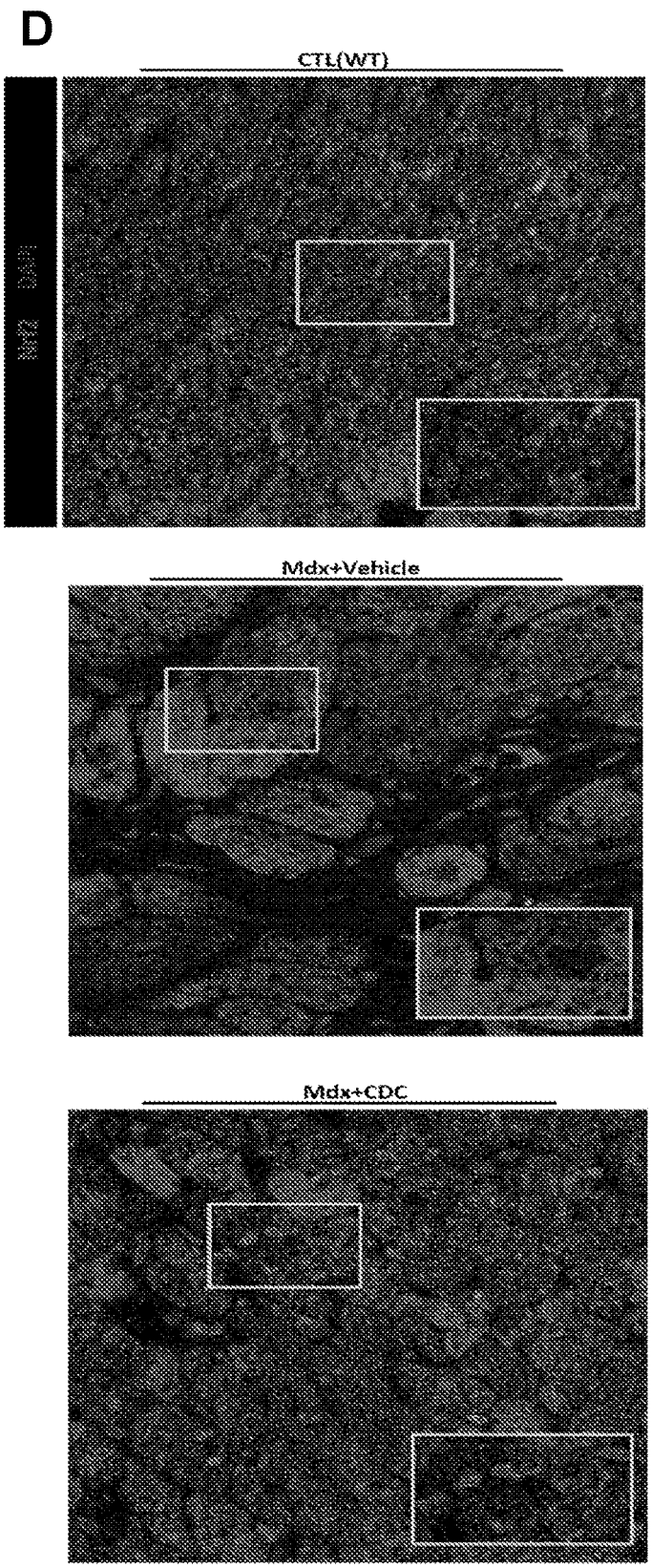
Figure 23:
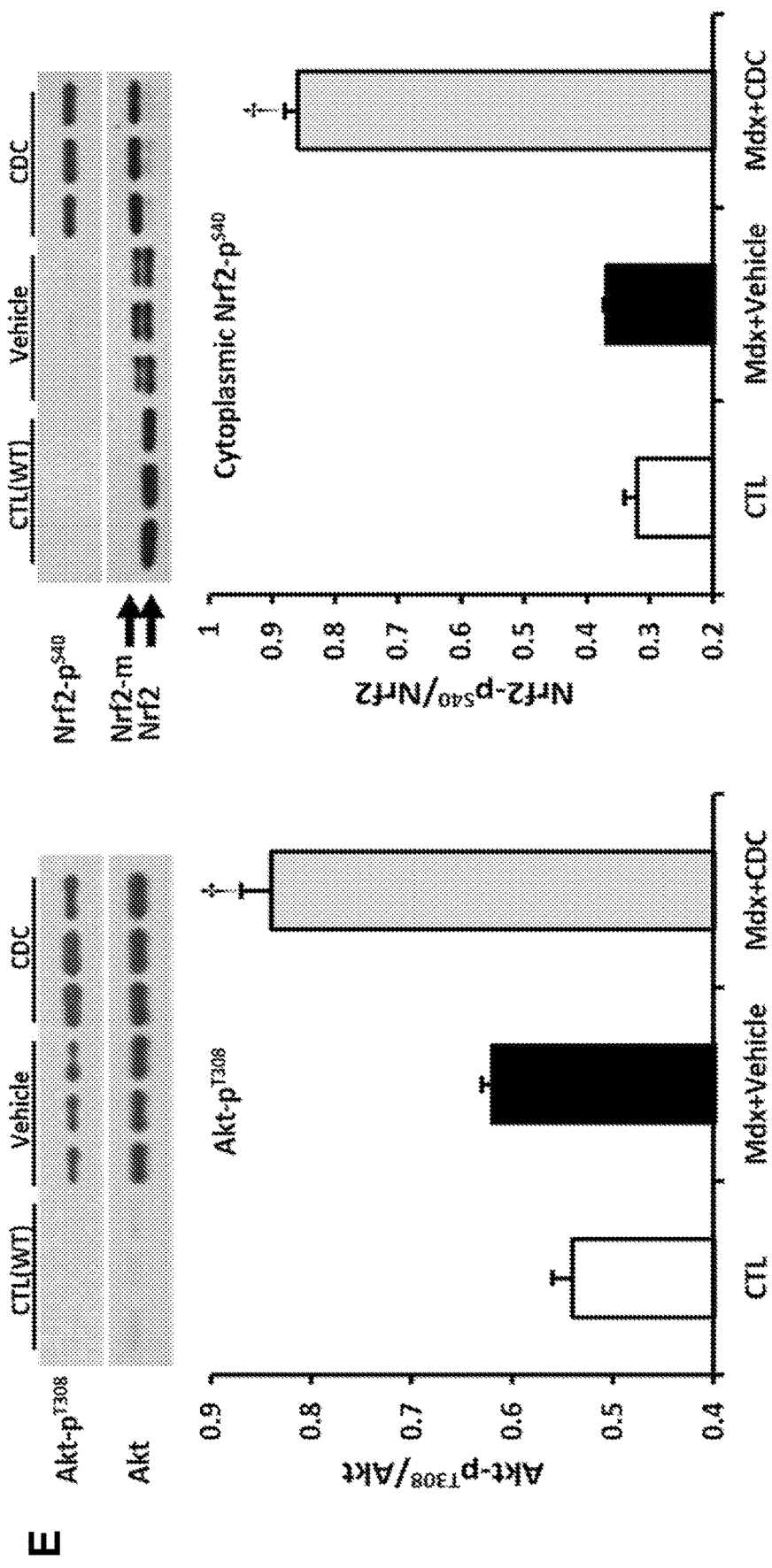
Figure 23E:
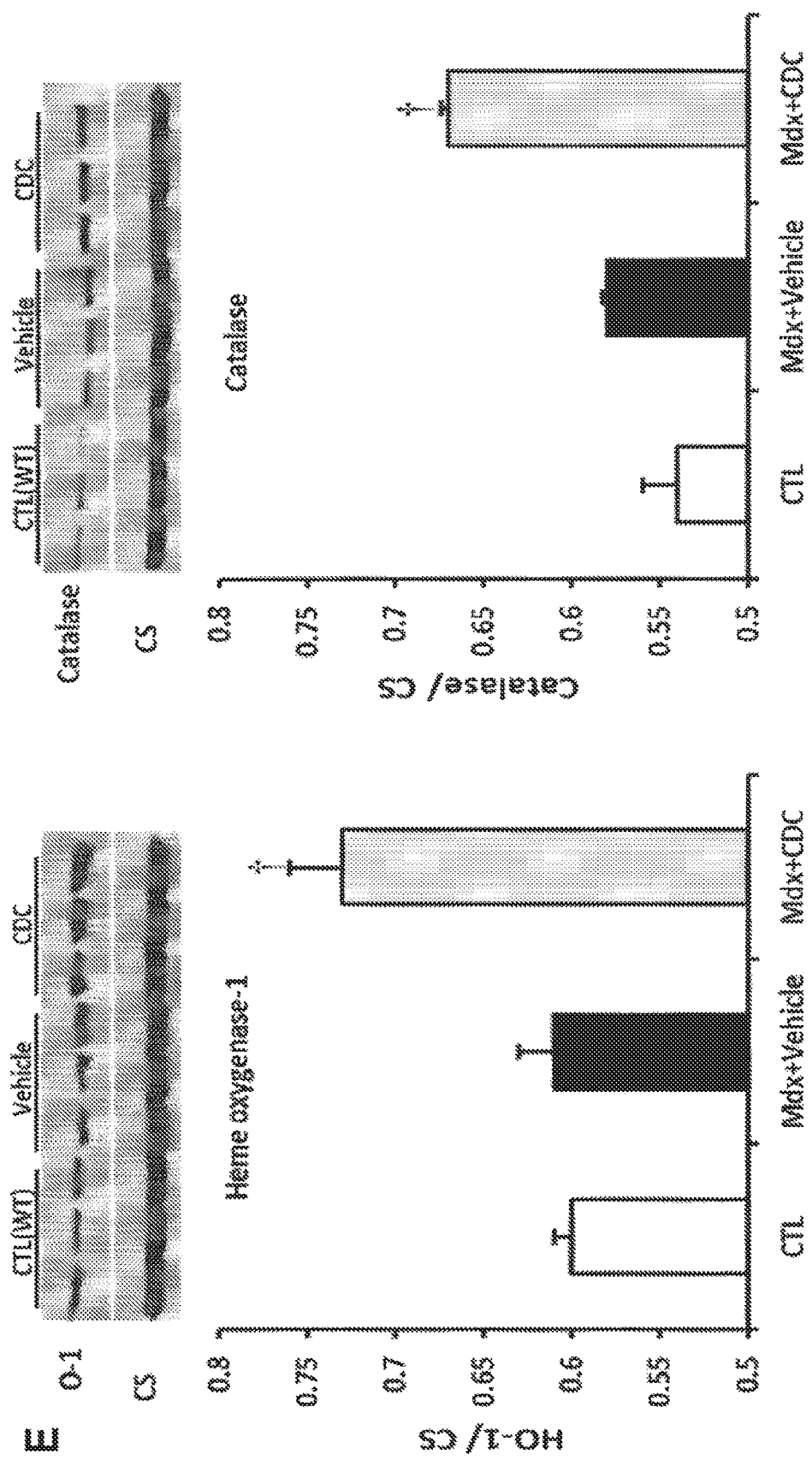
Figure 23E:
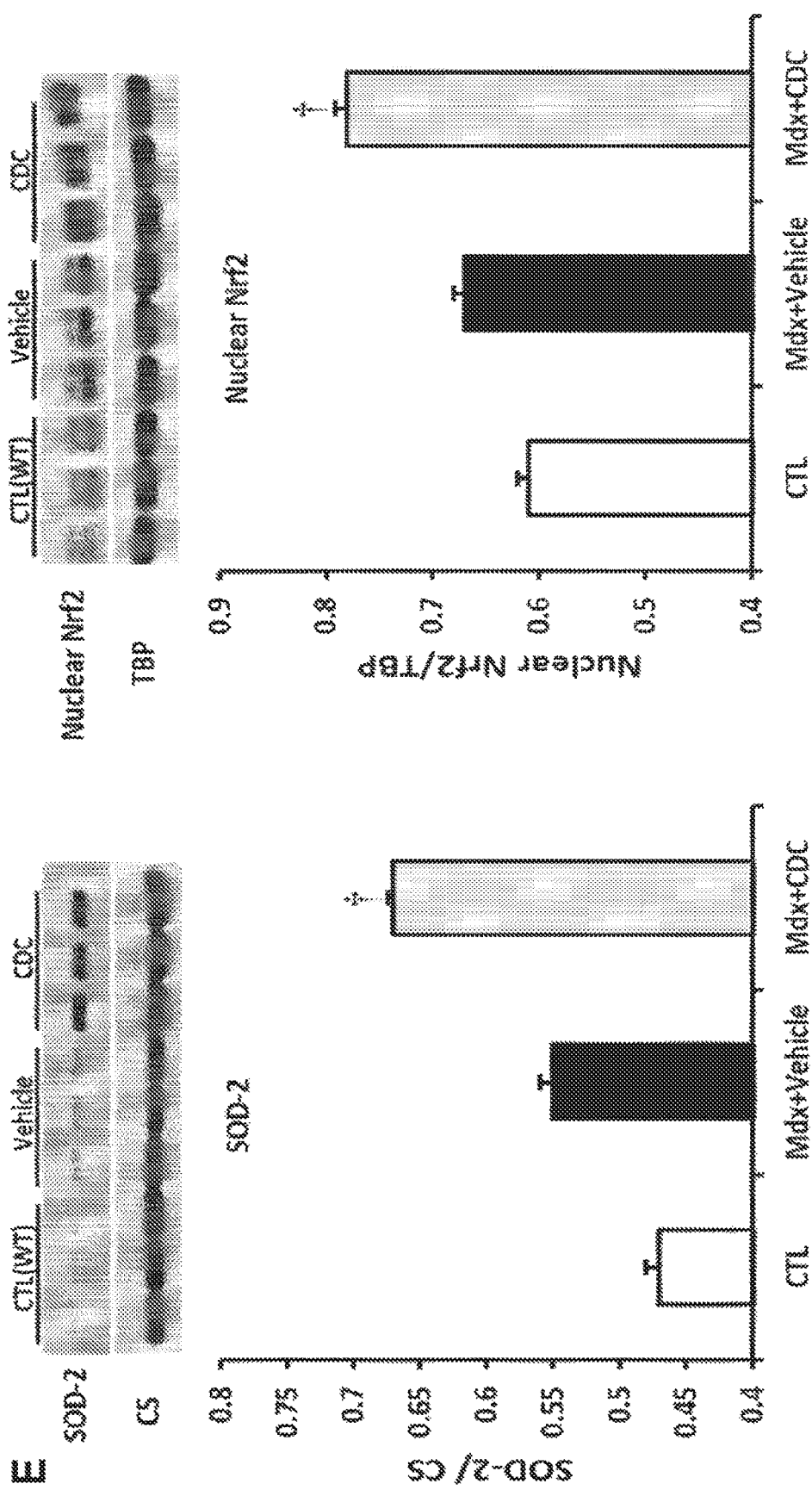
Figure 23:
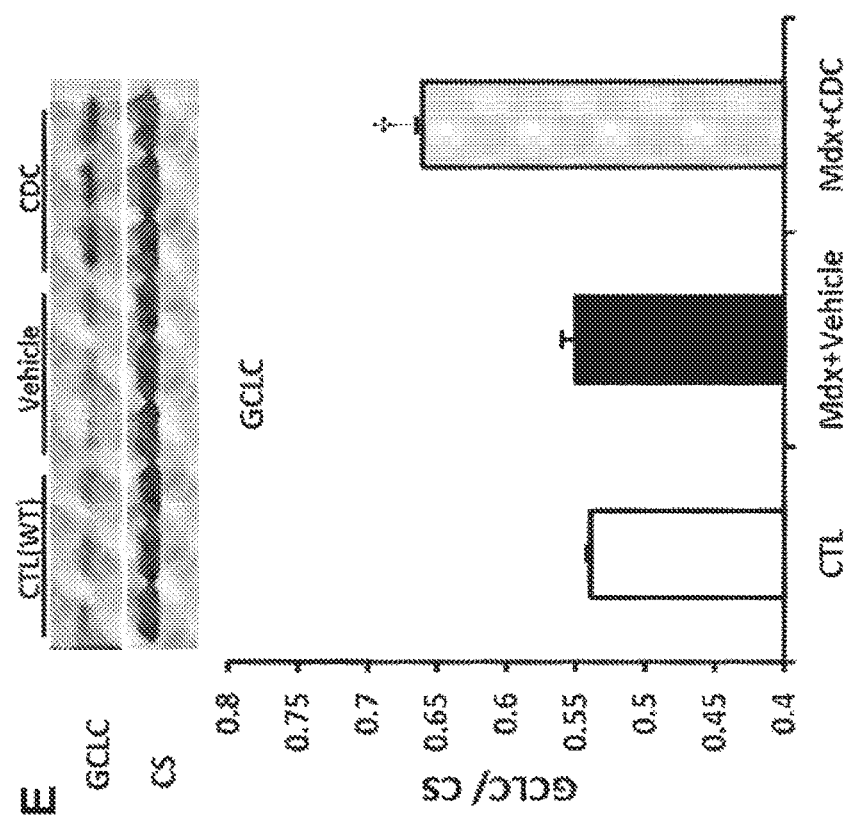
Figure 23:
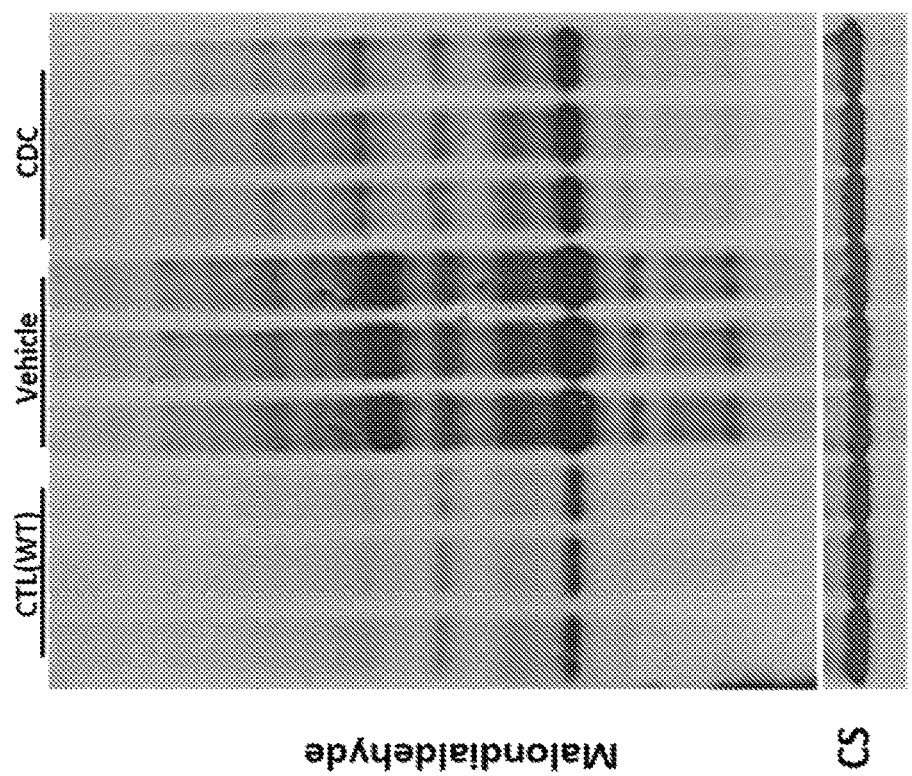
Figure 23:
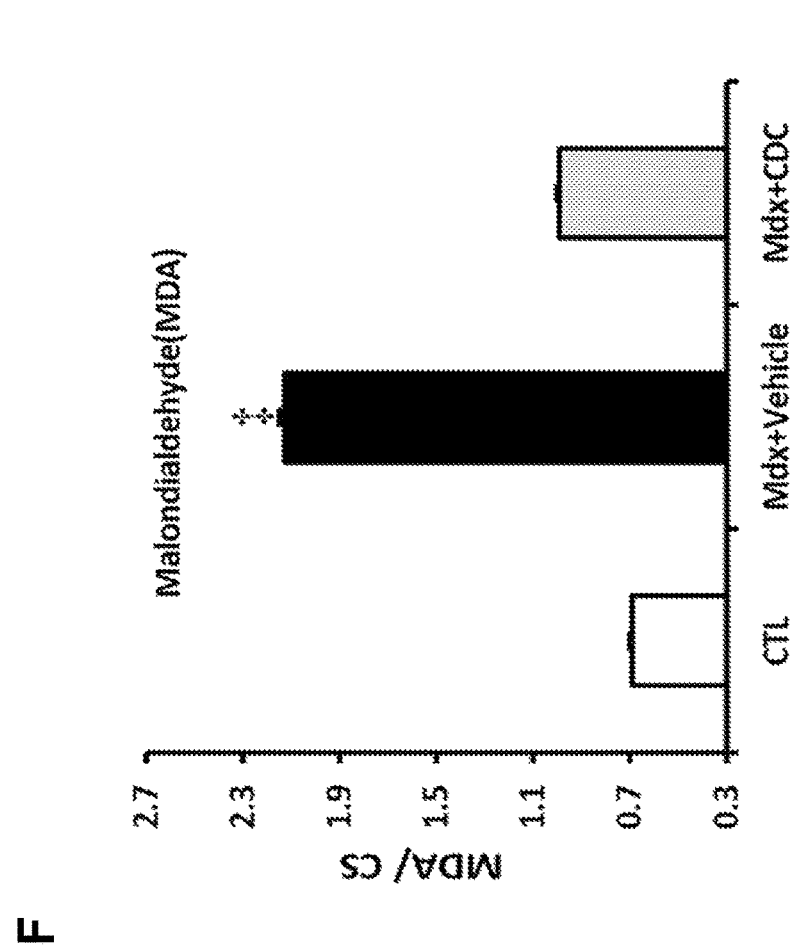

Function, Survival and Antioxidant Pathways Improved by CDC Transplantation in mdx Mice Intramyocardial injection of first and second (lower) doses of CDCs in mdx mice produced a sustained improvement of left ventricular function (as manifested by ejection fraction [EF]) and volumes, relative to placebo, for at least 6 months (FIG. 23A). The CDC-induced improvement in EF persisted beyond the point at which no surviving CDCs were detectable in mdx hearts (3 weeks after CDC delivery). In addition to improving EF, CDC injection enhanced ambulatory function (FIG. 23B). Age-matched wild-type mice (CTL) and 10-month-old mdx mice (distinct from the mdx mice studied for evaluation of cardiac function) were subjected to weekly high-intensity treadmill exercise, starting 3 weeks after CDC or vehicle administration. CDC-treated mdx mice showed a substantial increase in maximal exercise capacity, relative to vehicle-treated mdx mice, over the 3 mos that it was measured; survival also differed in the two groups (FIG. 23C). By ~23 mos of age all vehicle-treated mdx mice had died, whereas >50% of CDC-treated mdx mice remained alive (FIG. 23C). Injection of CDCs led to activation of the Nrf2 anti-oxidant pathway and upregulation of downstream gene products (FIG. 23E). Concomitantly, oxidative stress was attenuated (FIG. 23F). Nrf2 is normally sequestered in the cytoplasm via binding to its repressor molecule, Keap1. Oxidative stress (as well as Nrf2 phosphorylation by protein kinases such as Akt) causes dissociation of the Nrf2-Keap1 complex, which culminates in nuclear translocation of Nrf2 and transcriptional activation of antioxidant enzymes. In mdx hearts, levels of phosphorylated Akt and cytoplasmic and nuclear Nrf2 were high (as expected in response to oxidative stress); CDC treatment further increased their protein levels (FIG. 23E). As a consequence, downstream effectors heme oxygenase-1 (HO-1), catalase, superoxide dismutase-2 (SOD-2), and the catalytic subunit of glutamate-cysteine ligase (GCLC) were upregulated (FIG. 23E), leading to a profound reduction of malondialdehyde adducts (fatty acid peroxidation end products; FIG. 23F) in CDC-treated mdx heart. Histological analysis revealed extensive fibrosis in a typical vehicle-treated mdx heart, but much less in a CDC-treated mdx heart (comparable to an age-matched wild-type [WT] control). Likewise, Western blot analysis showed that CDC treatment largely reversed the accumulation of collagens I and III in mdx heart tissue 3 weeks after treatment.

Example 34

Figure 24:
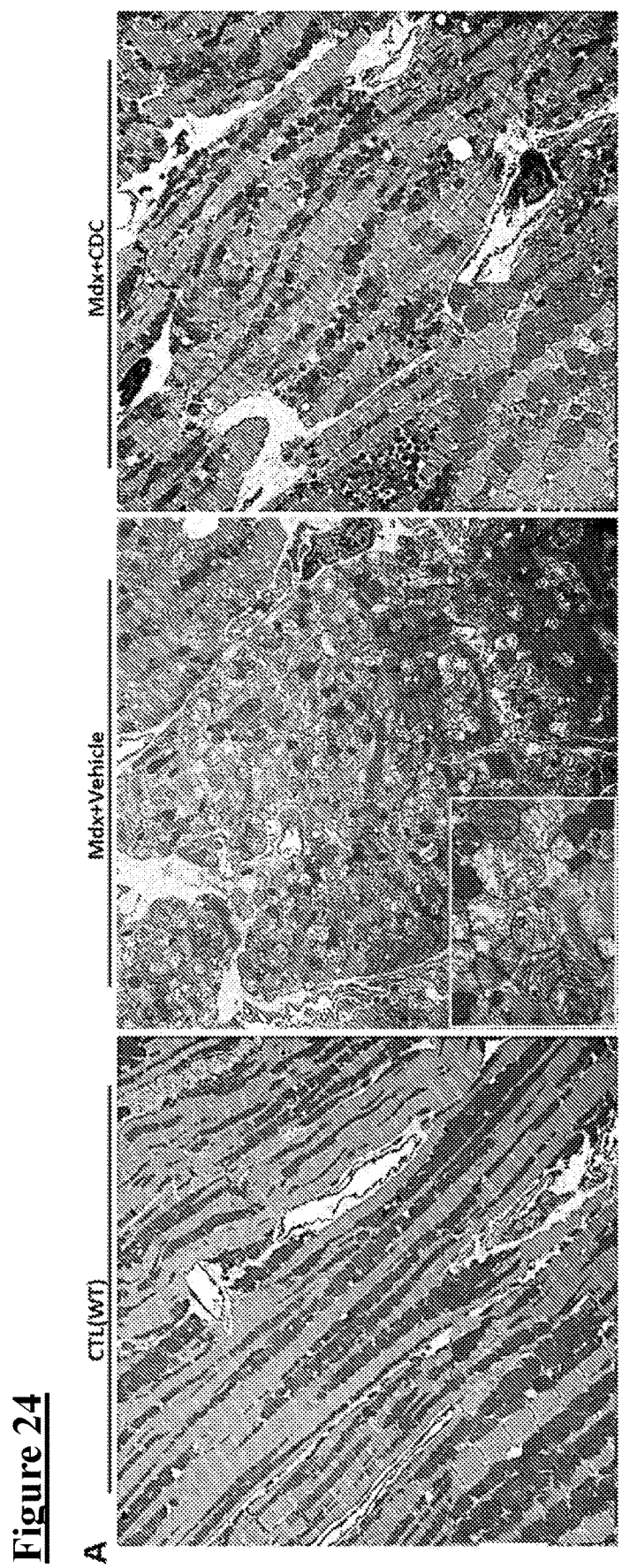
FIG. 24. Mitochondrial dysfunction and inflammation attenuated by CDC transplantation in mdx mouse hearts. A: Transmission electron microscopy (TEM) images from mdx mouse hearts 3 weeks after administration of vehicle (Mdx+Vehicle) or CDC (Mdx+CDC). Age-matched wild-type mice (CTL) served as control. B: Numbers of mitochondria from TEM images. C: Mitochondrial DNA copy numbers (per nuclear genome) in the heart tissue 3 weeks after treatment. D: Representative western blots and pooled data for mitochondrial respiratory chain subunits in heart tissue from CTL and mdx mice 3 wks after treatment (n=4-6 per group). E: Oxygen consumption rate (OCR) of mitochondria isolated from the hearts of CTL and CDC- or vehicle-treated mdx mice 3 weeks after treatment (CTL: n=3; Mdx+Vehicle & Mdx+CDC: n=8 each). Substrates (pyruvate, malate and ADP), a selective uncoupler (FCCP) and blockers (Oligomycin [Olig.]; Antimycin & Rotenone [Anti. & Rot.]) of oxidative phosphorylation were applied when indicated. F: Western blots and pooled data depicting protein abundance of mitochondrial PINK1 and nuclear PPARγ co-activator-1 (PGC-1) 3 days and 3 weeks after CDC administration in mdx mouse hearts (n=4-6). G: Immunohistochemical images of hearts stained for inflammatory cell markers CD68, CD20 and CD3. H: Western blots, pooled data and bar graph (lower right) representing average number of indicated inflammatory cells in mdx mouse hearts. In CDC-treated mice, accumulation of CD68$^+$ macrophages (upper row) and CD3$^-$ T cells (lower row) was reduced in association with inhibition of NF-κB pathway. Data are means±SEM. †P<0.05 vs. Mdx+Vehicle and CTL (WT, wild type mice); ‡P<0.003 vs. Mdx+CDC and CTL (WT, wild type mice); *P<0.05 vs. Mdx+CDC. Scale bars: 5 μm(A); 10 μm (G).
Figure 24:
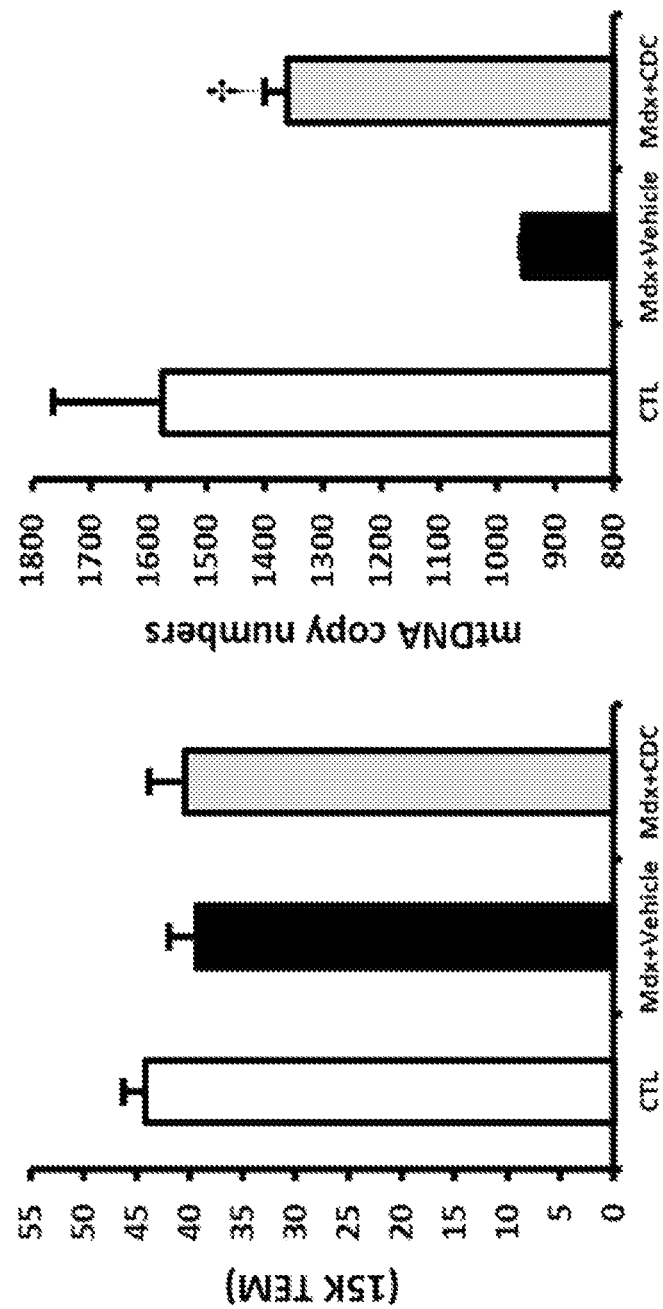
Figure 24:
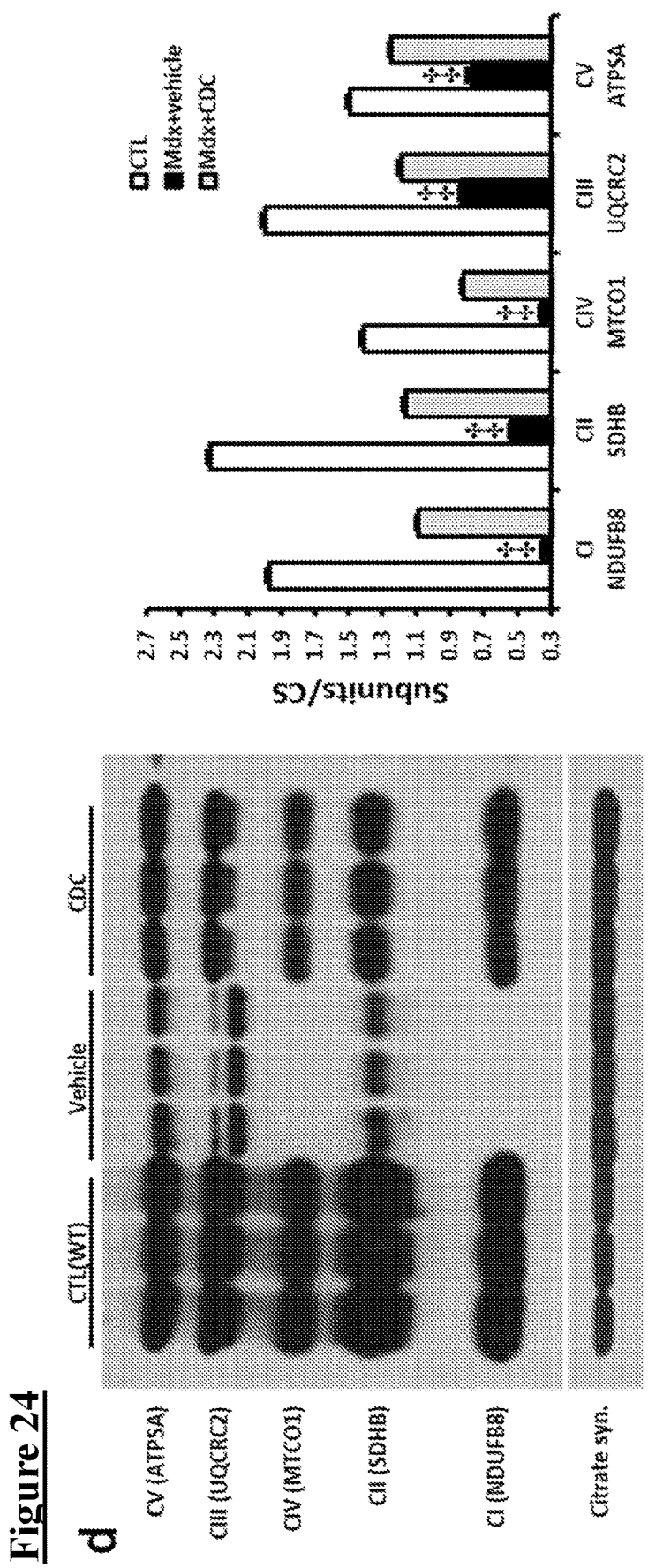
Figure 24:
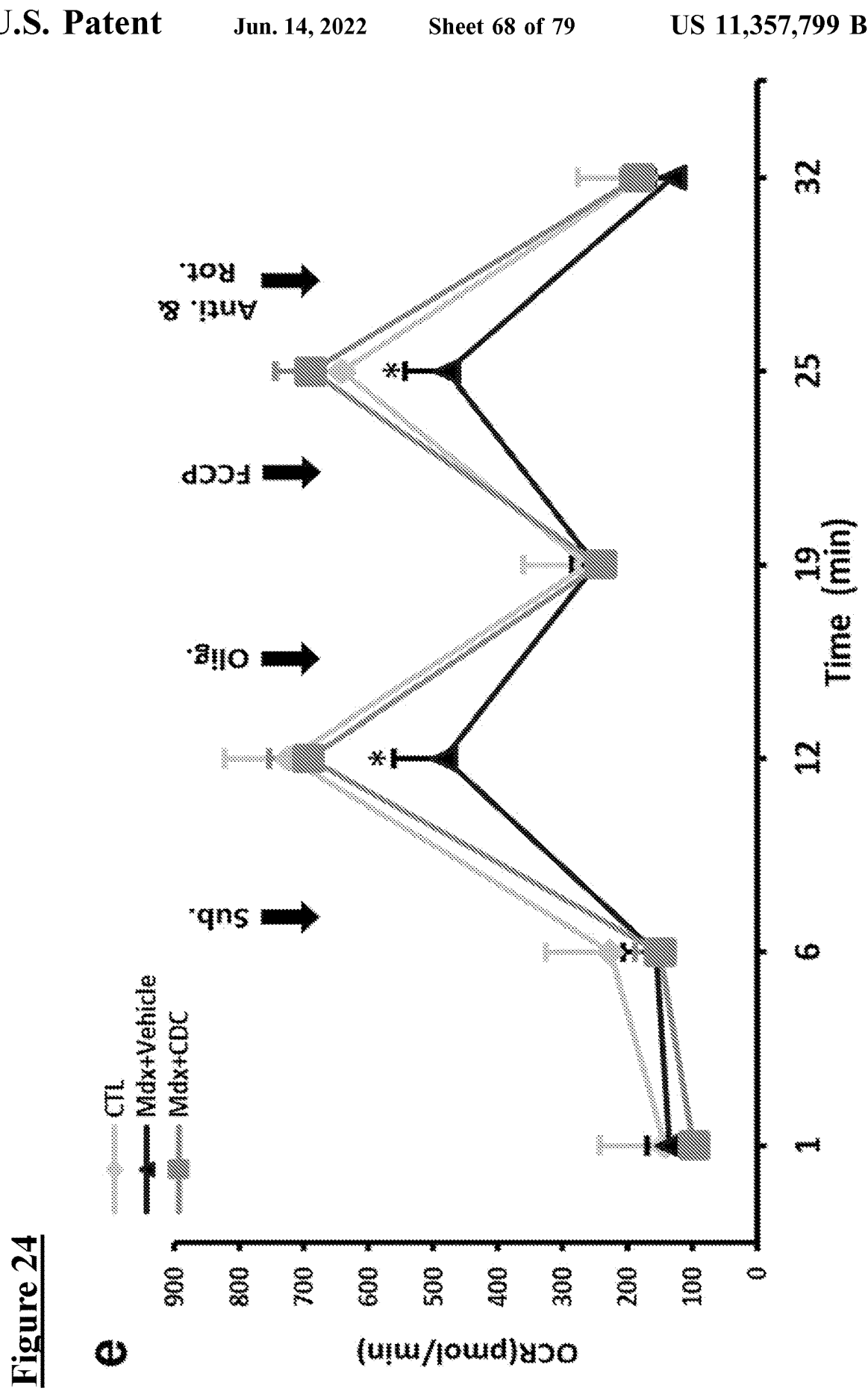
Figure 24:
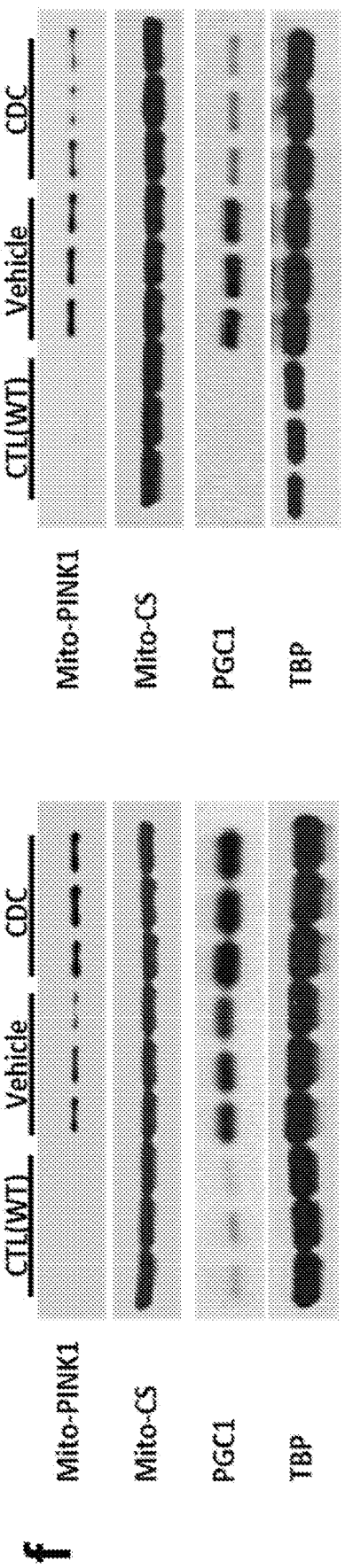
Figure 24:
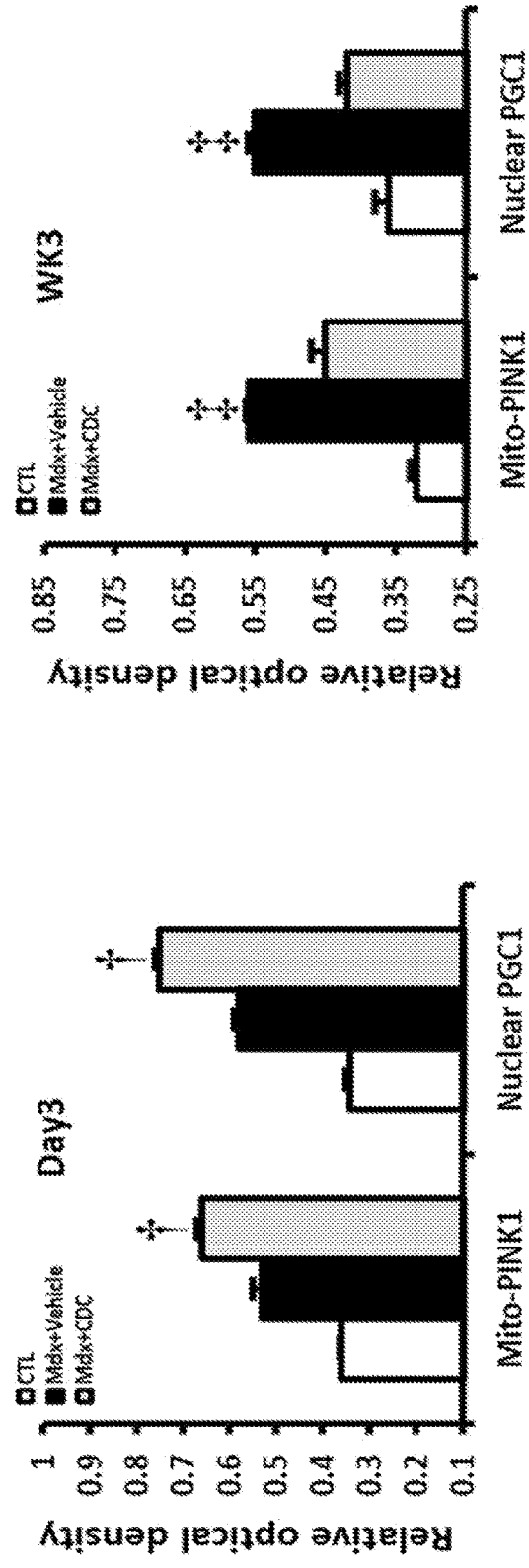
Figure 24:
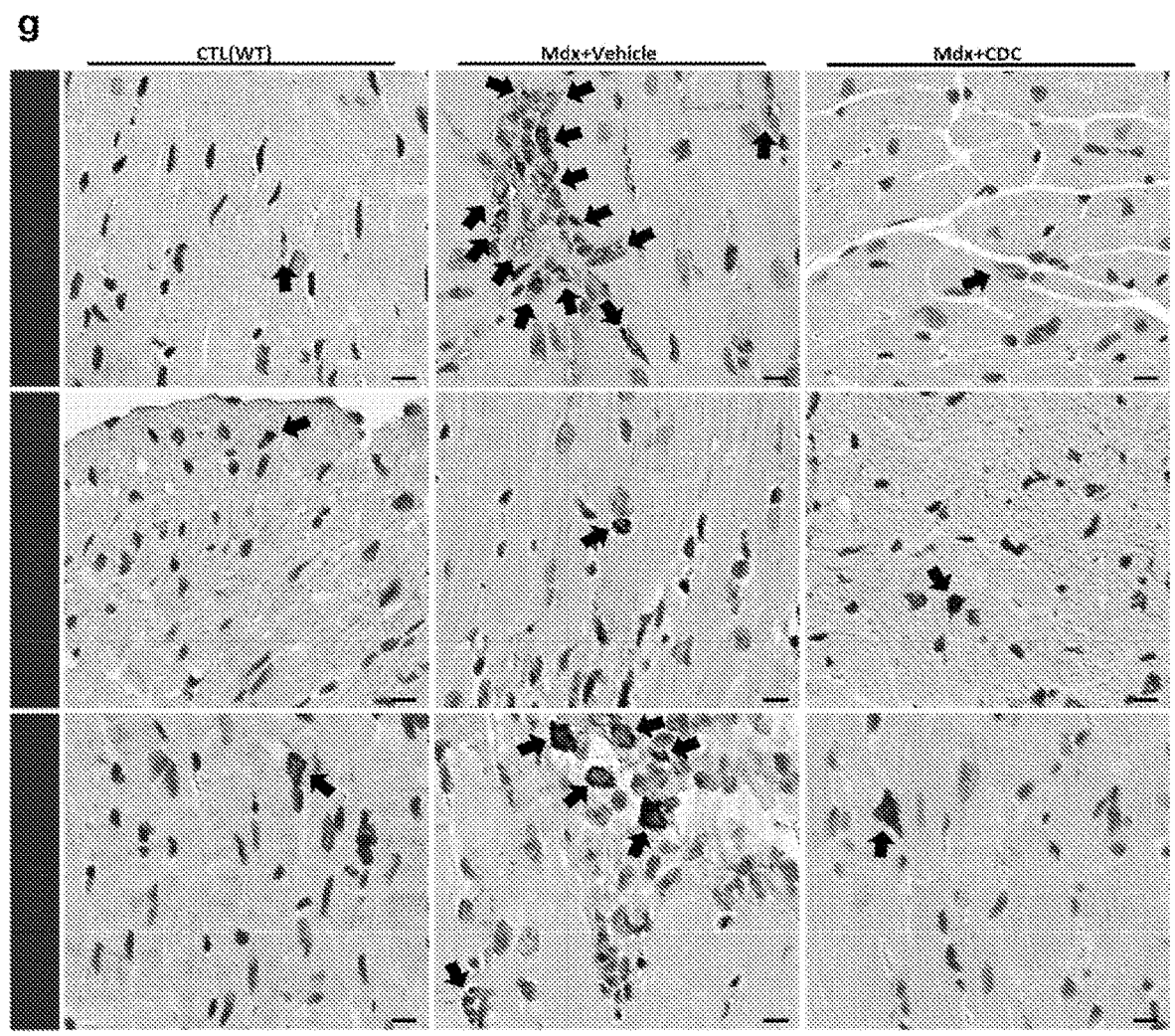
Figure 24:
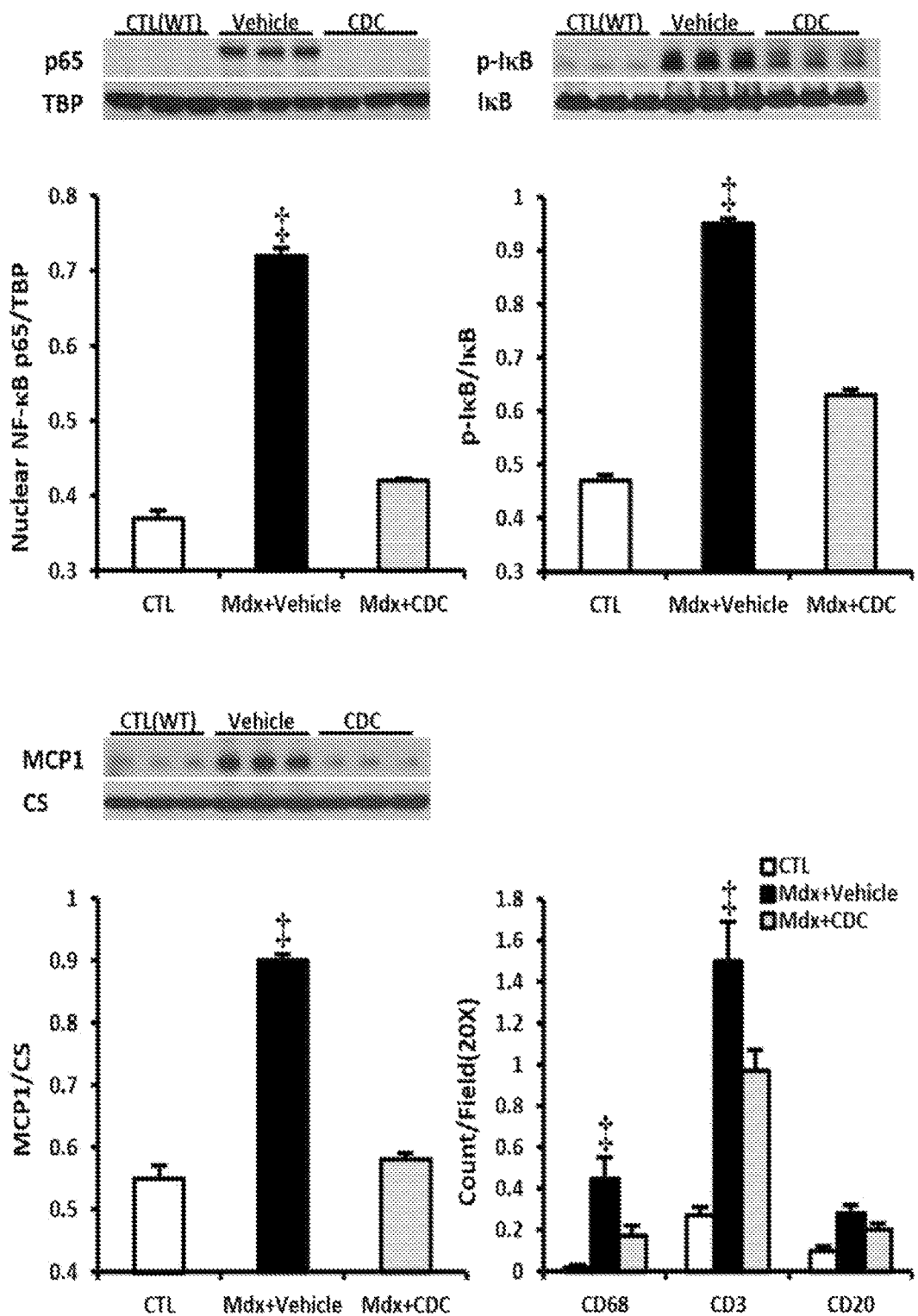

Mitochondrial Dysfunction and Inflammation Attenuated by CDC Transplantation in mdx Mouse Hearts Mitochondrial structure and function are abnormal in muscular dystrophy-associated heart failure. In mdx hearts, mitochondrial integrity improved 3 weeks after CDC injection: CDCs restored mitochondrial ultrastructure (FIG. 24A), increased mitochondrial DNA copy numbers (but not mitochondrial number; FIGS. 24B & C), augmented levels of respiratory chain subunits (FIG. 24D) and normalized the deficient respiratory capacity of isolated mdx mitochondria (FIG. 24E).

Key regulators of mitochondrial biogenesis and mitophagy, PGC-1 (nuclear PPARγ co-activator 1) and PINK1, respectively, were upregulated 3 days and down-regulated 3 weeks after CDC treatment (FIG. 24F), consistent with an initial turnover of damaged mitochondria followed by repopulation with stable competent mitochondria. Of note, the improved mitochondrial integrity and decreased mitochondrial turnover observed 3 weeks after CDC treatment in mdx mouse hearts were associated with upregulation of antioxidant enzymes and reductions of oxidative stress and inflammation (FIGS. 24G & H). NFκB, the master regulator of pro-inflammatory cytokines and chemokines, was activated in vehicle mdx hearts: Increases in phosphorylated IκB and nuclear p65 contents were accompanied by marked upregulation of MCPJ (monocyte chemoattractant proteinl) and accumulation of CD68$^+$ macrophages and CD3$^+$ T cells. CDC treatment reversed activation of NFκB and decreased the number of inflammatory cells in mdx hearts 3 weeks after CDC injection (FIGS. 24G & H). The Inventors also probed the effects of CDCs on cardiomyogenesis. Vehicle-treated mdx hearts exhibited a several-fold increase in the numbers of cycling (Ki67$^+$) and proliferating (aurora B$^+$) cardiomyocytes, presumably as a compensation for ongoing cardiomyocyte loss. CDCs are known to increase endogenous cardiomyogenesis in ischemic and non-ischemic models. Likewise, CDC treatment promoted cardiomyogenesis in the mdx heart, as evidenced by a marked increase in Ki67$^+$ and aurora B$^+$ cardiomyocytes.

Example 35

CDC-Secreted Exosomes Reproduce Benefits of CDCs in mdx Mice

Figure 25:
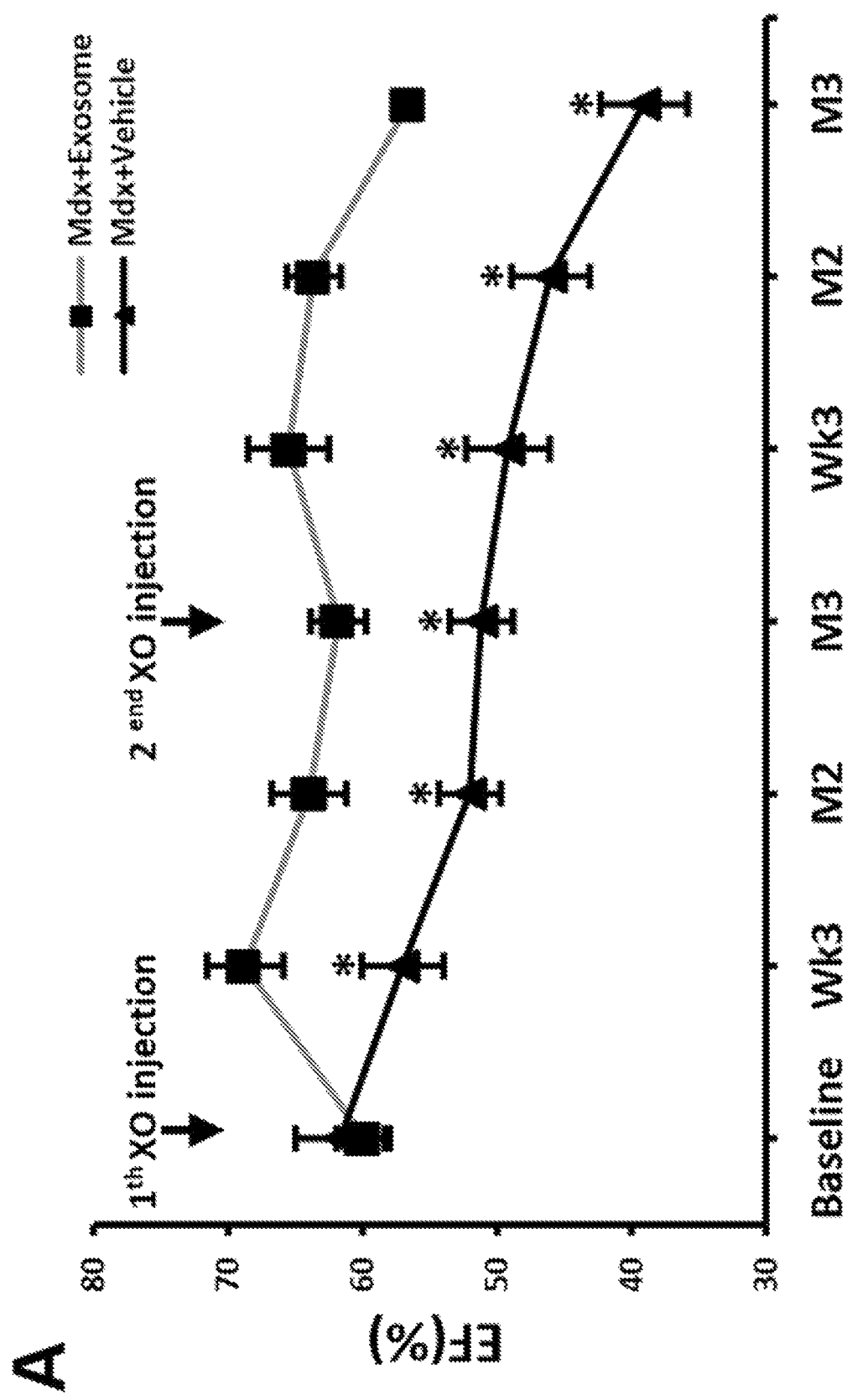
FIG. 25. CDC exosomes reproduce benefits of CDCs in mdx mice. A: Sustained functional benefit for at least 3 months with each of two sequential CDC exosome injections in mdx mice (n=11). B&C: Diminished cardiac collagen content (B) and enhanced cardiomyogenesis (C) 3 weeks after CDC exosome injection. Western blots and pooled data for cardiac collagen IA and IIIA (B), and immunohistochemical images and pooled data (C: CTL [wild type], vehicle and CDCexosome-treated [Mdx+XO] mdx mouse hearts stained for Ki67[C1] and Aurora B [C2]; n=4-6 per group). Arrows point to Ki67$^+$ (C1) and Aurora B$^+$ (C2) cardiomyocytes. WGA (Wheat germ agglutinin) was applied for staining and delineation of cell membrane. Data are means±SEM; *P<0.05 vs. Mdx+XO; †P<0.02 vs. Mdx+Vehicle and CTL (WT, wild type mice); ‡P<0.01 vs. Mdx+XO and CTL (WT, wild type mice), scale bar: 10 μm.
Figure 25:
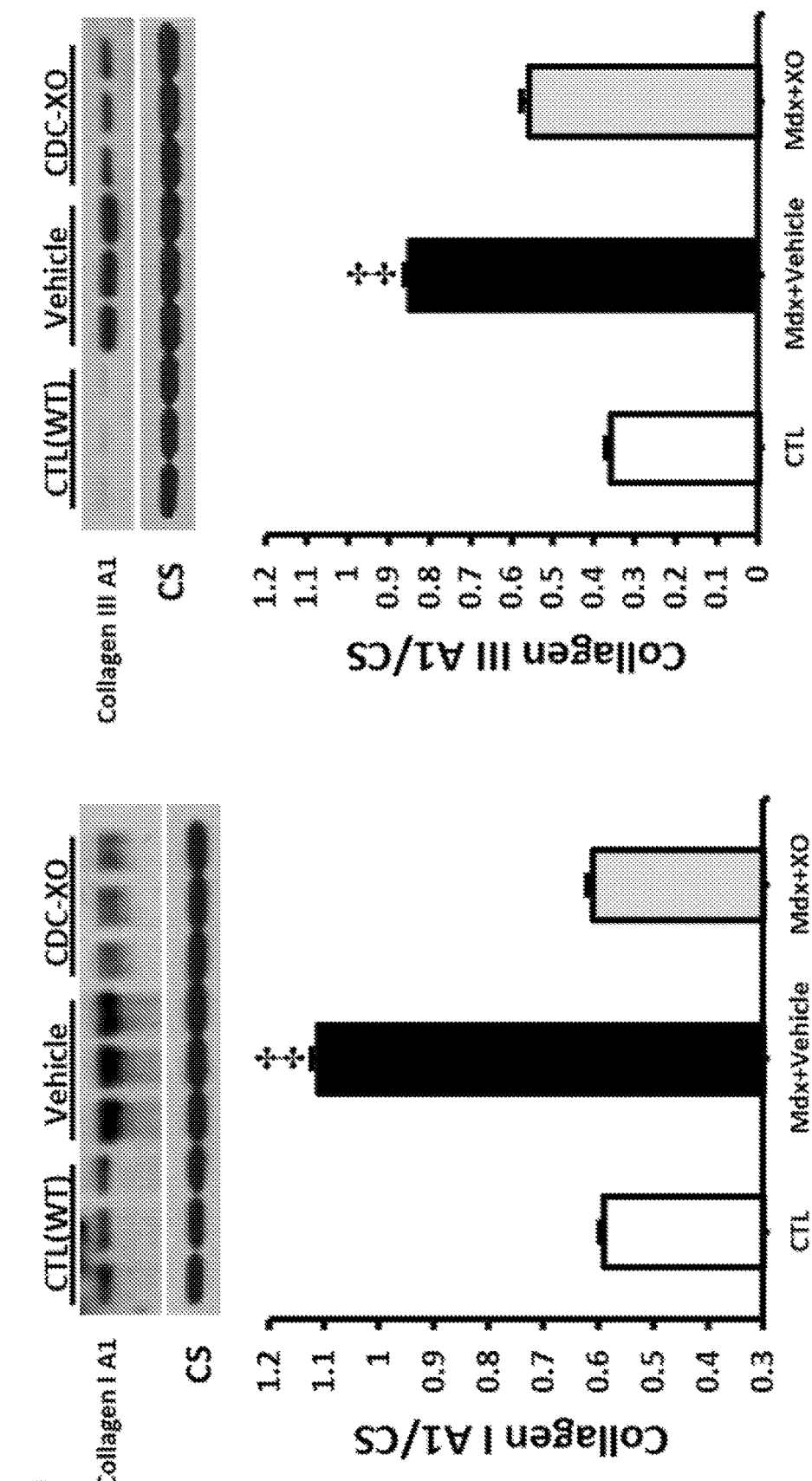
Figure 25:
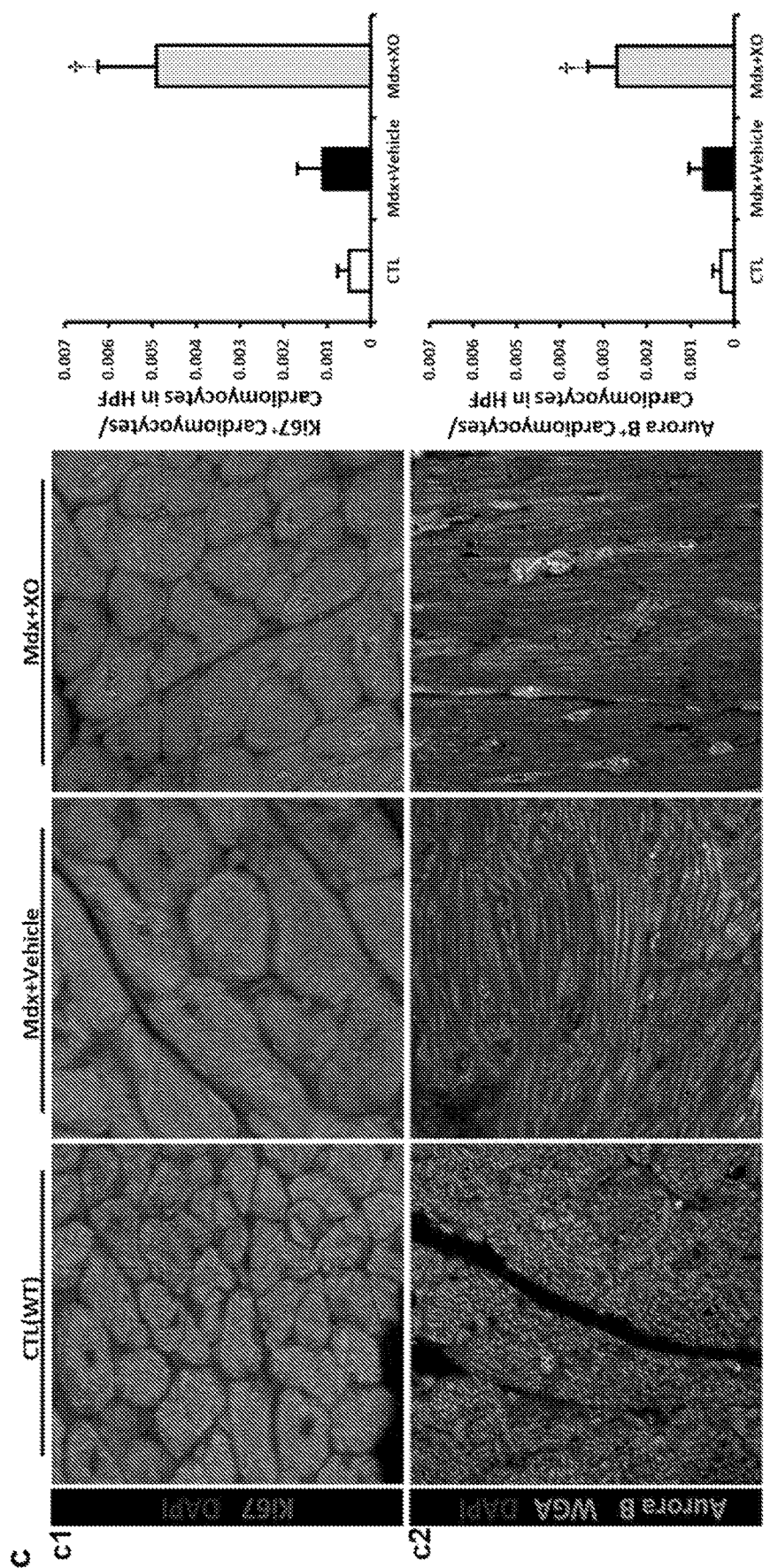

Exosomes secreted by CDCs (CDC-exosomes) mimic the functional and structural benefits of CDCs in a murine model of myocardial infarction. In the mdx mouse model of DMD, likewise, functional, anti-fibrotic, and cardiomyogenic benefits of CDCs are reproduced by administration of exosomes isolated from media conditioned by hypoxic CDCs. Intramyocardial injection of two repeat doses of human CDC-exosomes (separated by 3 months) led to sustained improvement in EF in mdx mice, relative to vehicle-treated mice (FIG. 25A). Meanwhile, the amounts of collagen I and III decreased in CDC-exosome-injected mdx hearts (FIG. 25B), along with marked increases in the numbers of cycling (Ki67$^+$, FIG. 25C1) and proliferating (aurora B$^+$, FIG. 25C2) cardiomyocytes.

Example 36

CDC-Exosomes in Human Duchenne Cardiomyocytes and miR-148a in mdx Mice

Figure 26:
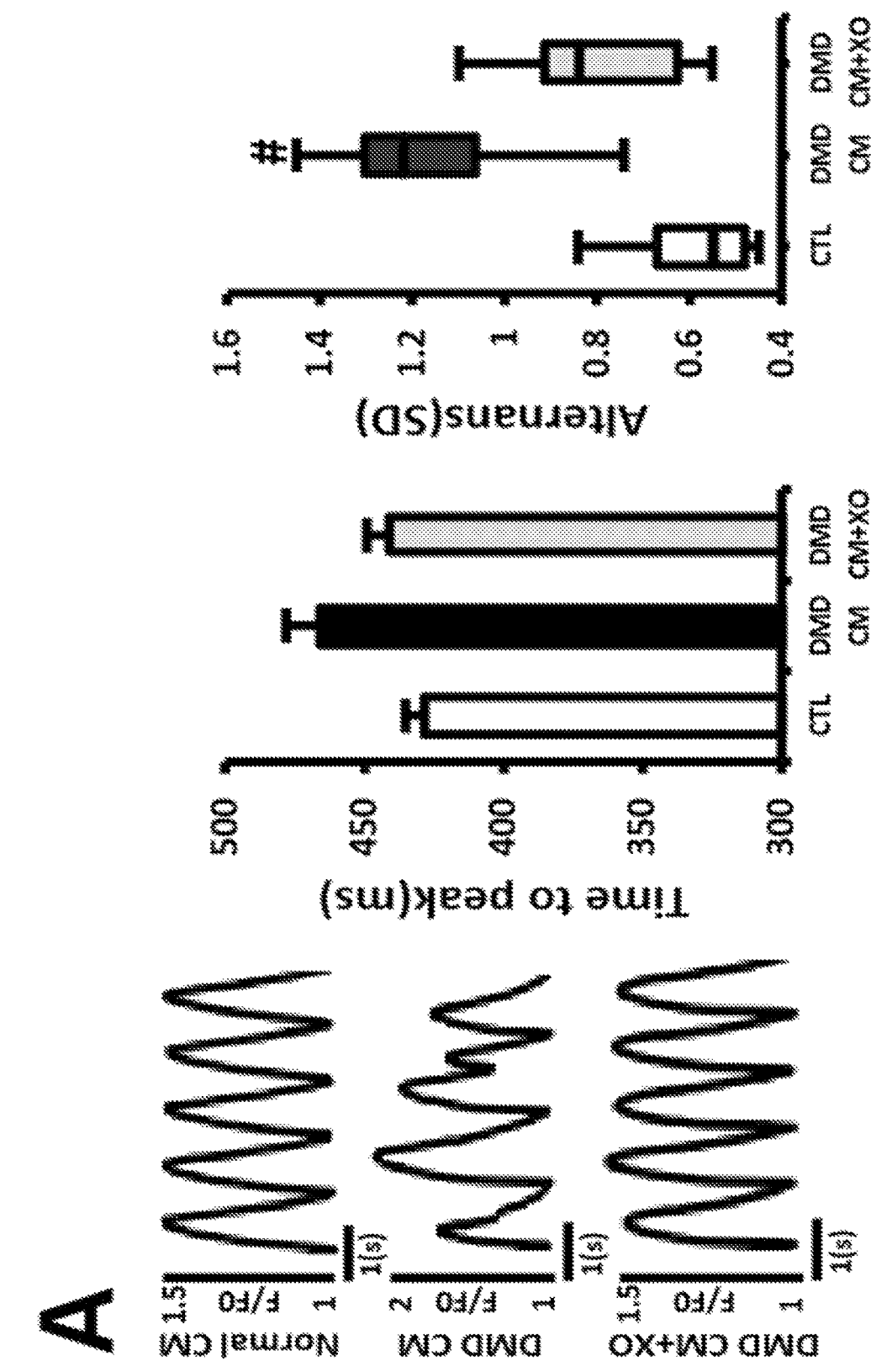
FIG. 26. CDC exosomes in human Duchenne cardiomyocytes and miR-148 in mdx mice. A: Calcium transients from normal and Duchenne human iPS-derived cardiomyocytes measured during 1 Hz burst pacing. Duchenne cardiomyocytes primed with vehicle (DMD CM) or CDC exosomes 1 week before assessment (DMD CM+XO). Bar graphs of calcium transient: time to peak and alternans (variation in beat-to-beat calcium transient amplitude). B: Oxygen consumption rate (OCR) in human Duchenne cardiomyocytes primed with CDC exosomes [DMD CM (CDC-XO$^+$)] or exosomes from normal human dermal fibroblasts [NHDF, as control; DMD CM (NHDF-XO$^+$)] 1 week before OCR measurement. Normal (Normal CM) and non-treated Duchenne cardiomyocytes (DMD CM) were studied in parallel. See FIG. 2 legend for abbreviations. C: Differential expression of microRNAs in CDC exosomes isolated from hypoxic conditioned media (2% $O_2$) compared to CDC exosomes isolated from normoxic conditioned media (n=2), including only miRs with >20 sequence hits. D: Injection of miR-148 mimic intramyocardially partially restored cardiac function in mdx mouse hearts 3 weeks after treatment. E: Western blots and pooled data for nuclear p65 (left) and phosphorylated Akt (right) in mdx mouse hearts 3 weeks after miR-148 treatment. F: Schematic of pathophysiological mechanisms operative in Duchenne cardiomyopathy and the cellular mechanisms recruited by CDCs and their exosomes (XO). All data are means±SEM except for the box plot (means±SD).
Figure 26:
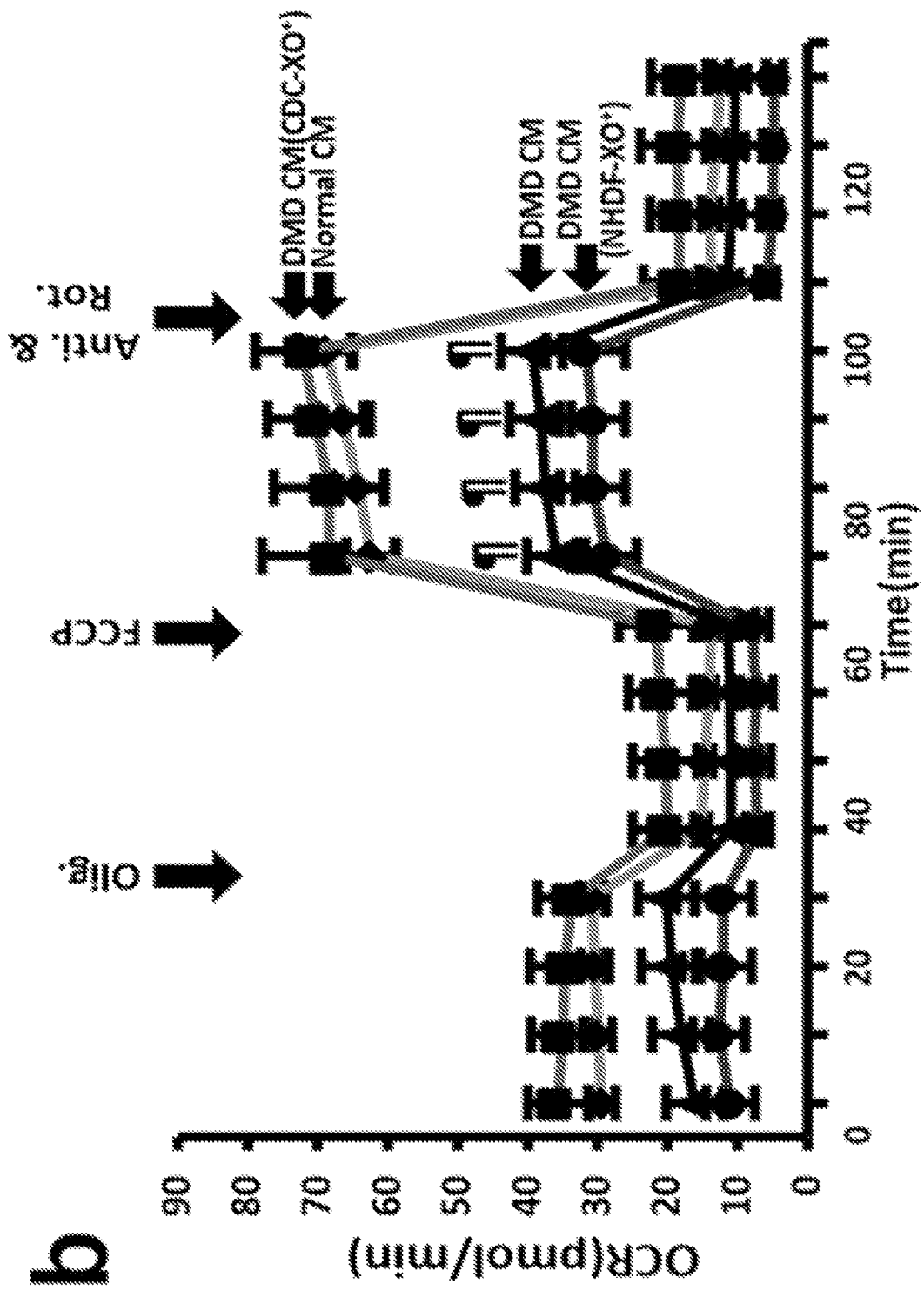
Figure 26:
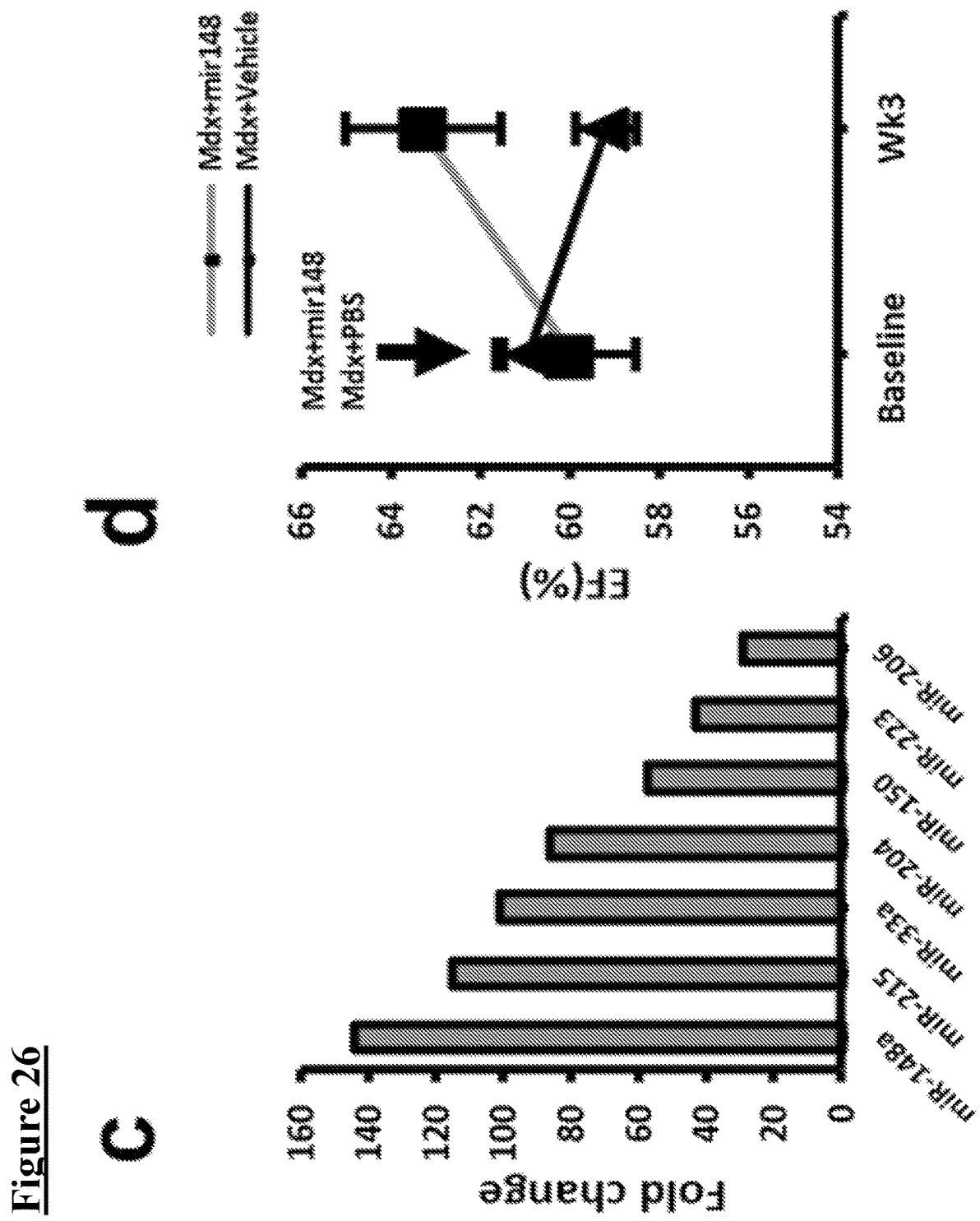
Figure 26:
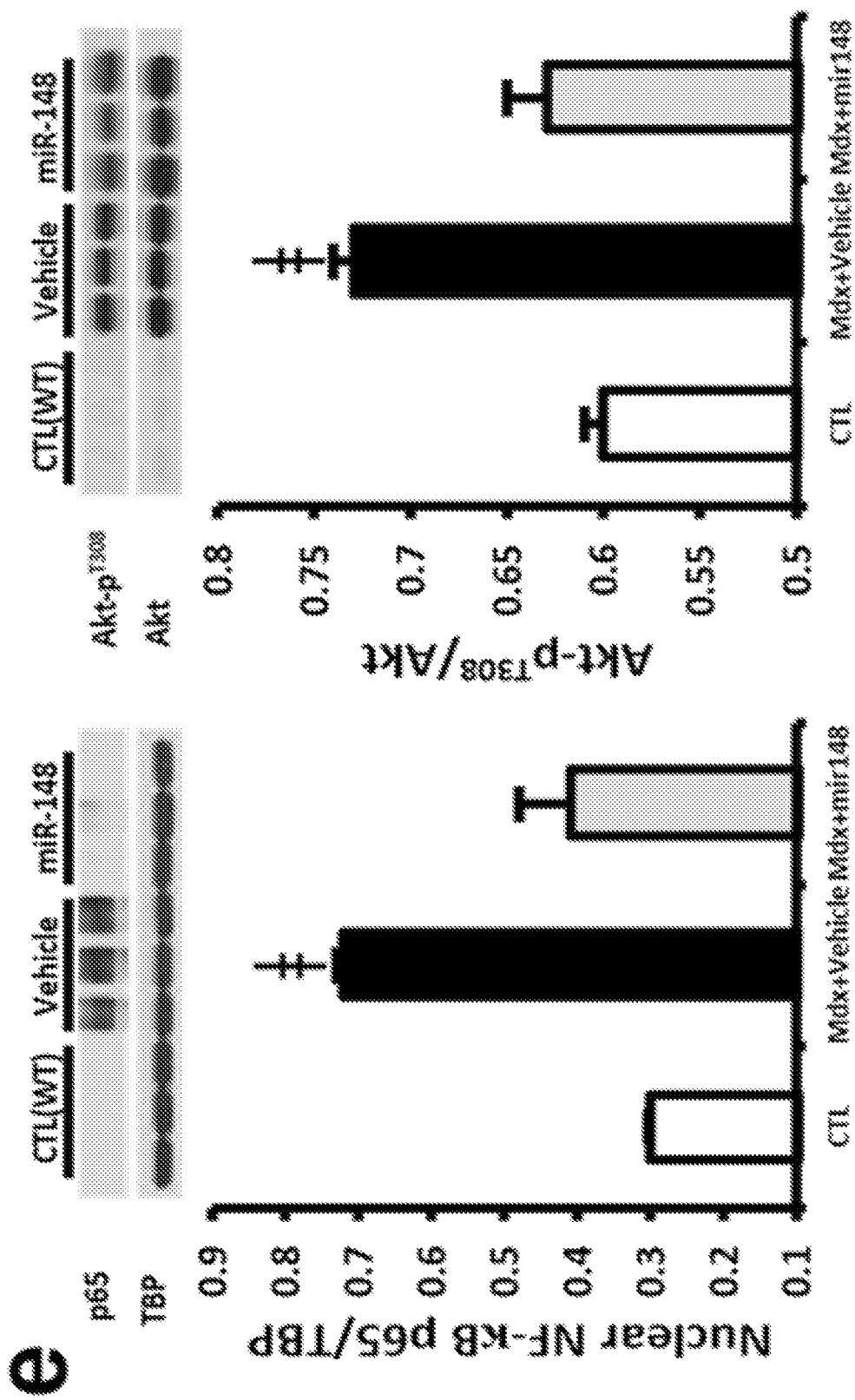
Figure 26:
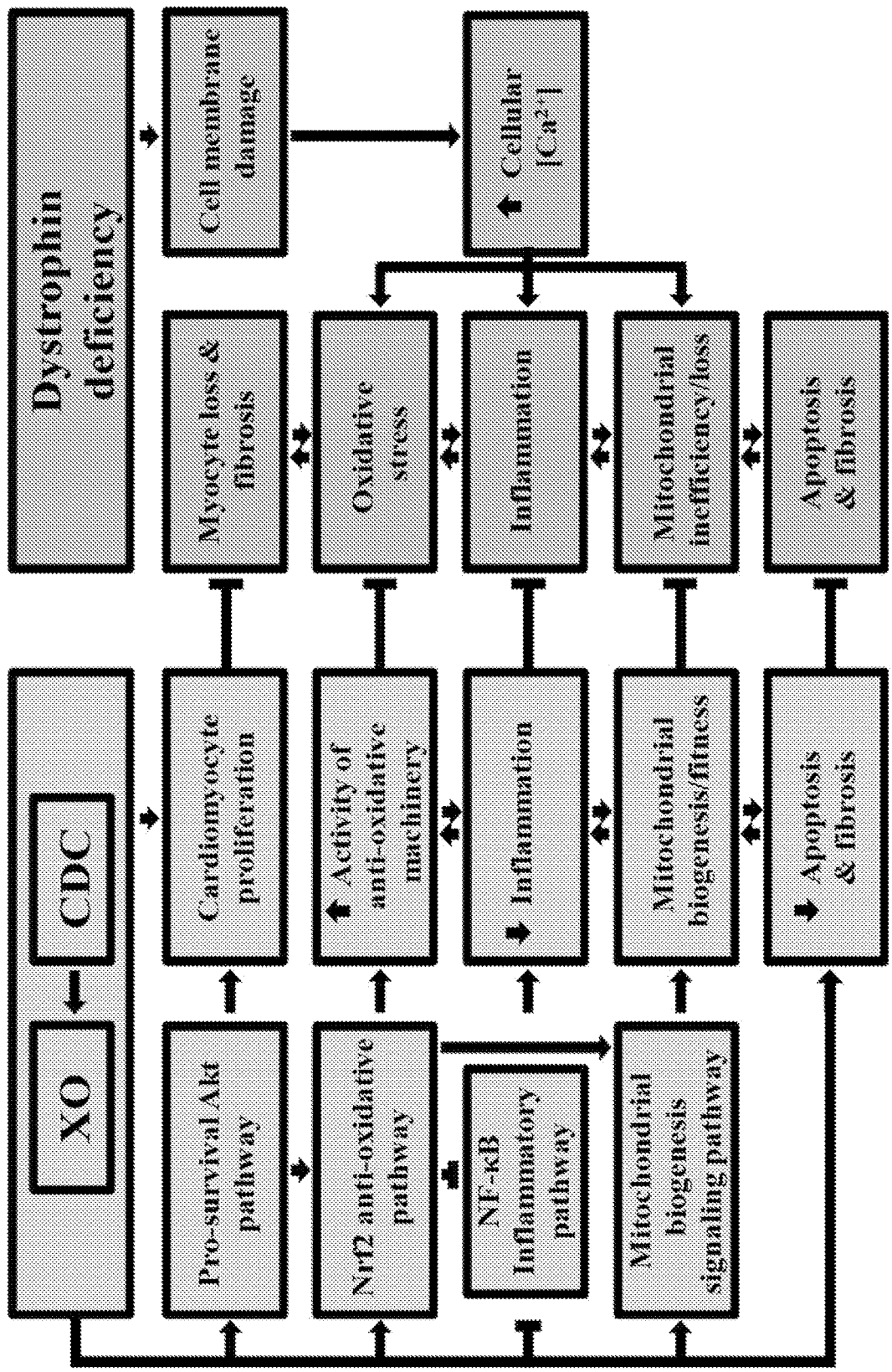

Duchenne human iPS-derived cardiomyocytes (DMD CMs) exhibit a number of phenotypic deficits also seen in mdx mouse hearts. Decreased oxygen consumption rate (OCR), reminiscent of that observed in mdx heart mitochondria (FIG. 24E), and abnormal calcium cycling are among the reported deficits[21]. Priming DMD CMs with CDC-exosomes one week earlier normalized OCR, but priming with exosomes from normal human dermal fibroblasts (NHDFexosomes) had no effect. Beat-to-beat calcium transient alternans during 1 Hz burst pacing, a measure of arrhythmogenicity, was likewise suppressed by priming DMD CMs with CDCexosomes (FIGS. 26A & B). Comparison of microRNA (miR) content of CDC-exosomes isolated from hypoxic versus normoxic CDCs revealed differences in miR expression (FIG. 26C), with notable augmentation of miR-148a in hypoxia. Given that the Inventors' CDC-exosomes were grown under hypoxia, the Inventors tested the effects of miR-148a administration. Three weeks after intramyocardial injection of miR-148a mimic, EF fraction was partially restored, and NFκB was suppressed, by miR-148a, but phospho-Akt level decreased (FIGS. 26D & E). The phospho-Akt changes are directionally opposite to those seen with CDC injection (FIG. 23E), indicating that miR-148a mimics some, but not all, of the effects of CDCs and CDC-exosomes.

TABLE 2

| 95% Confidence interval of difference | | | |
|---|---|---|---|
| *pAkt(CDC) | *pNrf2 | *Nuclear Nrf2 | *HO-1 |
| 1 (0.20, 0.43) | 1 (0.46, 0.62) | 1 (0.14, 0.20) | 1 (0.04, 0.23) |
| 2 (0.11, 0.31) | 2 (0.42, 0.56) | 2 (0.06, 0.13) | 2 (0.02, 0.23) |
| MDA | p-IκB | p65 | MCP-1 |
| 1 (1.37, 1.50) | 1 (0.43, 0.52) | 1 (0.32, 0.36) | 1 (0.28, 0.41) |
| 3 (1.08, 1.21) | 3 (0.28, 0.37) | 3 (0.28, 0.32) | 3 (0.27, 0.36) |
| CIII | CV | Collagen I(CDC) | Collagen III(CDC) |
| 1 (−1.27, −1.07) | 1 (−0.82, −0.63) | 1 (0.10, 0.19) | 1 (0.05, 0.23) |
| 3 (−0.42, −0.29) | 3 (−0.57, −0.39) | 3 (0.07, 0.14) | 3 (0.05, 0.11) |
| PINK1(Wk3) | *PGC-1(D3) | PGC-1(Wk3) | Collagen I(XO) |
| 1 (0.22, 0.26) | 1 (0.36, 0.46) | 1 (0.13, 0.26) | 1 (0.38, 0.71) |
| 3 (0.05, 0.16) | 2 (0.13, 0.22) | 3 (0.11, 0.17) | 3 (0.36, 0.69) |
| CD3 | *AuroraB(CDC) | *Ki67(CDC) | *AuroraB(XO) |
| 1 (0.79, 1.73) | 1 (0.001, 0.01) | 1 (0.001, 0.01) | 1 (0.001, 0.004) |
| 3 (0.04, 1.08) | 2 (0.0001, 0.004) | 2 (0.0001, 0.01) | 2 (0.0002, 0.004) |
| *Catalase | *SOD-2 | *GCLC | |
| 1 (0.04, 0.21) | 1 (0.16, 0.25) | 1 (0.09, 0.13) | |
| 2 (0.07, 0.11) | 2 (0.10, 0.14) | 2 (0.08, 0.15) | |

TABLE 2-continued

| 95% Confidence interval of difference | | |
|---|---|---|
| CI | CII | CIV |
| 1 (−1.69, −1.56) | 1 (−1.85, −1.72) | 1 (−1.14, −0.97) |
| 3 (−0.79, −0.70) | 3 (−0.70, −0.54) | 3 (−0.51, −0.41) |
| P65(miR-148) | pAkt(miR-148) | *PINK1(D3) |
| 1 (0.37, 0.46) | 1 (0.096, 0.15) | 1 (0.25, 0.34) |
| 3 (0.08, 0.53) | 3 (0.054, 0.15) | 2 (0.05, 0.19) |
| Collagen III(XO) | Alternans | CD68 |
| 1 (0.36, 0.59) | 1 (−0.024, 0.83) | 1 (0.18, 0.67) |
| 3 (0.25, 0.35) | 3 (−0.59, 0.37) | 3 (0.01, 0.56) |
| *Ki67(XO) | | |
| 1 (0.001, 0.01) | | |
| 2 (0.0001, 0.01) | | |

1: Wild type
2: Mdx + Vehicle
3: Mdx + CDC or Mdx + CDC-exosome or Mdx + miR148
*95% confidence interval (CI) for the difference between 3 vs 1; 3 vs 2. The rest denotes 95% CI for the difference between 2 vs 1, 2 vs 3.

Example 37

Discussion

Although heart disease may not be apparent in DMD patients for a decade or more after the diagnosis of skeletal myopathy, cardiomyopathy progresses rapidly once it becomes evident. Serial cardiac magnetic resonance imaging studies have revealed that fibrosis, while often initially restricted to just one segment of the heart, spreads quickly and inexorably thereafter[23]. The result is impairment of global heart function and early death. There is no effective treatment to reverse, prevent, or slow the progression of DMD cardiomyopathy. Recognizing that CDCs exert regenerative effects that may be salutary in DMD, the Inventors tested the effects of CDC injection early in the course of DMD cardiomyopathy. The Inventors discovered that CDCs attenuate fibrosis and inflammation in the mdx heart, while improving pump function, increasing exercise capacity and enhancing survival. The salient benefits of CDCs were reproduced by CDC-exosomes. The Inventors' findings support the hypothesis that CDCs act by secreting exosomes laden with genetic signals, including (but not limited to) miR-148a. These exosomes are taken up by the surrounding myocardium, where they antagonize multiple pathophysiological pathways that underlie DMD cardiomyopathy. The constellation of effects is synergistic: oxidative stress, inflammation and fibrosis are blunted, while cardiomyogenesis and mitochondrial function are augmented. The results are notable in that CDCs and their exosomes not only forestall progression, but actually reverse the central functional deficits of DMD cardiomyopathy. Major improvements in mortality and exercise capacity occur without targeting dystrophin, providing proof of concept that the root genetic cause need not be corrected in order for DMD therapies to be highly effective. Given that CDCs are already in advanced clinical testing, the Inventors' results support the initiation of clinical trials of CDCs in patients with DMD cardiomyopathy. Indeed, based upon the present findings, the HOPE-Duchenne trial will soon investigate the safety and tolerability of allogeneic CDCs administered by multi-vessel intracoronary infusion in subjects with heart failure secondary to DMD.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of cardiosphere derived cells, the use of alternative sources such as cells derived directly from heart biopsies (explant-derived cells), or from self-assembling clusters of heart-derived cells (cardiospheres), exosomes produced by such cells, method of isolating, characterizing or altering exosomes produced by such cells, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treating heart failure secondary to muscular dystrophy, comprising:
administering a composition comprising cardiosphere-derived cells (CDCs) to a subject in need of treatment for heart failure secondary to muscular dystrophy, wherein administration of the composition treats the subject.

2. The method of claim 1, wherein the muscular dystrophy is Duchenne muscular dystrophy.

3. The method of claim 1, wherein administering a composition comprises about $1\times10^5$ to about $1\times10^8$ or more CDCs in a single dose.

4. The method of claim 3, wherein administering a composition comprises myocardial infusion.

5. The method of claim 4, wherein myocardial infusion is intracoronary.

6. The method of claim 4 wherein myocardial infusion is intra-arterial or intravenous.

7. The method of claim 1, wherein treatment of the subject results in decreased fibrosis, decreased inflammation, increased mitochondrial function and/or increased cardiomyogenesis.

* * * * *